(12) United States Patent
Chand et al.

(10) Patent No.: US 11,680,098 B2
(45) Date of Patent: Jun. 20, 2023

(54) ANTIBODIES THAT SPECIFICALLY BIND HUMAN CD96

(71) Applicant: Agenus Inc., Lexington, MA (US)

(72) Inventors: Dhan Sidhartha Chand, Woburn, MA (US); Randi Barbara Gombos, Wilmington, MA (US); Olga Ignatovich, Cambridge (GB); Nicola Anne Ramsay, Cambridge (GB); K. Mark Bushell, Saffron Walden (GB); Emmanuel Cyrille Pascal Briend, Cambridge (GB)

(73) Assignee: AGENUS INC., Lexington, MA (US)

( * ) Notice: Subject to any disclaimer, the term of this patent is extended or adjusted under 35 U.S.C. 154(b) by 243 days.

(21) Appl. No.: 17/007,238

(22) Filed: Aug. 31, 2020

(65) Prior Publication Data

US 2021/0101977 A1   Apr. 8, 2021

Related U.S. Application Data

(60) Provisional application No. 62/931,476, filed on Nov. 6, 2019, provisional application No. 62/894,334, filed on Aug. 30, 2019.

(51) Int. Cl.
| | |
|---|---|
| *C07K 16/28* | (2006.01) |
| *A61K 39/00* | (2006.01) |
| *A61K 47/68* | (2017.01) |
| *A61K 31/713* | (2006.01) |
| *C12N 15/63* | (2006.01) |
| *C12N 5/10* | (2006.01) |
| *A61K 45/06* | (2006.01) |

(52) U.S. Cl.
CPC ........ *C07K 16/2803* (2013.01); *A61K 31/713* (2013.01); *A61K 39/001129* (2018.08); *A61K 47/6803* (2017.08); *A61K 47/6849* (2017.08); *C12N 5/10* (2013.01); *C12N 15/63* (2013.01); *A61K 45/06* (2013.01); *A61K 2039/507* (2013.01); *C07K 2317/21* (2013.01); *C07K 2317/31* (2013.01); *C07K 2317/565* (2013.01)

(58) Field of Classification Search
CPC ............ C07K 16/2803; C07K 2317/21; C07K 2317/565; A61K 31/713; A61K 39/001129; A61K 45/06; C12N 5/10; C12N 5/63
See application file for complete search history.

(56) References Cited

U.S. PATENT DOCUMENTS

| | | | |
|---|---|---|---|
| 7,767,410 B2 | 8/2010 | Weissman et al. | |
| 8,232,071 B2 | 7/2012 | Weissman et al. | |

FOREIGN PATENT DOCUMENTS

| | | |
|---|---|---|
| EP | 3712170 A1 | 9/2020 |
| WO | WO-2013184912 A2 | 12/2013 |
| WO | WO-2015024060 A1 | 2/2015 |
| WO | WO-2019030377 A1 | 2/2019 |
| WO | WO-2019091449 A1 | 5/2019 |
| WO | WO-2020132034 A1 | 6/2020 |
| WO | WO-2021042019 A1 | 3/2021 |

OTHER PUBLICATIONS

PCT International Search Report and Written Opinion from PCT/US2020/048700, dated Nov. 26, 2020.

*Primary Examiner* — Robert S Landsman
(74) *Attorney, Agent, or Firm* — Dechert LLP; Andrew T. Wilkins; Kayla Metzger

(57) ABSTRACT

The instant disclosure provides antibodies that specifically bind to CD96 (e.g., human CD96) and antagonize CD96 function. Also provided are pharmaceutical compositions comprising these antibodies, nucleic acids encoding these antibodies, expression vectors and host cells for making these antibodies, and methods of treating a subject using these antibodies.

22 Claims, 42 Drawing Sheets
Specification includes a Sequence Listing.

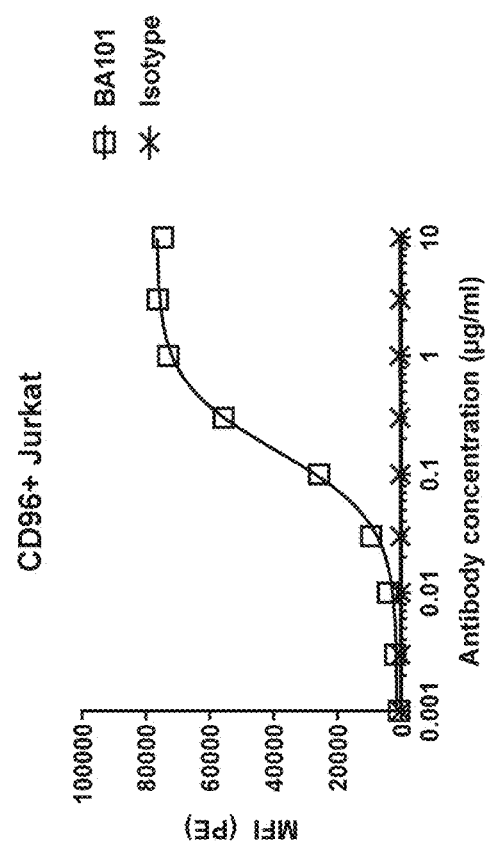
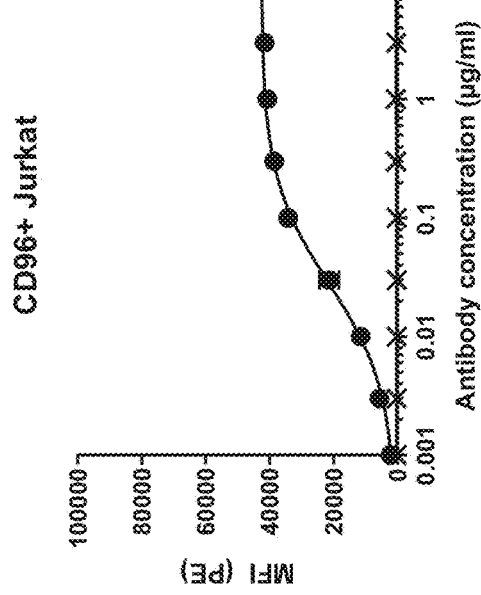
Fig. 1A, Fig. 1B. Binding of parental anti-CD96 antibodies to Jurkat cells expressing human isoform 2 of CD96

Binding of parental anti-CD96 antibodies to CHO cells expressing human isoform 1 of CD96

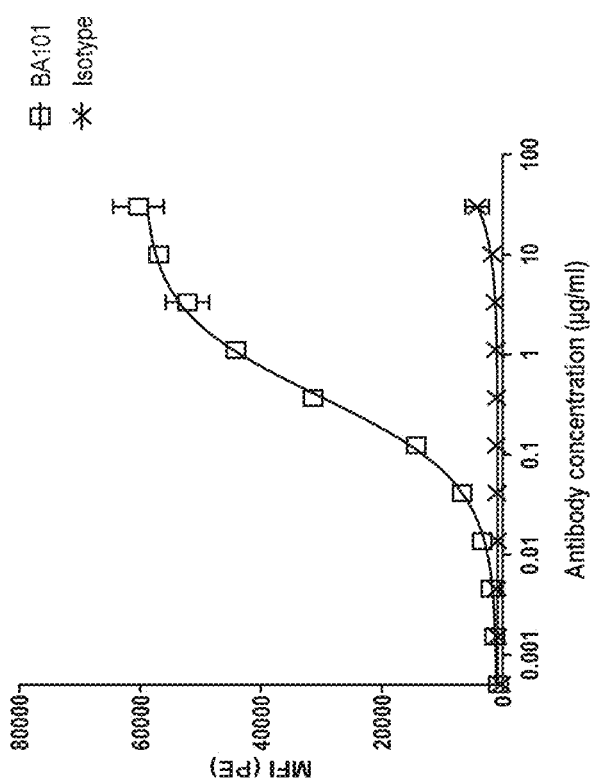
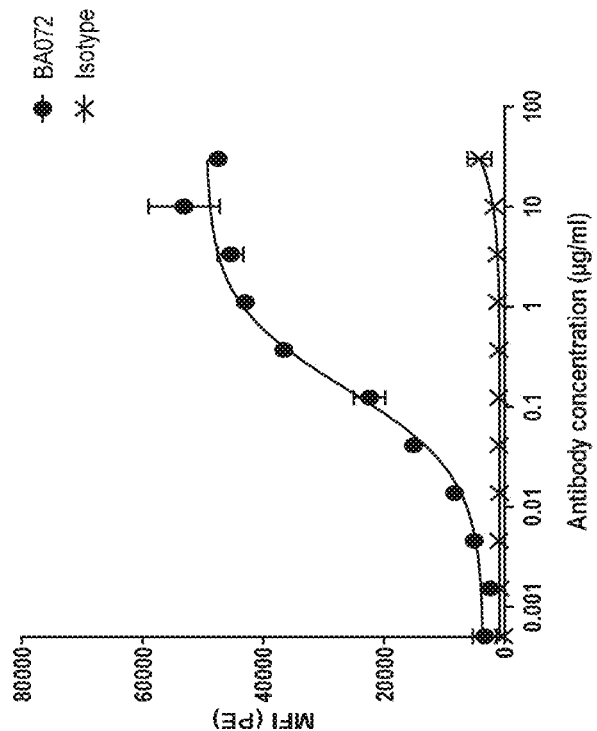
Fig. 3A, Fig. 3B: Binding of parental anti-CD96 antibodies to CHO cells expressing human isoform 2 of CD96

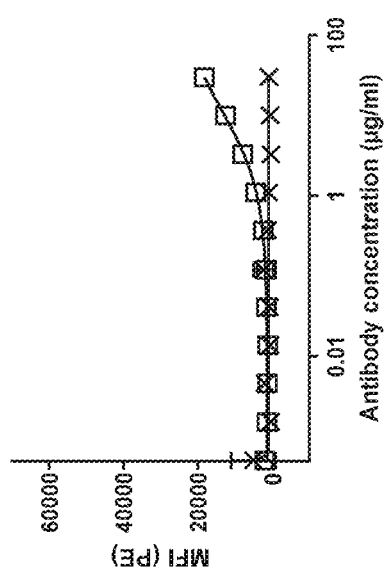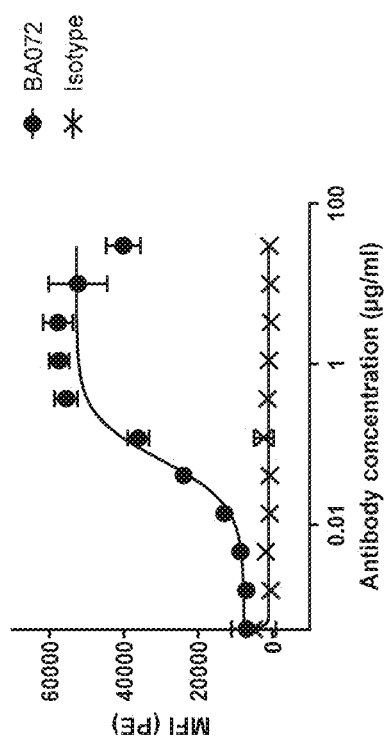
Fig. 4A / Fig. 4B: Binding of parental anti-CD96 antibodies to CHO cells expressing isoform 2 of cynomolgus monkey CD96

Binding of parental anti-CD96 antibodies to activated primary human T cells expressing CD96

Binding of anti-CD96 antibodies to activated human primary T cells expressing CD96

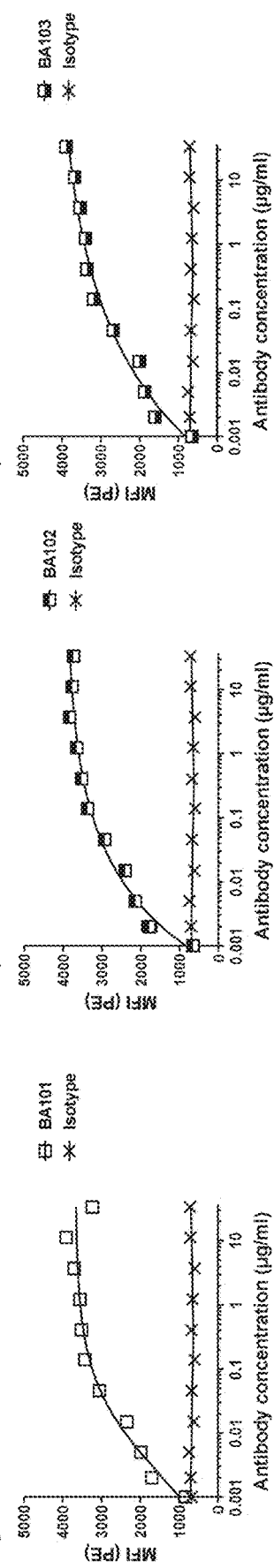
Fig. 7A–7F. Binding of anti-CD96 antibodies to human primary cells expressing CD96

Binding of anti-CD96 antibodies to NY-ESO-1 transfected CD8⁺ T cells expressing CD96

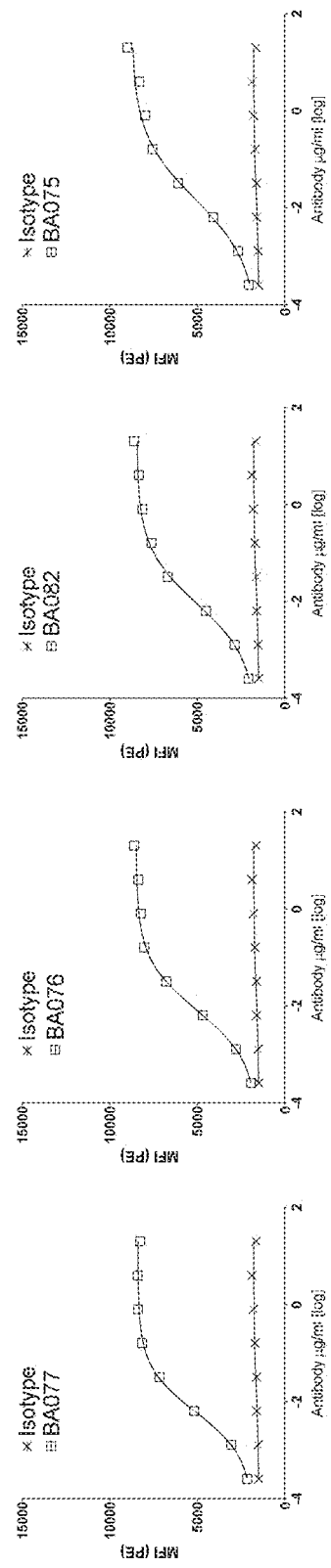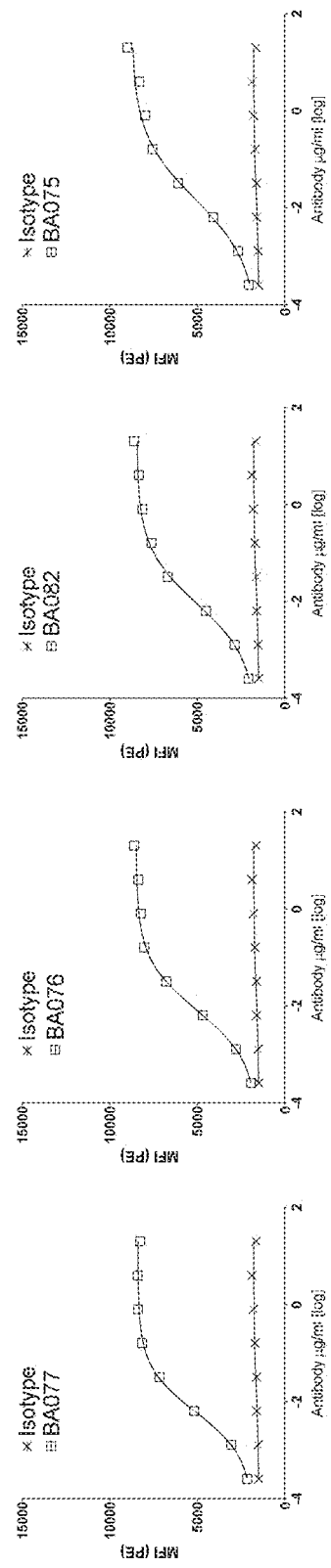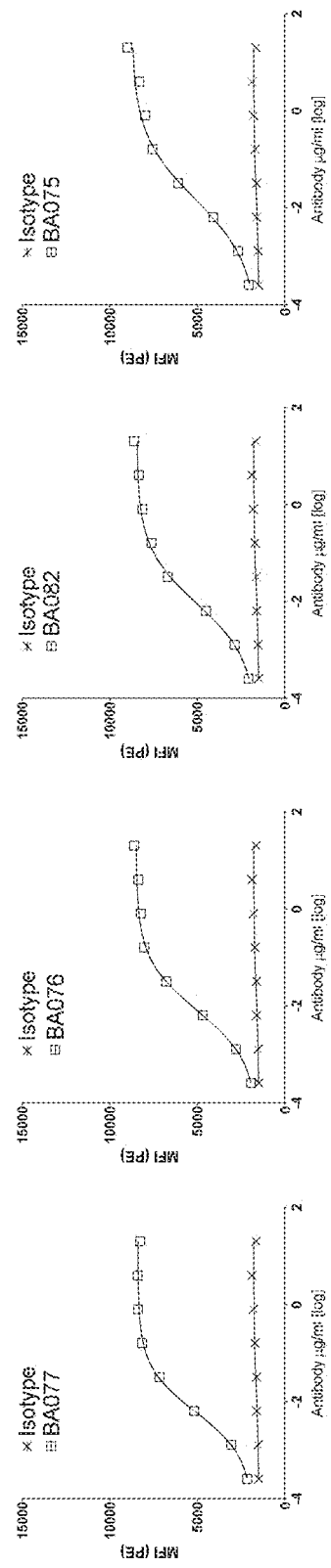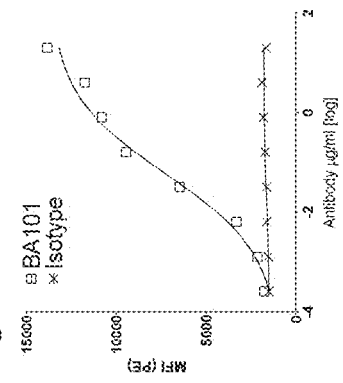

Binding of parental anti-CD96 antibodies to cynomolgus primary cells expressing CD96

Blocking by parental anti-CD96 antibodies of binding between PVR-Fc and CHO cells expressing human isoform 2 of CD96

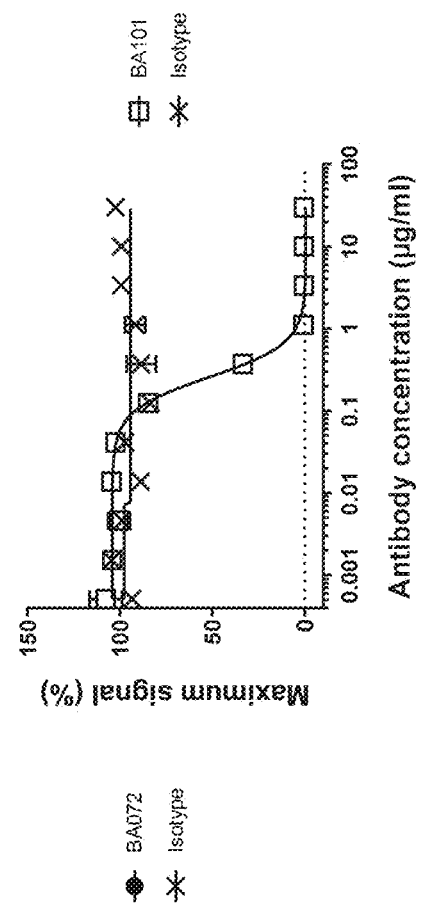
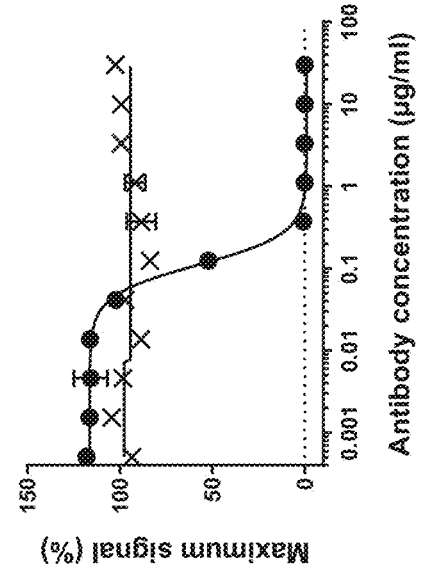
Fig. 11A, Fig. 11B: Blocking by parental anti-CD96 antibodies of binding between PVR-His and CHO cells expressing human isoform 2 of CD96

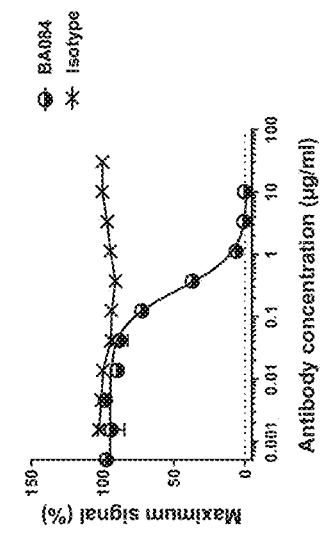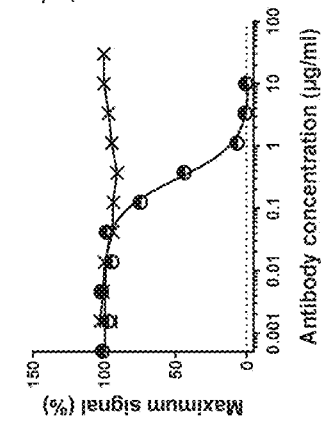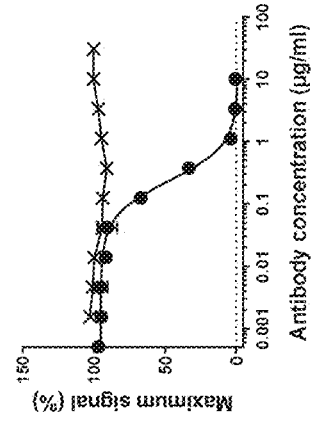
Fig. 12A, Fig. 12B, Fig. 12C: Blocking by anti-CD96 antibodies of the binding between PVR-Fc and CHO cells expressing human isoform 2 of CD96

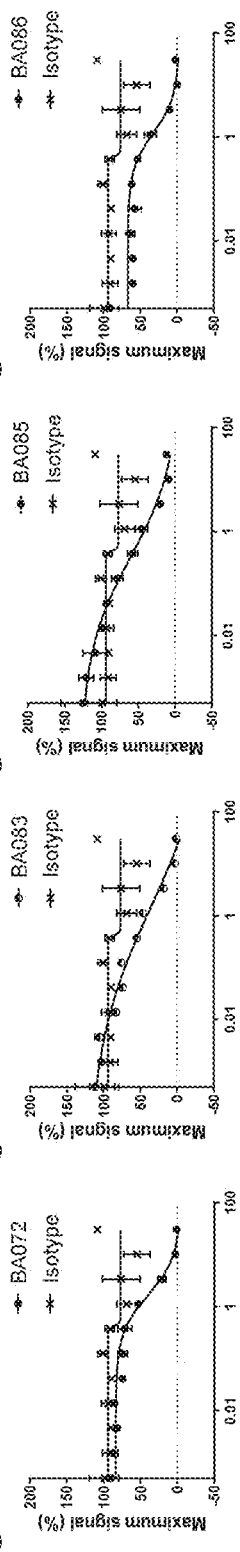
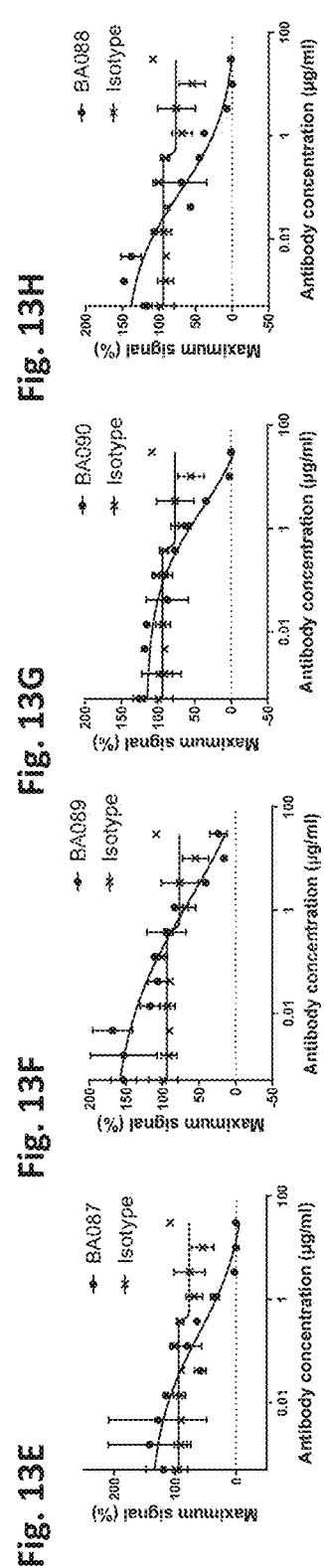
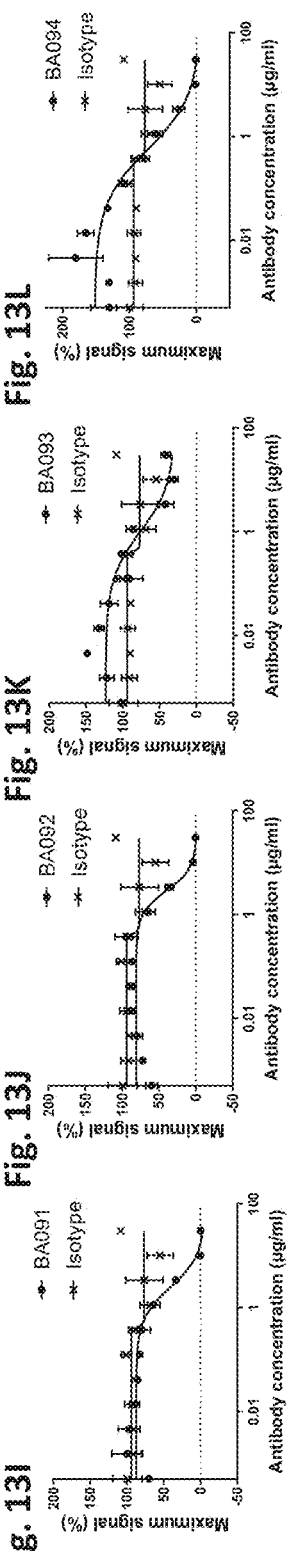
Fig. 13A–Fig. 13L. Blocking by anti-CD96 antibodies of the binding between PVR-Fc and CHO cells expressing human isoform 2 of CD96.

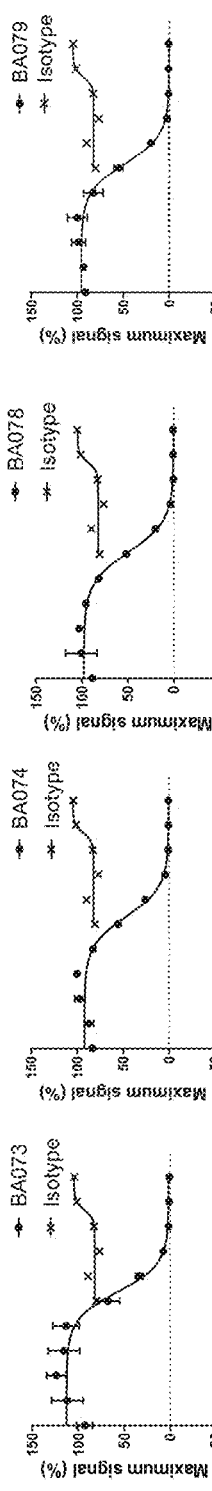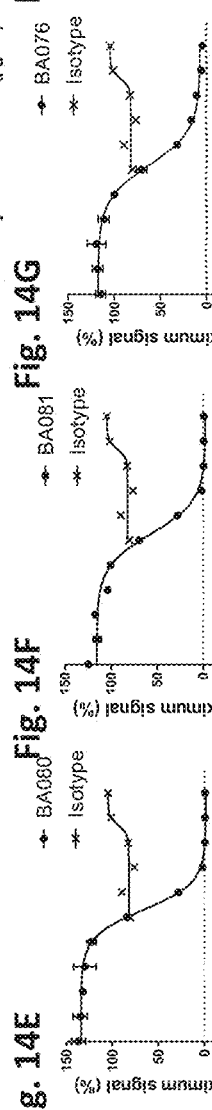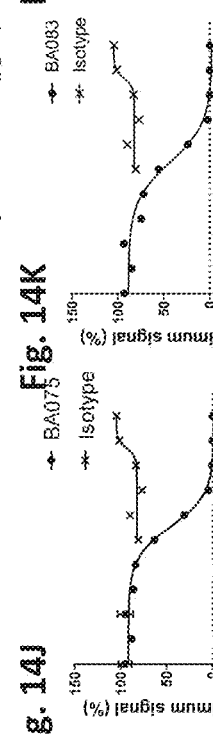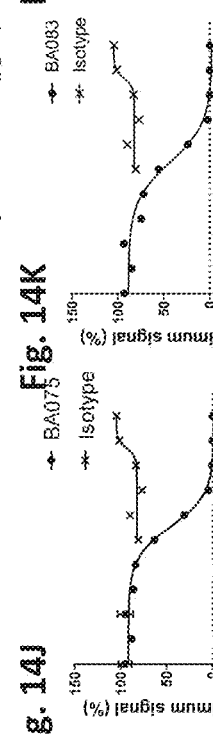
Fig. 14A Fig. 14B Fig. 14C Fig. 14D
Fig. 14E Fig. 14F Fig. 14G Fig. 14H
Fig. 14I Fig. 14J Fig. 14K Fig. 14L
Blocking by anti-CD96 antibodies of the binding between PVR-Fc and CHO cells expressing human isoform 1 of CD96

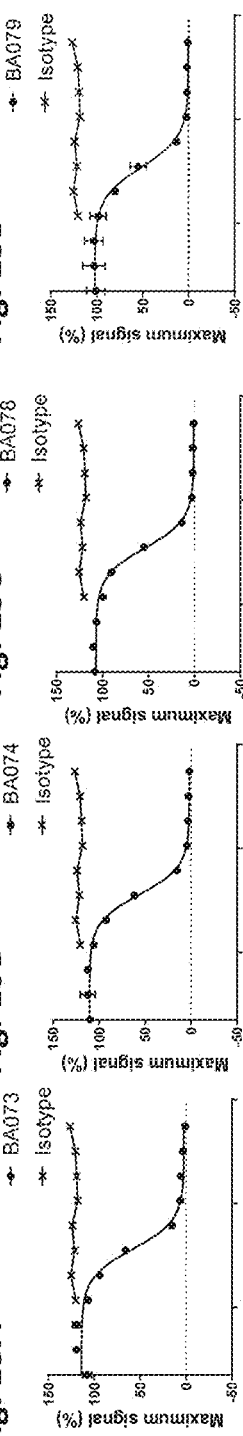
Fig. 15A – Fig. 15L. Blocking by anti-CD96 antibodies of the binding between PVR-Fc and CHO cells expressing human isoform 2 of CD96.

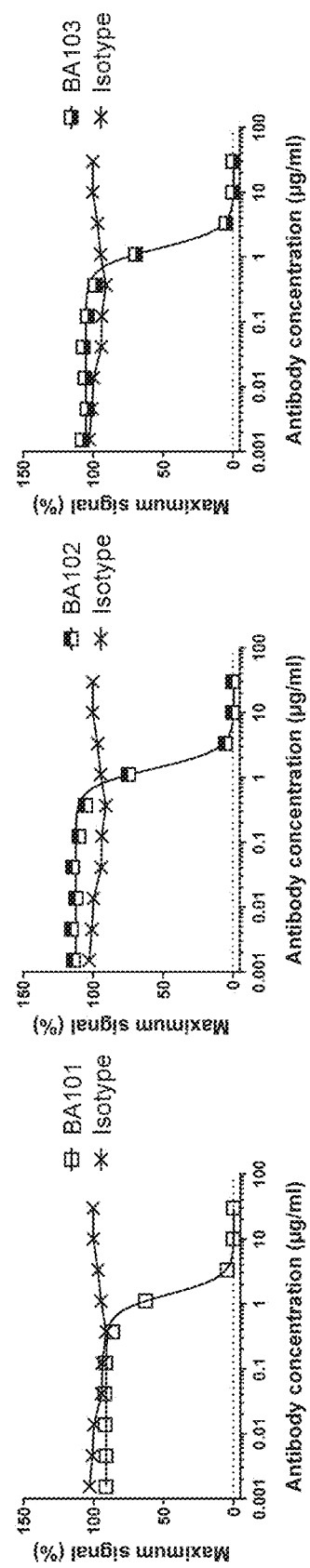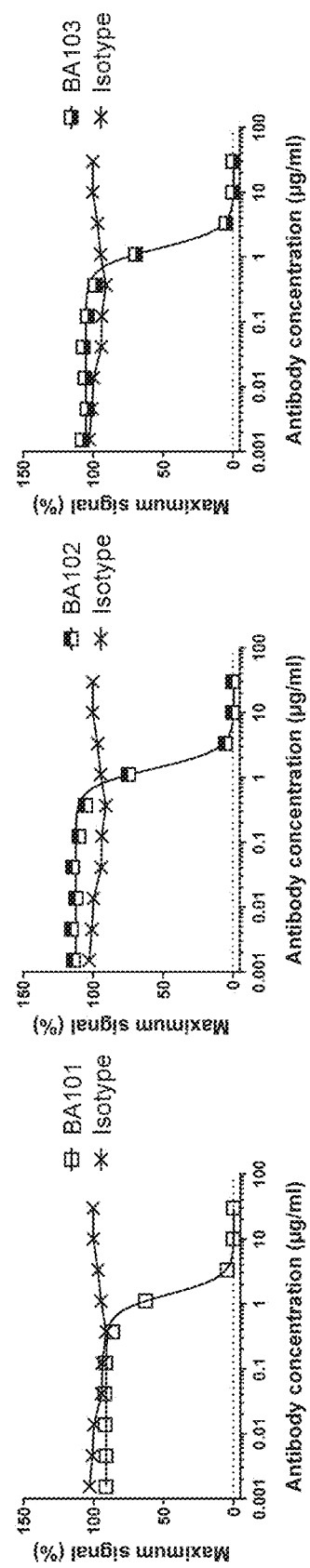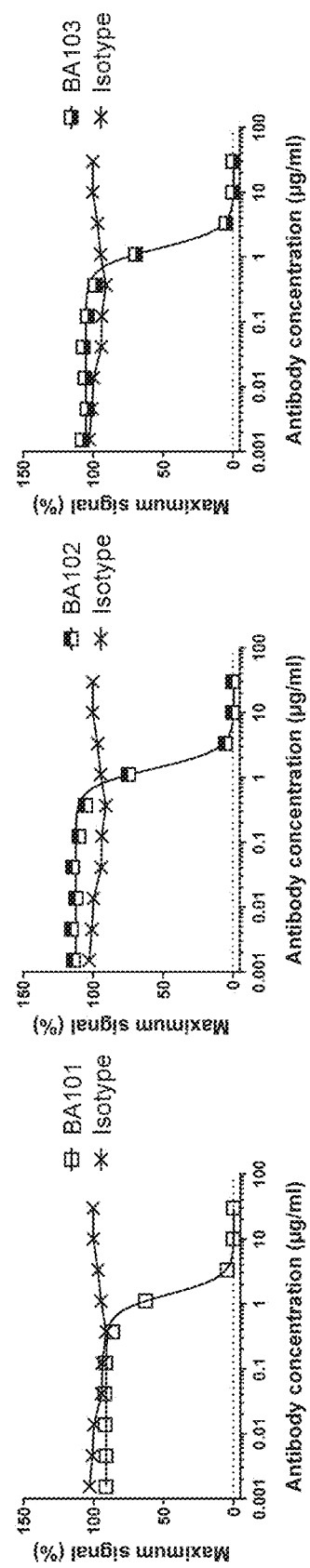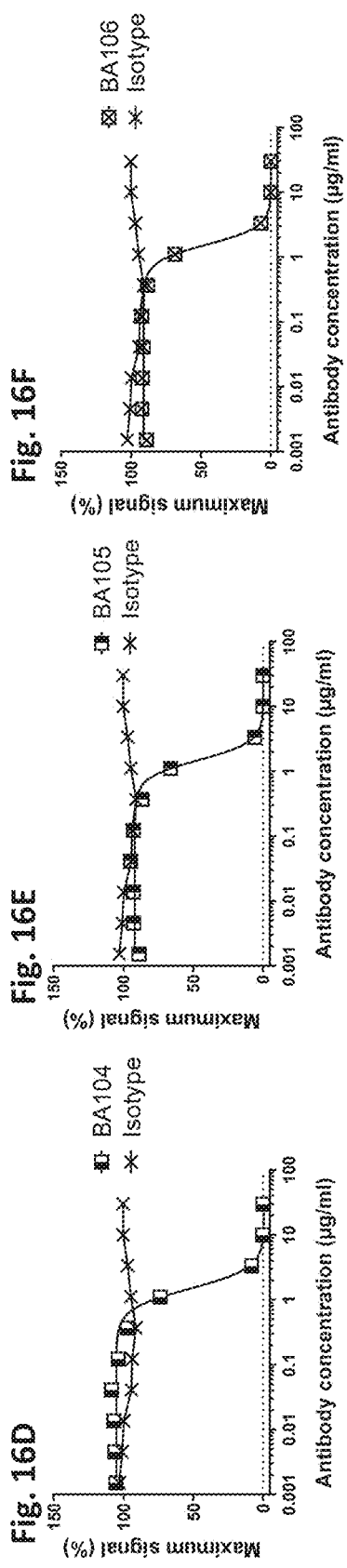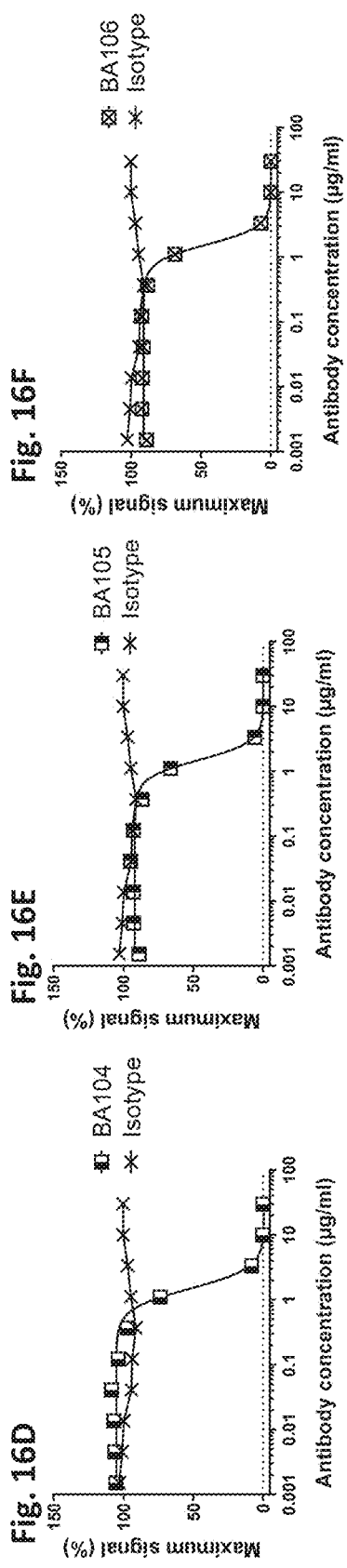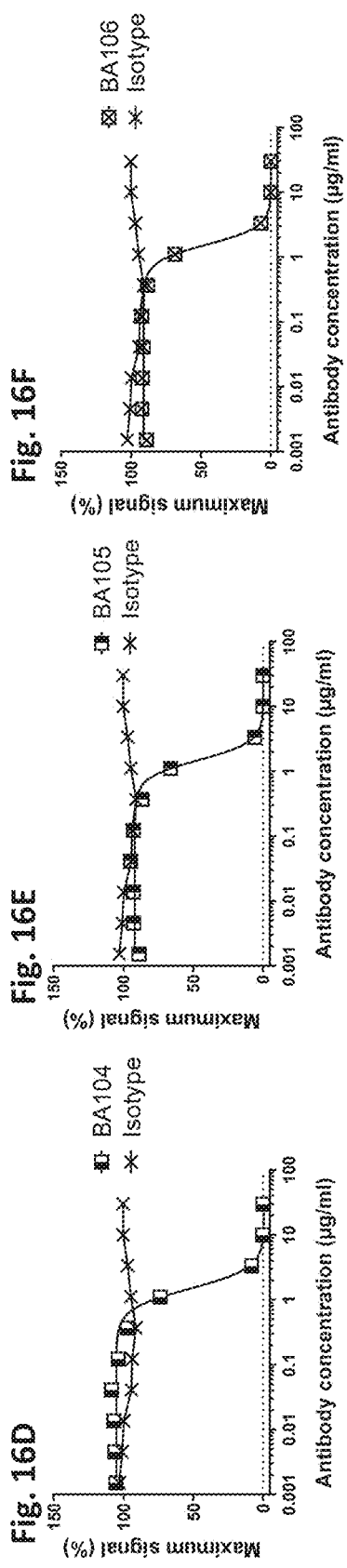
Fig. 16A, Fig. 16B, Fig. 16C, Fig. 16D, Fig. 16E, Fig. 16F. Blocking by anti-CD96 antibodies of the binding between PVR-Fc and CHO cells expressing human isoform 2 of CD96.

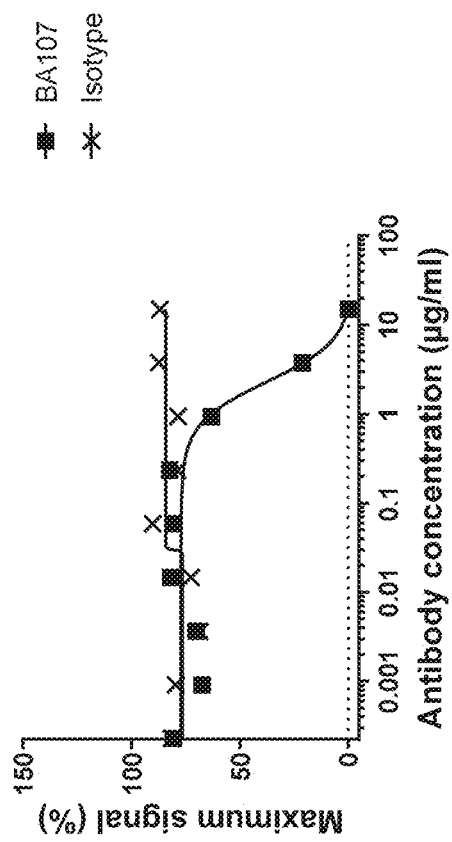
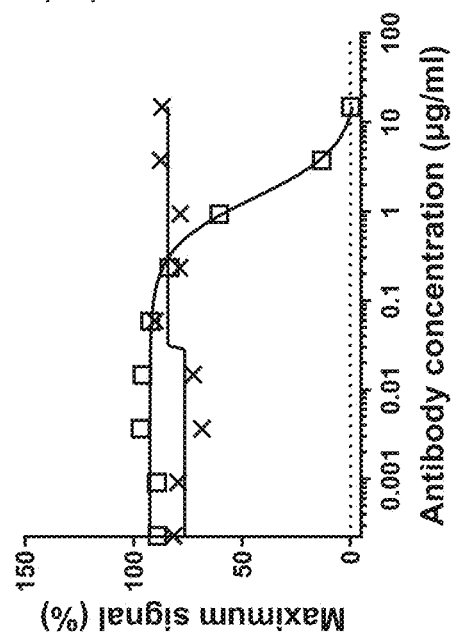
Fig. 17A, Fig. 17B. Blocking by anti-CD96 antibodies of the binding between PVR-Fc and CHO cells expressing human isoform 2 of CD96

Blocking by anti-CD96 antibodies of the binding between PVR-Fc and CHO cells expressing cynomolgus isoform 2 of CD96

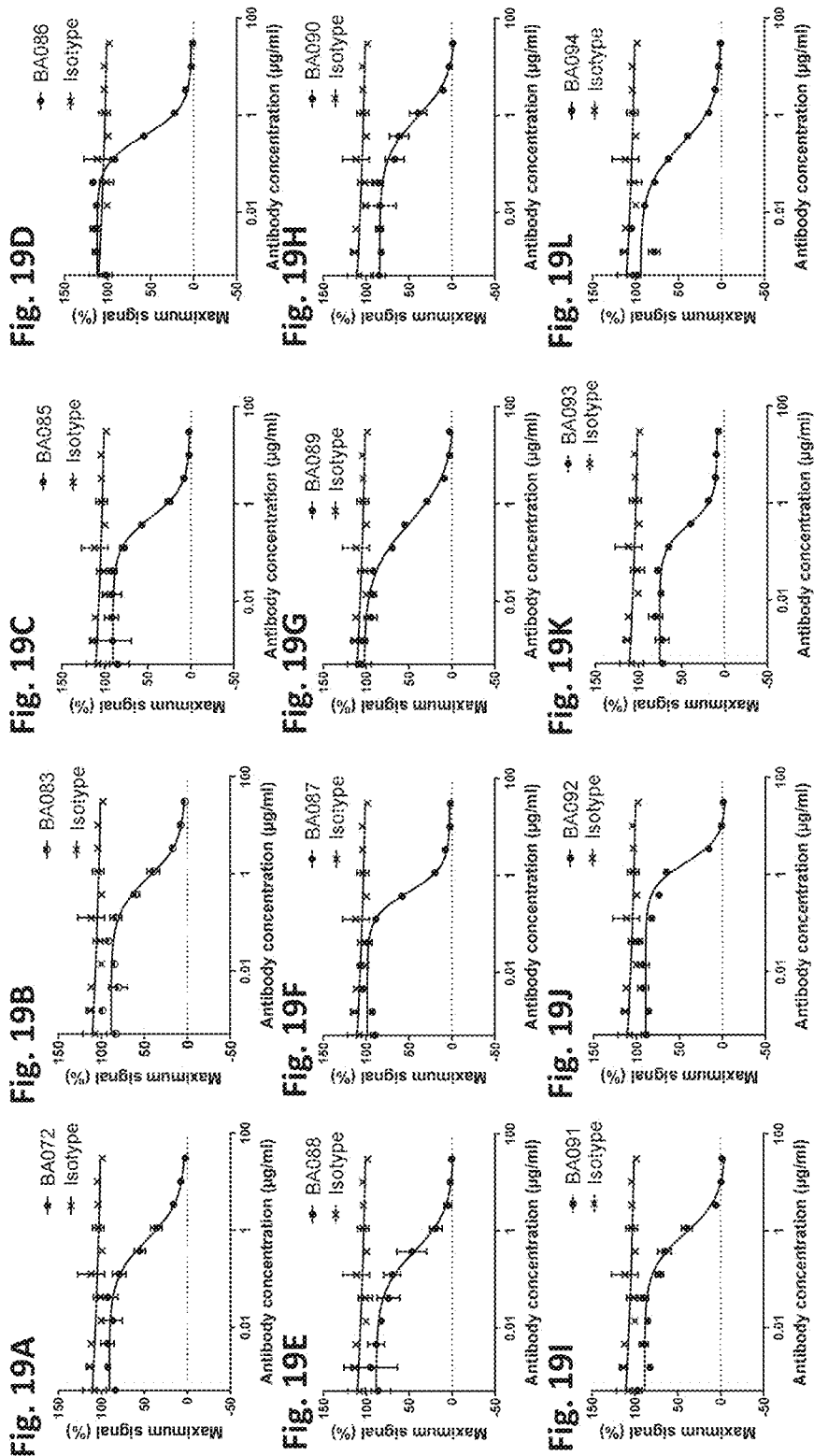

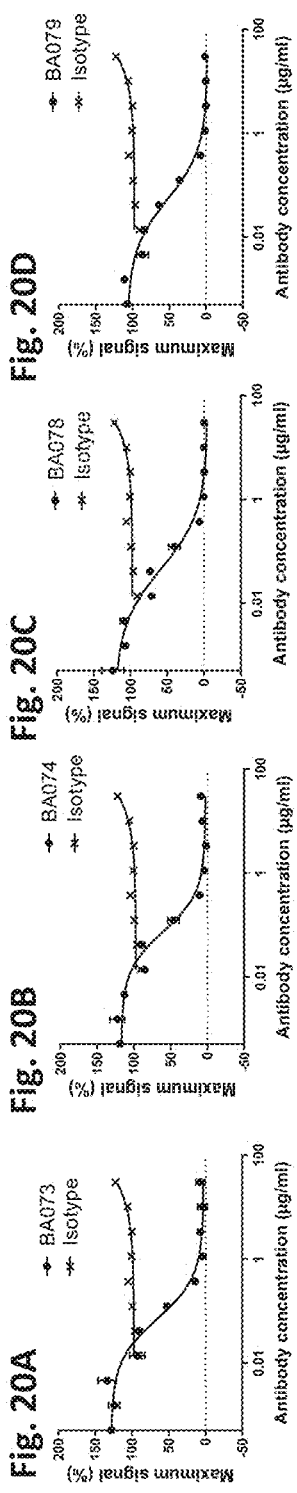
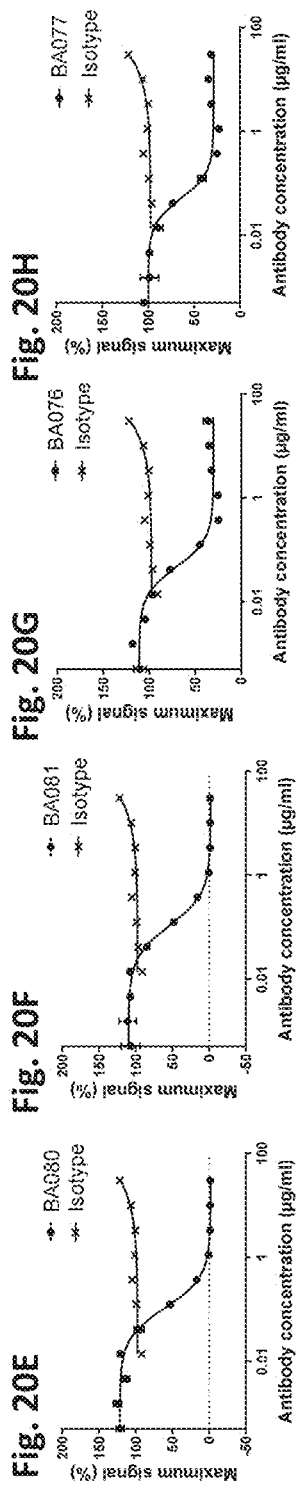
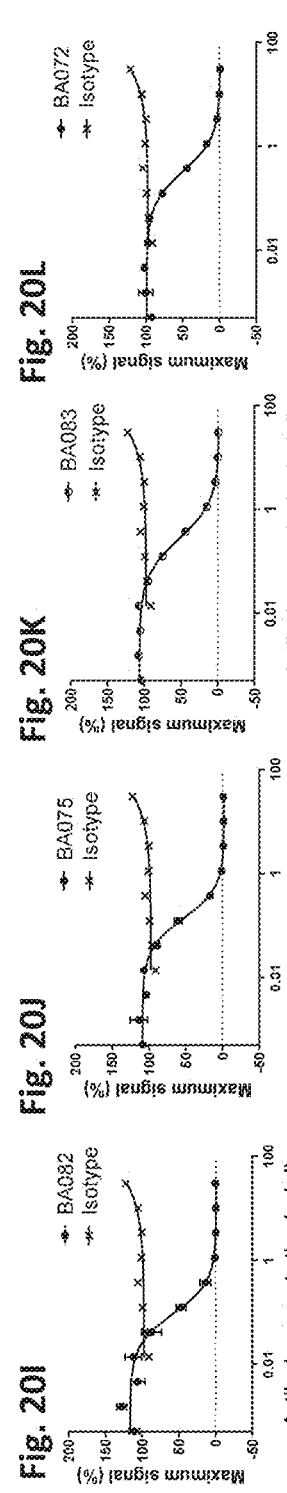
Fig. 20A–20L. Blocking by anti-CD96 antibodies of the binding between PVR-Fc and CHO cells expressing cynomolgus isoform 1 of CD96.

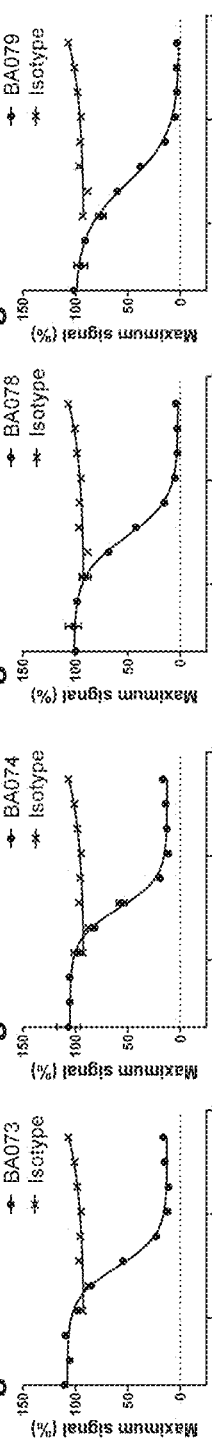
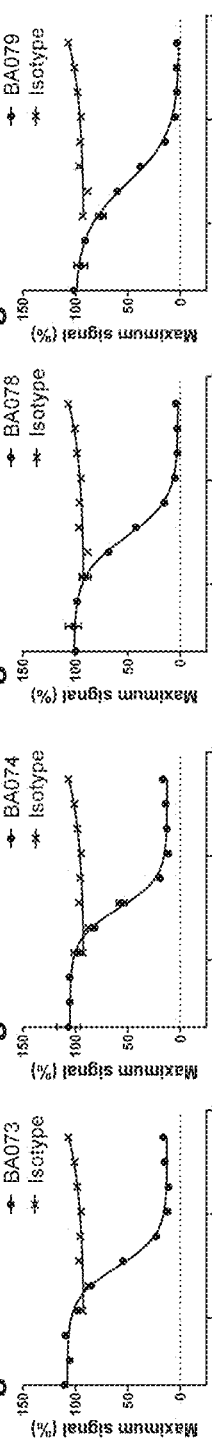
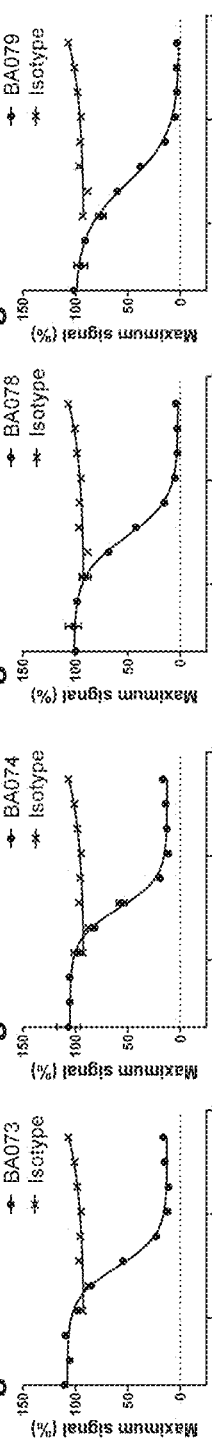
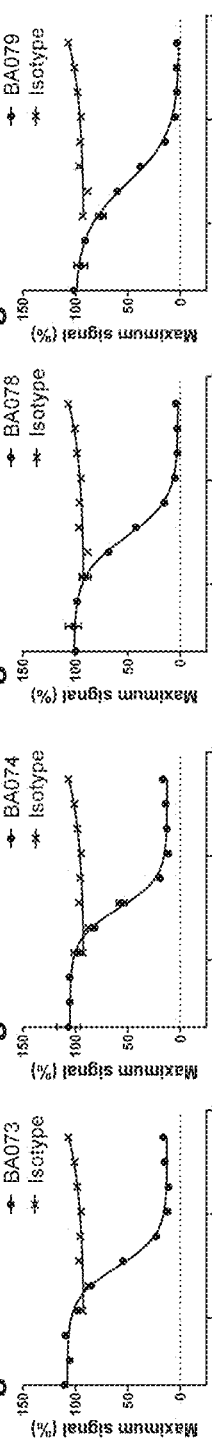
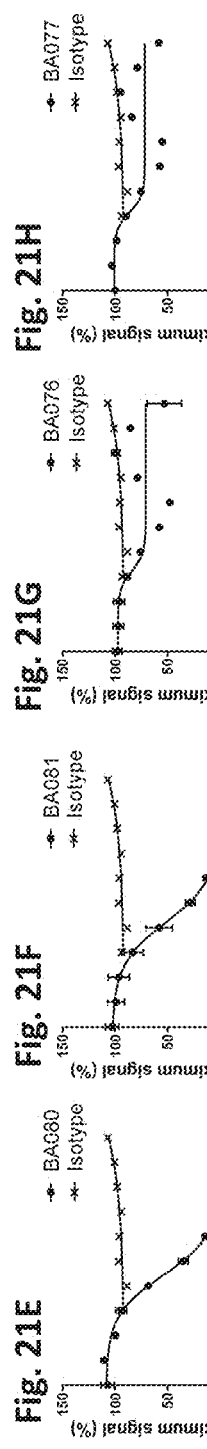
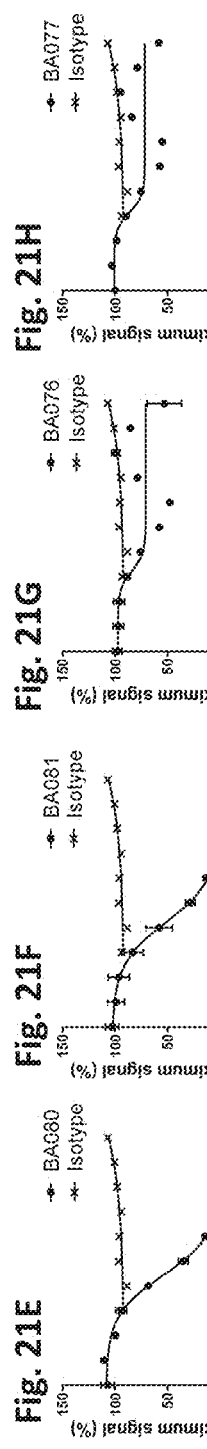
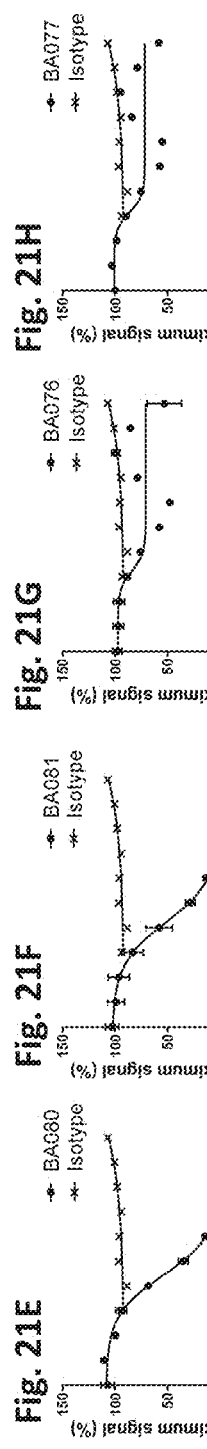
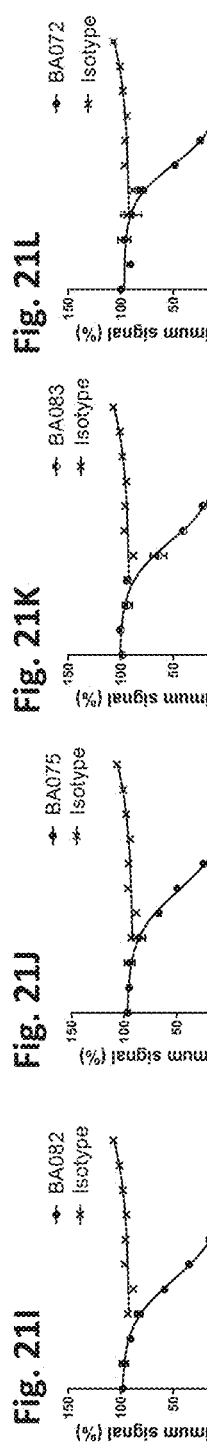
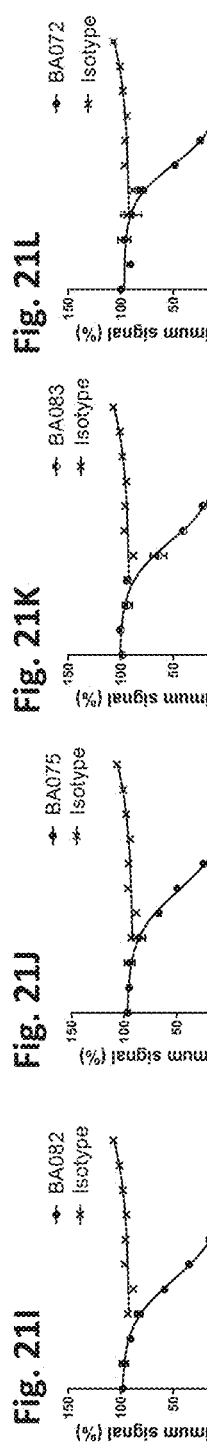
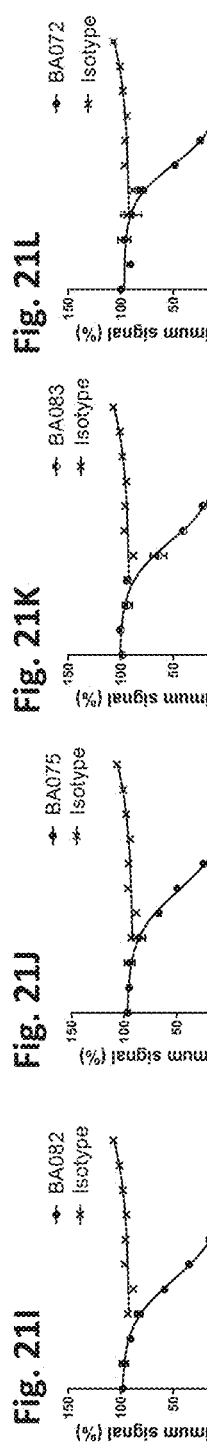
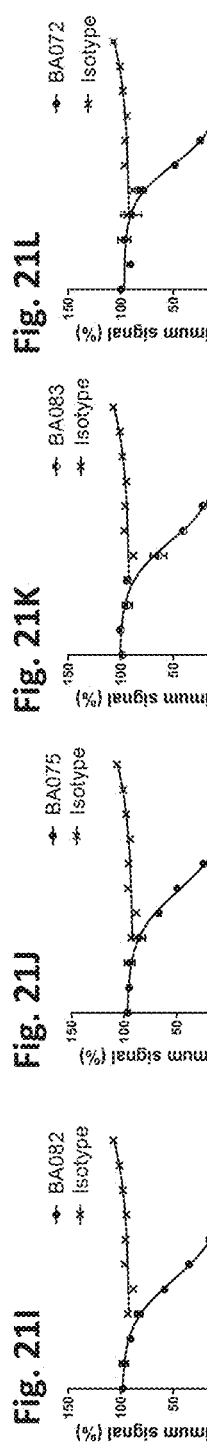
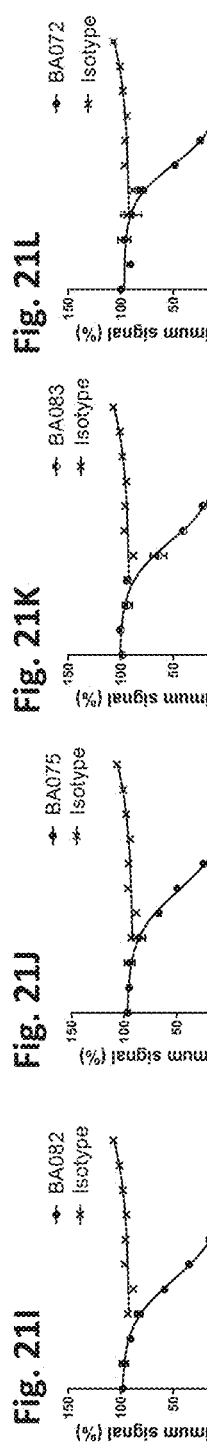
Blocking by anti-CD96 antibodies of the binding between PVR-Fc and CHO cells expressing cynomolgus isoform 2 of CD96

Blocking by parental anti-CD96 antibodies of the conjugation between CHO cells expressing human isoform 2 of CD96 or PVR

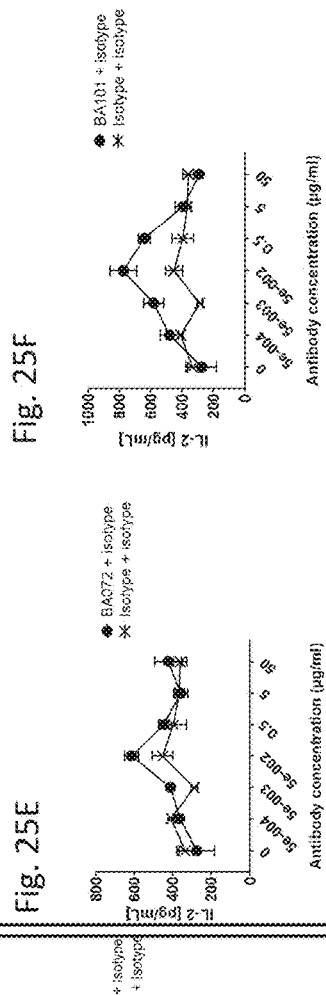
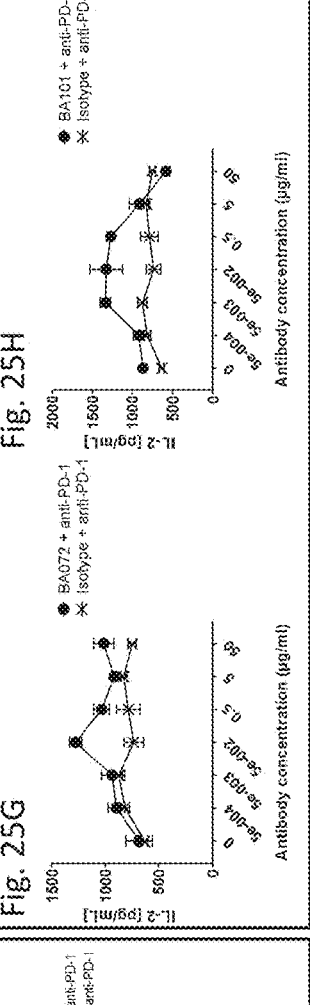
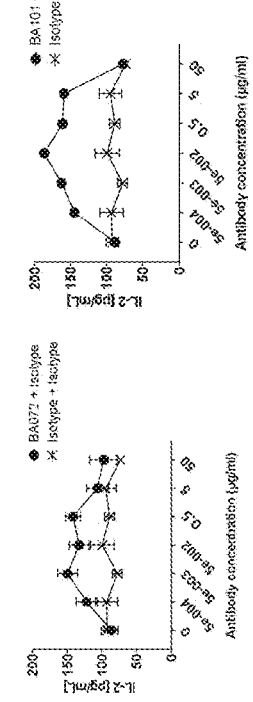
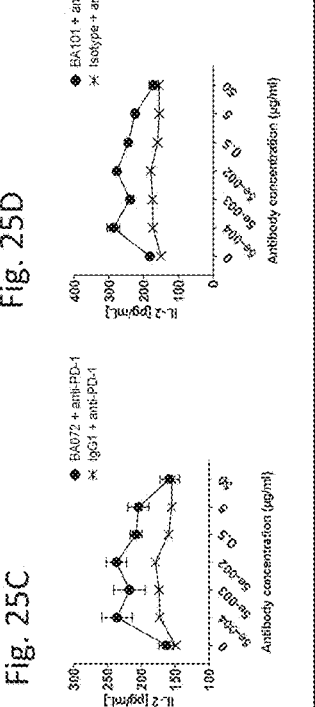
Fig. 25A – Fig. 25H. T cell responses with parental anti-CD96 in primary T cell:APC co-culture assay in two different donors over a range of doses.

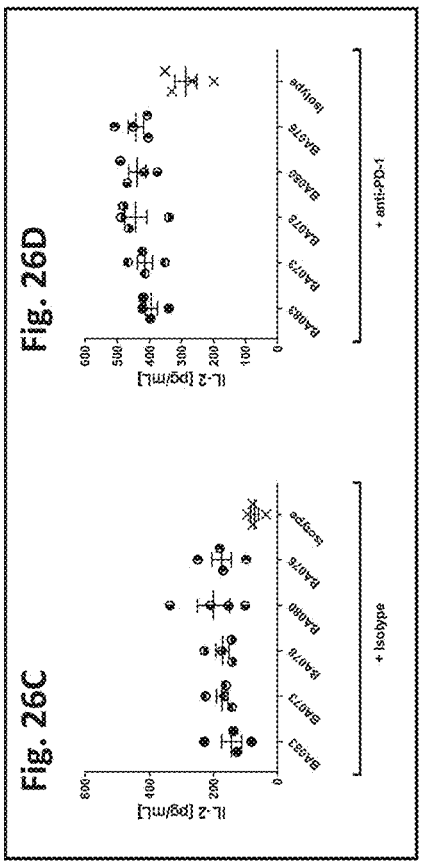
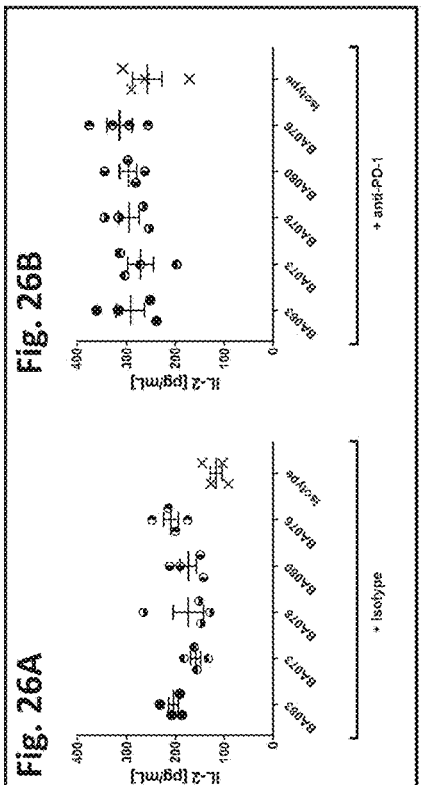
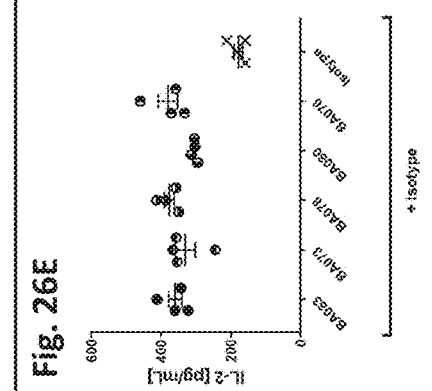

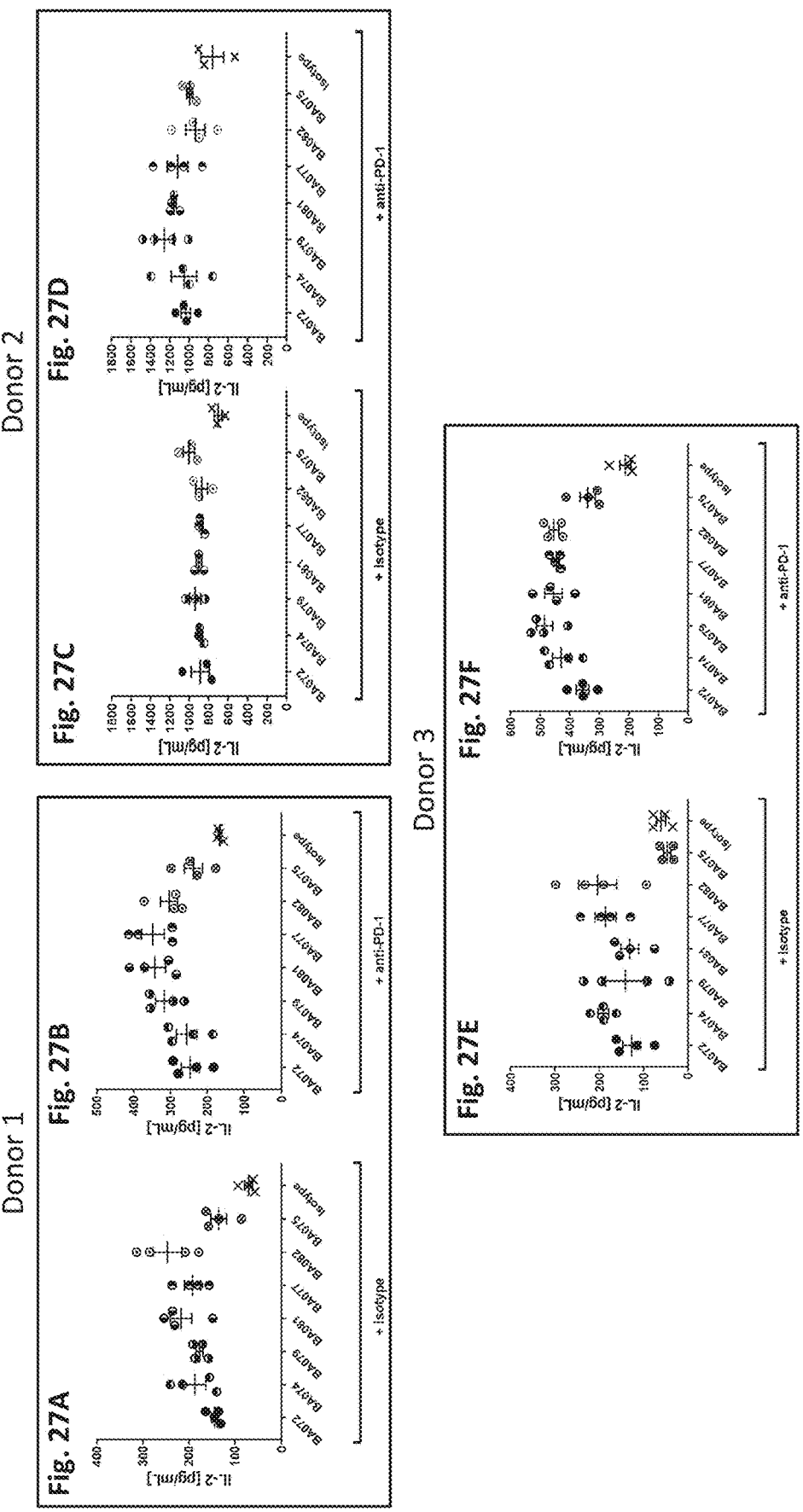

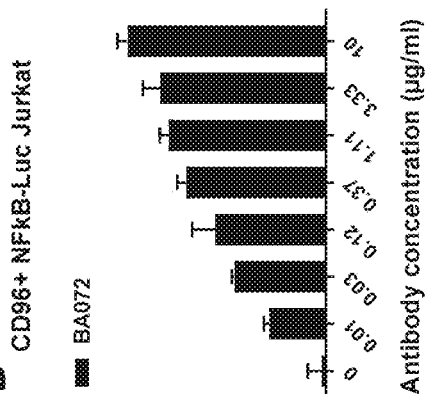
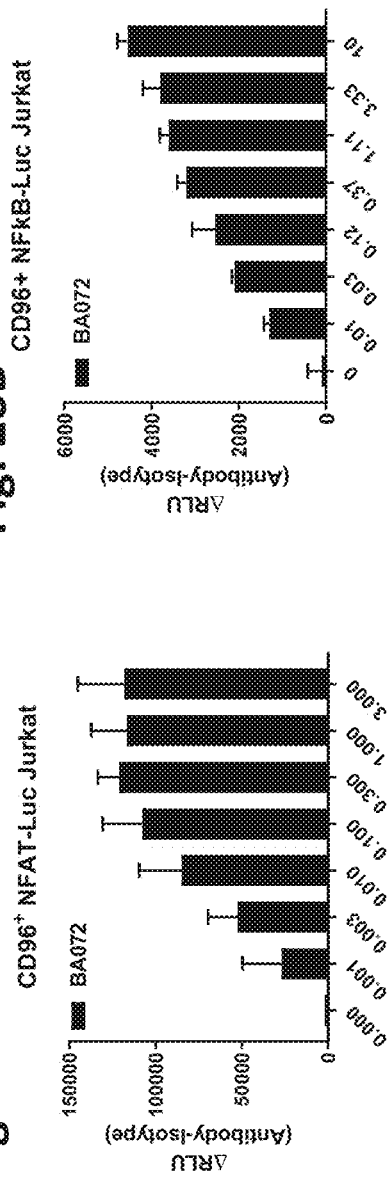
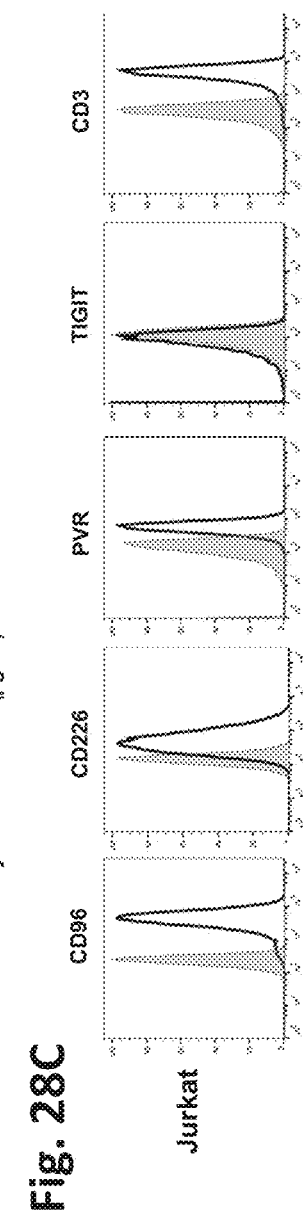

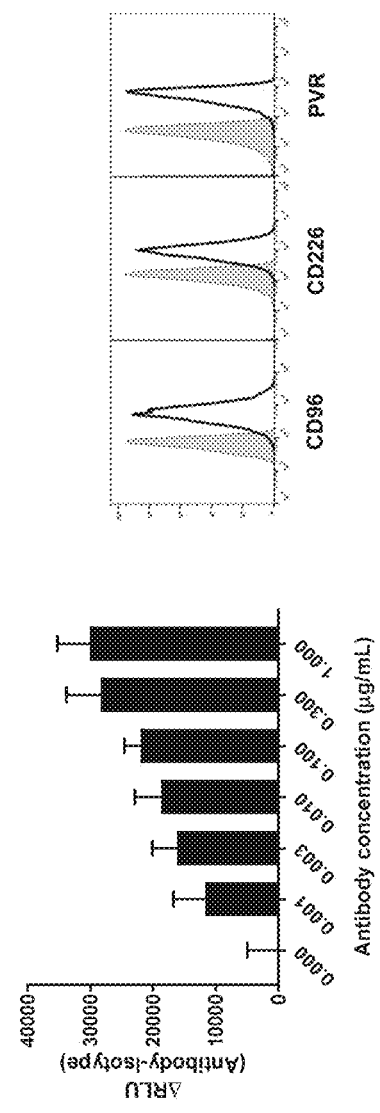
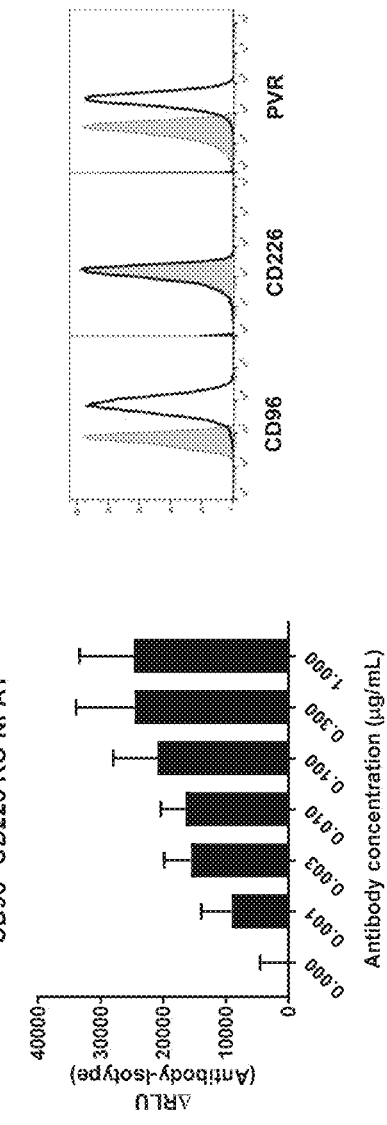

Induction of ADCC by Fc variants of anti-CD96 antibodies

Signalling by Fc variants of anti-CD96 antibodies in Jurkat reporter cell line

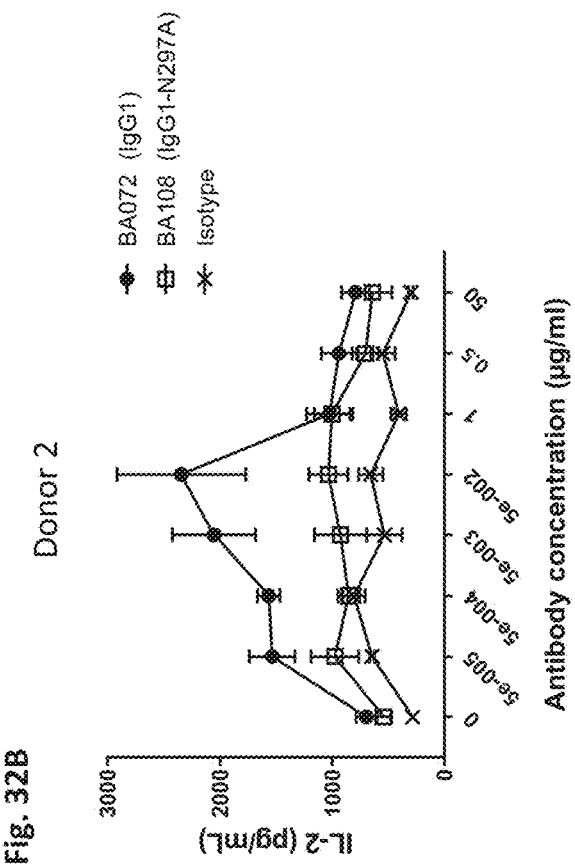
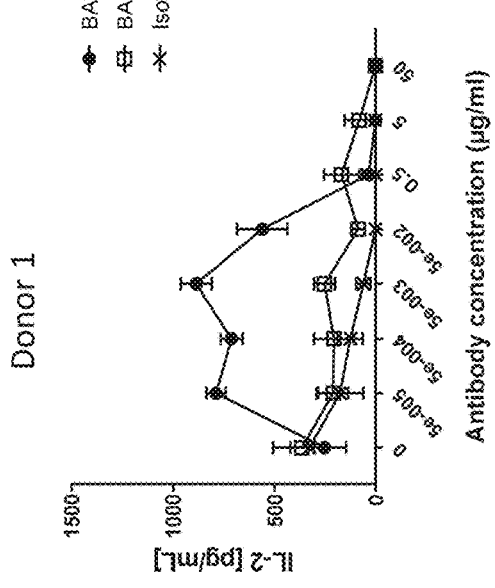

Internalization of CD96 in CD96-overexpressing Jurkat cells

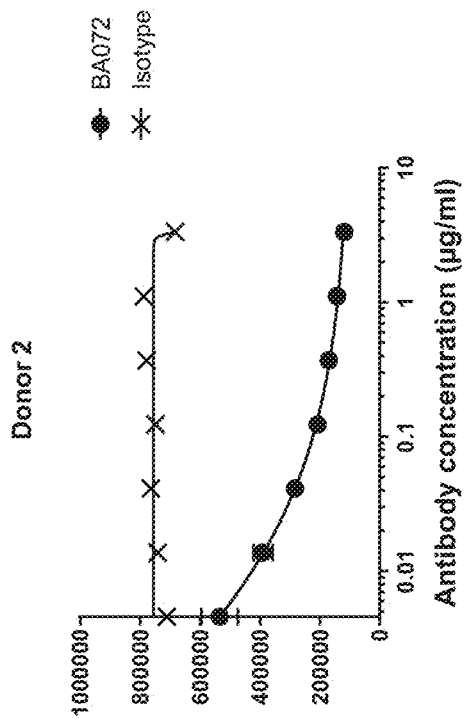
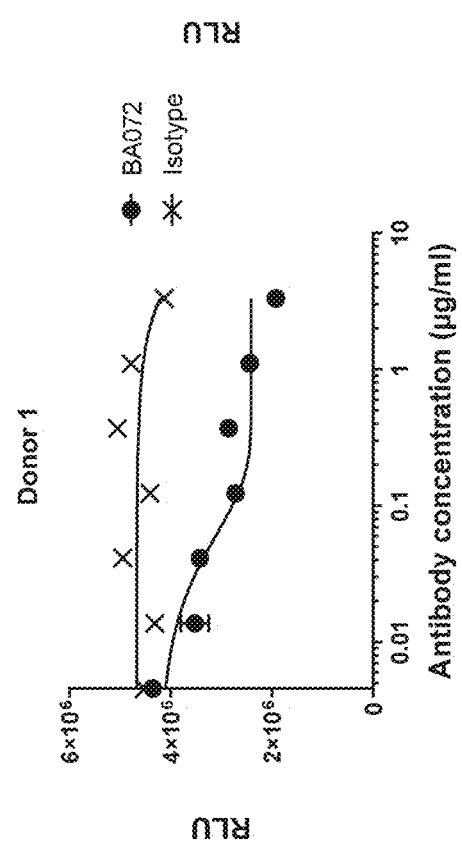
Fig. 35A / Fig. 35B. Anti-CD96 antibody-mediated internalization in primary T cells

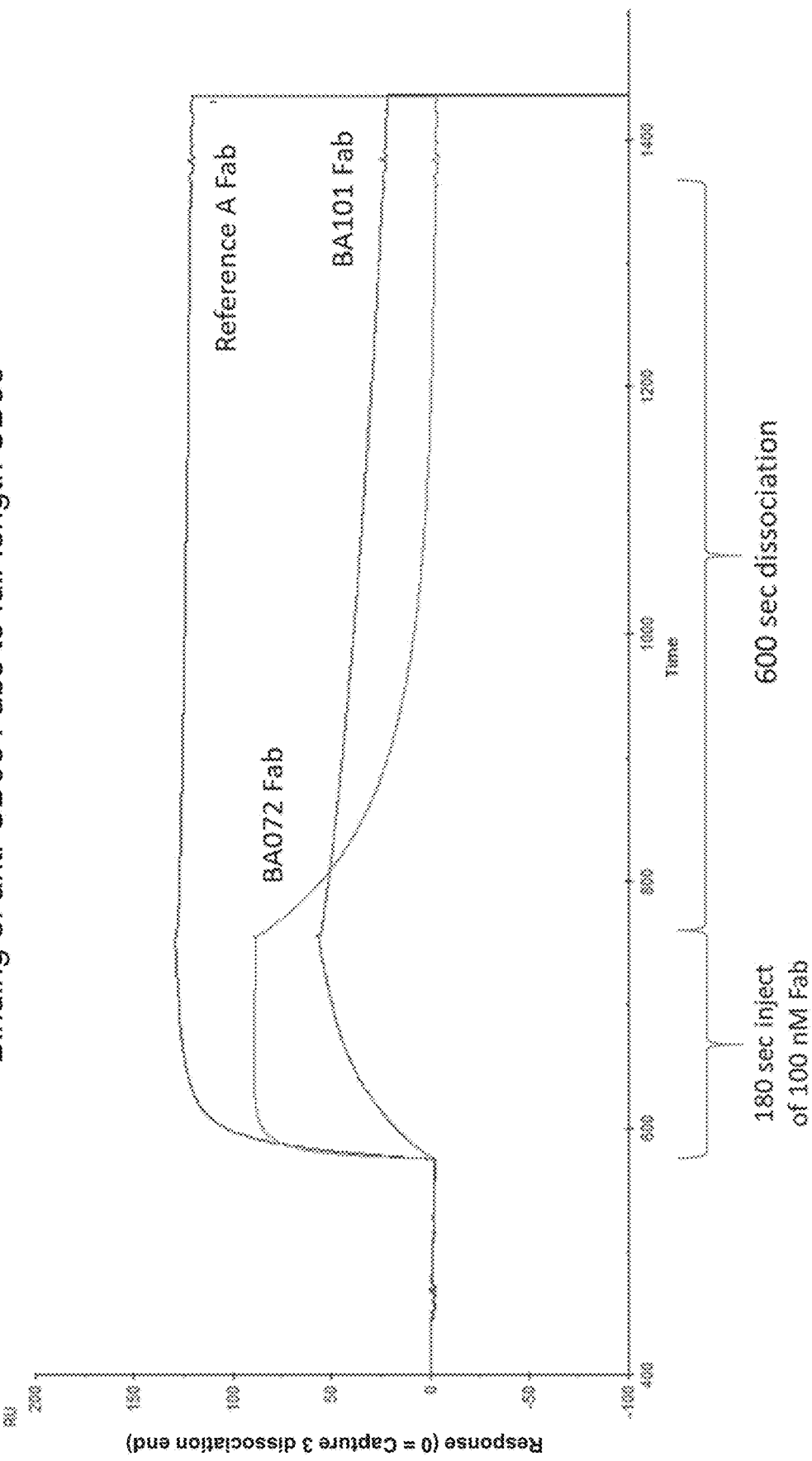

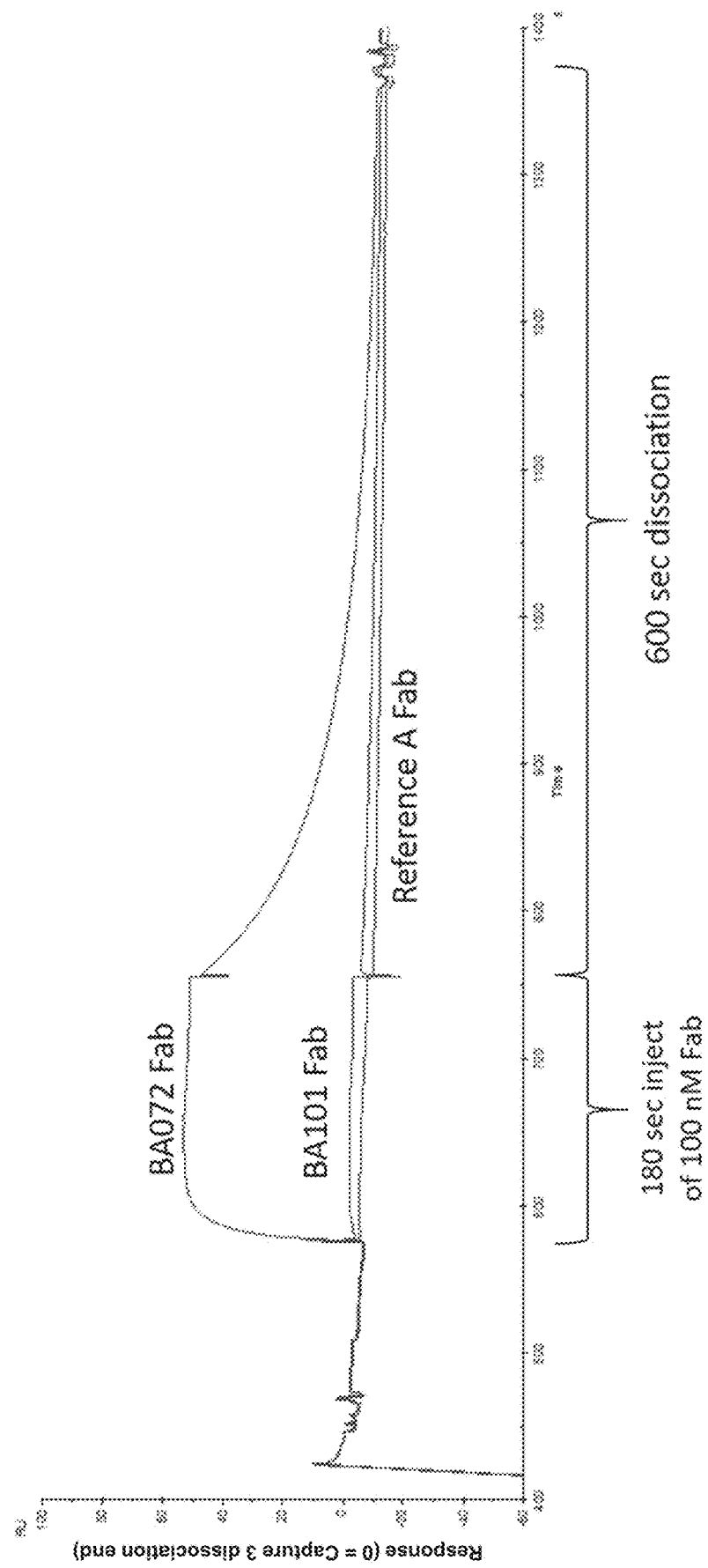

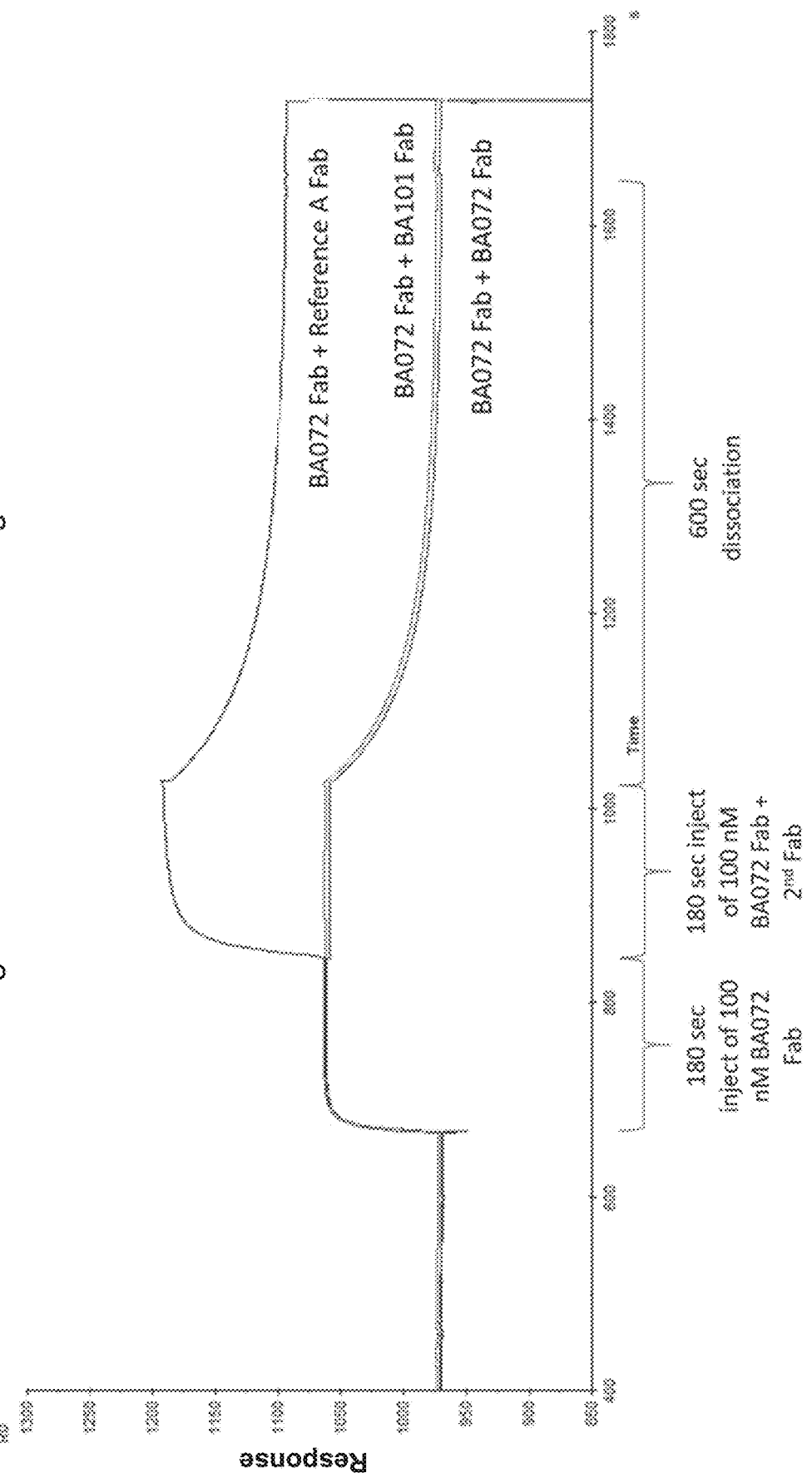

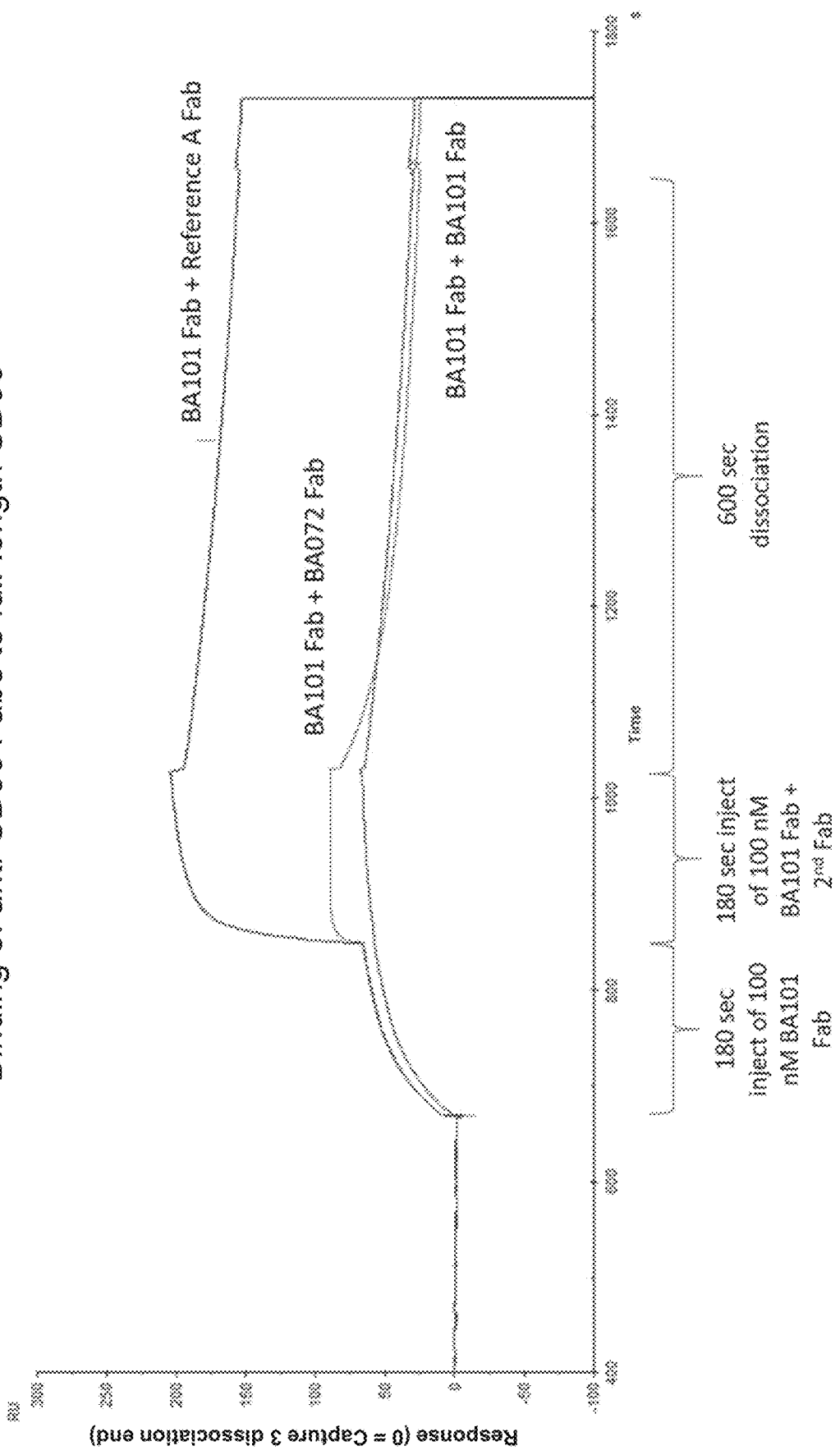

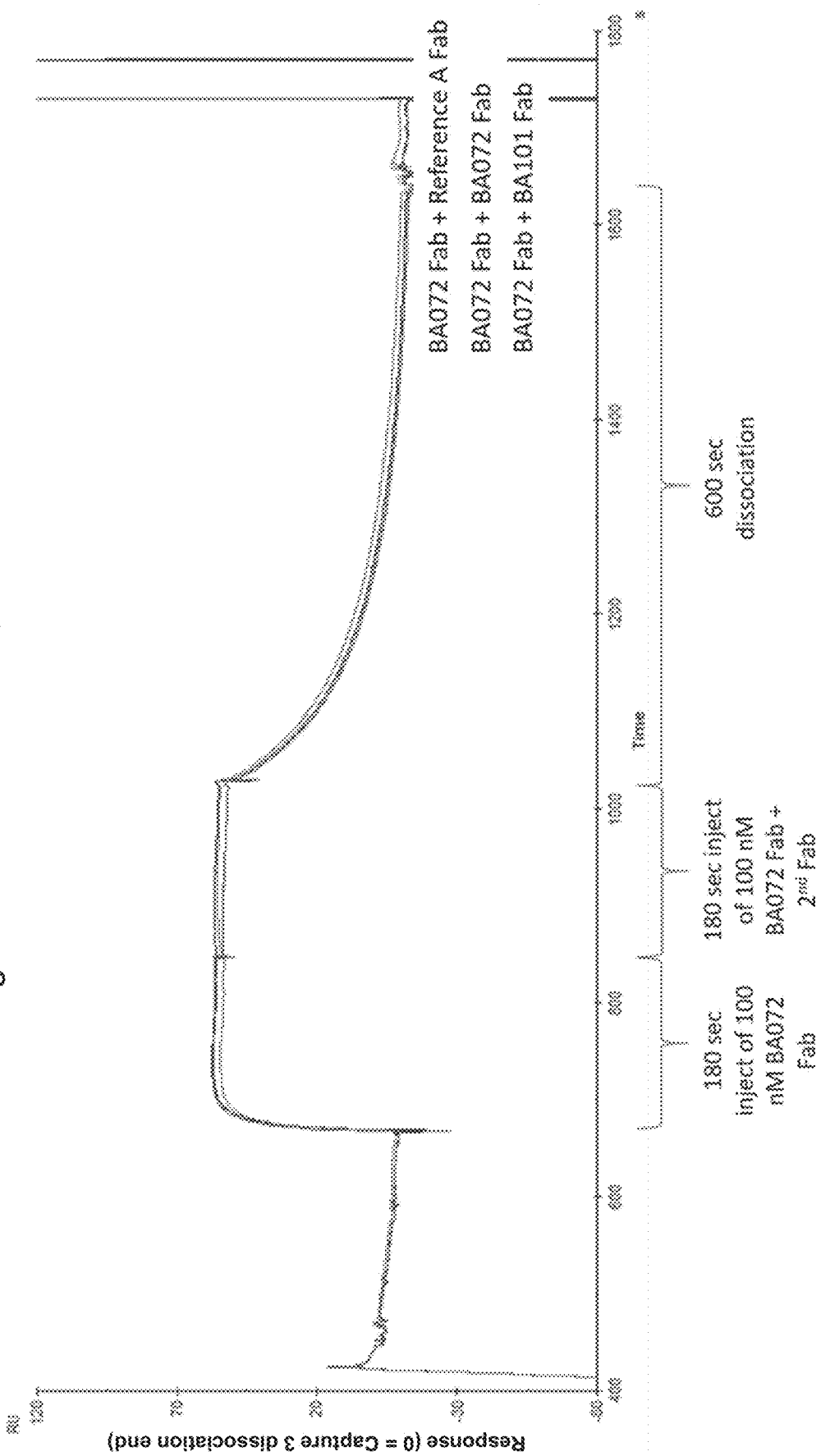

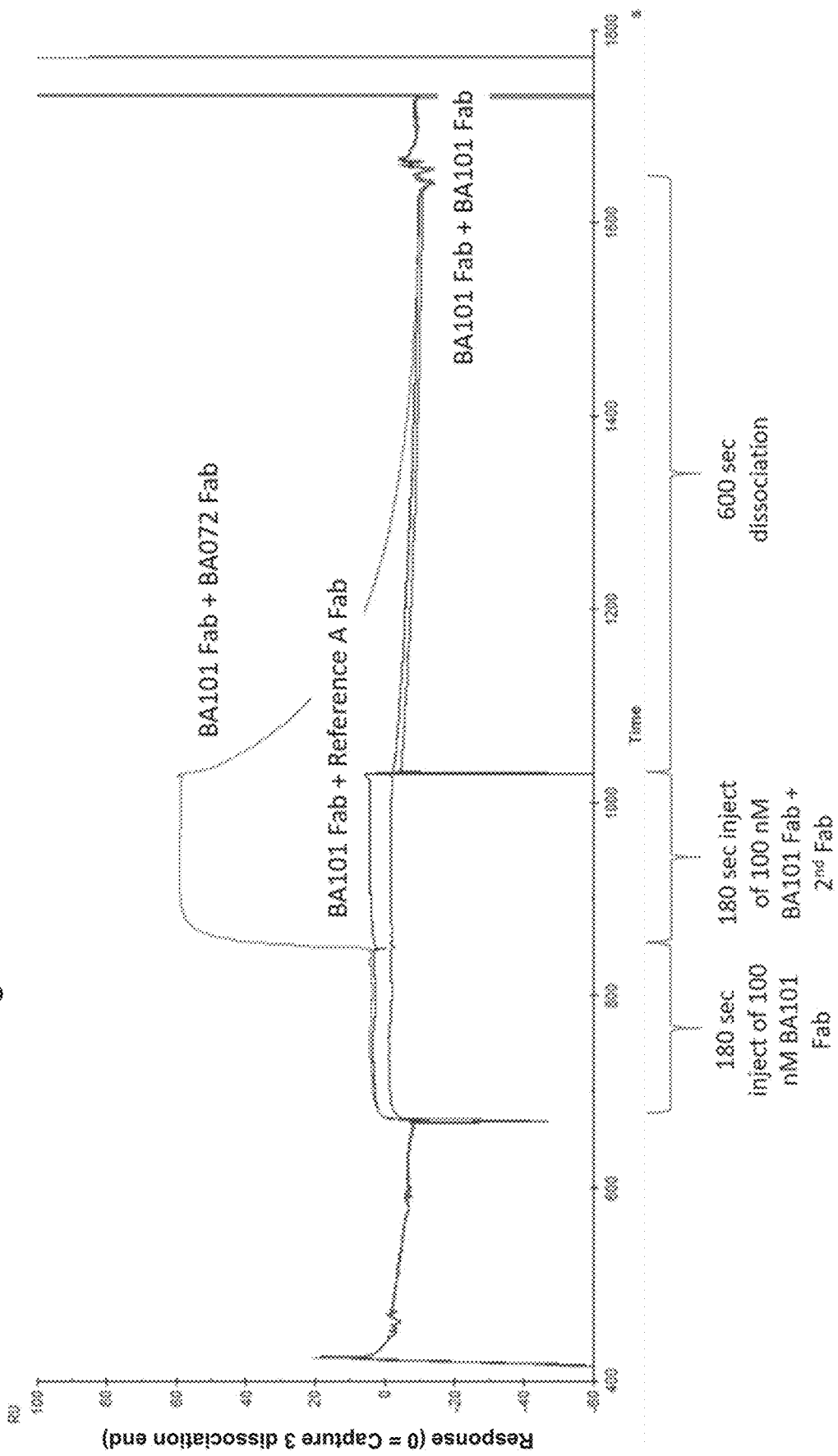

ANTIBODIES THAT SPECIFICALLY BIND HUMAN CD96

RELATED APPLICATIONS

This application claims the benefit of U.S. Provisional Application Nos. 62/894,334, filed Aug. 30, 2019, and 62/931,476, filed Nov. 6, 2019, each of which is incorporated by reference herein in its entirety.

1. FIELD

The instant disclosure relates to antibodies that specifically bind to CD96 (e.g., human CD96) and methods of using the same.

2. BACKGROUND

CD96 (Cluster of Differentiation 96), also known as TACTILE (T cell-activation, increased late expression), is a type I transmembrane protein in the immunoglobulin (Ig) superfamily. It has a single Ig domain, a type I transmembrane domain, a single intracellular immunoreceptor tyrosine-based inhibitory motif (ITIM), and a single YXXM phosphorylation motif, and is expressed on the surface of T cells and natural killer (NK) cells.

CD96 is believed to play a role in the regulation of immune cells (e.g., NK cells and T cells) and tumor metastasis. In particular, it has been shown that blockade of CD96 function suppressed primary tumor growth in several mouse tumor models in a CD8+ T cell-dependent manner.

Given the role of human CD96 in modulating immune responses, therapeutic agents designed to block CD96 ligand interactions hold great promise for the treatment of diseases that involve immune suppression.

3. SUMMARY

The instant disclosure provides antibodies that specifically bind to CD96 (e.g., human CD96) and modulate CD96 function, e.g., CD96-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing immune cell activation, and hence, are useful for treating cancer in a subject or treating or preventing an infectious disease in a subject.

Accordingly, in one aspect, the instant disclosure provides an isolated antibody that specifically binds to human CD96, the antibody comprising a heavy chain variable region (VH) comprising complementarity determining regions (CDRs) CDRH1, CDRH2, and CDRH3, and a light chain variable region (VL) comprising CDRs CDRL1, CDRL2, and CDRL3, wherein:

(a) CDRH1 comprises the amino acid sequence of $X_1YX_2X_3X_4$ (SEQ ID NO: 135), wherein
  $X_1$ is Q or S;
  $X_2$ is A or S;
  $X_3$ is M or I; and
  $X_4$ is H or S;
(b) CDRH2 comprises the amino acid sequence of $X_1IX_2X_3X_4X_5X_6X_7X_8X_9YX_{10}QKFQG$ (SEQ ID NO: 137), wherein
  $X_1$ is W or G;
  $X_2$ is N or I;
  $X_3$ is A, E, V, or P;
  $X_4$ is V, G, W, or I;
  $X_5$ is S, Y, T, N, or F;
  $X_6$ is G or W;
  $X_7$ is D, Y, N, or T;
  $X_8$ is T or A;
  $X_9$ is K or N; and
  $X_{10}$ is S or A;
(c) CDRH3 comprises the amino acid sequence of NWGX$_1$SYGX$_2$DV (SEQ ID NO: 180), GYDSRPLDV (SEQ ID NO: 19), or GYDSRPLDY (SEQ ID NO: 20), wherein
  $X_1$ is M or L; and
  $X_2$ is M or L;
(d) CDRL1 comprises the amino acid sequence of RASQSIX$_1$X$_2$YLN (SEQ ID NO: 139) or GGNNIGSKIVH (SEQ ID NO: 26), wherein
  $X_1$ is S, T, or L; and
  $X_2$ is S, P, or W;
(e) CDRL2 comprises the amino acid sequence of $X_1X_2$SSLQS (SEQ ID NO: 141) or DDRDRPS (SEQ ID NO: 32), wherein
  $X_1$ is S or A; and
  $X_2$ is A, S, or E; and/or
(f) CDRL3 comprises the amino acid sequence of QQX$_1$YSTPALX$_2$ (SEQ ID NO: 143) or QVWDINVHHVI (SEQ ID NO: 35), wherein
  $X_1$ is S or A; and
  $X_2$ is T or S,
optionally wherein the amino acid immediately N-terminal to CDRH1 is N, T, S, D, or A.

In certain embodiments:
(a) CDRH1 comprises the amino acid sequence of $X_1YX_2MH$ (SEQ ID NO: 136), wherein
  $X_1$ is Q or S; and
  $X_2$ is A or S;
(b) CDRH2 comprises the amino acid sequence of WINX$_1$X$_2$X$_3$X$_4$X$_5$TKYSQKFQG (SEQ ID NO: 138), wherein
  $X_1$ is A, V, or E;
  $X_2$ is V, W, or G;
  $X_3$ is S, Y, T, or N;
  $X_4$ is G or W; and
  $X_5$ is D, N, Y, or T;
(c) CDRH3 comprises the amino acid sequence of NWGX$_1$SYGX$_2$DV (SEQ ID NO: 180), wherein
  $X_1$ is M or L; and
  $X_2$ is M or L;
(d) CDRL1 comprises the amino acid sequence of RASQSIX$_1$X$_2$YLN (SEQ ID NO: 139), wherein
  $X_1$ is S, T, or L; and
  $X_2$ is S, P, or W;
(e) CDRL2 comprises the amino acid sequence of $X_1X_2$SSLQS (SEQ ID NO: 141), wherein
  $X_1$ is S or A; and
  $X_2$ is A, S, or E; and/or
(f) CDRL3 comprises the amino acid sequence of QQSYSTPALT (SEQ ID NO: 33) or QQAYSTPALS (SEQ ID NO: 34).

In certain embodiments:
(a) CDRH1 comprises the amino acid sequence of SEQ ID NO: 4;
(b) CDRH2 comprises the amino acid sequence of SEQ ID NO: 17;
(c) CDRH3 comprises the amino acid sequence of SEQ ID NO: 19 or 20;

(d) CDRL1 comprises the amino acid sequence of SEQ ID NO: 26;

(e) CDRL2 comprises the amino acid sequence of SEQ ID NO: 32; and/or (f) CDRL3 comprises the amino acid sequence of SEQ ID NO: 35.

In certain embodiments, CDRH1, CDRH2, and CDRH3 comprise the amino acid sequences of SEQ ID NOs: 1, 5, and 18; 2, 6, and 18; 2, 8, and 18; 2, 9, and 18; 2, 10, and 18; 1, 7, and 18; 2, 11, and 18; 1, 12, and 18; 1, 13, and 18; 1, 14, and 18; 3, 15, and 18; 1, 16, and 18; 1, 5, and 140; 1, 5, and 142; 1, 5, and 179; 4, 17, and 19; or 4, 17, and 20, respectively.

In certain embodiments, CDRL1, CDRL2, and CDRL3 comprise the amino acid sequences of SEQ ID NOs: 21, 28, and 33; 21, 29, and 33; 21, 30, and 33; 21, 31, and 33; 22, 29, and 33; 24, 29, and 33; 23, 29, and 33; 25, 28, and 34; or 26, 32, and 35, respectively.

In certain embodiments, CDRH1, CDRH2, CDRH3, CDRL1, CDRL2, and CDRL3 comprise the amino acid sequences of SEQ ID NOs: 1, 5, 18, 21, 28, and 33; 1, 5, 18, 21, 29, and 33; 1, 5, 18, 22, 29, and 33; 1, 5, 18, 23, 29, and 33; 1, 5, 18, 24, 29, and 33; 1, 5, 18, 25, 28, and 34; 1, 5, 140, 21, 28, and 33; 1, 5, 142, 21, 28, and 33; 1, 5, 179, 21, 28, and 33; 1, 7, 18, 21, 29, and 33; 1, 12, 18, 21, 28, and 33; 1, 13, 18, 21, 28, and 33; 1, 14, 18, 21, 28, and 33; 1, 16, 18, 21, 28, and 33; 2, 6, 18, 21, 29, and 33; 2, 8, 18, 21, 29, and 33; 2, 9, 18, 21, 30, and 33; 2, 10, 18, 21, 29, and 33; 2, 11, 18, 21, 31, and 33; 3, 15, 18, 21, 28, and 33; 4, 17, 19, 26, 32, and 35; or 4, 17, 20, 26, 32, and 35, respectively.

In certain embodiments, the antibody comprises a VH comprising an amino acid sequence that is at least 75%, 80%, 85%, 90%, 95%, 99%, or 100% identical to the amino acid sequence of SEQ ID NO: 36, 37, 38, 39, 40, 41, 42, 43, 44, 45, 46, 47, 48, 49, 50, 51, 52, 53, 54, 55, 56, 57, 58, 59, 60, or 61. In certain embodiments, the amino acid sequence of the VH consists of the amino acid sequence of SEQ ID NO: 36, 37, 38, 39, 40, 41, 42, 43, 44, 45, 46, 47, 48, 49, 50, 51, 52, 53, 54, 55, 56, 57, 58, 59, 60, or 61. In certain embodiments, the X in any one of SEQ ID NOs: 36, 37, 38, 39, 40, 41, 42, 43, 44, 45, 46, 47, 48, 49, 50, 51, 52, 53, 54, 55, 56, 57, 58, 59, 60, or 61 is glutamine. In certain embodiments, the X in any one of SEQ ID NOs: 36, 37, 38, 39, 40, 41, 42, 43, 44, 45, 46, 47, 48, 49, 50, 51, 52, 53, 54, 55, 56, 57, 58, 59, 60, or 61 is pyroglutamate.

In certain embodiments, the antibody comprises a VL comprising an amino acid sequence that is at least 75%, 80%, 85%, 90%, 95%, 99%, or 100% identical to the amino acid sequence of SEQ ID NO: 62, 63, 64, 65, 66, 67, 68, 69, 70, 71, 72, 73, 74, or 75. In certain embodiments, the amino acid sequence of the VL consists of the amino acid sequence of SEQ ID NO: 62, 63, 64, 65, 66, 67, 68, 69, 70, 71, 72, 73, 74, or 75.

In another aspect, the instant disclosure provides an isolated antibody that specifically binds to human CD96, the antibody comprising: a VH comprising the amino acid sequence of SEQ ID NO: 36, 37, 38, 39, 40, 41, 42, 43, 44, 45, 46, 47, 48, 49, 50, 51, 52, 53, 54, 55, 56, 57, 58, 59, 60, or 61; and/or a VL comprising the amino acid sequence of SEQ ID NO: 62, 63, 64, 65, 66, 67, 68, 69, 70, 71, 72, 73, 74, or 75. In certain embodiments, the VH and VL comprise the amino acid sequences of SEQ ID NOs: 36 and 62; 37 and 62; 37 and 63; 37 and 66; 37 and 67; 37 and 68; 37 and 69; 38 and 63; 39 and 63; 40 and 63; 41 and 63; 42 and 63; 43 and 64; 44 and 64; 45 and 63; 46 and 63; 47 and 65; 48 and 62; 49 and 62; 50 and 62; 51 and 62; 52 and 62; 53 and 62; 54 and 62; 55 and 62; 56 and 62; 57 and 62; 58 and 62; 59 and 62; 60 and 70; 60 and 71; 60 and 72; 60 and 73; 60 and 74; 60 and 75; or 61 and 70, respectively. In certain embodiments, the amino acid sequences of the VH and VL consist of the amino acid sequences of SEQ ID NOs: 36 and 62; 37 and 62; 37 and 63; 37 and 66; 37 and 67; 37 and 68; 37 and 69; 38 and 63; 39 and 63; 40 and 63; 41 and 63; 42 and 63; 43 and 64; 44 and 64; 45 and 63; 46 and 63; 47 and 65; 48 and 62; 49 and 62; 50 and 62; 51 and 62; 52 and 62; 53 and 62; 54 and 62; 55 and 62; 56 and 62; 57 and 62; 58 and 62; 59 and 62; 60 and 70; 60 and 71; 60 and 72; 60 and 73; 60 and 74; 60 and 75; or 61 and 70, respectively. In certain embodiments, the X in any one of SEQ ID NOs: 36, 37, 38, 39, 40, 41, 42, 43, 44, 45, 46, 47, 48, 49, 50, 51, 52, 53, 54, 55, 56, 57, 58, 59, 60, or 61 is glutamine. In certain embodiments, the X in any one of SEQ ID NOs: 36, 37, 38, 39, 40, 41, 42, 43, 44, 45, 46, 47, 48, 49, 50, 51, 52, 53, 54, 55, 56, 57, 58, 59, 60, or 61 is pyroglutamate.

In certain embodiments, the antibody specifically binds to the amino acid sequence of SEQ ID NO: 130 or 131. In certain embodiments, the antibody binds to the amino acid sequence of SEQ ID NO: 134.

In certain embodiments, the antibody is internalized upon binding to cells expressing human CD96.

In another aspect, the instant disclosure provides an isolated antibody that specifically binds the amino acid sequence of SEQ ID NO: 130 or 131. In certain embodiments, the antibody binds to the amino acid sequence of SEQ ID NO: 134.

In another aspect, the instant disclosure provides an isolated antibody that specifically binds to human CD96, wherein the antibody is internalized upon binding to cells expressing human CD96.

In certain embodiments, the antibody comprises a heavy chain constant region selected from the group consisting of human IgG1, IgG2, IgG3, IgG4, IgA1, and IgA2. In certain embodiments, the antibody comprises an IgG1 heavy chain constant region. In certain embodiments, the amino acid sequence of the IgG1 heavy chain constant region comprises an N297A mutation, numbered according to the EU numbering system. In certain embodiments, the antibody comprises a heavy chain constant region comprising the amino acid sequence of SEQ ID NO: 124 or 176. In certain embodiments, the amino acid sequence of the IgG1 heavy chain constant region comprises S239D, A330L, and I332E mutations, numbered according to the EU numbering system. In certain embodiments, the antibody comprises a heavy chain constant region comprising the amino acid sequence of SEQ ID NO: 125 or 177. In certain embodiments, the amino acid sequence of the IgG1 heavy chain constant region comprises S267E and L328F mutations, numbered according to the EU numbering system. In certain embodiments, the antibody comprises a heavy chain constant region comprising the amino acid sequence of SEQ ID NO: 126 or 178. In certain embodiments, the antibody comprises a heavy chain constant region that is a variant of a wild type heavy chain constant region, wherein the variant heavy chain constant region binds to an FcγR with higher affinity than the wild type heavy chain constant region binds to the FcγR. In certain embodiments, the FcγR is FcγRIIB.

In certain embodiments, the antibody comprises a heavy chain comprising the amino acid sequence of SEQ ID NO: 76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, or 169. In certain embodiments, the amino acid sequence of the heavy chain consists of the amino acid sequence of SEQ ID NO:

76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, or 169. In certain embodiments, the X in any one of SEQ ID NOs: 76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, and 169 is glutamine. In certain embodiments, the X in any one of SEQ ID NOs: 76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, and 169 is pyroglutamate.

In certain embodiments, the antibody comprises a light chain constant region comprising the amino acid sequence of SEQ ID NO: 122 or 123. In certain embodiments, the antibody comprises a light chain comprising the amino acid sequence of SEQ ID NO: 102, 103, 104, 105, 106, 107, 108, 109, 110, 111, 112, 113, 114, or 115. In certain embodiments, the amino acid sequence of the light chain consists of the amino acid sequence of SEQ ID NO: 102, 103, 104, 105, 106, 107, 108, 109, 110, 111, 112, 113, 114, or 115.

In another aspect, the instant disclosure provides an isolated antibody that specifically binds to human CD96, the antibody comprising: a heavy chain comprising the amino acid sequence of SEQ ID NO: 76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, or 169; and/or a light chain comprising the amino acid sequence of SEQ ID NO: 102, 103, 104, 105, 106, 107, 108, 109, 110, 111, 112, 113, 114, or 115. In certain embodiments, the amino acid sequence of the heavy chain consists of the amino acid sequence of SEQ ID NO: 76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, or 169; and/or the amino acid sequence of the light chain consists of the amino acid sequence of SEQ ID NO: 102, 103, 104, 105, 106, 107, 108, 109, 110, 111, 112, 113, 114, or 115. In certain embodiments, the heavy chain and light chain comprise the amino acid sequences of SEQ ID NOs: 76 and 102; 79 and 103; 78 and 103; 82 and 103; 84 and 104; 83 and 104; 86 and 103; 85 and 103; 81 and 103; 80 and 103; 87 and 105; 77 and 102; 88 and 102; 77 and 106; 77 and 107; 77 and 108; 77 and 103; 89 and 102; 90 and 102; 91 and 102; 92 and 102; 93 and 102; 77 and 109; 94 and 102; 95 and 102; 96 and 102; 97 and 102; 98 and 102; 99 and 102; 100 and 110; 100 and 111; 100 and 112; 100 and 113; 100 and 114; 100 and 115; 101 and 110; 144 and 102; 147 and 103; 146 and 103; 150 and 103; 152 and 104; 151 and 104; 154 and 103; 153 and 103; 149 and 103; 148 and 103; 155 and 105; 145 and 102; 156 and 102; 145 and 106; 145 and 107; 145 and 108; 145 and 103; 157 and 102; 158 and 102; 159 and 102; 160 and 102; 161 and 102; 145 and 109; 162 and 102; 163 and 102; 164 and 102; 165 and 102; 166 and 102; 167 and 102; 168 and 110; 168 and 111; 168 and 112; 168 and 113; 168 and 114; 168 and 115; or 169 and 110, respectively. In certain embodiments, the amino acid sequences of the heavy chain and the light chain consist of the amino acid sequences of SEQ ID NOs: 76 and 102; 79 and 103; 78 and 103; 82 and 103; 84 and 104; 83 and 104; 86 and 103; 85 and 103; 81 and 103; 80 and 103; 87 and 105; 77 and 102; 88 and 102; 77 and 106; 77 and 107; 77 and 108; 77 and 103; 89 and 102; 90 and 102; 91 and 102; 92 and 102; 93 and 102; 77 and 109; 94 and 102; 95 and 102; 96 and 102; 97 and 102; 98 and 102; 99 and 102; 100 and 110; 100 and 111; 100 and 112; 100 and 113; 100 and 114; 100 and 115; 101 and 110; 144 and 102; 147 and 103; 146 and 103; 150 and 103; 152 and 104; 151 and 104; 154 and 103; 153 and 103; 149 and 103; 148 and 103; 155 and 105; 145 and 102; 156 and 102; 145 and 106; 145 and 107; 145 and 108; 145 and 103; 157 and 102; 158 and 102; 159 and 102; 160 and 102; 161 and 102; 145 and 109; 162 and 102; 163 and 102; 164 and 102; 165 and 102; 166 and 102; 167 and 102; 168 and 110; 168 and 111; 168 and 112; 168 and 113; 168 and 114; 168 and 115; or 169 and 110, respectively. In certain embodiments, the X in any one of SEQ ID NOs: 76-101 or 144-169 is glutamine. In certain embodiments, the X in any one of SEQ ID NOs: 76-101 or 144-169 is pyroglutamate.

In another aspect, the instant disclosure provides an isolated antibody that specifically binds to human CD96, wherein the antibody binds to the same epitope of human CD96 as an antibody disclosed herein.

In another aspect, the instant disclosure provides an isolated antibody that specifically binds to human CD96, wherein the antibody competes for binding to human CD96 with an antibody disclosed herein.

In certain embodiments, the antibody is a human antibody. In certain embodiments, the antibody is a multispecific antibody. In certain embodiments, the antibody is conjugated to a cytotoxic agent, cytostatic agent, toxin, radionuclide, or detectable label. In certain embodiments, the antibody is conjugated to a second antibody.

In another aspect, the instant disclosure provides an isolated polynucleotide encoding a VH and/or a VL of an antibody disclosed herein. In another aspect, the instant disclosure provides a vector comprising the polynucleotide. In another aspect, the instant disclosure provides a recombinant host cell comprising the polynucleotide or the vector. In another aspect, the instant disclosure provides a method of producing an antibody that specifically binds to human CD96, the method comprising culturing the host cell under suitable conditions so that the polynucleotide is expressed and the antibody is produced.

In another aspect, the instant disclosure provides a pharmaceutical composition comprising an antibody, a polynucleotide, a vector, or a host cell disclosed herein; and a pharmaceutically acceptable carrier or excipient.

In another aspect, the instant disclosure provides a method of increasing an immune response in a subject, the method comprising administering to the subject an effective amount of an antibody, a polynucleotide, a vector, a host cell, or a pharmaceutical composition disclosed herein.

In another aspect, the instant disclosure provides a method of treating cancer in a subject, the method comprising administering to the subject an effective amount of an antibody, a polynucleotide, a vector, a host cell, or a pharmaceutical composition disclosed herein.

In another aspect, the instant disclosure provides a method of treating an infectious disease in a subject, the method comprising administering to the subject an antibody, a polynucleotide, a vector, a host cell, or a pharmaceutical composition disclosed herein In certain embodiments of the foregoing methods, the antibody, polynucleotide, vector, host cell, or pharmaceutical composition is administered, systemically, intravenously, subcutaneously, intratumorally, or is delivered to a tumor draining lymph node.

In certain embodiments of the foregoing methods, the methods further comprise administering an additional therapeutic agent to the subject. In certain embodiments, the additional therapeutic agent is a chemotherapeutic agent. In certain embodiments, the additional therapeutic agent is a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-VISTA antibody, an antagonist anti-TIGIT antibody, an antagonist anti-CEACAM1 antibody, an antagonist anti-CD96 antibody, an agonist anti-GITR antibody, and an agonist anti-OX40 antibody. In certain embodiments, the additional therapeutic agent is an anti-PD-1 antibody, optionally wherein the anti-PD-1 antibody is pembrolizumab or nivolumab. In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 protein and is complexed with a tumor-associated antigenic peptide, wherein the HSPPC is derived from a tumor obtained from a subject.

4. BRIEF DESCRIPTION OF THE DRAWINGS

FIGS. 1A and 1B are graphs showing the binding of the anti-CD96 antibodies BA072 or BA101, or an IgG1 isotype control antibody, to Jurkat cells engineered to express high levels of cell surface human isoform 2 of CD96. The levels of Jurkat cell binding of BA072 (FIG. 1A) or BA101 (FIG. 1B), as assessed by median fluorescence intensity (MFI), in each case in comparison with Jurkat cell binding of an IgG1 isotype control antibody, are plotted against the concentrations of the respective antibody incubated with the cells.

FIGS. 2A and 2B are graphs showing the binding of the anti-CD96 antibodies BA072 or BA101, or an IgG1 isotype control antibody, to CHO cells engineered to express high levels of cell surface isoform 1 of human CD96. The levels of binding of BA072 (FIG. 2A) or BA101 (FIG. 2B), as assessed by median fluorescence intensity (MFI), in each case in comparison with CHO cell binding of an IgG1 isotype control antibody, are plotted against the concentrations of the respective antibody incubated with the cells.

FIGS. 3A and 3B are graphs showing the binding of the anti-CD96 antibodies BA072 or BA101, or an IgG1 isotype control antibody, to CHO cells engineered to express high levels of cell surface isoform 2 of human CD96. The levels of binding of BA072 (FIG. 3A) or BA101 (FIG. 3B), as assessed by median fluorescence intensity (MFI), in each case in comparison with CHO cell binding of an IgG1 isotype control antibody, are plotted against the concentrations of the respective antibody incubated with the cells.

FIGS. 4A and 4B are graphs showing the binding of the anti-CD96 antibodies BA072 or BA101, or an IgG1 isotype control antibody, to CHO cells engineered to express high levels of cell surface isoform 2 of cynomolgus monkey CD96. The levels of binding of BA072 (FIG. 4A) or BA101 (FIG. 4B), as assessed by median fluorescence intensity (MFI), in each case in comparison with CHO cell binding of an IgG1 isotype control antibody, are plotted against the concentrations of the respective antibody incubated with the cells.

FIGS. 5A and 5B are graphs showing the binding of the anti-CD96 antibodies BA072 or BA101, or an IgG1 isotype control antibody, to activated primary human T cells expressing cell surface CD96. The levels of binding of BA072 (FIG. 5A) or BA101 (FIG. 5B), as assessed by median fluorescence intensity (MFI), in each case in comparison with activated primary human T cell binding of an IgG1 isotype control antibody, are plotted against the concentrations of the respective antibody incubated with the cells.

FIGS. 6A, 6B, and 6C are a series of graphs showing the binding of the anti-CD96 antibodies BA072, BA083, or BA084, or an IgG1 isotype control antibody, to activated primary human T cells expressing cell surface CD96. The levels of binding of BA072 (FIG. 6A), BA083 (FIG. 6B), or BA084 (FIG. 6C), as assessed by median fluorescence intensity (MFI), in each case in comparison with activated primary human T cell binding of an IgG1 isotype control antibody, are plotted against the concentrations of the respective antibody incubated with the cells.

FIGS. 7A-7F are a series of graphs showing the binding of the anti-CD96 antibodies BA101, BA102, BA103, BA104, BA105, or BA106, or an IgG1 isotype control antibody, to activated primary human T cells expressing cell surface CD96. The levels of binding of BA101 (FIG. 7A), BA102 (FIG. 7B), BA103 (FIG. 7C), BA104 (FIG. 7D), BA105 (FIG. 7E), or BA106 (FIG. 7F), as assessed by median fluorescence intensity (MFI), in each case in comparison with activated primary human T cell binding of an IgG1 isotype control antibody, are plotted against the concentrations of the respective antibody incubated with the cells.

FIGS. 8A-8M are a series of graphs showing the binding of affinity-matured anti-CD96 antibodies, BA074, BA073, BA079, BA078, BA081, BA080, BA077, BA076, BA082, or BA075, parental antibodies BA072 or BA101, germlined antibody BA083, or an IgG1 isotype control antibody, to NY-ESO-1 transfected CD8+ T cells expressing cell surface CD96. The levels of binding of BA072 (FIG. 8A), BA083 (FIG. 8B), BA074 (FIG. 8C), BA073 (FIG. 8D), BA079 (FIG. 8E), BA078 (FIG. 8F), BA081 (FIG. 8G), BA080 (FIG. 8H), BA077 (FIG. 8I), BA076 (FIG. 8J), BA082 (FIG. 8K), BA075 (FIG. 8L), or BA101 (FIG. 8M), as assessed by median fluorescence intensity (MFI), in each case in comparison with NY-ESO-1 transfected CD8+ T cell binding of an IgG1 isotype control antibody, are plotted against the concentrations of the respective antibody incubated with the cells.

FIGS. 9A and 9B are graphs showing the binding of the anti-CD96 antibodies BA072 or BA101, or an IgG1 isotype control antibody, to activated cynomolgus monkey primary T cells expressing cell surface cynomolgus monkey CD96. The levels of binding of BA072 (FIG. 9A) or BA101 (FIG. 9B), as assessed by median fluorescence intensity (MFI), in each case in comparison with activated primary cynomolgus T cell binding of an IgG1 isotype control antibody, are plotted against the concentrations of the respective antibody incubated with the cells.

FIGS. 10A and 10B are graphs showing the blockade of PVR-Fc binding to CHO cells, engineered to express high levels of cell surface isoform 2 of human CD96, by the anti-CD96 antibodies BA072 (FIG. 10A) or BA101 (FIG. 10B). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 11A and 11B are graphs showing the blockade PVR-His binding to CHO cells, engineered to express high levels of cell surface isoform 2 of human CD96, by the anti-CD96 antibodies BA072 (FIG. 11A) or BA101 (FIG. 11B). The levels of binding of PVR-His, as assessed by median fluorescence intensity (MFI), in each case in comparison with blockade by an IgG1 isotype control antibody, are plotted as % maximal response against the concentrations of the respective antibody incubated with the cells.

FIGS. 12A-12C are a series of graphs showing the blockade of PVR-Fc binding to CHO cells, engineered to express high levels of cell surface isoform 2 of human CD96, by the anti-CD96 antibodies BA072 (FIG. 12A), BA083 (FIG. 12B), or BA084 (FIG. 12C). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 13A-13L are a series of graphs showing the blockade of human PVR-Fc binding to CHO cells, engineered to express high levels of cell surface isoform 2 of human CD96, by the anti-CD96 antibodies BA072 (FIG. 13A), BA083 (FIG. 13B), BA085 (FIG. 13C), BA086 (FIG. 13D), BA087 (FIG. 13E), BA089 (FIG. 13F), BA090 (FIG. 13G), BA088 (FIG. 13H), BA091 (FIG. 13I), BA092 (FIG. 13J), BA093 (FIG. 13K), or BA094 (FIG. 13L). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 14A-14L are a series of graphs showing the blockade of human PVR-Fc binding to CHO cells, engineered to express high levels of cell surface isoform 1 of human CD96, by the anti-CD96 antibodies BA073 (FIG. 14A), BA074 (FIG. 14B), BA078 (FIG. 14C), BA079 (FIG. 14D), BA080 (FIG. 14E), BA081 (FIG. 14F), BA076 (FIG. 14G), BA077 (FIG. 14H), BA082 (FIG. 14I), BA075 (FIG. 14J), BA083 (FIG. 14K), or BA072 (FIG. 14L). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 15A-15L are a series of graphs showing the blockade of human PVR-Fc binding to CHO cells, engineered to express high levels of cell surface isoform 2 of human CD96, by the anti-CD96 antibodies BA073 (FIG. 15A), BA074 (FIG. 15B), BA078 (FIG. 15C), BA079 (FIG. 15D), BA080 (FIG. 15E), BA081 (FIG. 15F), BA076 (FIG. 15G), BA077 (FIG. 15H), BA082 (FIG. 15I), BA075 (FIG. 15J), BA083 (FIG. 15K), or BA072 (FIG. 15L). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 16A-16F are a series of graphs showing the blockade of PVR-Fc binding to CHO cells, engineered to express high levels of cell surface human isoform 2 of CD96, by the anti-CD96 antibodies BA101 (FIG. 16A), BA102 (FIG. 16B), BA103 (FIG. 16C), BA104 (FIG. 16D), BA105 (FIG. 16E), or BA106 (FIG. 16F). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 17A and 17B are graphs showing the blockade of PVR-Fc binding to CHO cells, engineered to express high levels of cell surface human isoform 2 of CD96, by the anti-CD96 antibodies BA101 (FIG. 17A) or BA107 (FIG. 17B). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 18A-18C are a series of graphs showing the blockade of PVR-Fc binding to CHO cells, engineered to express high levels of cell surface isoform 2 of cynomolgus monkey CD96, by the anti-CD96 antibodies BA072 (FIG. 18A), BA083 (FIG. 18B), or BA084 (FIG. 18C). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 19A-19L are a series of graphs showing the blockade of human PVR-Fc binding to CHO cells, engineered to express high levels of cell surface isoform 2 of cynomolgus monkey CD96, by the anti-CD96 antibodies BA072 (FIG. 19A), BA083 (FIG. 19B), BA085 (FIG. 19C), BA086 (FIG. 19D), BA088 (FIG. 19E), BA087 (FIG. 19F), BA089 (FIG. 19G), BA090 (FIG. 19H), BA091 (FIG. 19I), BA092 (FIG. 19J), BA093 (FIG. 19K), or BA094 (FIG. 19L). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 20A-20L are a series of graphs showing the blockade of human PVR-Fc binding to CHO cells, engineered to express high levels of cell surface isoform 1 of cynomolgus CD96, by the anti-CD96 antibodies BA073 (FIG. 20A), BA074 (FIG. 20B), BA078 (FIG. 20C), BA079 (FIG. 20D), BA080 (FIG. 20E), BA081 (FIG. 20F), BA076 (FIG. 20G), BA077 (FIG. 20H), BA082 (FIG. 20I), BA075 (FIG. 20J), BA083 (FIG. 20K), or BA072 (FIG. 20L). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 21A-21L are a series of graphs showing the blockade of human PVR-Fc binding to CHO cells, engineered to express high levels of cell surface isoform 2 of cynomolgus CD96, by the anti-CD96 antibodies BA073 (FIG. 21A), BA074 (FIG. 21B), BA078 (FIG. 21C), BA079 (FIG. 21D), BA080 (FIG. 21E), BA081 (FIG. 21F), BA076 (FIG. 21G), BA077 (FIG. 21H), BA082 (FIG. 21I), BA075 (FIG. 21J), BA083 (FIG. 21K), or BA072 (FIG. 21L). The levels of binding of PVR-Fc, as assessed by median fluorescence intensity (MFI), in each case in comparison with blockade by an IgG1 isotype control antibody, are plotted as % maximal response against the concentrations of the respective antibody incubated with the cells.

FIGS. 22A and 22B are graphs showing the conjugate formation of CHO cells, engineered to express high levels of isoform 2 of human CD96 or PVR, in the presence of the anti-CD96 antibodies BA072 (FIG. 22A) or BA101 (FIG.

22B), or an IgG1 isotype control antibody. The percent of conjugates formed, in each case in comparison to IgG1 isotype control, are plotted against the concentrations of the respective antibody incubated with the cells. FIG. 22C are scatter plots showing conjugate formation in quadrant Q2 in the presence of isotype control, and not in the presence of blocking antibody.

FIG. 23 is a graph showing the conjugate formation of CHO cells, engineered to express high levels of isoform 2 of human CD96 or PVR, in the presence of the anti-CD96 antibodies BA072, BA083, BA084, or an IgG1 isotype control antibody. The percent of conjugates formed, in each case in comparison to IgG1 isotype control, are plotted against the concentrations of the respective antibody incubated with the cells.

FIGS. 25A-25H are a series of graphs showing that the anti-CD96 antibodies BA072 and BA101 promote IL-2 secretion by SEA-stimulated PBMCs in a dose-dependent manner, when administered with and without an anti-PD-1 antibody, in two different donors. FIGS. 25A-D represent a first experiment with a first donor, and FIGS. 25E-H represent a second experiment with a second donor.

FIGS. 26A-26F are a series of graphs showing that the affinity-matured BA073, BA078, BA080, and BA076 antibodies and the germlined antibody BA083 promote IL-2 secretion by SEA-stimulated PBMCs both with and without an anti-PD-1 antibody. FIGS. 26A and 26B represent one experiment without (FIG. 26A) and with (FIG. 26B) an anti-PD-1 antibody. FIGS. 26C and 26D represent a second experiment, with a different donor, without (FIG. 26C) and with (FIG. 26D) an anti-PD-1 antibody. FIGS. 26E and 26F represent a third experiment, with a different donor, without (FIG. 26E) and with (FIG. 26F) an anti-PD-1 antibody.

FIGS. 27A-27F are a series of graphs showing the ability of affinity-matured BA074, BA079, BA077, BA081, BA082, and BA075 antibodies and the parental BA072 antibody to promote IL-2 secretion by SEA-stimulated PBMCs. FIGS. 27A and 278B represent one experiment without (FIG. 27A) and with (FIG. 27B) an anti-PD-1 antibody. FIGS. 27C and 27D represent a second experiment, with a different donor, without (FIG. 27C) and with (FIG. 27D) an anti-PD-1 antibody. FIGS. 27E and 27F represent a third experiment, with a different donor, without (FIG. 27E) and with (FIG. 27F) an anti-PD-1 antibody.

FIGS. 28A and 28B are graphs showing the increase in NFAT-Luciferase (FIG. 28A) and NFκB-Luciferase (FIG. 28B) signaling on CD96-expressing Jurkat reporter cells in the presence of BA072 and PVR and anti-CD3 expressing CHO cells. The delta relative light units (RLU) between BA072 and isotype control is plotted against antibody concentration. FIG. 28C is a series of histograms showing cell surface expression of CD96, CD226, PVR, and CD3.

FIGS. 29A and 29B are a series of graphs showing the increase in NFAT-Luciferase signaling on CD96-expressing Jurkat reporter cells, with (FIG. 29A) and without (FIG. 29B) CD226 surface expression, in the presence of BA072 and PVR and anti-CD3 expressing CHO cells. The delta relative light units (RLU) between BA072 and isotype control is plotted against antibody concentration.

Figure 30A:
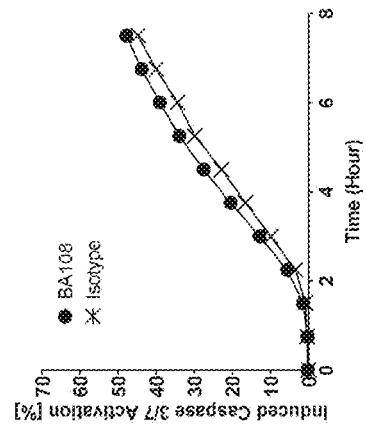
Figure 30B:
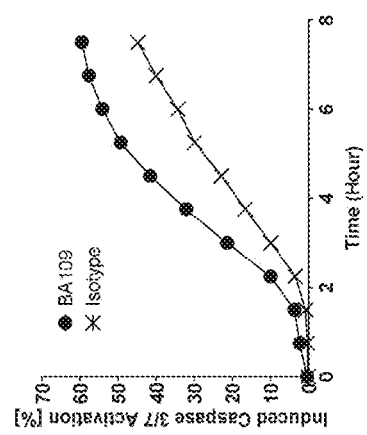
Figure 30C:
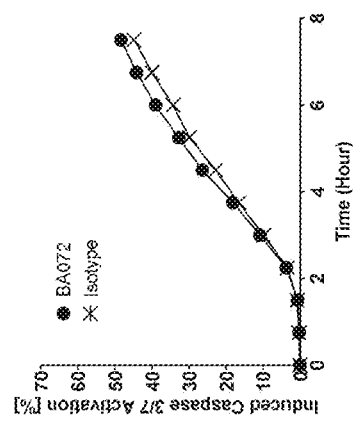

FIGS. 30A-30C are a series of graph showing promotion of antibody-dependent cell-mediated cytotoxicity (ADCC) of CD96-expressing cells in the presence of primary NK cells as measured by induction of caspase 3/7 activation by BA072 IgG1 (FIG. 30A), Fc-enhanced BA072 (BA109) (FIG. 30B), or the Fc-silent variant of BA072 (BA108) (FIG. 30C), in each case in comparison to an isotype control. The % induced caspase 3/7 activation is plotted against time (h).

Figures 31A, 31B, 31C:
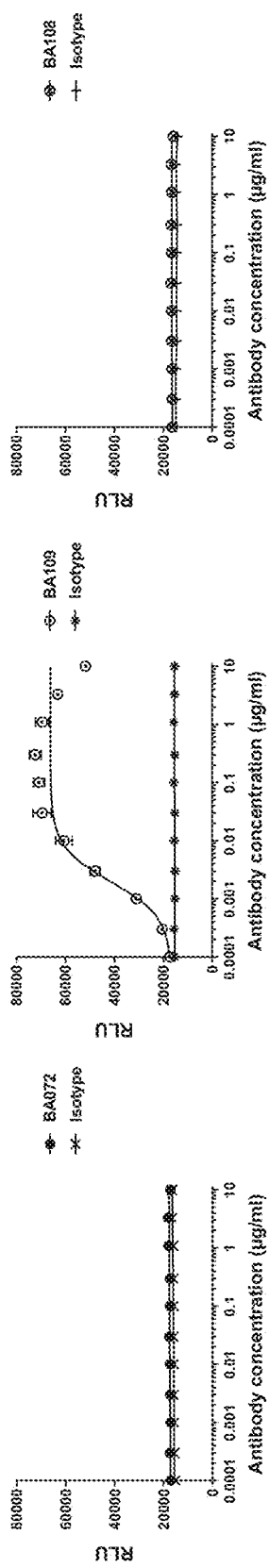

FIGS. 31A-31C are a series of graphs showing FcγRIIIA-mediated NFAT signaling from FcγRIIIA-expressing Jurkat reporter cells in the presence of anti-CD96 BA072 Fc variants, Fc-enhanced BA072 variant (BA109) (FIG. 31B), Fc-silent variant of BA072 (BA108) (FIG. 31C), or BA072 IgG1 (FIG. 31A), bound to CD96-expressing target cells (4:1 E:T ratio). The relative light units (RLU) is plotted against antibody concentration.

FIGS. 32A and 32B are graphs showing the extent of IL-2 secretion elicited by BA072 (FIG. 32A) and BA108 (an Fc silent variant of BA072; FIG. 32B) in T cell:APC co-culture assays using PBMCs from two human donors.

Figure 33A:
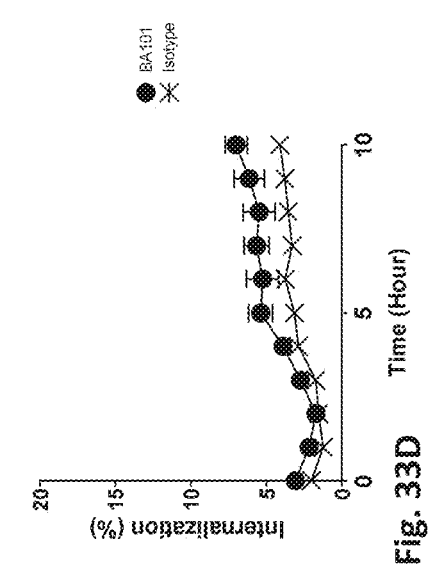
Figure 33B:
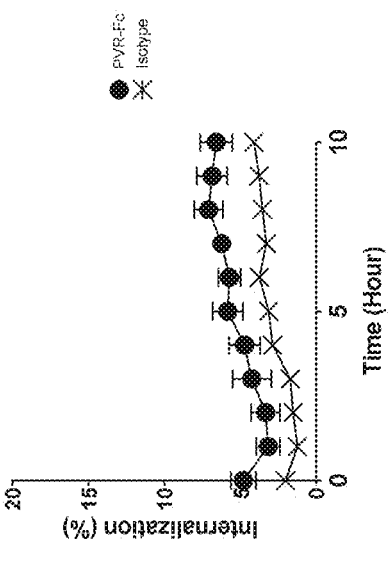
Figure 33C:
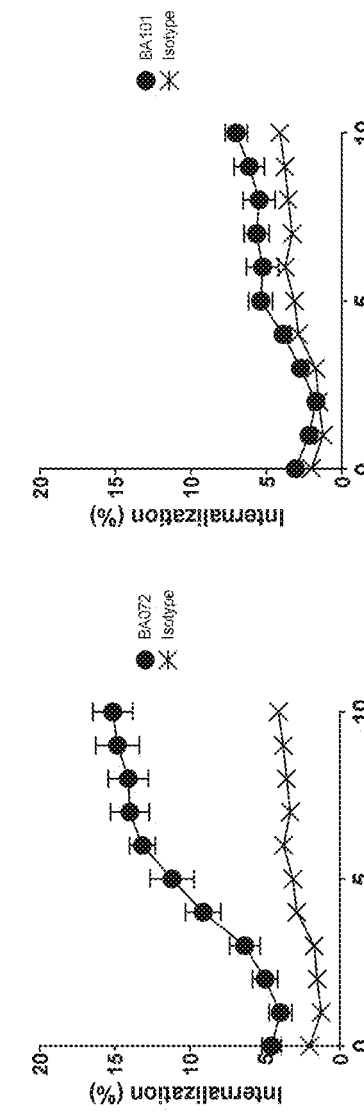
Figure 33D:
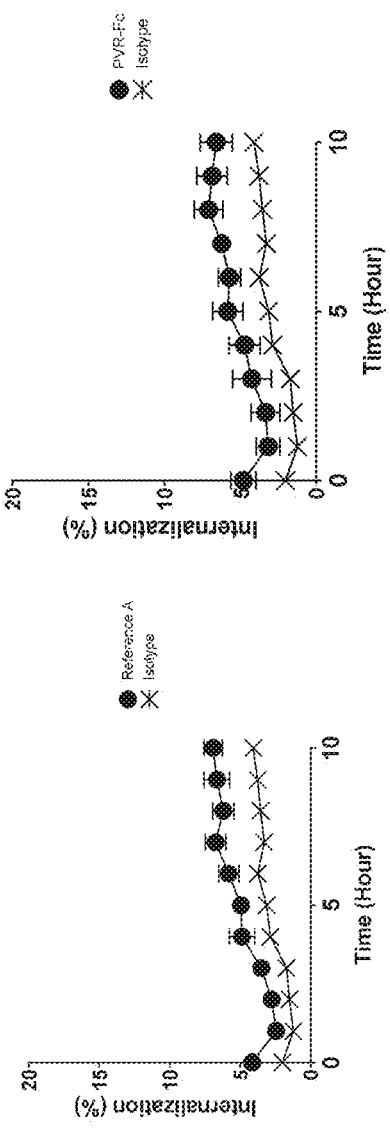

FIGS. 33A-33D are a series of graphs showing percent internalization of CD96 using CD96-expressing Jurkat cells in the presence of BA072 (FIG. 33A), BA101 (FIG. 33B), the reference antibody Reference A (FIG. 33C), or PVR-Fc (FIG. 33D).

Figure 34A:
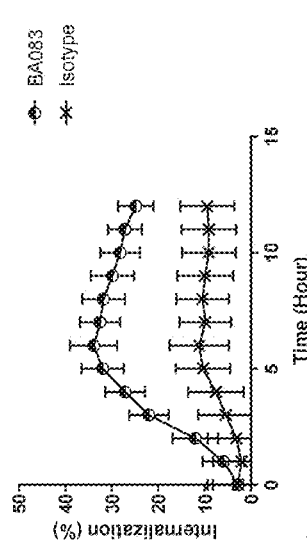
Figure 34B:
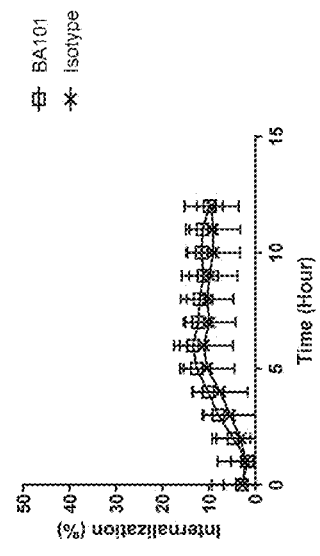
Figure 34C:
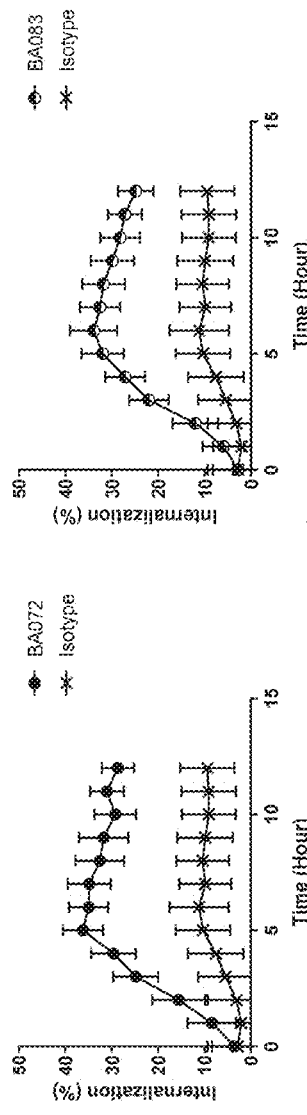
Figure 34D:
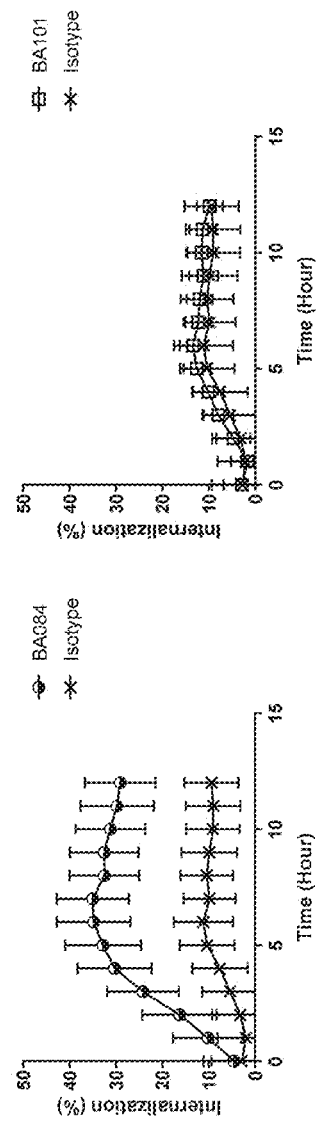

FIGS. 34A-34D are a series of graphs showing the percent internalization of CD96 using CD96-expressing Jurkat cells in the presence of parental antibodies BA072 (FIG. 34A) or BA101 (FIG. 34D), or germline variants BA083 (FIG. 34B) or BA084 (FIG. 34C).

FIGS. 35A and 35B are graphs showing internalization of CD96 by CD96-expressing primary T cells in the presence of BA072 in donor 1 (FIG. 35A) and donor 2 (FIG. 35B).

FIGS. 36A and 36B are sensorgrams showing binding of BA072 Fab, BA101 Fab, and Reference A Fab to Fc-tagged full-length human CD96 (FIG. 36A) or Fc-tagged domain 1 of human CD96 (FIG. 36B).

FIGS. 37A-37D are a series of sensorgrams showing binding of BA072 Fab, BA101 Fab, and Reference A Fab to Fc-tagged full-length human CD96 (FIGS. 37A and 37B) or Fc-tagged domain 1 human CD96 (FIGS. 37C and 37D). FIGS. 37A and 37C represent experiments where initial association was with BA072. FIGS. 37B and 37D represent experiments where initial association was with BA101.

5. DETAILED DESCRIPTION

The instant disclosure provides antibodies that specifically bind to CD96 (e.g., human CD96 or cynomolgus CD96) and antagonize CD96 function, e.g., CD96-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing immune cell activation, and hence, are useful for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides"

described herein are additionally contemplated as polynucleotides that may be, but need not be, isolated.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "CD96" refers to Cluster of Differentiation 96, also known as TACTILE (T cell-activation, increased late expression), that in humans is encoded by the CD96 gene. As used herein, the term "human CD96" refers to a CD96 protein encoded by a wild-type human CD96 gene (e.g., GenBank™ accession number NM_005816.5), a fragment, or a variant thereof. Exemplary extracellular portions of human CD96 are provided herein as SEQ ID NOs: 127, 128, 129, 130, and 131. Exemplary extracellular portions of cynomolgus CD96 are provided herein as SEQ ID NOs: 132, 133, and 134.

As used herein, the terms "CD155", "polio virus receptor", and "PVR" are used interchangeably and refer to a CD155 protein encoded by a CD155 gene (e.g., GenBank™ accession number NMn_006505.5), a fragment, or a variant thereof.

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affibodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies, or a class (e.g., human IgG1 or IgG4) or subclass thereof. In a specific embodiment, the antibody is a humanized monoclonal antibody. In another specific embodiment, the antibody is a human monoclonal antibody.

As used herein, the terms "VH region" and "VL region" refer, respectively, to single antibody heavy and light chain variable regions, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus CD96). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat or MacCallum definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain, which is not directly involved in binding of an antibody to antigen but which can exhibit various effector functions, such as interaction with an Fc receptor (e.g., Fc gamma receptor).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., IgG1, IgG2, IgG3, and IgG4.

As used herein, the term "light chain" when used in reference to an antibody can refer to any distinct type, e.g., kappa (κ) or lambda (λ), based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA. As used herein, a "lower affinity" refers to a larger $K_D$.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs (e.g., factors of 10), 2.5 logs, 3 logs, 4 logs or greater than the $K_A$ when the molecules bind non-specifically to another antigen.

In another specific embodiment, molecules that specifically bind to an antigen do not cross react with other proteins under similar binding conditions. In another specific embodiment, molecules that specifically bind to CD96 do not cross react with other non-CD96 proteins. In a specific embodiment, provided herein is an antibody that binds to CD96 (e.g., human CD96) with higher affinity than to another unrelated antigen. In certain embodiments, provided herein is an antibody that binds to CD96 (e.g., human CD96) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-CD96 antibody described herein to an unrelated, non-CD96 protein is less than 10%, 15%, or 20% of the binding of the antibody to CD96 protein as measured by, e.g., a radioimmunoassay.

As used herein, an "epitope" is a term in the art and refers to a region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics. In a specific embodiment, the epitope of an antibody is determined by protein mutagenesis, e.g., by generating switch mutants of an antigen with portions of its ortholog from another species and then testing the switch mutants for loss of antibody binding (e.g., by a FACS-based cell binding assay, as described herein).

As used herein, the terms "T cell receptor" and "TCR" are used interchangeably and refer to full-length heterodimeric αβ or γδ TCRs, antigen-binding fragments of full-length TCRs, and molecules comprising TCR CDRs or variable regions. Examples of TCRs include, but are not limited to, full-length TCRs, antigen-binding fragments of full-length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multispecific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "internalization" or 'internalized" refers to the uptake of an antibody into an intracellular compartment of a cell upon binding of the antibody to an antigen expressed at the surface of the cell.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the world-wide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

5.2 Anti-CD96 Antibodies

In one aspect, the instant disclosure provides antibodies that specifically bind to CD96 (e.g., human CD96 or cynomolgus CD96) and antagonize CD96 function. The amino acid sequences of exemplary antibodies are set forth in Table 1, herein.

TABLE 1

Amino acid sequences of exemplary anti-CD96 antibodies.

| Description | Amino Acid Sequence | SEQ ID NO: |
|---|---|---|
| CDRH1 consensus sequence 1 | $X_1YX_2X_3X_4$, wherein<br>$X_1$ is Q or S;<br>$X_2$ is A or S;<br>$X_3$ is M or I; and<br>$X_4$ is S or H. | 135 |

TABLE 1-continued

Amino acid sequences of exemplary anti-CD96 antibodies.

| Description | Amino Acid Sequence | SEQ ID NO: |
|---|---|---|
| CDRH1 consensus sequence 2 | $X_1YX_2MH$, wherein<br>$X_1$ is Q or S; and<br>$X_2$ is A or S. | 136 |
| CDRH2 consensus sequence 1 | $X_1IX_2X_3X_4X_5X_6X_7X_8X_9YX_{10}QKFQG$, wherein<br>$X_1$ is W or G;<br>$X_2$ is N or I;<br>$X_3$ is A, E, V, or P;<br>$X_4$ is V, G, W, or I;<br>$X_5$ is S, Y, T, N, or F;<br>$X_6$ is G or W;<br>$X_7$ is D, Y, N, or T;<br>$X_8$ is T or A;<br>$X_9$ is K or N; and<br>$X_{10}$ is S or A. | 137 |
| CDRH2 consensus sequence 2 | $WINX_1X_2X_3X_4X_5TKYSQKFQG$, wherein<br>$X_1$ is A, V, or E;<br>$X_2$ is V, W, or G;<br>$X_3$ is S, Y, T, or N;<br>$X_4$ is G or W; and<br>$X_5$ is D, N, Y, or T. | 138 |
| CDRH3 consensus sequence | $NWGX_1SYGX_2DV$, wherein<br>$X_1$ is M or L; and<br>$X_2$ is M or L. | 180 |
| CDRL1 consensus sequence | $RASQSIX_1X_2YLN$, wherein<br>$X_1$ is S, T, or L; and<br>$X_2$ is S, P, or W. | 139 |
| CDRL2 consensus sequence | $X_1X_2SSLQS$, wherein<br>$X_1$ is S or A; and<br>$X_2$ is A, S, or E. | 141 |
| CDRL3 consensus sequence | $QQX_1YSTPALX_2$, wherein<br>$X_1$ is S or A; and<br>$X_2$ is T or S. | 143 |
| CDRH1 - BA072, BA083, BA081, BA080, BA084, BA085, BA086, BA087, BA088, BA089, BA090, BA091, BA093, BA094, BA095, BA096, BA097, BA098, BA099, BA100 | SYAMH | 1 |
| CDRH1 - BA074, BA073, BA075, BA077, BA076, BA079, BA078, BA082 | QYAMH | 2 |
| CDRH1 - BA092 | SYSMH | 3 |
| CDRH1 - BA101, BA102, BA103, BA104, BA105, BA106, BA107 | SYAIS | 4 |
| CDRH2 - BA072, BA083, BA084, BA085, BA086, BA087, BA088, BA094, BA095, BA096, BA097, BA098, BA099, BA100 | WINAGNGNTKYSQKFQG | 5 |
| CDRH2 - BA074, BA073 | WINAVSGDTKYSQKFQG | 6 |
| CDRH2 - BA081, BA080 | WINAGTGDTKYSQKFQG | 7 |
| CDRH2 - BA075 | WINEGYGNTKYSQKFQG | 8 |

TABLE 1-continued

Amino acid sequences of exemplary anti-CD96 antibodies.

| Description | Amino Acid Sequence | SEQ ID NO: |
| --- | --- | --- |
| CDRH2 - BA077, BA076 | WINAGYGYTKYSQKFQG | 9 |
| CDRH2 - BA079, BA078 | WINAGTGNTKYSQKFQG | 10 |
| CDRH2 - BA082 | WINAGYGNTKYSQKFQG | 11 |
| CDRH2 - BA089 | WINAWNGNTKYSQKFQG | 12 |
| CDRH2 - BA090 | WINVGTGTTKYSQKFQG | 13 |
| CDRH2 - BA091 | WINAVNGNTKYSQKFQG | 14 |
| CDRH2 - BA092 | WINAGNWNTKYSQKFQG | 15 |
| CDRH2 - BA093 | WINAWTGNTKYSQKFQG | 16 |
| CDRH2 - BA101, BA102, BA103, BA104, BA105, BA106, BA107 | GIIPIFGTANYAQKFQG | 17 |
| CDRH3 - BA072, BA083, BA074, BA073, BA081, BA080, BA075, BA77, BA076, BA079, BA78, BA082, BA084, BA085, BA086, BA087, BA088, BA089, BA090, BA091, BA092, BA093, BA094 | NWGMSYGMDV | 18 |
| CDRH3 - BA095, BA098 | NWGMSYGLDV | 140 |
| CDRH3 - BA096, BA099 | NWGLSYGMDV | 142 |
| CDRH3 - BA097, BA100 | NWGLSYGLDV | 179 |
| CDRH3 - BA101, BA102, BA103, BA104, BA105, BA106 | GYDSRPLDV | 19 |
| CDRH3 - BA107 | GYDSRPLDY | 20 |
| CDRL1 - BA072, BA083, BA074, BA073, BA081, BA080, BA075, BA77, BA076, BA079, BA78, BA082, BA084, BA088, BA089, BA090, BA091, BA092, BA093, BA095, BA096, BA097, BA098, BA099, BA100 | RASQSISSYLN | 21 |
| CDRL1 - BA085 | RASQSISPYLN | 22 |
| CDRL1 - BA087 | RASQSILSYLN | 23 |
| CDRL1 - BA086 | RASQSISWYLN | 24 |
| CDRL1 - BA094 | RASQSITSYLN | 25 |
| CDRL1 - BA101, BA102, BA103, BA104, BA105, BA106, BA107 | GGNNIGSKIVH | 26 |
| CDRL2 - BA072, BA083, BA084, BA089, BA090, BA091, BA092, BA093, BA094, BA095, BA096, BA097, BA098, BA099, BA100 | AASSLQS | 28 |

TABLE 1-continued

Amino acid sequences of exemplary anti-CD96 antibodies.

| Description | Amino Acid Sequence | SEQ ID NO: |
|---|---|---|
| CDRL2 - BA074, BA073, BA081, BA080, BA075, BA079, BA078, BA085, BA086, BA087, BA088 | SASSLQS | 29 |
| CDRL2 - BA077, BA076 | SESSLQS | 30 |
| CDRL2 - BA082 | SSSSLQS | 31 |
| CDRL2 - BA101, BA102, BA103, BA104, BA105, BA106, BA107 | DDRDRPS | 32 |
| CDRL3 - BA072, BA083, BA074, BA073, BA081, BA080, BA075, BA77, BA076, BA079, BA78, BA082, BA084, BA085, BA086, BA087, BA088, BA089, BA090, BA091, BA092, BA093, BA095, BA096, BA097, BA098, BA099, BA100 | QQSYSTPALT | 33 |
| CDRL3 - BA094 | QQAYSTPALS | 34 |
| CDRL3 - BA101, BA102, BA103, BA104, BA105, BA106, BA107 | QVWDINVHHVI | 35 |
| VH - BA072 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGMDVWGQGTMVTVSS, wherein X is glutamine (Q) or pyroglutamate (pE) | 36 |
| VH - BA083, BA085, BA086, BA087, BA088, BA094 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGMSYGMDVWGQGTTVTVSS, wherein X is glutamine (Q) or pyroglutamate (pE) | 37 |
| VH - BA074 | XVQLVQSGAEVKKPGASVKVSCKASGYTFTQYA MHWVRQAPGQRLEWMGWINAVSGDTKYSQKFQ GRVTITRDTSTSTAYMELRSLRSDDTAMYYCARN WGMSYGMDVWGQGTMVTVSS, wherein X is glutamine (Q) or pyroglutamate (pE) | 38 |
| VH - BA073 | XVQLVQSGAEVKKPGASVKVSCKASGYTFTQYA MHWVRQAPGQRLEWMGWINAVSGDTKYSQKFQ GRVTITRDTSASTAYMELSSLRSEDTAVYYCARN WGMSYGMDVWGQGTTVTVSS, wherein X is glutamine (Q) or pyroglutamate (pE) | 39 |
| VH - BA081 | XVQLVQSGAEVKKPGASVKVSCKASGYTFTSYA MHWVRQAPGQRLEWMGWINAGTGDTKYSQKFQ GRVTITRDTSTSTAYMELRSLRSDDTAMYYCARN WGMSYGMDVWGQGTMVTVSS, wherein X is glutamine (Q) or pyroglutamate (pE) | 40 |
| VH - BA080 | XVQLVQSGAEVKKPGASVKVSCKASGYTFTSYA MHWVRQAPGQRLEWMGWINAGTGDTKYSQKFQ GRVTITRDTSASTAYMELSSLRSEDTAVYYCARN WGMSYGMDVWGQGTTVTVSS, wherein X is glutamine (Q) or pyroglutamate (pE) | 41 |
| VH - BA075 | XVQLVQSGAEVKKPGASVKVSCKASGYTFNQYA MHWVRQAPGQRLEWMGWINEGYGNTKYSQKFQ GRVTITRDTSTSTAYMELRSLRSDDTAMYYCARN WGMSYGMDVWGQGTMVTVSS, wherein X is glutamine (Q) or pyroglutamate (pE) | 42 |

TABLE 1-continued

Amino acid sequences of exemplary anti-CD96 antibodies.

| Description | Amino Acid Sequence | SEQ ID NO: |
|---|---|---|
| VH - BA077 | XVQLVQSGAEVKKPGASVKVSCKASGYTFTQYA MHWVRQAPGQRLEWMGWINAGYGYTKYSQKFQ GRVTITRDTSTSTAYMELRSLRSDDTAMYYCARN WGMSYGMDVWGQGTMVTVSS, wherein X is glutamine (Q) or pyroglutamate (pE) | 43 |
| VH - BA076 | XVQLVQSGAEVKKPGASVKVSCKASGYTFTQYA MHWVRQAPGQRLEWMGWINAGYGYTKYSQKFQ GRVTITRDTSASTAYMELSSLRSEDTAVYYCARN WGMSYGMDVWGQGTTVTVSS, wherein X is glutamine (Q) or pyroglutamate (pE) | 44 |
| VH - BA079 | XVQLVQSGAEVKKPGASVKVSCKASGYTFSQYA MHWVRQAPGQRLEWMGWINAGTGNTKYSQKFQ GRVTITRDTSTSTAYMELRSLRSDDTAMYYCARN WGMSYGMDVWGQGTMVTVSS, wherein X is glutamine (Q) or pyroglutamate (pE) | 45 |
| VH - BA078 | XVQLVQSGAEVKKPGASVKVSCKASGYTFSQYA MHWVRQAPGQRLEWMGWINAGTGNTKYSQKFQ GRVTITRDTSASTAYMELSSLRSEDTAVYYCARN WGMSYGMDVWGQGTTVTVSS, wherein X is glutamine (Q) or pyroglutamate (pE) | 46 |
| VH - BA082 | XVQLVQSGAEVKKPGASVKVSCKASGYTFDQYA MHWVRQAPGQRLEWMGWINAGYGNTKYSQKFQ GRVTITRDTSTSTAYMELRSLRSDDTAMYYCARN WGMSYGMDVWGQGTMVTVSS, wherein X is glutamine (Q) or pyroglutamate (pE) | 47 |
| VH - BA084 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAVYYCARN WGMSYGMDVWGQGTTVTVSS, wherein X is glutamine (Q) or pyroglutamate (pE) | 48 |
| VH - BA089 | XVQLVQSGAEVKKPGASVKVSCKASGYTFTSYA MHWVRQAPGQRLEWMGWINAWNGNTKYSQKF QGRVTITRDTSASTAYMELSSLRSEDTAVYYCAR NWGMSYGMDVWGQGTTVTVSS, wherein X is glutamine (Q) or pyroglutamate (pE) | 49 |
| VH - BA090 | XVQLVQSGAEVKKPGASVKVSCKASGYTFTSYA MHWVRQAPGQRLEWMGWINVGTGTTKYSQKFQ GRVTITRDTSASTAYMELSSLRSEDTAVYYCARN WGMSYGMDVWGQGTTVTVSS, wherein X is glutamine (Q) or pyroglutamate (pE) | 50 |
| VH - BA091 | XVQLVQSGAEVKKPGASVKVSCKASGYTFSSYA MHWVRQAPGQRLEWMGWINAVNGNTKYSQKFQ GRVTITRDTSASTAYMELSSLRSEDTAVYYCARN WGMSYGMDVWGQGTTVTVSS, wherein X is glutamine (Q) or pyroglutamate (pE) | 51 |
| VH - BA092 | XVQLVQSGAEVKKPGASVKVSCKASGYTFASYS MHWVRQAPGQRLEWMGWINAGNWNTKYSQKF QGRVTITRDTSASTAYMELSSLRSEDTAVYYCAR NWGMSYGMDVWGQGTTVTVSS, wherein X is glutamine (Q) or pyroglutamate (pE) | 52 |
| VH - BA093 | XVQLVQSGAEVKKPGASVKVSCKASGYTFTSYA MHWVRQAPGQRLEWMGWINAWTGNTKYSQKF QGRVTITRDTSASTAYMELSSLRSEDTAVYYCAR NWGMSYGMDVWGQGTTVTVSS, wherein X is glutamine (Q) or pyroglutamate (pE) | 53 |
| VH - BA095 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGLDVWGQGTMVTVSS, wherein X is glutamine (Q) or pyroglutamate (pE) | 54 |
| VH - BA096 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN | 55 |

TABLE 1-continued

Amino acid sequences of exemplary anti-CD96 antibodies.

| Description | Amino Acid Sequence | SEQ ID NO: |
|---|---|---|
| | WGLSYGMDVWGQGTMVTVSS, wherein X is glutamine (Q) or pyroglutamate (pE) | |
| VH - BA097 | XVQLVQSGAEVKKPGASVKVSCKASGYTFTSYAMHWVRQAPGQRLEWMGWINAGNGNTKYSQKFQGRVTITRDTSTSTAYMELRSLRSDDTAMYYCARNWGLSYGLDVWGQGTMVTVSS, wherein X is glutamine (Q) or pyroglutamate (pE) | 56 |
| VH - BA098 | XVQLVQSGAEVKKPGASVKVSCKASGYTFTSYAMHWVRQAPGQRLEWMGWINAGNGNTKYSQKFQGRVTITRDTSASTAYMELSSLRSEDTAVYYCARNWGMSYGLDVWGQGTTVTVSS, wherein X is glutamine (Q) or pyroglutamate (pE) | 57 |
| VH - BA099 | XVQLVQSGAEVKKPGASVKVSCKASGYTFTSYAMHWVRQAPGQRLEWMGWINAGNGNTKYSQKFQGRVTITRDTSASTAYMELSSLRSEDTAVYYCARNWGLSYGMDVWGQGTTVTVSS, wherein X is glutamine (Q) or pyroglutamate (pE) | 58 |
| VH - BA100 | XVQLVQSGAEVKKPGASVKVSCKASGYTFTSYAMHWVRQAPGQRLEWMGWINAGNGNTKYSQKFQGRVTITRDTSASTAYMELSSLRSEDTAVYYCARNWGLSYGLDVWGQGTTVTVSS, wherein X is glutamine (Q) or pyroglutamate (pE) | 59 |
| VH - BA101, BA102, BA103, BA104, BA105, BA106 | XVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARGYDSRPLDVWGQGTLVTVSS, wherein X is glutamine (Q) or pyroglutamate (pE) | 60 |
| VH - BA107 | XVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARGYDSRPLDYWGQGTLVTVSS, wherein X is glutamine (Q) or pyroglutamate (pE) | 61 |
| VL - BA072, BA083, BA084, BA089, BA090, BA091, BA092, BA093 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPALTFGGGTKVDIK | 62 |
| VL - BA074, BA073, BA081, BA080, BA075, BA079, BA078, BA088 | DIQMTQSPSSLSASVGDRVTITCRASQSISSYLNWYQQKPGKAPKLLIYSASSLQSGVPSRFSGSGSGTDFTLTISSLQPEDFATYYCQQSYSTPALTFGGGTKVDIK | 63 |
| VL - BA077, BA076 | DIQMTQSPSSLSASVGDRVTITCRASQSISSYLNWYQQKPGKAPKLLIYSESSLQSGVPSRFSGSGSGTDFTLTISSLQPEDFATYYCQQSYSTPALTFGGGTKVDIK | 64 |
| VL - BA082 | DIQMTQSPSSLSASVGDRVTITCRASQSISSYLNWYQQKPGKAPKLLIYSSSSLQSGVPSRFSGSGSGTDFTLTISSLQPEDFATYYCQQSYSTPALTFGGGTKVDIK | 65 |
| VL - BA085 | DIQMTQSPSSLSASVGDRVTITCRASQSISPYLNWYQQKPGKAPKLLIYSASSLQSGVPSRFSGSGSGTDFTLTISSLQPEDFATYYCQQSYSTPALTFGGGTKVDIK | 66 |
| VL - BA086 | DIQMTQSPSSLSASVGDRVTITCRASQSISWYLNWYQQKPGKAPKLLIYSASSLQSGVPSRFSGSGSGTDFTLTISSLQPEDFATYYCQQSYSTPALTFGGGTKVDIK | 67 |
| VL - BA087 | DIQMTQSPSSLSASVGDRVTITCRASQSILSYLNWYQQKPGKAPKLLIYSASSLQSGVPSRFSGSGSGTDFTLTISSLQPEDFATYYCQQSYSTPALTFGGGTKVDIK | 68 |
| VL - BA094 | DIQMTQSPSSLSASVGDRVTITCRASQSITSYLNWYQQKPGKAPKLLIYAASSLQSGVPSRFSGSGSGTDFTLTISSLQPEDFATYYCQQAYSTPALSFGGGTKVDIK | 69 |

TABLE 1-continued

Amino acid sequences of exemplary anti-CD96 antibodies.

| Description | Amino Acid Sequence | SEQ ID NO: |
|---|---|---|
| VL - BA101, BA107 | SYELTQPLSVSVALGQTASITCGGNNIGSKIVHWYQQKSGQAPVLVVSDDRDRPSGIPERFSGSNSGNTATLTINTVEAGDEADYYCQVWDINVHHVIFGGGTKVTVL | 70 |
| VL - BA102 | SYELTQPLSVSVALGQTASITCGGNNIGSKIVHWYQQKPGQAPVLVVSDDRDRPSGIPERFSGSNSGNTATLTISRVEAGDEADYYCQVWDINVHHVIFGGGTKLTVL | 71 |
| VL - BA103 | SYELTQPLSVSVALGQTASITCGGNNIGSKIVHWYQQKSGQAPVLVIYDDRDRPSGIPERFSGSNSGNTATLTINTVEAGDEADYYCQVWDINVHHVIFGGGTKLTVL | 72 |
| VL - BA104 | SYELTQPLSVSVALGQTASITCGGNNIGSKIVHWYQQKPGQAPVLVVSDDRDRPSGIPERFSGSNSGNTATLTINTVEAGDEADYYCQVWDINVHHVIFGGGTKLTVL | 73 |
| VL - BA105 | SYELTQPLSVSVALGQTASITCGGNNIGSKIVHWYQQKSGQAPVLVVSDDRDRPSGIPERFSGSNSGNTATLTISRVEAGDEADYYCQVWDINVHHVIFGGGTKLTVL | 74 |
| VL - BA106 | SYELTQPLSVSVALGQTASITCGGNNIGSKIVHWYQQKSGQAPVLVVSDDRDRPSGIPERFSGSNSGNTATLTISRAQAGDEADYYCQVWDINVHHVIFGGGTKLTVL | 75 |
| full-length heavy chain (with C-terminal lysine) - BA072 | XVQLVQSGAEVKKPGASVKVSCKASGYTFTSYAMHWVRQAPGQRLEWMGWINAGNGNTKYSQKFQGRVTITRDTSTSTAYMELRSLRSDDTAMYYCARNWGMSYGMDVWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK, wherein X is glutamine (Q) or pyroglutamate (pE) | 76 |
| full-length heavy chain (without C-terminal lysine) - BA072 | XVQLVQSGAEVKKPGASVKVSCKASGYTFTSYAMHWVRQAPGQRLEWMGWINAGNGNTKYSQKFQGRVTITRDTSTSTAYMELRSLRSDDTAMYYCARNWGMSYGMDVWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG, wherein X is glutamine (Q) or pyroglutamate (pE) | 144 |
| full-length heavy chain (with C-terminal lysine) - BA083, BA085, BA086, BA087, BA088, BA094 | XVQLVQSGAEVKKPGASVKVSCKASGYTFTSYAMHWVRQAPGQRLEWMGWINAGNGNTKYSQKFQGRVTITRDTSASTAYMELSSLRSEDTAVYYCARNWGMSYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQ | 77 |

TABLE 1-continued

Amino acid sequences of exemplary anti-CD96 antibodies.

| Description | Amino Acid Sequence | SEQ ID NO: |
|---|---|---|
| | KSLSLSPGK, wherein X is glutamine (Q) or pyroglutamate (pE) | |
| full-length heavy chain (without C-terminal lysine) - BA083, BA085, BA086, BA087, BA088, BA094 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 145 |
| full-length heavy chain (with C-terminal lysine) - BA074 | XVQLVQSGAEVKKPGASVKVSCKASGYTFTQYA MHWVRQAPGQRLEWMGWINAVSGDTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 78 |
| full-length heavy chain (without C-terminal lysine) - BA074 | XVQLVQSGAEVKKPGASVKVSCKASGYTFTQYA MHWVRQAPGQRLEWMGWINAVSGDTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 146 |
| full-length heavy chain (with C-terminal lysine) - BA073 | XVQLVQSGAEVKKPGASVKVSCKASGYTFTQYA MHWVRQAPGQRLEWMGWINAVSGDTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 79 |
| full-length heavy chain (without C-terminal lysine) - BA073 | XVQLVQSGAEVKKPGASVKVSCKASGYTFTQYA MHWVRQAPGQRLEWMGWINAVSGDTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE | 147 |

TABLE 1-continued

Amino acid sequences of exemplary anti-CD96 antibodies.

| Description | Amino Acid Sequence | SEQ ID NO: |
|---|---|---|
| | DPEVKFNWYVDGVEVHNAKTKPREEQYNSTYRV<br>VSVLTVLHQDWLNGKEYKCKVSNKALPAPIEKTI<br>SKAKGQPREPQVYTLPPSREEMTKNQVSLTCLVK<br>GFYPSDIAVEWESNGQPENNYKTTPPVLDSDGSFF<br>LYSKLTVDKSRWQQGNVFSCSVMHEALHNHYTQ<br>KSLSLSPG, wherein X is glutamine (Q) or<br>pyroglutamate (pE) | |
| full-length heavy chain (with C-terminal lysine) - BA081 | XVQLVQSGAEVKKPGASVKVSCKASGYTFTSYA<br>MHWVRQAPGQRLEWMGWINAGTGDTKYSQKFQ<br>GRVTITRDTSTSTAYMELRSLRSDDTAMYYCARN<br>WGMSYGMDVWGQGTMVTVSSASTKGPSVFPLAP<br>SSKSTSGGTAALGCLVKDYFPEPVTVSWNSGALT<br>SGVHTFPAVLQSSGLYSLSSVVTVPSSSLGTQTYIC<br>NVNHKPSNTKVDKRVEPKSCDKTHTCPPCPAPEL<br>LGGPSVFLFPPKPKDTLMISRTPEVTCVVVDVSHE<br>DPEVKFNWYVDGVEVHNAKTKPREEQYNSTYRV<br>VSVLTVLHQDWLNGKEYKCKVSNKALPAPIEKTI<br>SKAKGQPREPQVYTLPPSREEMTKNQVSLTCLVK<br>GFYPSDIAVEWESNGQPENNYKTTPPVLDSDGSFF<br>LYSKLTVDKSRWQQGNVFSCSVMHEALHNHYTQ<br>KSLSLSPGK, wherein X is glutamine (Q) or<br>pyroglutamate (pE) | 80 |
| full-length heavy chain (without C-terminal lysine) - BA081 | XVQLVQSGAEVKKPGASVKVSCKASGYTFTSYA<br>MHWVRQAPGQRLEWMGWINAGTGDTKYSQKFQ<br>GRVTITRDTSTSTAYMELRSLRSDDTAMYYCARN<br>WGMSYGMDVWGQGTMVTVSSASTKGPSVFPLAP<br>SSKSTSGGTAALGCLVKDYFPEPVTVSWNSGALT<br>SGVHTFPAVLQSSGLYSLSSVVTVPSSSLGTQTYIC<br>NVNHKPSNTKVDKRVEPKSCDKTHTCPPCPAPEL<br>LGGPSVFLFPPKPKDTLMISRTPEVTCVVVDVSHE<br>DPEVKFNWYVDGVEVHNAKTKPREEQYNSTYRV<br>VSVLTVLHQDWLNGKEYKCKVSNKALPAPIEKTI<br>SKAKGQPREPQVYTLPPSREEMTKNQVSLTCLVK<br>GFYPSDIAVEWESNGQPENNYKTTPPVLDSDGSFF<br>LYSKLTVDKSRWQQGNVFSCSVMHEALHNHYTQ<br>KSLSLSPG, wherein X is glutamine (Q) or<br>pyroglutamate (pE) | 148 |
| full-length heavy chain (with C-terminal lysine) - BA080 | XVQLVQSGAEVKKPGASVKVSCKASGYTFTSYA<br>MHWVRQAPGQRLEWMGWINAGTGDTKYSQKFQ<br>GRVTITRDTSASTAYMELSSLRSEDTAVYYCARN<br>WGMSYGMDVWGQGTTVTVSSASTKGPSVFPLAP<br>SSKSTSGGTAALGCLVKDYFPEPVTVSWNSGALT<br>SGVHTFPAVLQSSGLYSLSSVVTVPSSSLGTQTYIC<br>NVNHKPSNTKVDKRVEPKSCDKTHTCPPCPAPEL<br>LGGPSVFLFPPKPKDTLMISRTPEVTCVVVDVSHE<br>DPEVKFNWYVDGVEVHNAKTKPREEQYNSTYRV<br>VSVLTVLHQDWLNGKEYKCKVSNKALPAPIEKTI<br>SKAKGQPREPQVYTLPPSREEMTKNQVSLTCLVK<br>GFYPSDIAVEWESNGQPENNYKTTPPVLDSDGSFF<br>LYSKLTVDKSRWQQGNVFSCSVMHEALHNHYTQ<br>KSLSLSPGK, wherein X is glutamine (Q) or<br>pyroglutamate (pE) | 81 |
| full-length heavy chain (without C-terminal lysine) - BA080 | XVQLVQSGAEVKKPGASVKVSCKASGYTFTSYA<br>MHWVRQAPGQRLEWMGWINAGTGDTKYSQKFQ<br>GRVTITRDTSASTAYMELSSLRSEDTAVYYCARN<br>WGMSYGMDVWGQGTTVTVSSASTKGPSVFPLAP<br>SSKSTSGGTAALGCLVKDYFPEPVTVSWNSGALT<br>SGVHTFPAVLQSSGLYSLSSVVTVPSSSLGTQTYIC<br>NVNHKPSNTKVDKRVEPKSCDKTHTCPPCPAPEL<br>LGGPSVFLFPPKPKDTLMISRTPEVTCVVVDVSHE<br>DPEVKFNWYVDGVEVHNAKTKPREEQYNSTYRV<br>VSVLTVLHQDWLNGKEYKCKVSNKALPAPIEKTI<br>SKAKGQPREPQVYTLPPSREEMTKNQVSLTCLVK<br>GFYPSDIAVEWESNGQPENNYKTTPPVLDSDGSFF<br>LYSKLTVDKSRWQQGNVFSCSVMHEALHNHYTQ<br>KSLSLSPG, wherein X is glutamine (Q) or<br>pyroglutamate (pE) | 149 |
| full-length heavy chain (with C-terminal lysine) - BA075 | XVQLVQSGAEVKKPGASVKVSCKASGYTFNQYA<br>MHWVRQAPGQRLEWMGWINEGYGNTKYSQKFQ<br>GRVTITRDTSTSTAYMELRSLRSDDTAMYYCARN | 82 |

TABLE 1-continued

Amino acid sequences of exemplary anti-CD96 antibodies.

| Description | Amino Acid Sequence | SEQ ID NO: |
|---|---|---|
| | WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | |
| full-length heavy chain (without C-terminal lysine) - BA075 | XVQLVQSGAEVKKPGASVKVSCKASGYTFNQYA MHWVRQAPGQRLEWMGWINEGYGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 150 |
| full-length heavy chain (with C-terminal lysine) - BA077 | XVQLVQSGAEVKKPGASVKVSCKASGYTFTQYA MHWVRQAPGQRLEWMGWINAGYGYTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 83 |
| full-length heavy chain (without C-terminal lysine) - BA077 | XVQLVQSGAEVKKPGASVKVSCKASGYTFTQYA MHWVRQAPGQRLEWMGWINAGYGYTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 151 |
| full-length heavy chain (with C-terminal lysine) - BA076 | XVQLVQSGAEVKKPGASVKVSCKASGYTFTQYA MHWVRQAPGQRLEWMGWINAGYGYTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ | 84 |

TABLE 1-continued

Amino acid sequences of exemplary anti-CD96 antibodies.

| Description | Amino Acid Sequence | SEQ ID NO: |
|---|---|---|
| | KSLSLSPGK, wherein X is glutamine (Q) or pyroglutamate (pE) | |
| full-length heavy chain (without C-terminal lysine) - BA076 | XVQLVQSGAEVKKPGASVKVSCKASGYTFTQYA MHWVRQAPGQRLEWMGWINAGYGYTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 152 |
| full-length heavy chain (with C-terminal lysine) - BA079 | XVQLVQSGAEVKKPGASVKVSCKASGYTFSQYA MHWVRQAPGQRLEWMGWINAGTGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 85 |
| full-length heavy chain (without C-terminal lysine) - BA079 | XVQLVQSGAEVKKPGASVKVSCKASGYTFSQYA MHWVRQAPGQRLEWMGWINAGTGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 153 |
| full-length heavy chain (with C-terminal lysine) - BA078 | XVQLVQSGAEVKKPGASVKVSCKASGYTFSQYA MHWVRQAPGQRLEWMGWINAGTGNTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 86 |
| full-length heavy chain (without C-terminal lysine) - BA078 | XVQLVQSGAEVKKPGASVKVSCKASGYTFSQYA MHWVRQAPGQRLEWMGWINAGTGNTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE | 154 |

TABLE 1-continued

Amino acid sequences of exemplary anti-CD96 antibodies.

| Description | Amino Acid Sequence | SEQ ID NO: |
|---|---|---|
| | DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | |
| full-length heavy chain (with C-terminal lysine) - BA082 | XVQLVQSGAEVKKPGASVKVSCKASGYTFDQYA MHWVRQAPGQRLEWMGWINAGYGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 87 |
| full-length heavy chain (without C-terminal lysine) - BA082 | XVQLVQSGAEVKKPGASVKVSCKASGYTFDQYA MHWVRQAPGQRLEWMGWINAGYGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 155 |
| full-length heavy chain (with C-terminal lysine) - BA084 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 88 |
| full-length heavy chain (without C-terminal lysine) - BA084 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 156 |
| full-length heavy chain (with C-terminal lysine) - BA089 | XVQLVQSGAEVKKPGASVKVSCKASGYTFTSYA MHWVRQAPGQRLEWMGWINAWNGNTKYSQKF QRVTITRDTSASTAYMELSSLRSEDTAVYYCAR | 89 |

TABLE 1-continued

Amino acid sequences of exemplary anti-CD96 antibodies.

| Description | Amino Acid Sequence | SEQ ID NO: |
|---|---|---|
| | NWGMSYGMDVWGQGTTVTVSSASTKGPSVFPLA PSSKSTSGGTAALGCLVKDYFPEPVTVSWNSGAL TSGVHTFPAVLQSSGLYSLSSVVTVPSSSLGTQTYI CNVNHKPSNTKVDKRVEPKSCDKTHTCPPCPAPE LLGGPSVFLFPPKPKDTLMISRTPEVTCVVVDVSH EDPEVKFNWYVDGVEVHNAKTKPREEQYNSTYR VVSVLTVLHQDWLNGKEYKCKVSNKALPAPIEKT ISKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | |
| full-length heavy chain (without C-terminal lysine) - BA089 | XVQLVQSGAEVKKPGASVKVSCKASGYTFTSYA MHWVRQAPGQRLEWMGWINAWNGNTKYSQKF QGRVTITRDTSASTAYMELSSLRSEDTAVYYCAR NWGMSYGMDVWGQGTTVTVSSASTKGPSVFPLA PSSKSTSGGTAALGCLVKDYFPEPVTVSWNSGAL TSGVHTFPAVLQSSGLYSLSSVVTVPSSSLGTQTYI CNVNHKPSNTKVDKRVEPKSCDKTHTCPPCPAPE LLGGPSVFLFPPKPKDTLMISRTPEVTCVVVDVSH EDPEVKFNWYVDGVEVHNAKTKPREEQYNSTYR VVSVLTVLHQDWLNGKEYKCKVSNKALPAPIEKT ISKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 157 |
| full-length heavy chain (with C-terminal lysine) - BA090 | XVQLVQSGAEVKKPGASVKVSCKASGYTFTSYA MHWVRQAPGQRLEWMGWINVGTGTTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 90 |
| full-length heavy chain (without C-terminal lysine) - BA090 | XVQLVQSGAEVKKPGASVKVSCKASGYTFTSYA MHWVRQAPGQRLEWMGWINVGTGTTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 158 |
| full-length heavy chain (with C-terminal lysine) - BA091 | XVQLVQSGAEVKKPGASVKVSCKASGYTFSSYA MHWVRQAPGQRLEWMGWINAVNGNTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ | 91 |

TABLE 1-continued

Amino acid sequences of exemplary anti-CD96 antibodies.

| Description | Amino Acid Sequence | SEQ ID NO: |
|---|---|---|
| | KSLSLSPGK, wherein X is glutamine (Q) or pyroglutamate (pE) | |
| full-length heavy chain (without C-terminal lysine) - BA091 | XVQLVQSGAEVKKPGASVKVSCKASGYTFSSYA MHWVRQAPGQRLEWMGWINAVNGNTKYSQKFQ GRVTITRDTSASTAYMELSSLRSEDTAVYYCARN WGMSYGMDVWGQGTTVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 159 |
| full-length heavy chain (with C-terminal lysine) - BA092 | XVQLVQSGAEVKKPGASVKVSCKASGYTFASYS MHWVRQAPGQRLEWMGWINAGNWNTKYSQKF QGRVTITRDTSASTAYMELSSLRSEDTAVYYCAR NWGMSYGMDVWGQGTTVTVSSASTKGPSVFPLA PSSKSTSGGTAALGCLVKDYFPEPVTVSWNSGAL TSGVHTFPAVLQSSGLYSLSSVVTVPSSSLGTQTYI CNVNHKPSNTKVDKRVEPKSCDKTHTCPPCPAPE LLGGPSVFLFPPKPKDTLMISRTPEVTCVVVDVSH EDPEVKFNWYVDGVEVHNAKTKPREEQYNSTYR VVSVLTVLHQDWLNGKEYKCKVSNKALPAPIEKT ISKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 92 |
| full-length heavy chain (without C-terminal lysine) - BA092 | XVQLVQSGAEVKKPGASVKVSCKASGYTFASYS MHWVRQAPGQRLEWMGWINAGNWNTKYSQKF QGRVTITRDTSASTAYMELSSLRSEDTAVYYCAR NWGMSYGMDVWGQGTTVTVSSASTKGPSVFPLA PSSKSTSGGTAALGCLVKDYFPEPVTVSWNSGAL TSGVHTFPAVLQSSGLYSLSSVVTVPSSSLGTQTYI CNVNHKPSNTKVDKRVEPKSCDKTHTCPPCPAPE LLGGPSVFLFPPKPKDTLMISRTPEVTCVVVDVSH EDPEVKFNWYVDGVEVHNAKTKPREEQYNSTYR VVSVLTVLHQDWLNGKEYKCKVSNKALPAPIEKT ISKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 160 |
| full-length heavy chain (with C-terminal lysine) - BA093 | XVQLVQSGAEVKKPGASVKVSCKASGYTFTSYA MHWVRQAPGQRLEWMGWINAWTGNTKYSQKF QGRVTITRDTSASTAYMELSSLRSEDTAVYYCAR NWGMSYGMDVWGQGTTVTVSSASTKGPSVFPLA PSSKSTSGGTAALGCLVKDYFPEPVTVSWNSGAL TSGVHTFPAVLQSSGLYSLSSVVTVPSSSLGTQTYI CNVNHKPSNTKVDKRVEPKSCDKTHTCPPCPAPE LLGGPSVFLFPPKPKDTLMISRTPEVTCVVVDVSH EDPEVKFNWYVDGVEVHNAKTKPREEQYNSTYR VVSVLTVLHQDWLNGKEYKCKVSNKALPAPIEKT ISKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 93 |
| full-length heavy chain (without C-terminal lysine) - BA093 | XVQLVQSGAEVKKPGASVKVSCKASGYTFTSYA MHWVRQAPGQRLEWMGWINAWTGNTKYSQKF QGRVTITRDTSASTAYMELSSLRSEDTAVYYCAR NWGMSYGMDVWGQGTTVTVSSASTKGPSVFPLA PSSKSTSGGTAALGCLVKDYFPEPVTVSWNSGAL TSGVHTFPAVLQSSGLYSLSSVVTVPSSSLGTQTYI CNVNHKPSNTKVDKRVEPKSCDKTHTCPPCPAPE LLGGPSVFLFPPKPKDTLMISRTPEVTCVVVDVSH | 161 |

TABLE 1-continued

Amino acid sequences of exemplary anti-CD96 antibodies.

| Description | Amino Acid Sequence | SEQ ID NO: |
|---|---|---|
| | EDPEVKFNWYVDGVEVHNAKTKPREEQYNSTYR VVSVLTVLHQDWLNGKEYKCKVSNKALPAPIEKT ISKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | |
| full-length heavy chain (with C-terminal lysine) - BA095 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGLDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 94 |
| full-length heavy chain (without C-terminal lysine) - BA095 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGLDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 162 |
| full-length heavy chain (with C-terminal lysine) - BA096 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGLSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 95 |
| full-length heavy chain (without C-terminal lysine) - BA096 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGLSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 163 |
| full-length heavy chain (with C-terminal lysine) - BA097 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN | 96 |

TABLE 1-continued

Amino acid sequences of exemplary anti-CD96 antibodies.

| Description | Amino Acid Sequence | SEQ ID NO: |
|---|---|---|
| | WGLSYGLDVWGQGTMVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPGK, wherein X is glutamine (Q) or pyroglutamate (pE) | |
| full-length heavy chain (without C-terminal lysine) - BA097 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGLSYGLDVWGQGTMVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG, wherein X is glutamine (Q) or pyroglutamate (pE) | 164 |
| full-length heavy chain (with C-terminal lysine) - BA098 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGMSYGLDVWGQGTTVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPGK, wherein X is glutamine (Q) or pyroglutamate (pE) | 97 |
| full-length heavy chain (without C-terminal lysine) - BA098 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGMSYGLDVWGQGTTVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG, wherein X is glutamine (Q) or pyroglutamate (pE) | 165 |
| full-length heavy chain (with C-terminal lysine) - BA099 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGLSYGMDVWGQGTTVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK | 98 |

TABLE 1-continued

Amino acid sequences of exemplary anti-CD96 antibodies.

| Description | Amino Acid Sequence | SEQ ID NO: |
|---|---|---|
| | SLSLSPGK, wherein X is glutamine (Q) or pyroglutamate (pE) | |
| full-length heavy chain (without C-terminal lysine) - BA099 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGLSYGMDVWGQGTTVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG, wherein X is glutamine (Q) or pyroglutamate (pE) | 166 |
| full-length heavy chain (with C-terminal lysine) - BA100 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGLSYGLDVWGQGTTVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPGK, wherein X is glutamine (Q) or pyroglutamate (pE) | 99 |
| full-length heavy chain (without C-terminal lysine) - BA100 | XVQLVQSGAEVKKPGASVKVSCKASGYTFTSYA MHWVRQAPGQRLEWMGWINAGNGNTKYSQKFQ GRVTITRDTSASTAYMELSSLRSEDTAVYYCARN WGLSYGLDVWGQGTTVTVSSASTKGPSVFPLAPS SKSTSGGTAALGCLVKDYFPEPVTVSWNSGALTS GVHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG, wherein X is glutamine (Q) or pyroglutamate (pE) | 167 |
| full-length heavy chain (with C-terminal lysine) - BA101, BA102, BA103, BA104, BA105, BA106 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYDSRP LDVWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPSVFL FPPKPKDTLMISRTPEVTCVVVDVSHEDPEVKFN WYVDGVEVHNAKTKPREEQYNSTYRVVSVLTVL HQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP GK, wherein X is glutamine (Q) or pyroglutamate (pE) | 100 |
| full-length heavy chain (without C-terminal lysine) - BA101, BA102, BA103, BA104, BA105, BA106 | XVQ LVQ SGAEVKKPGSSVKVSCKASGGTFSSYAIS WVRQAPGQGLEWMGGIIPIFGTANYAQKFQGRVT ITADKSTSTAYMELSSLRSEDTAVYYCARGYDSRP LDVWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPSVFL FPPKPKDTLMISRTPEVTCVVVDVSHEDPEVKFN WYVDGVEVHNAKTKPREEQYNSTYRVVSVLTVL | 168 |

TABLE 1-continued

Amino acid sequences of exemplary anti-CD96 antibodies.

| Description | Amino Acid Sequence | SEQ ID NO: |
|---|---|---|
| | HQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP G, wherein X is glutamine (Q) or pyroglutamate (pE) | |
| full-length heavy chain (with C-terminal lysine) - BA107 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYDSRP LDYWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPSVFL FPPKPKDTLMISRTPEVTCVVVDVSHEDPEVKFN WYVDGVEVHNAKTKPREEQYNSTYRVVSVLTVL HQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP GK, wherein X is glutamine (Q) or pyroglutamate (pE) | 101 |
| full-length heavy chain (without C-terminal lysine) - BA107 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYDSRP LDYWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPSVFL FPPKPKDTLMISRTPEVTCVVVDVSHEDPEVKFN WYVDGVEVHNAKTKPREEQYNSTYRVVSVLTVL HQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP G, wherein X is glutamine (Q) or pyroglutamate (pE) | 169 |
| full-length light chain - BA072, BA083, BA084, BA089, BA090, BA091, BA092, BA093 | DIQMTQSPSSLSASVGDRVTITCRASQSISSYLNWY QQKPGKAPKLLIYAASSLQSGVPSRFSGSGSGTDF TLTISSLQPEDFATYYCQQSYSTPALTFGGGTKVDI KRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKSF NRGEC | 102 |
| full-length light chain - BA074, BA073, BA081, BA080, BA075, BA079, BA078, BA088 | DIQMTQSPSSLSASVGDRVTITCRASQSISSYLNWY QQKPGKAPKLLIYSASSLQSGVPSRFSGSGSGTDFT LTISSLQPEDFATYYCQQSYSTPALTFGGGTKVDIK RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 103 |
| full-length light chain - BA077, BA076 | DIQMTQSPSSLSASVGDRVTITCRASQSISSYLNWY QQKPGKAPKLLIYSESSLQSGVPSRFSGSGSGTDFT LTISSLQPEDFATYYCQQSYSTPALTFGGGTKVDIK RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 104 |
| full-length light chain - BA082 | DIQMTQSPSSLSASVGDRVTITCRASQSISSYLNWY QQKPGKAPKLLIYSSSSLQSGVPSRFSGSGSGTDFT LTISSLQPEDFATYYCQQSYSTPALTFGGGTKVDIK RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 105 |
| full-length light chain - BA085 | DIQMTQSPSSLSASVGDRVTITCRASQSISPYLNWY QQKPGKAPKLLIYSASSLQSGVPSRFSGSGSGTDFT LTISSLQPEDFATYYCQQSYSTPALTFGGGTKVDIK RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 106 |

TABLE 1-continued

Amino acid sequences of exemplary anti-CD96 antibodies.

| Description | Amino Acid Sequence | SEQ ID NO: |
|---|---|---|
| full-length light chain - BA086 | DIQMTQSPSSLSASVGDRVTITCRASQSISWYLNW YQQKPGKAPKLLIYSASSLQSGVPSRFSGSGSGTD FTLTISSLQPEDFATYYCQQSYSTPALTFGGGTKV DIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC | 107 |
| full-length light chain - BA087 | DIQMTQSPSSLSASVGDRVTITCRASQSILSYLNW YQQKPGKAPKLLIYSASSLQSGVPSRFSGSGSGTD FTLTISSLQPEDFATYYCQQSYSTPALTFGGGTKV DIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC | 108 |
| full-length light chain - BA094 | DIQMTQSPSSLSASVGDRVTITCRASQSITSYLNW YQQKPGKAPKLLIYAASSLQSGVPSRFSGSGSGTD FTLTISSLQPEDFATYYCQQAYSTPALSFGGGTKV DIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC | 109 |
| full-length light chain - BA101, BA107 | SYELTQPLSVSVALGQTASITCGGNNIGSKIVHWY QQKSGQAPVLVVSDDRDRPSGIPERFSGSNSGNTA TLTINTVEAGDEADYYCQVWDINVHHVIFGGGTK VTVLGQPKAAPSVTLFPPSSEELQANKATLVCLIS DFYPGAVTVAWKADSSPVKAGVETTTPSKQSNN KYAASSYLSLTPEQWKSHRSYSCQVTHEGSTVEK TVAPTECS | 110 |
| full-length light chain - BA102 | SYELTQPLSVSVALGQTASITCGGNNIGSKIVHWY QQKPGQAPVLVVSDDRDRPSGIPERFSGSNSGNTA TLTISRVEAGDEADYYCQVWDINVHHVIFGGGTK LTVLGQPKAAPSVTLFPPSSEELQANKATLVCLISD FYPGAVTVAWKADSSPVKAGVETTTPSKQSNNK YAASSYLSLTPEQWKSHRSYSCQVTHEGSTVEKT VAPTECS | 111 |
| full-length light chain - BA103 | SYELTQPLSVSVALGQTASITCGGNNIGSKIVHWY QQKSGQAPVLVIYDDRDRPSGIPERFSGSNSGNTA TLTINTVEAGDEADYYCQVWDINVHHVIFGGGTK LTVLGQPKAAPSVTLFPPSSEELQANKATLVCLISD FYPGAVTVAWKADSSPVKAGVETTTPSKQSNNK YAASSYLSLTPEQWKSHRSYSCQVTHEGSTVEKT VAPTECS | 112 |
| full-length light chain - BA104 | SYELTQPLSVSVALGQTASITCGGNNIGSKIVHWY QQKPGQAPVLVVSDDRDRPSGIPERFSGSNSGNTA TLTINTVEAGDEADYYCQVWDINVHHVIFGGGTK LTVLGQPKAAPSVTLFPPSSEELQANKATLVCLISD FYPGAVTVAWKADSSPVKAGVETTTPSKQSNNK YAASSYLSLTPEQWKSHRSYSCQVTHEGSTVEKT VAPTECS | 113 |
| full-length light chain - BA105 | SYELTQPLSVSVALGQTASITCGGNNIGSKIVHWY QQKSGQAPVLVVSDDRDRPSGIPERFSGSNSGNTA TLTISRVEAGDEADYYCQVWDINVHHVIFGGGTK LTVLGQPKAAPSVTLFPPSSEELQANKATLVCLISD FYPGAVTVAWKADSSPVKAGVETTTPSKQSNNK YAASSYLSLTPEQWKSHRSYSCQVTHEGSTVEKT VAPTECS | 114 |
| full-length light chain - BA106 | SYELTQPLSVSVALGQTASITCGGNNIGSKIVHWY QQKSGQAPVLVVSDDRDRPSGIPERFSGSNSGNTA TLTISRAQAGDEADYYCQVWDINVHHVIFGGGTK LTVLGQPKAAPSVTLFPPSSEELQANKATLVCLISD FYPGAVTVAWKADSSPVKAGVETTTPSKQSNNK YAASSYLSLTPEQWKSHRSYSCQVTHEGSTVEKT VAPTECS | 115 |
| IgG1 N297A variant full-length heavy chain (with | XVQLVQSGAEVKKPGASVKVSCKASGYTFTSYA MHWVRQAPGQRLEWMGWINAGNGNTKYSQKFQ | 116 |

TABLE 1-continued

Amino acid sequences of exemplary anti-CD96 antibodies.

| Description | Amino Acid Sequence | SEQ ID NO: |
|---|---|---|
| C-terminal lysine) - BA072 | GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYASTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | |
| IgG1 N297A variant full-length heavy chain (without C-terminal lysine) - BA072 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYASTYRV VSVLTVLHQDWLNGKEYKCKVSNKALPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 170 |
| IgG1 N297A variant full-length heavy chain (with C-terminal lysine) - BA101 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYD SRP LDVWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPSVFL FPPKPKDTLMISRTPEVTCVVVDVSHEDPEVKFN WYVDGVEVHNAKTKPREEQYASTYRVVSVLTVL HQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP GK, wherein X is glutamine (Q) or pyroglutamate (pE) | 117 |
| IgG1 N297A variant full-length heavy chain (without C-terminal lysine) - BA101 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYD SRP LDVWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPSVFL FPPKPKDTLMISRTPEVTCVVVDVSHEDPEVKFN WYVDGVEVHNAKTKPREEQYASTYRVVSVLTVL HQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP G, wherein X is glutamine (Q) or pyroglutamate (pE) | 171 |
| IgG1 S239D/A330L/I332E variant full-length heavy chain (with C-terminal lysine) - BA072 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPDVFLFPPKPKDTLMISRTPEVTCVVVDVSHE DPEVKFNWYVDGVEVHNAKTKPREEQYNSTYRV VSVLTVLHQDWLNGKEYKCKVSNKALPLPEEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 118 |

TABLE 1-continued

Amino acid sequences of exemplary anti-CD96 antibodies.

| Description | Amino Acid Sequence | SEQ ID NO: |
|---|---|---|
| IgG1 S239D/A330L/I332E variant full-length heavy chain (without C-terminal lysine) - BA072 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPDVFLFPPKPKDTLMISRTPEVTCVVVDVSHE DPEVKFNWYVDGVEVHNAKTKPREEQYNSTYRV VSVLTVLHQDWLNGKEYKCKVSNKALPLPEEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPG, wherein X is glutamine (Q) or pyroglutamate (pE) | 172 |
| IgG1 S239D/A330L/I332E variant full-length heavy chain (with C-terminal lysine) - BA101 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYDSRP LDVWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPDVFL FPPKPKDTLMISRTPEVTCVVVDVSHEDPEVKFN WYVDGVEVHNAKTKPREEQYNSTYRVVSVLTVL HQDWLNGKEYKCKVSNKALPLPEEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP GK, wherein X is glutamine (Q) or pyroglutamate (pE) | 119 |
| IgG1 S239D/A330L/I332E variant full-length heavy chain (without C-terminal lysine) - BA101 | XVQLVQSGAEVKKPGSSVKVSCKASGGTFSSYAIS WVRQAPGQGLEWMGGIIPIFGTANYAQKFQGRVT ITADKSTSTAYMELSSLRSEDTAVYYCARGYDSRP LDVWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKPS NTKVDKRVEPKSCDKTHTCPPCPAPELLGGPDVFL FPPKPKDTLMISRTPEVTCVVVDVSHEDPEVKFN WYVDGVEVHNAKTKPREEQYNSTYRVVSVLTVL HQDWLNGKEYKCKVSNKALPLPEEKTISKAKGQP REPQVYTLPPSREEMTKNQVSLTCLVKGFYPSDIA VEWESNGQPENNYKTTPPVLDSDGSFFLYSKLTV DKSRWQQGNVFSCSVMHEALHNHYTQKSLSLSP G, wherein X is glutamine (Q) or pyroglutamate (pE) | 173 |
| IgG1 S267E L328F variant full-length heavy chain (with C-terminal lysine) - BA072 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVEHE DPEVKFNWYVDGVEVHNAKTKPREEQYNSTYRV VSVLTVLHQDWLNGKEYKCKVSNKAFPAPIEKTI SKAKGQPREPQVYTLPPSREEMTKNQVSLTCLVK GFYPSDIAVEWESNGQPENNYKTTPPVLDSDGSFF LYSKLTVDKSRWQQGNVFSCSVMHEALHNHYTQ KSLSLSPGK, wherein X is glutamine (Q) or pyroglutamate (pE) | 120 |
| IgG1 S267E L328F variant full-length heavy chain (without C-terminal lysine) - BA072 | XVQLVQSGAEVKKPGASVKVSCKASGYTFTSYA MHWVRQAPGQRLEWMGWINAGNGNTKYSQKFQ GRVTITRDTSTSTAYMELRSLRSDDTAMYYCARN WGMSYGMDVWGQGTMVTVSSASTKGPSVFPLAP SSKSTSGGTAALGCLVKDYFPEPVTVSWNSGALT SGVHTFPAVLQSSGLYSLSSVVTVPSSSLGTQTYIC NVNHKPSNTKVDKRVEPKSCDKTHTCPPCPAPEL LGGPSVFLFPPKPKDTLMISRTPEVTCVVVDVEHE DPEVKFNWYVDGVEVHNAKTKPREEQYNSTYRV VSVLTVLHQDWLNGKEYKCKVSNKAFPAPIEKTI SKAKGQPREPQVYTLPPSREEMTKNQVSLTCLVK GFYPSDIAVEWESNGQPENNYKTTPPVLDSDGSFF | 174 |

TABLE 1-continued

Amino acid sequences of exemplary anti-CD96 antibodies.

| Description | Amino Acid Sequence | SEQ ID NO: |
|---|---|---|
| | LYSKLTVDKSRWQQGNVFSCSVMHEALHNHYTQ KSLSLSPG, wherein X is glutamine (Q) or pyroglutamate (pE) | |
| heavy chain constant region (with C-terminal lysine) - BA072, BA101 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKRVEPKSCDK THTCPPCPAPELLGGPSVFLFPPKPKDTLMISRTPE VTCVVVDVSHEDPEVKFNWYVDGVEVHNAKTKP REEQYNSTYRVVSVLTVLHQDWLNGKEYKCKVS NKALPAPIEKTISKAKGQPREPQVYTLPPSREEMT KNQVSLTCLVKGFYPSDIAVEWESNGQPENNYKT TPPVLDSDGSFFLYSKLTVDKSRWQQGNVFSCSV MHEALHNHYTQKSLSLSPGK | 121 |
| heavy chain constant region (without C-terminal lysine) - BA072, BA101 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKRVEPKSCDK THTCPPCPAPELLGGPSVFLFPPKPKDTLMISRTPE VTCVVVDVSHEDPEVKFNWYVDGVEVHNAKTKP REEQYNSTYRVVSVLTVLHQDWLNGKEYKCKVS NKALPAPIEKTISKAKGQPREPQVYTLPPSREEMT KNQVSLTCLVKGFYPSDIAVEWESNGQPENNYKT TPPVLDSDGSFFLYSKLTVDKSRWQQGNVFSCSV MHEALHNHYTQKSLSLSPG | 175 |
| light chain constant region - BA072 | RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 122 |
| light chain constant region - BA101 | GQPKAAPSVTLFPPSSEELQANKATLVCLISDFYPG AVTVAWKADSSPVKAGVETTTPSKQSNNKYAAS SYLSLTPEQWKSHRSYSCQVTHEGSTVEKTVAPTE CS | 123 |
| IgG1 N297A variant constant region (with C-terminal lysine) - BA072 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKRVEPKSCDK THTCPPCPAPELLGGPSVFLFPPKPKDTLMISRTPE VTCVVVDVSHEDPEVKFNWYVDGVEVHNAKTKP REEQYASTYRVVSVLTVLHQDWLNGKEYKCKVS NKALPAPIEKTISKAKGQPREPQVYTLPPSREEMT KNQVSLTCLVKGFYPSDIAVEWESNGQPENNYKT TPPVLDSDGSFFLYSKLTVDKSRWQQGNVFSCSV MHEALHNHYTQKSLSLSPGK | 124 |
| IgG1 N297A variant constant region (without C-terminal lysine) - BA072 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKRVEPKSCDK THTCPPCPAPELLGGPSVFLFPPKPKDTLMISRTPE VTCVVVDVSHEDPEVKFNWYVDGVEVHNAKTKP REEQYASTYRVVSVLTVLHQDWLNGKEYKCKVS NKALPAPIEKTISKAKGQPREPQVYTLPPSREEMT KNQVSLTCLVKGFYPSDIAVEWESNGQPENNYKT TPPVLDSDGSFFLYSKLTVDKSRWQQGNVFSCSV MHEALHNHYTQKSLSLSPG | 176 |
| IgG1 5239D/A330L/I332E variant constant region (with C-terminal lysine) - BA072 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKRVEPKSCDK THTCPPCPAPELLGGPDVFLFPPKPKDTLMISRTPE VTCVVVDVSHEDPEVKFNWYVDGVEVHNAKTKP REEQYNSTYRVVSVLTVLHQDWLNGKEYKCKVS NKALPLPEEKTISKAKGQPREPQVYTLPPSREEMT KNQVSLTCLVKGFYPSDIAVEWESNGQPENNYKT TPPVLDSDGSFFLYSKLTVDKSRWQQGNVFSCSV MHEALHNHYTQKSLSLSPGK | 125 |
| IgG1 5239D/A330L/I332E variant constant region (without C-terminal lysine) - BA072 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKRVEPKSCDK THTCPPCPAPELLGGPDVFLFPPKPKDTLMISRTPE VTCVVVDVSHEDPEVKFNWYVDGVEVHNAKTKP REEQYNSTYRVVSVLTVLHQDWLNGKEYKCKVS | 177 |

TABLE 1-continued

Amino acid sequences of exemplary anti-CD96 antibodies.

| Description | Amino Acid Sequence | SEQ ID NO: |
|---|---|---|
| | NKALPLPEEKTISKAKGQPREPQVYTLPPSREEMT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPG | |
| IgG1 S267E L328F variant constant region (with C-terminal lysine) - BA072 | ASTKGPSVFPLAPSSKSTSGGTAALGCLVKDYFPE<br>PVTVSWNSGALTSGVHTFPAVLQSSGLYSLSSVVT<br>VPSSSLGTQTYICNVNHKPSNTKVDKRVEPKSCDK<br>THTCPPCPAPELLGGPSVFLFPPKPKDTLMISRTPE<br>VTCVVVDVEHEDPEVKFNWYVDGVEVHNAKTKP<br>REEQYNSTYRVVSVLTVLHQDWLNGKEYKCKVS<br>NKAFPAPIEKTISKAKGQPREPQVYTLPPSREEMT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPGK | 126 |
| IgG1 S267E L328F variant constant region (without C-terminal lysine) - BA072 | ASTKGPSVFPLAPSSKSTSGGTAALGCLVKDYFPE<br>PVTVSWNSGALTSGVHTFPAVLQSSGLYSLSSVVT<br>VPSSSLGTQTYICNVNHKPSNTKVDKRVEPKSCDK<br>THTCPPCPAPELLGGPSVFLFPPKPKDTLMISRTPE<br>VTCVVVDVEHEDPEVKFNWYVDGVEVHNAKTKP<br>REEQYNSTYRVVSVLTVLHQDWLNGKEYKCKVS<br>NKAFPAPIEKTISKAKGQPREPQVYTLPPSREEMT<br>KNQVSLTCLVKGFYPSDIAVEWESNGQPENNYKT<br>TPPVLDSDGSFFLYSKLTVDKSRWQQGNVFSCSV<br>MHEALHNHYTQKSLSLSPG | 178 |

TABLE 2

Exemplary sequences of CD96.

| Description | Amino Acid Sequence | SEQ ID NO: |
|---|---|---|
| Exemplary Human CD96 extracellular domain isoform 1 sequence [1] | VWEKTVNTEENVYATLGSDVNLTCQTQTVGFFV<br>QMQWSKVTNKIDLIAVYHPQYGFYCAYGRPCESL<br>VTFTETPENGSKWTLHLRNMSCSVSGRYECMLVL<br>YPEGIQTKIYNLLIQTHVTADEWNSNHTIEIEINQT<br>LEIPCFQNSSSKISSEFTYAWSVENSSTDSWVLLSK<br>GIKEDNGTQETLISQNHLISNSTLLKDRVKLGTDY<br>RLHLSPVQIFDDGRKFSCHIRVGPNKILRSSTTVKV<br>FAKPEIPVIVENNSTDVLVERRFTCLLKNVFPKANI<br>TWFIDGSFLHDEKEGIYITNEERKGKDGFLELKSV<br>LTRVHSNKPAQSDNLTIWCMALSPVPGNKVWNIS<br>SEKITFLLGSEISSTDPPLSVTESTLDTQPSPASSVSP<br>ARYPATSSVTLVDVSALRPNTTPQPSNSSMTTRGF<br>NYPWTSSGTDTKKSVSRIPSETYSSSPSGAGSTLH<br>DNVFTSTARAFSEVPTTANGSTKTNHVHITGIVVN<br>KPKDGM | 127 |
| Exemplary Human CD96 extracellular domain isoform 2 sequence [1] | VWEKTVNTEENVYATLGSDVNLTCQTQTVGFFV<br>QMQWSKVTNKIDLIAVYHPQYGFYCAYGRPCESL<br>VTFTETPENGSKWTLHLRNMSCSVSGRYECMLVL<br>YPEGIQTKIYNLLIQTHVTADEWNSNHTIEIEINQT<br>LEIPCFQNSSSKISSEFTYAWSVEDNGTQETLISQN<br>HLISNSTLLKDRVKLGTDYRLHLSPVQIFDDGRKF<br>SCHIRVGPNKILRSSTTVKVFAKPEIPVIVENNSTD<br>VLVERRFTCLLKNVFPKANITWFIDGSFLHDEKEG<br>IYITNEERKGKDGFLELKSVLTRVHSNKPAQSDNL<br>TIWCMALSPVPGNKVWNISSEKITFLLGSEISSTDP<br>PLSVTESTLDTQPSPASSVSPARYPATSSVTLVDVS<br>ALRPNTTPQPSNSSMTTRGFNYPWTSSGTDTKKSV<br>SRIPSETYSSSPSGAGSTLHDNVFTSTARAFSEVPT<br>TANGSTKTNHVHITGIVVNKPKDGM | 128 |
| Exemplary Human CD96 extracellular domain isoform 2 C89S [1] | VWEKTVNTEENVYATLGSDVNLTCQTQTVGFFV<br>QMQWSKVTNKIDLIAVYHPQYGFYCAYGRPCESL<br>VTFTETPENGSKWTLHLRNMSSSVSGRYECMLVL<br>YPEGIQTKIYNLLIQTHVTADEWNSNHTIEIEINQT<br>LEIPCFQNSSSKISSEFTYAWSVEDNGTQETLISQN<br>HLISNSTLLKDRVKLGTDYRLHLSPVQIFDDGRKF<br>SCHIRVGPNKILRSSTTVKVFAKPEIPVIVENNSTD | 129 |

TABLE 2-continued

Exemplary sequences of CD96.

| Description | Amino Acid Sequence | SEQ ID NO: |
|---|---|---|
| | VLVERRFTCLLKNVFPKANITWFIDGSFLHDEKEG IYITNEERKGKDGFLELKSVLTRVHSNKPAQSDNL TIWCMALSPVPGNKVWNISSEKITFLLGSEISSTDP PLSVTESTLDTQPSPASSVSPARYPATSSVTLVDVS ALRPNTTPQPSNSSMTTRGFNYPWTSSGTDTKKSV SRIPSETYSSSPSGAGSTLHDNVFTSTARAFSEVPT TANGSTKTNHVHITGIVVNKPKDGM | |
| Exemplary Human CD96 domain 1 [1] | VWEKTVNTEENVYATLGSDVNLTCQTQTVGFFV QMQWSKVTNKIDLIAVYHPQYGFYCAYGRPCESL VTFTETPENGSKWTLHLRNMSCSVSGRYECMLVL YPEGIQTKIYNLLIQTHV | 130 |
| Exemplary Human CD96 domain 1 C89S [1] | VWEKTVNTEENVYATLGSDVNLTCQTQTVGFFV QMQWSKVTNKIDLIAVYHPQYGFYCAYGRPCESL VTFTETPENGSKWTLHLRNMSSSVSGRYECMLVL YPEGIQTKIYNLLIQTHV | 131 |
| Exemplary Cyno CD96 extracellular domain [2] | VWGKPFNTEENIYATLGSDVNLTCQTQAKGFLVQ MQWSKVTDKADLIALYHPQYGFHCAYGSPCESL VTFTQTPENGSKWTLHLRNMSSSVSGRYECMLTL YPEGMQTKIYNLLIQTHVTPDEWKSNHTIEIEINQT LEIPCFQNSSSEISSEFTYAWLVVKNSSTDSWVLLS KGKRYDNGTQQTLISQDHLISSSTLLKDRVKVGID YRLHLSPVQIFDDGRKFSCHIRVGPDKILRSSTTIK VFAKPEIPMIVENNSTDVLVERTFTCLLKNVFPKA NIIWFIDGSFLHDEKEGIYITNEERKGKDGFLELKS VLTRVHSDKPAQSDNLTIWCMALSPVPGNKVWNI SSEKITFLLGSEMSTTDLPPSVTESTLDTQPSPASSV SPTRYPATSSVTLADVSALRPNTTPQSSSSSVTTQD FNYPWTSSGTDAKKSFSQIPSETYSSSPSGAGSTLH DNVFTSTTRALSEVPTTANGSTKTNHVHITGIVVS KPKDGM | 132 |
| Exemplary Cyno CD96 extracellular domain sequence isoform 2 [2] | VWGKPFNTEENIYATLGSDVNLTCQTQAKGFLVQ MQWSKVTDKADLIALYHPQYGFHCAYGSPCESL VTFTQTPENGSKWTLHLRNMSSSVSGRYECMLTL YPEGMQTKIYNLLIQTHVTPDEWKSNHTIEIEINQT LEIPCFQNSSSETSSEFTYAWLVEDNGTQQTLISQD HLISSSTLLKDRVKVGIDYRLHLSPVQIFDDGRKFS CHIRVGPDKILRSSTTIKVFAKPEIPMIVENNSTDVL VERTFTCLLKNVFPKANIIWFIDGSFLHDEKEGIYI TNEERKGKDGFLELKSVLTRVHSDKPAQSDNLTI WCMALSPVPGNKVWNISSEKITFLLGSEMSTTDLP PSVTESTLDTQPSPASSVSPTRYPATSSVTLADVSA LRPNTTPQSSSSSVTTQDFNYPWTSSGTDAKKSFS QIPSETYSSSPSGAGSTLHDNVFTSTTRALSEVPTT ANGSTKTNHVHITGIVVSKPKDGM | 133 |
| Exemplary Cyno CD96 domain 1 [2] | VWGKPFNTEENIYATLGSDVNLTCQTQAKGFLVQ MQWSKVTDKADLIALYHPQYGFHCAYGSPCESL VTFTQTPENGSKWTLHLRNMSSSVSGRYECMLTL YPEGMQTKIYNLLIQTHV | 134 |

[1] Domains assigned based on UniProt description of domains for hCD96.
[2] For cyCD96 sequence homology between the hCD96 sequence & the cyCD96 sequence was used to define domain 1, domain 2 or domain 3.

In certain embodiments, the instant disclosure provides an isolated antibody that specifically binds to CD96 (e.g., human CD96 or cynomolgus CD96), the antibody comprising a VH comprising one, two, or all three of the CDRs of a VH set forth in Table 1 herein. In certain embodiments, the antibody comprises the CDRH1 of a VH set forth in Table 1. In certain embodiments, the antibody comprises the CDRH2 of a VH set forth in Table 1. In certain embodiments, the antibody comprises the CDRH3 of a VH set forth in Table 1.

In certain embodiments, the instant disclosure provides an isolated antibody that specifically binds to CD96 (e.g., human CD96 or cynomolgus CD96), the antibody comprising a VL comprising one, two, or all three of the CDRs of a VL disclosed in Table 1 herein. In certain embodiments, the antibody comprises the CDRL1 of a VL set forth in Table 1. In certain embodiments, the antibody comprises the CDRL2 of a VL set forth in Table 1. In certain embodiments, the antibody comprises the CDRL3 of a VL set forth in Table 1.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety. In certain embodiments, the light chain CDRs of an antibody are determined according to Kabat and the heavy chain CDRs of an antibody are determined according to MacCallum (supra). In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus CD96).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the instant disclosure provides an isolated antibody that specifically binds to CD96 (e.g., human CD96 or cynomolgus CD96), the antibody comprising the Chothia VH CDRs of a VH disclosed in Table 1 herein. In certain embodiments, the instant disclosure provides an isolated antibody that specifically binds to CD96 (e.g., human CD96 or cynomolgus CD96), the antibody comprising the Chothia VL CDRs of a VL disclosed in Table 1 herein. In certain embodiments, the instant disclosure provides an isolated antibody that specifically binds to CD96 (e.g., human CD96 or cynomolgus CD96), the antibody comprising the Chothia VH CDRs and Chothia VL CDRs of an antibody disclosed in Table 1 herein. In certain embodiments, antibodies that specifically bind to CD96 (e.g., human CD96 or cynomolgus CD96) comprise one or more CDRs, in which the Chothia and Kabat CDRs have the same amino acid sequence. In certain embodiments, the instant disclosure provides an isolated antibody that specifically binds to CD96 (e.g., human CD96 or cynomolgus CD96) and comprises combinations of Kabat CDRs and Chothia CDRs.

In certain embodiments, the CDRs of an antibody can be determined according to the IMGT numbering system as described in: Lefranc M-P, (1999) The Immunologist 7: 132-136; Lefranc M-P et al., (1999) Nucleic Acids Res 27: 209-212, each of which is herein incorporated by reference in its entirety; and Lefranc M-P et al., (2009) Nucleic Acids Res 37: D1006-D1012.

In certain embodiments, the instant disclosure provides antibodies that specifically bind to CD96 (e.g., human CD96 or cynomolgus CD96) and comprise CDRs of an antibody disclosed in Table 1 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to CD96 (e.g., human CD96 or cynomolgus CD96) and comprise CDRs of an antibody disclosed in Table 1 herein as determined by the AbM numbering scheme.

In certain embodiments, the instant disclosure provides an isolated antibody that specifically binds to CD96 (e.g., human CD96 or cynomolgus CD96), wherein the antibody comprises a VH comprising the CDRH1, CDRH2, and CDRH3 region amino acid sequences of a VH set forth in SEQ ID NO: 36, 37, 38, 39, 40, 41, 42, 43, 44, 45, 46, 47, 48, 49, 50, 51, 52, 53, 54, 55, 56, 57, 58, 59, 60, or 61, and a VL comprising the CDRL1, CDRL2, and CDRL3 region amino acid sequences of a VL set forth in SEQ ID NO: 62, 63, 64, 65, 66, 67, 68, 69, 70, 71, 72, 73, 74, or 75, wherein each CDR is defined in accordance with the MacCallum definition, the Kabat definition, the Chothia definition, the IMGT numbering system, the AbM definition of CDR, structural analysis, or a combination thereof, wherein the structural analysis identifies residues in the variable region(s) predicted to make contact with an epitope region of CD96 (e.g., human CD96 or cynomolgus CD96). In certain embodiments, the instant disclosure provides an isolated antibody that specifically binds to CD96 (e.g., human CD96 or cynomolgus CD96) and comprises a combination of CDRs defined by the Kabat definition and CDRs defined by structural analysis of the antibody, wherein the structural analysis identifies residues in the variable region(s) predicted to make contact with an epitope region of CD96 (e.g., human CD96 or cynomolgus CD96).

In certain embodiments, the instant disclosure provides an isolated antibody that specifically binds to CD96 (e.g., human CD96 or cynomolgus CD96), the antibody comprising:

(a) CDRH1 comprises the amino acid sequence of $X_1YX_2X_3X_4$ (SEQ ID NO: 135), wherein
    $X_1$ is Q or S;
    $X_2$ is A or S;
    $X_3$ is M or I; and
    $X_4$ is H or S;

(b) CDRH2 comprises the amino acid sequence of $X_1IX_2X_3X_4X_5X_6X_7X_8X_9YX_{10}QKFQG$ (SEQ ID NO: 137), wherein
    $X_1$ is W or G;
    $X_2$ is N or I;
    $X_3$ is A, E, V, or P;
    $X_4$ is V, G, W, or I;
    $X_5$ is S, Y, T, N, or F;
    $X_6$ is G or W;
    $X_7$ is D, Y, N, or T;
    $X_8$ is T or A;
    $X_9$ is K or N; and
    $X_{10}$ is S or A;

(c) CDRH3 comprises the amino acid sequence of NWGX$_1$SYGX$_2$DV (SEQ ID NO: 180), GYDSRPLDV (SEQ ID NO: 19), or GYDSRPLDY (SEQ ID NO: 20), wherein
X$_1$ is M or L; and
X$_2$ is M or L;
(d) CDRL1 comprises the amino acid sequence of RASQSIX$_1$X$_2$YLN (SEQ ID NO: 139) or GGNNIGSKIVH (SEQ ID NO: 26), wherein
X$_1$ is S, T, or L; and
X$_2$ is S, P, or W;
(e) CDRL2 comprises the amino acid sequence of X$_1$X$_2$SSLQS (SEQ ID NO: 141) or DDRDRPS (SEQ ID NO: 32), wherein
X$_1$ is S or A; and
X$_2$ is A, S, or E; and/or
(f) CDRL3 comprises the amino acid sequence of QQX$_1$YSTPALX$_2$ (SEQ ID NO: 143) or QVWDINVHHVI (SEQ ID NO: 35), wherein
X$_1$ is S or A; and
X$_2$ is T or S.

In certain embodiments of the antibodies disclosed herein, the amino acid immediately N-terminal to CDRH1 (e.g., as described in Table 1 herein) is N, T, S, D, or A.

In certain embodiments, the instant disclosure provides an isolated antibody that specifically binds to CD96 (e.g., human CD96 or cynomolgus CD96), the antibody comprising:
(a) CDRH1 comprises the amino acid sequence of X$_1$YX$_2$X$_3$X$_4$ (SEQ ID NO: 135), wherein
X$_1$ is Q or S;
X$_2$ is A or S;
X$_3$ is M or I; and
X$_4$ is H or S;
(b) CDRH2 comprises the amino acid sequence of X$_1$IX$_2$X$_3$X$_4$X$_5$X$_6$X$_7$X$_8$X$_9$YX$_{10}$QKFQG (SEQ ID NO: 137), wherein
X$_1$ is W or G;
X$_2$ is N or I;
X$_3$ is A, E, V, or P;
X$_4$ is V, G, W, or I;
X$_5$ is S, Y, T, N, or F;
X$_6$ is G or W;
X$_7$ is D, Y, N, or T;
X$_8$ is T or A;
X$_9$ is K or N; and
X$_{10}$ is S or A;
(c) CDRH3 comprises the amino acid sequence of NWGX$_1$SYGX$_2$DV (SEQ ID NO: 180), GYDSRPLDV (SEQ ID NO: 19), or GYDSRPLDY (SEQ ID NO: 20), wherein
X$_1$ is M or L; and
X$_2$ is M or L;
(d) CDRL1 comprises the amino acid sequence of RASQSIX$_1$X$_2$YLN (SEQ ID NO: 139) or GGNNIGSKIVH (SEQ ID NO: 26), wherein
X$_1$ is S, T, or L; and
X$_2$ is S, P, or W;
(e) CDRL2 comprises the amino acid sequence of X$_1$X$_2$SSLQS (SEQ ID NO: 141) or DDRDRPS (SEQ ID NO: 32), wherein
X$_1$ is S or A; and
X$_2$ is A, S, or E; and
(f) CDRL3 comprises the amino acid sequence of QQX$_1$YSTPALX$_2$ (SEQ ID NO: 143) or QVWDINVHHVI (SEQ ID NO: 35), wherein
X$_1$ is S or A; and
X$_2$ is T or S.

In certain embodiments, the instant disclosure provides an isolated antibody that specifically binds to CD96 (e.g., human CD96 or cynomolgus CD96), wherein the antibody comprises a VH comprising the CDRH1, CDRH2 and CDRH3 amino acid sequences set forth in SEQ ID NOs: 1, 5, and 18; 2, 6, and 18; 2, 8, and 18; 2, 9, and 18; 2, 10, and 18; 1, 7, and 18; 2, 11, and 18; 1, 12, and 18; 1, 13, and 18; 1, 14, and 18; 3, 15, and 18; 1, 16, and 18; 1, 5, and 140; 1, 5, and 142; 1, 5, and 179; 4, 17, and 19; or 4, 17, and 20, respectively.

In certain embodiments, the instant disclosure provides an isolated antibody that specifically binds to CD96 (e.g., human CD96 or cynomolgus CD96), wherein the antibody comprises a VL comprising the CDRL1, CDRL2 and CDRL3 amino acid sequences set forth in SEQ ID NOs: 21, 28, and 33; 21, 29, and 33; 21, 30, and 33; 21, 31, and 33; 22, 29, and 33; 24, 29, and 33; 23, 29, and 33; 25, 28, and 34; or 26, 32, and 35, respectively.

In certain embodiments, the instant disclosure provides an isolated antibody that specifically binds to CD96 (e.g., human CD96 or cynomolgus CD96), wherein the antibody comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 5, 18, 21, 28, and 33; 1, 5, 18, 21, 29, and 33; 1, 5, 18, 22, 29, and 33; 1, 5, 18, 23, 29, and 33; 1, 5, 18, 24, 29, and 33; 1, 5, 18, 25, 28, and 34; 1, 5, 140, 21, 28, and 33; 1, 5, 142, 21, 28, and 33; 1, 5, 179, 21, 28, and 33; 1, 7, 18, 21, 29, and 33; 1, 12, 18, 21, 28, and 33; 1, 13, 18, 21, 28, and 33; 1, 14, 18, 21, 28, and 33; 1, 16, 18, 21, 28, and 33; 2, 6, 18, 21, 29, and 33; 2, 8, 18, 21, 29, and 33; 2, 9, 18, 21, 30, and 33; 2, 10, 18, 21, 29, and 33; 2, 11, 18, 21, 31, and 33; 3, 15, 18, 21, 28, and 33; 4, 17, 19, 26, 32, and 35; or 4, 17, 20, 26, 32, and 35, respectively.

In certain embodiments, the instant disclosure provides an isolated antibody that specifically binds to CD96 (e.g., human CD96 or cynomolgus CD96), comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 36, 37, 38, 39, 40, 41, 42, 43, 44, 45, 46, 47, 48, 49, 50, 51, 52, 53, 54, 55, 56, 57, 58, 59, 60, or 61. In certain embodiments, the instant disclosure provides an isolated antibody that specifically binds to CD96 (e.g., human CD96 or cynomolgus CD96), comprising a VH comprising an amino acid sequence set forth in SEQ ID NO: 36, 37, 38, 39, 40, 41, 42, 43, 44, 45, 46, 47, 48, 49, 50, 51, 52, 53, 54, 55, 56, 57, 58, 59, 60, or 61. In certain embodiments, the amino acid sequence of the VH consists of an amino acid sequence set forth in SEQ ID NO: 36, 37, 38, 39, 40, 41, 42, 43, 44, 45, 46, 47, 48, 49, 50, 51, 52, 53, 54, 55, 56, 57, 58, 59, 60, or 61. In certain embodiments, X in any one of SEQ ID NOs: 36-61 is glutamine. In certain embodiments, X in any one of SEQ ID NOs: 36-61 is pyroglutamate.

In certain embodiments, the instant disclosure provides an isolated antibody that specifically binds to CD96 (e.g., human CD96 or cynomolgus CD96), comprising a VL comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 62, 63, 64, 65, 66, 67, 68, 69, 70, 71, 72, 73, 74, or 75. In certain embodiments, the instant disclosure provides an isolated antibody that specifically binds to CD96 (e.g., human CD96 or cynomolgus CD96), comprising a VL comprising an amino acid sequence set forth in SEQ ID NO: 62, 63, 64, 65, 66, 67, 68, 69, 70, 71, 72, 73, 74, or 75. In certain embodiments, the amino acid sequence of the VL consists of an amino acid sequence set forth in SEQ ID NO: 62, 63, 64, 65, 66, 67, 68, 69, 70, 71, 72, 73, 74, or 75.

In certain embodiments, the instant disclosure provides an isolated antibody that specifically binds to CD96 (e.g., human CD96 or cynomolgus CD96), comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 36, 37, 38, 39, 40, 41, 42, 43, 44, 45, 46, 47, 48, 49, 50, 51, 52, 53, 54, 55, 56, 57, 58, 59, 60, or 61, and a VL comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 62, 63, 64, 65, 66, 67, 68, 69, 70, 71, 72, 73, 74, or 75. In certain embodiments, the instant disclosure provides an isolated antibody that specifically binds to CD96 (e.g., human CD96 or cynomolgus CD96), comprising a VH comprising an amino acid sequence of SEQ ID NO: 36, 37, 38, 39, 40, 41, 42, 43, 44, 45, 46, 47, 48, 49, 50, 51, 52, 53, 54, 55, 56, 57, 58, 59, 60, or 61, and a VL comprising an amino acid sequence of SEQ ID NO: 62, 63, 64, 65, 66, 67, 68, 69, 70, 71, 72, 73, 74, or 75. In certain embodiments, the amino acid sequence of the VH consists of an amino acid sequence set forth in SEQ ID NO: 36, 37, 38, 39, 40, 41, 42, 43, 44, 45, 46, 47, 48, 49, 50, 51, 52, 53, 54, 55, 56, 57, 58, 59, 60, or 61; and the amino acid sequence of the VL consists of an amino acid sequence set forth in SEQ ID NO: 62, 63, 64, 65, 66, 67, 68, 69, 70, 71, 72, 73, 74, or 75. In certain embodiments, X in any one of SEQ ID NOs: 36-61 is glutamine. In certain embodiments, X in any one of SEQ ID NOs: 36-61 is pyroglutamate.

In certain embodiments, the instant disclosure provides an isolated antibody that specifically binds to CD96 (e.g., human CD96 or cynomolgus CD96), comprising the VH and VL amino acid sequences set forth in SEQ ID NOs: 36 and 62; 37 and 62; 37 and 63; 37 and 66; 37 and 67; 37 and 68; 37 and 69; 38 and 63; 39 and 63; 40 and 63; 41 and 63; 42 and 63; 43 and 64; 44 and 64; 45 and 63; 46 and 63; 47 and 65; 48 and 62; 49 and 62; 50 and 62; 51 and 62; 52 and 62; 53 and 62; 54 and 62; 55 and 62; 56 and 62; 57 and 62; 58 and 62; 59 and 62; 60 and 70; 60 and 71; 60 and 72; 60 and 73; 60 and 74; 60 and 75; or 61 and 70, respectively. In certain embodiments, the amino acid sequences of VH and VL consist of the VH and VL amino acid sequences set forth in SEQ ID NOs: 36 and 62; 37 and 62; 37 and 63; 37 and 66; 37 and 67; 37 and 68; 37 and 69; 38 and 63; 39 and 63; 40 and 63; 41 and 63; 42 and 63; 43 and 64; 44 and 64; 45 and 63; 46 and 63; 47 and 65; 48 and 62; 49 and 62; 50 and 62; 51 and 62; 52 and 62; 53 and 62; 54 and 62; 55 and 62; 56 and 62; 57 and 62; 58 and 62; 59 and 62; 60 and 70; 60 and 71; 60 and 72; 60 and 73; 60 and 74; 60 and 75; or 61 and 70, respectively. In certain embodiments, X in any one of SEQ ID NOs: 36-61 is glutamine. In certain embodiments, X in any one of SEQ ID NOs: 36-61 is pyroglutamate.

In certain embodiments, the instant disclosure provides an isolated antibody that cross-competes for binding to CD96 (e.g., human CD96 or cynomolgus CD96) with an antibody comprising the VH and VL amino acid sequences set forth in SEQ ID NOs: 36 and 62; 37 and 62; 37 and 63; 37 and 66; 37 and 67; 37 and 68; 37 and 69; 38 and 63; 39 and 63; 40 and 63; 41 and 63; 42 and 63; 43 and 64; 44 and 64; 45 and 63; 46 and 63; 47 and 65; 48 and 62; 49 and 62; 50 and 62; 51 and 62; 52 and 62; 53 and 62; 54 and 62; 55 and 62; 56 and 62; 57 and 62; 58 and 62; 59 and 62; 60 and 70; 60 and 71; 60 and 72; 60 and 73; 60 and 74; 60 and 75; or 61 and 70, respectively.

In certain embodiments, the instant disclosure provides an isolated antibody that binds to the same or an overlapping epitope of CD96 (e.g., an epitope of human CD96 or an epitope of cynomolgus CD96) as an antibody described herein, e.g., an antibody comprising the VH and VL amino acid sequences set forth in SEQ ID NOs: 36 and 62; 37 and 62; 37 and 63; 37 and 66; 37 and 67; 37 and 68; 37 and 69; 38 and 63; 39 and 63; 40 and 63; 41 and 63; 42 and 63; 43 and 64; 44 and 64; 45 and 63; 46 and 63; 47 and 65; 48 and 62; 49 and 62; 50 and 62; 51 and 62; 52 and 62; 53 and 62; 54 and 62; 55 and 62; 56 and 62; 57 and 62; 58 and 62; 59 and 62; 60 and 70; 60 and 71; 60 and 72; 60 and 73; 60 and 74; 60 and 75; or 61 and 70, respectively. In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of CD96 (e.g., human CD96 or cynomolgus CD96) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as CD96 (e.g., human CD96 or cynomolgus CD96). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., CD96, such as human CD96 or cynomolgus CD96) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In certain embodiments, the antibody inhibits the binding of human CD96 to human CD155 (also known as poliovirus receptor (PVR)). In certain embodiments, the binding of human CD96 to human CD155 is reduced by more than 50%, 55%, 60%, 65%, 70%, 75%, 80%, 85%, 90%, 95%, 96%, 97%, 98%, or 99% in the presence of the antibody relative to the binding of human CD96 to human CD155 in the absence of the antibody.

In certain embodiments, the antibody inhibits a soluble fragment of human CD96 from binding to a soluble fragment of human CD155. In certain embodiments, the binding of a soluble fragment of human CD96 to a soluble fragment of human CD155 is reduced by more than 50%, 55%, 60%, 65%, 70%, 75%, 80%, 85%, 90%, 95%, 96%, 97%, 98%, or 99% in the presence of the antibody relative to the binding of a soluble fragment of human CD96 to a soluble fragment of human CD155 in the absence of the antibody.

In certain embodiments, the antibody inhibits a CD96-expressing cell from binding to a soluble fragment of human CD155. In certain embodiments, the binding of a CD96-expressing cell to a soluble fragment of human CD155 is reduced by more than 50%, 55%, 60%, 65%, 70%, 75%, 80%, 85%, 90%, 95%, 96%, 97%, 98%, or 99% in the presence of the antibody relative to the binding of a CD96-expressing cell to a soluble fragment of human CD155 in the absence of the antibody.

In certain embodiments, the antibody inhibits a CD96-expressing cell from binding to a cell expressing human CD155. In certain embodiments, the binding of a CD96-expressing cell to a CD155-expressing cell is reduced by more than 50%, 55%, 60%, 65%, 70%, 75%, 80%, 85%, 90%, 95%, 96%, 97%, 98%, or 99% in the presence of the antibody relative to the binding of a CD96-expressing cell to a CD155-expressing cell in the absence of the antibody.

In certain embodiments, the instant disclosure provides an isolated antibody that specifically binds to CD96 (e.g., human CD96 or cynomolgus CD96), the antibody comprising a heavy chain comprising the amino acid sequence set forth in SEQ ID NO: 76, 77, 78, 79, 80, 81, 82, 83, 84, 85, 86, 87, 88, 89, 90, 91, 92, 93, 94, 95, 96, 97, 98, 99, 100, 101, 144, 145, 146, 147, 148, 149, 150, 151, 152, 153, 154, 155, 156, 157, 158, 159, 160, 161, 162, 163, 164, 165, 166, 167, 168, or 169. In certain embodiments, the antibody comprises a heavy chain comprising the amino acid sequence set forth in SEQ ID NO: 76. In certain embodiments, the antibody comprises a heavy chain comprising the amino acid sequence set forth in SEQ ID NO: 77. In certain embodiments, the antibody comprises a heavy chain comprising the amino acid sequence set forth in SEQ ID NO: 78. In certain embodiments, the antibody comprises a heavy chain comprising the amino acid sequence set forth in SEQ ID NO: 79. In certain embodiments, the antibody comprises a heavy chain comprising the amino acid sequence set forth in SEQ ID NO: 80. In certain embodiments, the antibody comprises a heavy chain comprising the amino acid sequence set forth in SEQ ID NO: 81. In certain embodiments, the antibody comprises a heavy chain comprising the amino acid sequence set forth in SEQ ID NO: 82. In certain embodiments, the antibody comprises a heavy chain comprising the amino acid sequence set forth in SEQ ID NO: 83. In certain embodiments, the antibody comprises a heavy chain comprising the amino acid sequence set forth in SEQ ID NO: 84. In certain embodiments, the antibody comprises a heavy chain comprising the amino acid sequence set forth in SEQ ID NO: 85. In certain embodiments, the antibody comprises a heavy chain comprising the amino acid sequence set forth in SEQ ID NO: 86. In certain embodiments, the antibody comprises a heavy chain comprising the amino acid sequence set forth in SEQ ID NO: 87. In certain embodiments, the antibody comprises a heavy chain comprising the amino acid sequence set forth in SEQ ID NO: 88. In certain embodiments, the antibody comprises a heavy chain comprising the amino acid sequence set forth in SEQ ID NO: 89. In certain embodiments, the antibody comprises a heavy chain comprising the amino acid sequence set forth in SEQ ID NO: 90. In certain embodiments, the antibody comprises a heavy chain comprising the amino acid sequence set forth in SEQ ID NO: 91. In certain embodiments, the antibody comprises a heavy chain comprising the amino acid sequence set forth in SEQ ID NO: 92. In certain embodiments, the antibody comprises a heavy chain comprising the amino acid sequence set forth in SEQ ID NO: 93. In certain embodiments, the antibody comprises a heavy chain comprising the amino acid sequence set forth in SEQ ID NO: 94. In certain embodiments, the antibody comprises a heavy chain comprising the amino acid sequence set forth in SEQ ID NO: 95. In certain embodiments, the antibody comprises a heavy chain comprising the amino acid sequence set forth in SEQ ID NO: 96. In certain embodiments, the antibody comprises a heavy chain comprising the amino acid sequence set forth in SEQ ID NO: 97. In certain embodiments, the antibody comprises a heavy chain comprising the amino acid sequence set forth in SEQ ID NO: 98. In certain embodiments, the antibody comprises a heavy chain comprising the amino acid sequence set forth in SEQ ID NO: 99. In certain embodiments, the antibody comprises a heavy chain comprising the amino acid sequence set forth in SEQ ID NO: 100. In certain embodiments, the antibody comprises a heavy chain comprising the amino acid sequence set forth in SEQ ID NO: 101. In certain embodiments, the antibody comprises a heavy chain comprising the amino acid sequence set forth in SEQ ID NO: 144. In certain embodiments, the antibody comprises a heavy chain comprising the amino acid sequence set forth in SEQ ID NO: 145. In certain embodiments, the antibody comprises a heavy chain comprising the amino acid sequence set forth in SEQ ID NO: 146. In certain embodiments, the antibody comprises a heavy chain comprising the amino acid sequence set forth in SEQ ID NO: 147. In certain embodiments, the antibody comprises a heavy chain comprising the amino acid sequence set forth in SEQ ID NO: 148. In certain embodiments, the antibody comprises a heavy chain comprising the amino acid sequence set forth in SEQ ID NO: 149. In certain embodiments, the antibody comprises a heavy chain comprising the amino acid sequence set forth in SEQ ID NO: 150. In certain embodiments, the antibody comprises a heavy chain comprising the amino acid sequence set forth in SEQ ID NO: 151. In certain embodiments, the antibody comprises a heavy chain comprising the amino acid sequence set forth in SEQ ID NO: 152. In certain embodiments, the antibody comprises a heavy chain comprising the amino acid sequence set forth in SEQ ID NO: 153. In certain embodiments, the antibody comprises a heavy chain comprising the amino acid sequence set forth in SEQ ID NO: 154. In certain embodiments, the antibody comprises a heavy chain comprising the amino acid sequence set forth in SEQ ID NO: 155. In certain embodiments, the antibody comprises a heavy chain comprising the amino acid sequence set forth in SEQ ID NO: 156. In certain embodiments, the antibody comprises a heavy chain comprising the amino acid sequence set forth in SEQ ID NO: 157. In certain embodiments, the antibody comprises a heavy chain comprising the amino acid sequence set forth in SEQ ID NO: 158. In certain embodiments, the antibody comprises a heavy chain comprising the amino acid sequence set forth in SEQ ID NO: 159. In certain embodiments, the antibody comprises a heavy chain comprising the amino acid sequence set forth in SEQ ID NO: 160. In certain embodiments, the antibody comprises a heavy chain comprising the amino acid sequence set forth in SEQ ID NO: 161. In certain embodiments, the antibody comprises a heavy chain comprising the amino acid sequence set forth in SEQ ID NO: 162. In certain embodiments, the antibody comprises a heavy chain comprising the amino acid sequence set forth in SEQ ID NO: 163. In certain embodiments, the antibody comprises a heavy chain comprising the amino acid sequence set forth in SEQ ID NO: 164. In certain embodiments, the antibody comprises a heavy chain comprising the amino acid sequence set forth in SEQ ID NO: 165. In certain embodiments, the antibody comprises a heavy chain comprising the amino acid sequence set forth in SEQ ID NO: 166. In certain embodiments, the antibody comprises a heavy chain comprising the amino acid sequence set forth in SEQ ID NO: 167. In certain embodiments, the antibody comprises a heavy chain comprising the amino acid sequence set forth in SEQ ID NO: 168. In certain embodiments, the antibody comprises a heavy chain comprising the amino acid sequence set forth in SEQ ID NO: 169.

In certain embodiments, the amino acid sequence of the heavy chain consists of the amino acid sequence set forth in SEQ ID NO: 76. In certain embodiments, the amino acid sequence of the heavy chain consists of the amino acid sequence set forth in SEQ ID NO: 77. In certain embodiments, the amino acid sequence of the heavy chain consists of the amino acid sequence set forth in SEQ ID NO: 78. In certain embodiments, the amino acid sequence of the heavy chain consists of the amino acid sequence set forth in SEQ ID NO: 79. In certain embodiments, the amino acid sequence of the heavy chain consists of the amino acid sequence set forth in SEQ ID NO: 80. In certain embodiments, the amino acid sequence of the heavy chain consists of the amino acid sequence set forth in SEQ ID NO: 81. In certain embodiments, the amino acid sequence of the heavy chain consists of the amino acid sequence set forth in SEQ ID NO: 82. In certain embodiments, the amino acid sequence of the heavy chain consists of the amino acid sequence set forth in SEQ ID NO: 83. In certain embodiments, the amino acid sequence of the heavy chain consists of the amino acid sequence set forth in SEQ ID NO: 84. In certain embodiments, the amino acid sequence of the heavy chain consists of the amino acid sequence set forth in SEQ ID NO: 85. In certain embodiments, the amino acid sequence of the heavy chain consists of the amino acid sequence set forth in SEQ ID NO: 86. In certain embodiments, the amino acid sequence of the heavy chain consists of the amino acid sequence set forth in SEQ ID NO: 87. In certain embodiments, the amino acid sequence of the heavy chain consists of the amino acid sequence set forth in SEQ ID NO: 88. In certain embodiments, the amino acid sequence of the heavy chain consists of the amino acid sequence set forth in SEQ ID NO: 89. In certain embodiments, the amino acid sequence of the heavy chain consists of the amino acid sequence set forth in SEQ ID NO: 90. In certain embodiments, the amino acid sequence of the heavy chain consists of the amino acid sequence set forth in SEQ ID NO: 91. In certain embodiments, the amino acid sequence of the heavy chain consists of the amino acid sequence set forth in SEQ ID NO: 92. In certain embodiments, the amino acid sequence of the heavy chain consists of the amino acid sequence set forth in SEQ ID NO: 93. In certain embodiments, the amino acid sequence of the heavy chain consists of the amino acid sequence set forth in SEQ ID NO: 94. In certain embodiments, the amino acid sequence of the heavy chain consists of the amino acid sequence set forth in SEQ ID NO: 95. In certain embodiments, the amino acid sequence of the heavy chain consists of the amino acid sequence set forth in SEQ ID NO: 96. In certain embodiments, the amino acid sequence of the heavy chain consists of the amino acid sequence set forth in SEQ ID NO: 97. In certain embodiments, the amino acid sequence of the heavy chain consists of the amino acid sequence set forth in SEQ ID NO: 98. In certain embodiments, the amino acid sequence of the heavy chain consists of the amino acid sequence set forth in SEQ ID NO: 99. In certain embodiments, the amino acid sequence of the heavy chain consists of the amino acid sequence set forth in SEQ ID NO: 100. In certain embodiments, the amino acid sequence of the heavy chain consists of the amino acid sequence set forth in SEQ ID NO: 101. In certain embodiments, the amino acid sequence of the heavy chain consists of the amino acid sequence set forth in SEQ ID NO: 144. In certain embodiments, the amino acid sequence of the heavy chain consists of the amino acid sequence set forth in SEQ ID NO: 145. In certain embodiments, the amino acid sequence of the heavy chain consists of the amino acid sequence set forth in SEQ ID NO: 146. In certain embodiments, the amino acid sequence of the heavy chain consists of the amino acid sequence set forth in SEQ ID NO: 147. In certain embodiments, the amino acid sequence of the heavy chain consists of the amino acid sequence set forth in SEQ ID NO: 148. In certain embodiments, the amino acid sequence of the heavy chain consists of the amino acid sequence set forth in SEQ ID NO: 149. In certain embodiments, the amino acid sequence of the heavy chain consists of the amino acid sequence set forth in SEQ ID NO: 150. In certain embodiments, the amino acid sequence of the heavy chain consists of the amino acid sequence set forth in SEQ ID NO: 151. In certain embodiments, the amino acid sequence of the heavy chain consists of the amino acid sequence set forth in SEQ ID NO: 152. In certain embodiments, the amino acid sequence of the heavy chain consists of the amino acid sequence set forth in SEQ ID NO: 153. In certain embodiments, the amino acid sequence of the heavy chain consists of the amino acid sequence set forth in SEQ ID NO: 154. In certain embodiments, the amino acid sequence of the heavy chain consists of the amino acid sequence set forth in SEQ ID NO: 155. In certain embodiments, the amino acid sequence of the heavy chain consists of the amino acid sequence set forth in SEQ ID NO: 156. In certain embodiments, the amino acid sequence of the heavy chain consists of the amino acid sequence set forth in SEQ ID NO: 157. In certain embodiments, the amino acid sequence of the heavy chain consists of the amino acid sequence set forth in SEQ ID NO: 158. In certain embodiments, the amino acid sequence of the heavy chain consists of the amino acid sequence set forth in SEQ ID NO: 159. In certain embodiments, the amino acid sequence of the heavy chain consists of the amino acid sequence set forth in SEQ ID NO: 160. In certain embodiments, the amino acid sequence of the heavy chain consists of the amino acid sequence set forth in SEQ ID NO: 161. In certain embodiments, the amino acid sequence of the heavy chain consists of the amino acid sequence set forth in SEQ ID NO: 162. In certain embodiments, the amino acid sequence of the heavy chain consists of the amino acid sequence set forth in SEQ ID NO: 163. In certain embodiments, the amino acid sequence of the heavy chain consists of the amino acid sequence set forth in SEQ ID NO: 164. In certain embodiments, the amino acid sequence of the heavy chain consists of the amino acid sequence set forth in SEQ ID NO: 165. In certain embodiments, the amino acid sequence of the heavy chain consists of the amino acid sequence set forth in SEQ ID NO: 166. In certain embodiments, the amino acid sequence of the heavy chain consists of the amino acid sequence set forth in SEQ ID NO: 167. In certain embodiments, the amino acid sequence of the heavy chain consists of the amino acid sequence set forth in SEQ ID NO: 168. In certain embodiments, the amino acid sequence of the heavy chain consists of the amino acid sequence set forth in SEQ ID NO: 169. In certain embodiments, X in any one of SEQ ID NOs: 76-101 or 144-169 is glutamine. In certain embodiments, X in any one of SEQ ID NOs: 76-101 or 144-169 is pyroglutamate.

In certain embodiments, the instant disclosure provides an isolated antibody that specifically binds to CD96 (e.g., human CD96 or cynomolgus CD96), the antibody comprising a light chain comprising the amino acid sequence set forth in SEQ ID NO: 102, 103, 104, 105, 106, 107, 108, 109, 110, 111, 112, 113, 114, or 115. In certain embodiments, the amino acid sequence of the light chain consists of the amino acid sequence selected from the group consisting of SEQ ID NOs: 102, 103, 104, 105, 106, 107, 108, 109, 110, 111, 112, 113, 114, and 115.

In certain embodiments, the instant disclosure provides an isolated antibody that specifically binds to CD96 (e.g., human CD96 or cynomolgus CD96), comprising the heavy chain and light chain, wherein the heavy chain and light chain comprise the amino acid sequences of SEQ ID NOs: 76 and 102; 79 and 103; 78 and 103; 82 and 103; 84 and 104; 83 and 104; 86 and 103; 85 and 103; 81 and 103; 80 and 103; 87 and 105; 77 and 102; 88 and 102; 77 and 106; 77 and 107; 77 and 108; 77 and 103; 89 and 102; 90 and 102; 91 and 102; 92 and 102; 93 and 102; 77 and 109; 94 and 102; 95 and 102; 96 and 102; 97 and 102; 98 and 102; 99 and 102; 100 and 110; 100 and 111; 100 and 112; 100 and 113; 100 and 114; 100 and 115; 101 and 110; 144 and 102; 147 and 103; 146 and 103; 150 and 103; 152 and 104; 151 and 104; 154 and 103; 153 and 103; 149 and 103; 148 and 103; 155 and 105; 145 and 102; 156 and 102; 145 and 106; 145 and 107; 145 and 108; 145 and 103; 157 and 102; 158 and 102; 159 and 102; 160 and 102; 161 and 102; 145 and 109; 162 and 102; 163 and 102; 164 and 102; 165 and 102; 166 and 102; 167 and 102; 168 and 110; 168 and 111; 168 and 112; 168 and 113; 168 and 114; 168 and 115; or 169 and 110, respectively. In certain embodiments, wherein the amino acid sequences of the heavy chain and the light chain consist of the amino acid sequences of SEQ ID NOs: 76 and 102; 79 and 103; 78 and 103; 82 and 103; 84 and 104; 83 and 104; 86 and 103; 85 and 103; 81 and 103; 80 and 103; 87 and 105; 77 and 102; 88 and 102; 77 and 106; 77 and 107; 77 and 108; 77 and 103; 89 and 102; 90 and 102; 91 and 102; 92 and 102; 93 and 102; 77 and 109; 94 and 102; 95 and 102; 96 and 102; 97 and 102; 98 and 102; 99 and 102; 100 and 110; 100 and 111; 100 and 112; 100 and 113; 100 and 114; 100 and 115; 101 and 110; 144 and 102; 147 and 103; 146 and 103; 150 and 103; 152 and 104; 151 and 104; 154 and 103; 153 and 103; 149 and 103; 148 and 103; 155 and 105; 145 and 102; 156 and 102; 145 and 106; 145 and 107; 145 and 108; 145 and 103; 157 and 102; 158 and 102; 159 and 102; 160 and 102; 161 and 102; 145 and 109; 162 and 102; 163 and 102; 164 and 102; 165 and 102; 166 and 102; 167 and 102; 168 and 110; 168 and 111; 168 and 112; 168 and 113; 168 and 114; 168 and 115; or 169 and 110, respectively. In certain embodiments, X in any one of SEQ ID NOs: 76-101 or 144-169 is glutamine. In certain embodiments, X in any one of SEQ ID NOs: 76-101 or 144-169 is pyroglutamate.

In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 76 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 79 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 78 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 82 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 84 and a light chain comprising the amino acid sequence of SEQ ID NO: 104. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 83 and a light chain comprising the amino acid sequence of SEQ ID NO: 104. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 86 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 85 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 81 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 80 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 87 and a light chain comprising the amino acid sequence of SEQ ID NO: 105. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 77 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 88 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 77 and a light chain comprising the amino acid sequence of SEQ ID NO: 106. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 77 and a light chain comprising the amino acid sequence of SEQ ID NO: 107. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 77 and a light chain comprising the amino acid sequence of SEQ ID NO: 108. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 77 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 89 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 90 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 91 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 92 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 93 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 77 and a light chain comprising the amino acid sequence of SEQ ID NO: 109. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 94 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 95 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 96 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 97 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 98 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 99 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 100 and a light chain comprising the amino acid sequence of SEQ ID NO: 110. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 100 and a light chain comprising the amino acid sequence of SEQ ID NO: 111. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 100 and a light chain comprising the amino acid sequence of SEQ ID NO: 112. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 100 and a light chain comprising the amino acid sequence of SEQ ID NO: 113. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 100 and a light chain comprising the amino acid sequence of SEQ ID NO: 114. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 100 and a light chain comprising the amino acid sequence of SEQ ID NO: 115. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 101 and a light chain comprising the amino acid sequence of SEQ ID NO: 110. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 144 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 147 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 146 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 150 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 152 and a light chain comprising the amino acid sequence of SEQ ID NO: 104. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 151 and a light chain comprising the amino acid sequence of SEQ ID NO: 104. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 154 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 153 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 149 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 148 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 155 and a light chain comprising the amino acid sequence of SEQ ID NO: 105. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 145 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 156 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 145 and a light chain comprising the amino acid sequence of SEQ ID NO: 106. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 145 and a light chain comprising the amino acid sequence of SEQ ID NO: 107. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 145 and a light chain comprising the amino acid sequence of SEQ ID NO: 108. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 145 and a light chain comprising the amino acid sequence of SEQ ID NO: 103. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 157 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 158 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 159 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 160 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 161 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 145 and a light chain comprising the amino acid sequence of SEQ ID NO: 109. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 162 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 163 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 164 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 165 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 166 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 167 and a light chain comprising the amino acid sequence of SEQ ID NO: 102. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 168 and a light chain comprising the amino acid sequence of SEQ ID NO: 110. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 168 and a light chain comprising the amino acid sequence of SEQ ID NO: 111. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 168 and a light chain comprising the amino acid sequence of SEQ ID NO: 112. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 168 and a light chain comprising the amino acid sequence of SEQ ID NO: 113. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 168 and a light chain comprising the amino acid sequence of SEQ ID NO: 114. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 168 and a light chain comprising the amino acid sequence of SEQ ID NO: 115. In certain embodiments, the instant disclosure provides an isolated antibody that specifically binds to CD96 (e.g., human CD96 or cynomolgus CD96), the antibody comprising a heavy chain comprising the amino acid sequence of SEQ ID NO: 169 and a light chain comprising the amino acid sequence of SEQ ID NO: 110.

In certain embodiments, the amino acid sequences of the heavy chain and light chain consist of the amino acid sequences of SEQ ID NOs: 76 and 102, respectively. In certain embodiments, the amino acid sequences of the heavy chain and light chain consist of the amino acid sequences of SEQ ID NOs: 79 and 103, respectively. In certain embodiments, the amino acid sequences of the heavy chain and light chain consist of the amino acid sequences of SEQ ID NOs: 78 and 103, respectively. In certain embodiments, the amino acid sequences of the heavy chain and light chain consist of the amino acid sequences of SEQ ID NOs: 82 and 103, respectively. In certain embodiments, the amino acid sequences of the heavy chain and light chain consist of the amino acid sequences of SEQ ID NOs: 84 and 104, respectively. In certain embodiments, the amino acid sequences of the heavy chain and light chain consist of the amino acid sequences of SEQ ID NOs: 83 and 104, respectively. In certain embodiments, the amino acid sequences of the heavy chain and light chain consist of the amino acid sequences of SEQ ID NOs: 86 and 103, respectively. In certain embodiments, the amino acid sequences of the heavy chain and light chain consist of the amino acid sequences of SEQ ID NOs: 85 and 103, respectively. In certain embodiments, the amino acid sequences of the heavy chain and light chain consist of the amino acid sequences of SEQ ID NOs: 81 and 103, respectively. In certain embodiments, the amino acid sequences of the heavy chain and light chain consist of the amino acid sequences of SEQ ID NOs: 80 and 103, respectively. In certain embodiments, the amino acid sequences of the heavy chain and light chain consist of the amino acid sequences of SEQ ID NOs: 87 and 105, respectively. In certain embodiments, the amino acid sequences of the heavy chain and light chain consist of the amino acid sequences of SEQ ID NOs: 77 and 102, respectively. In certain embodiments, the amino acid sequences of the heavy chain and light chain consist of the amino acid sequences of SEQ ID NOs: 88 and 102, respectively. In certain embodiments, the amino acid sequences of the heavy chain and light chain consist of the amino acid sequences of SEQ ID NOs: 77 and 106, respectively. In certain embodiments, the amino acid sequences of the heavy chain and light chain consist of the amino acid sequences of SEQ ID NOs: 77 and 107, respectively. In certain embodiments, the amino acid sequences of the heavy chain and light chain consist of the amino acid sequences of SEQ ID NOs: 77 and 108, respectively. In certain embodiments, the amino acid sequences of the heavy chain and light chain consist of the amino acid sequences of SEQ ID NOs: 77 and 103, respectively. In certain embodiments, the amino acid sequences of the heavy chain and light chain consist of the amino acid sequences of SEQ ID NOs: 89 and 102, respectively. In certain embodiments, the amino acid sequences of the heavy chain and light chain consist of the amino acid sequences of SEQ ID NOs: 90 and 102, respectively. In certain embodiments, the amino acid sequences of the heavy chain and light chain consist of the amino acid sequences of SEQ ID NOs: 91 and 102, respectively. In certain embodiments, the amino acid sequences of the heavy chain and light chain consist of the amino acid sequences of SEQ ID NOs: 92 and 102, respectively. In certain embodiments, the amino acid sequences of the heavy chain and light chain consist of the amino acid sequences of SEQ ID NOs: 93 and 102, respectively. In certain embodiments, the amino acid sequences of the heavy chain and light chain consist of the amino acid sequences of SEQ ID NOs: 77 and 109, respectively. In certain embodiments, the amino acid sequences of the heavy chain and light chain consist of the amino acid sequences of SEQ ID NOs: 94 and 102, respectively. In certain embodiments, the amino acid sequences of the heavy chain and light chain consist of the amino acid sequences of SEQ ID NOs: 95 and 102, respectively. In certain embodiments, the amino acid sequences of the heavy chain and light chain consist of the amino acid sequences of SEQ ID NOs: 96 and 102, respectively. In certain embodiments, the amino acid sequences of the heavy chain and light chain consist of the amino acid sequences of SEQ ID NOs: 97 and 102, respectively. In certain embodiments, the amino acid sequences of the heavy chain and light chain consist of the amino acid sequences of SEQ ID NOs: 98 and 102, respectively. In certain embodiments, the amino acid sequences of the heavy chain and light chain consist of the amino acid sequences of SEQ ID NOs: 99 and 102, respectively. In certain embodiments, the amino acid sequences of the heavy chain and light chain consist of the amino acid sequences of SEQ ID NOs: 100 and 110, respectively. In certain embodiments, the amino acid sequences of the heavy chain and light chain consist of the amino acid sequences of SEQ ID NOs: 100 and 111, respectively. In certain embodiments, the amino acid sequences of the heavy chain and light chain consist of the amino acid sequences of SEQ ID NOs: 100 and 112, respectively. In certain embodiments, the amino acid sequences of the heavy chain and light chain consist of the amino acid sequences of SEQ ID NOs: 100 and 113, respectively. In certain embodiments, the amino acid sequences of the heavy chain and light chain consist of the amino acid sequences of SEQ ID NOs: 100 and 114, respectively. In certain embodiments, the amino acid sequences of the heavy chain and light chain consist of the amino acid sequences of SEQ ID NOs: 100 and 115, respectively. In certain embodiments, the amino acid sequences of the heavy chain and light chain consist of the amino acid sequences of SEQ ID NOs: 101 and 110, respectively. In certain embodiments, the amino acid sequences of the heavy chain and light chain consist of the amino acid sequences of SEQ ID NOs: 144 and 102, respectively. In certain embodiments, the amino acid sequences of the heavy chain and light chain consist of the amino acid sequences of SEQ ID NOs: 147 and 103, respectively. In certain embodiments, the amino acid sequences of the heavy chain and light chain consist of the amino acid sequences of SEQ ID NOs: 146 and 103, respectively. In certain embodiments, the amino acid sequences of the heavy chain and light chain consist of the amino acid sequences of SEQ ID NOs: 150 and 103, respectively. In certain embodiments, the amino acid sequences of the heavy chain and light chain consist of the amino acid sequences of SEQ ID NOs: 152 and 104, respectively. In certain embodiments, the amino acid sequences of the heavy chain and light chain consist of the amino acid sequences of SEQ ID NOs: 151 and 104, respectively. In certain embodiments, the amino acid sequences of the heavy chain and light chain consist of the amino acid sequences of SEQ ID NOs: 154 and 103, respectively. In certain embodiments, the amino acid sequences of the heavy chain and light chain consist of the amino acid sequences of SEQ ID NOs: 153 and 103, respectively. In certain embodiments, the amino acid sequences of the heavy chain and light chain consist of the amino acid sequences of SEQ ID NOs: 149 and 103, respectively. In certain embodiments, the amino acid sequences of the heavy chain and light chain consist of the amino acid sequences of SEQ ID NOs: 148 and 103, respectively. In certain embodiments, the amino acid sequences of the heavy chain and light chain consist of the amino acid sequences of SEQ ID NOs: 155 and 105, respectively. In certain embodiments, the amino acid sequences of the heavy chain and light chain consist of the amino acid sequences of SEQ ID NOs: 145 and 102, respectively. In certain embodiments, the amino acid sequences of the heavy chain and light chain consist of the amino acid sequences of SEQ ID NOs: 156 and 102, respectively. In certain embodiments, the amino acid sequences of the heavy chain and light chain consist of the amino acid sequences of SEQ ID NOs: 145 and 106, respectively. In certain embodiments, the amino acid sequences of the heavy chain and light chain consist of the amino acid sequences of SEQ ID NOs: 145 and 107, respectively. In certain embodiments, the amino acid sequences of the heavy chain and light chain consist of the amino acid sequences of SEQ ID NOs: 145 and 108, respectively. In certain embodiments, the amino acid sequences of the heavy chain and light chain consist of the amino acid sequences of SEQ ID NOs: 145 and 103, respectively. In certain embodiments, the amino acid sequences of the heavy chain and light chain consist of the amino acid sequences of SEQ ID NOs: 157 and 102, respectively. In certain embodiments, the amino acid sequences of the heavy chain and light chain consist of the amino acid sequences of SEQ ID NOs: 158 and 102, respectively. In certain embodiments, the amino acid sequences of the heavy chain and light chain consist of the amino acid sequences of SEQ ID NOs: 159 and 102, respectively. In certain embodiments, the amino acid sequences of the heavy chain and light chain consist of the amino acid sequences of SEQ ID NOs: 160 and 102, respectively. In certain embodiments, the amino acid sequences of the heavy chain and light chain consist of the amino acid sequences of SEQ ID NOs: 161 and 102, respectively. In certain embodiments, the amino acid sequences of the heavy chain and light chain consist of the amino acid sequences of SEQ ID NOs: 145 and 109, respectively. In certain embodiments, the amino acid sequences of the heavy chain and light chain consist of the amino acid sequences of SEQ ID NOs: 162 and 102, respectively. In certain embodiments, the amino acid sequences of the heavy chain and light chain consist of the amino acid sequences of SEQ ID NOs: 163 and 102, respectively. In certain embodiments, the amino acid sequences of the heavy chain and light chain consist of the amino acid sequences of SEQ ID NOs: 164 and 102, respectively. In certain embodiments, the amino acid sequences of the heavy chain and light chain consist of the amino acid sequences of SEQ ID NOs: 165 and 102, respectively. In certain embodiments, the amino acid sequences of the heavy chain and light chain consist of the amino acid sequences of SEQ ID NOs: 166 and 102, respectively. In certain embodiments, the amino acid sequences of the heavy chain and light chain consist of the amino acid sequences of SEQ ID NOs: 167 and 102, respectively. In certain embodiments, the amino acid sequences of the heavy chain and light chain consist of the amino acid sequences of SEQ ID NOs: 168 and 110, respectively. In certain embodiments, the amino acid sequences of the heavy chain and light chain consist of the amino acid sequences of SEQ ID NOs: 168 and 111, respectively. In certain embodiments, the amino acid sequences of the heavy chain and light chain consist of the amino acid sequences of SEQ ID NOs: 168 and 112, respectively. In certain embodiments, the amino acid sequences of the heavy chain and light chain consist of the amino acid sequences of SEQ ID NOs: 168 and 113, respectively. In certain embodiments, the amino acid sequences of the heavy chain and light chain consist of the amino acid sequences of SEQ ID NOs: 168 and 114, respectively. In certain embodiments, the amino acid sequences of the heavy chain and light chain consist of the amino acid sequences of SEQ ID NOs: 168 and 115, respectively. In certain embodiments, the amino acid sequences of the heavy chain and light chain consist of the amino acid sequences of SEQ ID NOs: 169 and 110, respectively.

Any antibody format can be used in the antibodies disclosed herein. In certain embodiments, the antibody is a single chain antibody or single-chain Fv (scFv). In certain embodiments, the antibody is a scFv fused with an Fc region (scFv-Fc). In certain embodiments, the antibody is a Fab fragment. In certain embodiments, the antibody is a F(ab')$_2$ fragment.

In certain embodiments, the antibody disclosed herein is a multispecific antibody (e.g., a bispecific antibody) which specifically binds to CD96 (e.g., human CD96 or cynomolgus CD96) and a second antigen.

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. In certain embodiments, the detectable label comprises a fluorescent moiety or a click chemistry handle.

Any immunoglobulin (Ig) constant region can be used in the antibodies disclosed herein. In certain embodiments, the Ig region is a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

In certain embodiments, the instant disclosure provides an isolated antibody that specifically binds to CD96 (e.g., human CD96 or cynomolgus CD96), the antibody comprising a heavy chain constant region comprising the amino acid sequence of SEQ ID NO: 121 or 175. In certain embodiments, the instant disclosure provides an isolated antibody that specifically binds to CD96 (e.g., human CD96 or cynomolgus CD96), the antibody comprising alight chain constant region comprising the amino acid sequence of SEQ ID NO: 122 or 123.

In certain embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1) and/or the hinge region, numbered according to the EU numbering system, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG1) and/or the third constant (CH3) domain (residues 341-447 of human IgG1), numbered according to the EU numbering system. In a specific embodiment, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild type heavy chain constant region, wherein the variant heavy chain constant region binds to FcγRIIB with higher affinity than the wild type heavy chain constant region binds to FcγRIIB. In certain embodiments, the variant heavy chain constant region is a variant human heavy chain constant region, e.g., a variant human IgG1, a variant human IgG2, or a variant human IgG4 heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F; according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant domain Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A332L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant domain of an IgG1 with an N297Q or N297A amino acid substitution, numbered according to the EU numbering system. In one embodiment, an antibody described herein comprises the constant domain of an IgG1 with a mutation selected from the group consisting of D265A, P329A, and a combination thereof, numbered according to the EU numbering system. In another embodiment, an antibody described herein comprises the constant domain of an IgG1 with a mutation selected from the group consisting of L234A, L235A, and a combination thereof, numbered according to the EU numbering system. In another embodiment, an antibody described herein comprises the constant domain of an IgG1 with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG1 heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG1 heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises a modified constant domain of an IgG1, wherein the modification increases the ability of the antibody to mediate antibody dependent cellular cytotoxicity (ADCC). In certain embodiments, 0.1, 1, or 10 µg/mL of the antibody is capable of inducing cell death of at least 20%, 25%, 30%, 35%, 40%, 45%, 50%, 55%, or 60% of CD96-expressing cells within 1, 2, or 3 hours, as assessed by methods described herein and/or known to a person of skill in the art. In certain embodiments, the modified constant domain of an IgG1 comprises S239D and I332E substitutions, numbered according to the EU numbering system. In certain embodiments, the modified constant domain of an IgG1 comprises S239D, A330L, and I332E substitutions, numbered according to the EU numbering system. In certain embodiments, the modified constant domain of an IgG1 comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, an antibody described herein comprises the constant region of an IgG4 antibody and the serine at amino acid residue 228 of the heavy chain, numbered according to the EU numbering system, is substituted for proline. In certain embodiments, the instant disclosure provides an isolated antibody that specifically binds to CD96 (e.g., human CD96 or cynomolgus CD96), the antibody comprising a heavy chain constant region comprising the amino acid sequence of SEQ ID NO: 26.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to CD96 (e.g., human CD96 or cynomolgus CD96) and functions as an antagonist (e.g., decreases or inhibits CD96 activity).

In certain embodiments, the instant disclosure provides an isolated antibody that specifically binds to CD96 (e.g., human CD96 or cynomolgus CD96) and decreases or inhibits CD96 (e.g., human CD96 or cynomolgus CD96) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to CD96 (e.g., human CD96 or cynomolgus CD96) activity without any antibody or with an unrelated antibody (e.g., an antibody that does not specifically bind to CD96 (e.g., human CD96 or cynomolgus CD96)). In certain embodiments, the instant disclosure provides an isolated antibody that specifically binds to CD96 (e.g., human CD96 or cynomolgus CD96) and decreases or inhibits CD96 (e.g., human CD96 or cynomolgus CD96) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to CD96 (e.g., human CD96 or cynomolgus CD96) activity without any antibody or with an unrelated antibody (e.g., an antibody that does not specifically bind to CD96 (e.g., human CD96)). Non-limiting examples of CD96 (e.g., human CD96 or cynomolgus CD96) activity can include CD96 (e.g., human CD96 or cynomolgus CD96) signaling; CD96 (e.g., human CD96 or cynomolgus CD96) binding to its ligand (e.g., CD155) or a fragment and/or fusion protein thereof); activation of a T cell (e.g., a T cell expressing human CD96); activation of a natural killer (NK) cell; decrease or inhibition of a Treg; increase of cytokine (e.g., IL-2) production; increase of the activity of CD155 (e.g., human CD155). In specific embodiments, an increase in a CD96 (e.g., human CD96 or cynomolgus CD96) activity is assessed as described in the Examples.

In specific embodiments, the instant disclosure provides an isolated antibody that specifically binds to CD96 (e.g., human CD96 or cynomolgus CD96) and decreases or inhibits CD96 (e.g., human or cynomolgus CD96) binding to its ligand (e.g., CD155) or a fragment and/or fusion protein thereof) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to CD96 (e.g., human CD96 or cynomolgus CD96) binding to this ligand without any antibody or with an unrelated antibody (e.g., an antibody that does not specifically bind to CD96 (e.g., human or cynomolgus CD96)). In specific embodiments, the instant disclosure provides an isolated antibody that specifically binds to CD96 (e.g., human or cynomolgus CD96) and increases CD96 (e.g., human or cynomolgus CD96) binding to its ligand (e.g., CD155 (e.g., human or cynomolgus CD155) or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to CD96 (e.g., human CD96) binding to this ligand without any antibody or with an unrelated antibody (e.g., an antibody that does not specifically bind to CD96 (e.g., human or cynomolgus CD96)).

In specific embodiments, the instant disclosure provides an isolated antibody that specifically binds to CD96 (e.g., human CD96 or cynomolgus CD96) and activates a T cell (e.g., a T cell expressing human CD96). In certain embodiments, the T cell is a memory T cell. In certain embodiments, the T cell is a primary CD3-expressing T cell. In certain embodiments, the T cell is a CD96-expressing Jurkat cell. In certain embodiments, the antibody disclosed herein increases the activity of nuclear factor of activated T-cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to NFAT activity without any antibody or with an unrelated antibody (e.g., an antibody that does not specifically bind to CD96 (e.g., human CD96 or cynomolgus CD96)). In certain embodiments, the antibody disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to NFAT activity without any antibody or with an unrelated antibody (e.g., an antibody that does not specifically bind to CD96 (e.g., human CD96 or cynomolgus CD96)). In certain embodiments, the antibody increases NFAT activity in the presence of a ligand of CD96 (e.g., CD155) or a fragment and/or fusion protein thereof, and/or a cell expressing a ligand of CD96 (e.g., a monocyte or a dendritic cell).

In specific embodiments, the instant disclosure provides an isolated antibody that specifically binds to CD96 (e.g., human CD96 or cynomolgus CD96) and increases cytokine production (e.g., IL-2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production without any antibody or with an unrelated antibody (e.g., an antibody that does not specifically bind to CD96 (e.g., human CD96 or cynomolgus CD96)). In specific embodiments, the instant disclosure provides an isolated antibody that specifically binds to CD96 (e.g., human CD96 or cynomolgus CD96) and increases cytokine production (e.g., IL-2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production without any antibody or with an unrelated antibody (e.g., an antibody that does not specifically bind to CD96 (e.g., human CD96 or cynomolgus CD96)). In certain embodiments, the antibody increases cytokine production (e.g., IL-2) in the presence of a ligand of CD96 (e.g., CD155) or a fragment and/or fusion protein thereof), and/or a cell expressing a ligand of CD96 (e.g., a monocyte or a dendritic cell). In certain embodiments, the antibody increases the production of IL-2 relative to IL-2 production without any antibody or with an unrelated antibody (e.g., an antibody that does not specifically bind to CD96 (e.g., human CD96 or cynomolgus CD96)).

In certain embodiments, the instant disclosure provides an isolated antibody that specifically binds to CD96 (e.g., human CD96 or cynomolgus CD96) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to IFNγ and/or IL-2 production without any antibody or with an unrelated antibody (e.g., an antibody that does not specifically bind to CD96 (e.g., human CD96 or cynomolgus CD96)).

In certain embodiments, human peripheral blood mononuclear cells (PBMCs) stimulated with *Staphylococcus* Enterotoxin A (SEA) in the presence of an antibody described herein, which specifically binds to CD96 (e.g., human CD96 or cynomolgus CD96), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any antibody or with an unrelated antibody (e.g., an antibody that does not specifically bind to CD96 (e.g., human CD96 or cynomolgus CD96)), as assessed by methods described herein or known to one of skill in the art.

In certain embodiments, the instant disclosure provides an isolated antibody that specifically binds to CD96 (e.g., human CD96 or cynomolgus CD96) and increases or promotes memory recall of a memory T cell. In certain embodiments, the memory T cell is a CD8 effector memory T cell. In certain embodiments, the memory T cell is a CD4 effector memory T cell. In certain embodiments, the antibody increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the number of proliferating memory T cells when the memory T cells are in contact with their cognate antigen(s) in the absence of any antibody or in the presence of an unrelated antibody (e.g., an antibody that does not specifically bind to CD96 (e.g., human CD96 or cynomolgus CD96)). In certain embodiments, the antibody increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the production of the cytokine from a memory T cell when the memory T cell is in contact with its cognate antigen in the absence of any antibody or in the presence of an unrelated antibody (e.g., an antibody that does not specifically bind to CD96 (e.g., human CD96 or cynomolgus CD96)).

In certain embodiments, the instant disclosure provides an isolated antibody that specifically binds to CD96 (e.g., human CD96 or cynomolgus CD96) and activates an NK cell. In certain embodiments, the NK cells are isolated. In certain embodiments, the NK cells are in a mixed culture of PBMCs. In certain embodiments, the antibody disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to the expression level of CD107a in NK cells without any antibody or with an unrelated antibody (e.g., an antibody that does not specifically bind to CD96 (e.g., human CD96 or cynomolgus CD96)). In certain embodiments, the antibody disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to the expression level of CD107a in NK cells without any antibody or with an unrelated antibody (e.g., an antibody that does not specifically bind to CD96 (e.g., human CD96 or cynomolgus CD96)). In certain embodiments, the antibody disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production (e.g., IFNγ and/or TNFα) from NK cells without any antibody or with an unrelated antibody (e.g., an antibody that does not specifically bind to CD96 (e.g., human CD96 or cynomolgus CD96)). In certain embodiments, the antibody disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production (e.g., IFNγ and/or TNFα) from NK cells without any antibody or with an unrelated antibody (e.g., an antibody that does not specifically bind to CD96 (e.g., human CD96 or cynomolgus CD96)).

5.3 Pharmaceutical Compositions

Provided herein are compositions comprising an anti-CD96 (e.g., human CD96 or cynomolgus CD96) antibody disclosed herein having the desired degree of purity in a physiologically acceptable carrier, excipient or stabilizer (see, e.g., Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-CD96 (e.g., human CD96 or cynomolgus CD96) antibody disclosed herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in increasing or promoting CD96 (e.g., human CD96 or cynomolgus CD96) activity and treating a condition, such as cancer or an infectious disease. In one embodiment, the present invention relates to a pharmaceutical composition of the present invention comprising an anti-CD96 antibody of the present invention for use as a medicament. In another embodiment, the present invention relates to a pharmaceutical composition of the present invention for use in a method for the treatment of cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-CD96 (e.g., human CD96 or cynomolgus CD96) antibody disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-CD96 (e.g., human CD96 or cynomolgus CD96) antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-CD96 (e.g., human CD96 or cynomolgus CD96) antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

5.4 Methods of Use and Uses

In another aspect, the instant disclosure provides a method of treating a subject using the anti-CD96 (e.g., human CD96 or cynomolgus CD96) antibodies disclosed herein. Any disease or disorder in a subject that would benefit from decrease of CD96 (e.g., human CD96 or cynomolgus CD96) function can be treated using the anti-CD96 (e.g., human CD96 or cynomolgus CD96) antibodies disclosed herein. In certain embodiments, the disease or disorder is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the disease or disorder is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

The anti-CD96 (e.g., human CD96) antibodies disclosed herein are particularly useful for inhibiting immune system tolerance to tumors, and accordingly can be used as an immunotherapy for subjects with cancer. For example, in certain embodiments, the instant disclosure provides a method of increasing T cell (e.g., $CD8^+$ cytotoxic T cells, $CD4^+$ helper T cells, NKT cells, effector T cells, or memory T cells) activation in response to an antigen in a subject, the method comprising administering to the subject an effective amount of an anti-CD96 (e.g., human CD96 or cynomolgus CD96) antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the anti-CD96 (e.g., human CD96 or cynomolgus CD96) antibodies or pharmaceutical compositions disclosed herein include, without limitation, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer. In certain embodiments, the cancer is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the cancer is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

In one embodiment, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In a specific embodiment, the cancer is a cervical cancer.

In one embodiment, the cancer is a hematological cancer, for example, a leukemia, a lymphoma, or a myeloma. In one embodiment, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplamacytic lymphoma, or extranodal marginal zone lymphoma. In one embodiment the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In one embodiment, the cancer is a lung cancer, e.g., a lung adenocarcinoma, non-small cell lung cancer, or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-CD96 (e.g., human CD96 or cynomolgus CD96) antibody or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an anti-CD96 (e.g., human CD96 or cynomolgus CD96) antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-CD96 (e.g., human CD96 or cynomolgus CD96) antibody described herein or a composition thereof is the only active agent administered to a subject. In certain embodiments, an anti-CD96 (e.g., human CD96 or cynomolgus CD96) antibody described herein or a composition thereof is used in combination with anti-infective interventions (e.g., antivirals, antibacterials, antifungals, or anti-helminthics) for the treatment of infectious diseases. Therefore, in a one embodiment, the present invention relates to an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by anti-CD96 (e.g., human CD96 or cynomolgus CD96) antibodies or pharmaceutical compositions disclosed herein are caused by infectious agents including but not limited to bacteria, parasites, fungi, protozae, and viruses. In a specific embodiment, the infectious disease treated and/or prevented by anti-CD96 (e.g., human CD96 or cynomolgus CD96) antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans,* and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans,* and *Pseudomonas aeruginosa*) that can be prevented and/or treated in accordance with the methods described herein include, but are not limited to, *Mycobacteria rickettsia, Mycoplasma, Neisseria, S. pneumonia, Borrelia burgdorferi* (Lyme disease), *Bacillus antracis* (anthrax), tetanus, *Streptococcus, Staphylococcus,* mycobacterium, pertussis, cholera, plague, diphtheria, chlamydia, *S. aureus* and legionella.

Protozoal diseases or protozoal infections caused by protozoa that can be prevented and/or treated in accordance with the methods described herein include, but are not limited to, leishmania, coccidiosis, trypanosoma schistosoma or malaria. Parasitic diseases or parasitic infections caused by parasites that can be prevented and/or treated in accordance with the methods described herein include, but are not limited to, chlamydia and rickettsia.

Fungal diseases or fungal infections that can be prevented and/or treated in accordance with the methods described herein include, but are not limited to, those caused by *Candida* infections, zygomycosis, *Candida mastitis*, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the chemotherapeutic agent is a DNA damage-inducing agent (e.g., gemcitabine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an agonist anti-CD137 antibody, an agonist anti-GITR antibody, and an agonist anti-OX40 antibody. In certain embodiments, the checkpoint targeting agent is selected from the group consisting of an antagonist anti-CTLA-4 antibody, an antagonist anti-PD-L1 antibody, an antagonist anti-PD-L2 antibody, and an antagonist anti-PD-1 antibody, wherein the anti-CD96 (e.g., human CD96 or cynomolgus CD96) antibodies or pharmaceutical compositions disclosed herein synergize with the checkpoint targeting agent.

In one embodiment, the present invention relates to an antibody and/or pharmaceutical composition of the present invention for use in a method of the present invention, wherein the method further comprises administering an additional therapeutic agent to the subject. In one embodiment, the present invention relates to (a) an antibody and/or pharmaceutical composition of the present invention and (b) an additional therapeutic agent for use as a medicament. In one embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one embodiment, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb.

In certain embodiments, an anti-CD96 (e.g., human CD96 or cynomolgus CD96) antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in one embodiment, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an anti-CD96 (e.g., human CD96) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, an anti-CD96 (e.g., human CD96 or cynomolgus CD96) antibody disclosed herein is administered to a subject in combination with a vaccine. The vaccine can be, e.g., a peptide vaccine, a DNA vaccine, or an RNA vaccine. In certain embodiments, the vaccine is a heat shock protein-based tumor vaccine or a heat shock protein-based pathogen vaccine. In a specific embodiment, an anti-CD96 (e.g., human CD96 or cynomolgus CD96) antibody disclosed herein is administered to a subject in combination with a heat shock protein-based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in one embodiment, the present invention relates to (a) an antibody and/or pharmaceutical composition of the present invention and (b) a vaccine for use as a medicament, for example for use in a method for the treatment of cancer. In one embodiment, the present invention relates to a pharmaceutical composition, kit or kit-of-parts comprising (a) an antibody and/or pharmaceutical composition of the present invention and (b) a vaccine. In one embodiment, the vaccine is a heat shock protein-based tumor vaccine. In one embodiment, the vaccine is a heat shock protein-based pathogen vaccine. In certain embodiments, the vaccine is as described in WO 2016/183486, incorporated herein by reference in its entirety.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-CD96 (e.g., human CD96 or cynomolgus CD96) antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in one embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In certain embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436,404, 6,447,780, 6,447,781 and 6,610,659.

In certain embodiments, an anti-CD96 (e.g., human CD96 or cynomolgus CD96) antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON.

In certain embodiments, an anti-CD96 (e.g., human CD96 or cynomolgus CD96) antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in one embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-CD96 (e.g., human CD96 or cynomolgus CD96) antibody disclosed herein is administered to a subject in combination with a cell expressing a chimeric antigen receptor (CAR). In certain embodiments, the cell is a T cell.

In certain embodiments, an anti-CD96 (e.g., human CD96 or cynomolgus CD96) antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an anti-CD96 (e.g., human CD96 or cynomolgus CD96) antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), optionally wherein the BiTE and/or DART comprises the VH and VL sequences of cetuximab. In certain embodiments, the tumor-associated antigen is Her2 (e.g., human Her2), optionally wherein the BiTE and/or DART comprises the VH and VL sequences of trastuzumab. In certain embodiments, the tumor-associated antigen is CD20 (e.g., human CD20).

The anti-CD96 (e.g., human CD96 or cynomolgus CD96) antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-CD96 (e.g., human CD96 or cynomolgus CD96) antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-CD96 (e.g., human CD96 or cynomolgus CD96) antibody described herein can also be used to assay CD96 (e.g., human CD96 or cynomolgus CD96) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-CD96 (e.g., human CD96 or cynomolgus CD96) antibody described herein can be labeled and used in combination with an anti-CD96 (e.g., human CD96 or cynomolgus CD96) antibody to detect CD96 (e.g., human CD96 or cynomolgus CD96) protein levels. Therefore, in one embodiment, the present invention relates to the use of an antibody of the present invention for in vitro detection of CD96 (e.g., human CD96 or cynomolgus CD96) protein in a biological sample. In a further embodiment, the present invention relates to the use of an anti-CD96 antibody of the invention, for assaying and/or detecting CD96 (e.g., human CD96 or cynomolgus CD96) protein levels in a biological sample in vitro, optionally wherein the anti-CD96 antibody is conjugated to a radionuclide or detectable label, and/or carries a label described herein, and/or wherein an immunohistological method is used.

Assaying for the expression level of CD96 (e.g., human CD96 or cynomolgus CD96) protein is intended to include qualitatively or quantitatively measuring or estimating the level of CD96 (e.g., human CD96 or cynomolgus CD96) protein in a first biological sample either directly (e.g., by determining or estimating absolute protein level) or relatively (e.g., by comparing to the disease associated protein level in a second biological sample). CD96 (e.g., human CD96 or cynomolgus CD96) polypeptide expression level in the first biological sample can be measured or estimated and compared to a standard CD96 (e.g., human CD96 or cynomolgus CD96) protein level, the standard being taken, for example, from a second biological sample obtained from an individual not having the disorder or being determined by averaging levels from a population of individuals not having the disorder. As will be appreciated in the art, once the "standard" CD96 (e.g., human CD96 or cynomolgus CD96) polypeptide level is known, it can be used repeatedly as a standard for comparison. Therefore, in a further embodiment, the present invention relates to an in vitro method for assaying and/or detecting CD96 protein levels, for example human CD96 protein levels, in a biological sample, comprising qualitatively or quantitatively measuring or estimating the level of CD96 protein, for example of human CD96 protein, in a biological sample, by an immunohistological method.

As used herein, the term "biological sample" refers to any biological sample obtained from a subject, cell line, tissue, or other source of cells potentially expressing CD96 (e.g., human CD96 or cynomolgus CD96). Methods for obtaining tissue biopsies and body fluids from animals (e.g., humans or cynomolgus monkeys) are well known in the art. Biological samples include peripheral blood mononuclear cells (PBMCs).

An anti-CD96 (e.g., human CD96 or cynomolgus CD96) antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-CD96 antibody and/or pharmaceutical composition of the present invention for use as a diagnostic. In one embodiment, the present invention relates to an anti-CD96 antibody and/or pharmaceutical composition of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-CD96 antibody of the invention, for predicting, diagnosing and/or monitoring of a subject having or suspected to have an immune system-dysfunction and/or with regard to an anticipated or desired immune system response, antigen response or vaccine response by assaying and/or detecting human CD96 protein levels in a biological sample of the subject in vitro.

In one embodiment, an anti-CD96 (e.g., human CD96 or cynomolgus CD96) antibody can be used in immunohistochemistry of biopsy samples. In one embodiment, the method is an in vitro method. In another embodiment, an anti-CD96 (e.g., human CD96 or cynomolgus CD96) antibody can be used to detect levels of CD96 (e.g., human CD96 or cynomolgus CD96), or levels of cells which contain CD96 (e.g., human CD96 or cynomolgus CD96) on their membrane surface, the levels of which can then be linked to certain disease symptoms. Anti-CD96 (e.g., human CD96 or cynomolgus CD96) antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-CD96 (e.g., human CD96 or cynomolgus CD96) antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-CD96 (e.g., human CD96 or cynomolgus CD96) antibody may carry or may be conjugated to a radioactive label or radionuclide, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$I, $^{117}$Lu, $^{121}$I, $^{124}$I, $^{125}$I, $^{131}$I, $^{198}$Au, $^{211}$At, $^{213}$K, $^{225}$Ac and $^{186}$Re. When radioactive labels are used, currently available counting procedures known in the art may be utilized to identify and quantitate the specific binding of anti-CD96 (e.g., human CD96 or cynomolgus CD96) antibody to CD96 (e.g., human CD96 or cynomolgus CD96). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-CD96 (e.g., human CD96 or cynomolgus CD96) antibody under conditions that allow for the formation of a complex between the antibody and CD96 (e.g., human CD96 or cynomolgus CD96). Any complexes formed between the antibody and CD96 (e.g., human CD96 or cynomolgus CD96) are detected and compared in the sample and the control. In light of the specific binding of the antibodies described herein for CD96 (e.g., human CD96 or cynomolgus CD96), the antibodies can be used to specifically detect CD96 (e.g., human CD96 or cynomolgus CD96) expression on the surface of cells. The antibodies described herein can also be used to purify CD96 (e.g., human CD96 or cynomolgus CD96) via immunoaffinity purification. Also included herein is an assay system which may be prepared in the form of a test kit, kit, or kit-of-parts for the quantitative analysis of the extent of the presence of, for instance, CD96 (e.g., human CD96 or cynomolgus CD96) or CD96 (e.g., human CD96 or cynomolgus CD96)/CD96 (e.g., human CD96 or cynomolgus CD96) ligand complexes. The system, test kit, kit or kit-of-parts may comprise a labeled component, e.g., a labeled antibody, and one or more additional immunochemical reagents.

5.5 Polynucleotides, Vectors and Methods of Producing Anti-CD96 Antibodies

In another aspect, provided herein are polynucleotides comprising a nucleotide sequence encoding an antibody. or a portion thereof, described herein or a fragment thereof (e.g., a VL and/or VH; and a light chain and/or heavy chain) that specifically binds to a CD96 (e.g., human CD96 or cynomolgus CD96) antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a CD96 (e.g., human CD96 or cynomolgus CD96) polypeptide and comprises an amino acid sequence as described herein, as well as antibodies which compete with such antibodies for binding to a CD96 (e.g., human CD96 or cynomolgus CD96) polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1).

Also provided herein are polynucleotides encoding an anti-CD96 (e.g., human CD96 or cynomolgus CD96) antibody that are optimized, e.g., by codon/RNA optimization, replacement with heterologous signal sequences, and elimination of mRNA instability elements. Methods to generate optimized nucleic acids encoding an anti-CD96 (e.g., human CD96 or cynomolgus CD96) antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-CD96 (e.g., human CD96 or cynomolgus CD96) antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-CD96 (e.g., human CD96 or cynomolgus CD96) antibody encoded by polynucleotides that have not been optimized.

In certain embodiments, an optimized polynucleotide sequence encoding an anti-CD96 (e.g., human CD96 or cynomolgus CD96) antibody described herein or a fragment thereof (e.g., VL domain and/or VH domain) can hybridize to an antisense (e.g., complementary) polynucleotide of an unoptimized polynucleotide sequence encoding an anti-CD96 (e.g., human CD96 or cynomolgus CD96) antibody described herein or a fragment thereof (e.g., VL domain and/or VH domain). In specific embodiments, an optimized nucleotide sequence encoding an anti-CD96 (e.g., human CD96 or cynomolgus CD96) antibody described herein or a fragment hybridizes under high stringency conditions to antisense polynucleotide of an unoptimized polynucleotide sequence encoding an anti-CD96 (e.g., human CD96 or cynomolgus CD96) antibody described herein or a fragment thereof. In a specific embodiment, an optimized nucleotide sequence encoding an anti-CD96 (e.g., human CD96 or cynomolgus CD96) antibody described herein or a fragment thereof hybridizes under high stringency, intermediate or lower stringency hybridization conditions to an antisense polynucleotide of an unoptimized nucleotide sequence encoding an anti-CD96 (e.g., human CD96 or cynomolgus CD96) antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-CD96 (e.g., human CD96 or cynomolgus CD96) antibodies described herein can be readily isolated and sequenced using conventional procedures (e.g., by using oligonucleotide probes that are capable of binding specifically to genes encoding the heavy and light chains of the anti-CD96 (e.g., human CD96 or cynomolgus CD96) antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-CD96 (e.g., human CD96 or cynomolgus CD96) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to CD96 (e.g., human CD96 or cynomolgus CD96) and related polynucleotides and expression vectors. Provided herein are vectors (e.g., expression vectors) comprising polynucleotides comprising nucleotide sequences encoding anti-CD96 (e.g., human CD96 or cynomolgus CD96) antibodies or a fragment for recombinant expression in host cells, preferably in mammalian cells (e.g., CHO cells). Also provided herein are host cells comprising such vectors for recombinantly expressing anti-CD96 (e.g., human CD96 or cynomolgus CD96) antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to CD96 (e.g., human CD96 or cynomolgus CD96) generally involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122, 464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-CD96 (e.g., human CD96 or cynomolgus CD96) antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-CD96 (e.g., human CD96 or cynomolgus CD96) antibody described herein, and a second vector comprising a polynucleotide encoding a heavy chain/heavy chain variable region of an anti-CD96 (e.g., human CD96 or cynomolgus CD96) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with, e.g., recombinant bacteriophage DNA, plasmid DNA or cosmid DNA expression vectors containing antibody coding sequences; yeast (e.g., *Saccharomyces* and *Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to CD96 (e.g., human CD96 or cynomolgus CD96) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-CD96 (e.g., human CD96 or cynomolgus CD96) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-CD96 (e.g., human CD96 or cynomolgus CD96) antibody described herein can be engineered. In specific embodiments, a cell provided herein stably expresses a light chain/light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CD96 (e.g., human CD96 or cynomolgus CD96) antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, NY (1994); Colbère-Garapin F et al., (1981) J Mol Biol 150: 1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Kohler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to CD96 (e.g., human CD96 or cynomolgus CD96) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to CD96 (e.g., human CD96 or cynomolgus CD96) comprising culturing a cell or host cell described herein. In one embodiment, the method is performed in vitro. In a certain aspect, provided herein is a method of making an antibody which specifically binds to CD96 (e.g., human CD96 or cynomolgus CD96) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to CD96 (e.g., human CD96 or cynomolgus CD96) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding domains, each monovalent binding domain capable of binding to an epitope on the antigen. Each monovalent binding domain can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., CD96 (e.g., human CD96 or cynomolgus CD96)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., CD96 (e.g., human CD96 or cynomolgus CD96)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against CD96 (e.g., human CD96 or cynomolgus CD96). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize a specific CD96 (e.g., human CD96 or cynomolgus CD96), and which can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab)$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG1, IgG2, IgG3 and IgG4. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is herein incorporated by reference in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a CD96 (e.g., human CD96 or cynomolgus CD96) antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of CD96 (e.g., human CD96 or cynomolgus CD96) as an anti-CD96 (e.g., human CD96 or cynomolgus CD96) antibody described herein, is a human antibody. In particular embodiments, an antibody described herein, which competitively blocks (e.g., in a dose-dependent manner) any one of the antibodies described herein, from binding to CD96 (e.g., human CD96 or cynomolgus CD96), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., CD96 (e.g., human CD96 or cynomolgus CD96)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569, 825, 5,661,016, 5,545,806, 5,814,318 and 5,939,598, all of which are herein incorporated by reference in their entireties. Examples of mice capable of producing human antibodies include the Xenomouse™ (Abgenix, Inc.; U.S. Pat. Nos. 6,075,181 and 6,150,184), the HuAb-Mouse™ (Medarex, Inc./Gen Pharm; U.S. Pat. Nos. 5,545,806 and 5,569, 825), the Trans Chromo Mouse™ (Kirin) and the KM Mouse™ (Medarex/Kirin), all of which are herein incorporated by reference in their entireties.

Human antibodies that specifically bind to CD96 (e.g., human CD96 or cynomolgus CD96) can be made by a variety of methods known in the art including the phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., CD96 (e.g., human CD96 or cynomolgus CD96)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

5.6 Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated CD96 (e.g., human CD96 or cynomolgus CD96) antigen as a control. In another specific embodiment, the kits described herein further comprise a control antibody which does not react with a CD96 (e.g., human CD96 or cynomolgus CD96) antigen. In another specific embodiment, kits described herein contain one or more elements for detecting the binding of an antibody to a CD96 (e.g., human CD96 or cynomolgus CD96) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CD96 (e.g., human CD96 or cynomolgus CD96) antigen. The CD96 (e.g., human CD96 or cynomolgus CD96) antigen provided in the kit can also be attached to a solid support. In a more specific embodiment, the detecting means of the above described kit includes a solid support to which a CD96 (e.g., human CD96 or cynomolgus CD96) antigen is attached. Such a kit can also include a non-attached reporter-labeled anti-human antibody or anti-mouse/rat antibody. In this embodiment, binding of the antibody to the CD96 (e.g., human CD96 or cynomolgus CD96) antigen can be detected by binding of the said reporter-labeled antibody. In one embodiment, the present invention relates to the use of a kit of the present invention for in vitro assaying and/or detecting CD96 antigen (e.g., human CD96 or cynomolgus CD96) in a biological sample.

6. EXAMPLES

The examples in this Section (i.e., Section 6) are offered by way of illustration and not by way of limitation.

6.1 Example 1: Characterization of Anti-CD96 Antibodies

This example describes the characterization of antibodies that specifically bind to human CD96. The amino acid sequences of these antibodies are set forth in Table 1.
6.1.1 Anti-Human CD96 Antibodies Bind to Purified Human and Cynomolgus Monkey CD96 Protein
Binding of Parental and Germlined Anti-CD96 Antibodies to His-Tagged Isoform 2 of Human CD96 with a C89S Mutation The binding affinity of the parental antibody BA072, and the germline variants BA083 and BA084, to full-length isoform 2 of human CD96 with a C89S mutation (SEQ ID NO: 129) with a His tag, was assessed by surface plasmon resonance.

Briefly, surface plasmon resonance experiments were performed using a Biacore T200 instrument, and the association rate ($K_a$), dissociation rate ($K_d$), and dissociation constant ($K_D$) were calculated from each experiment using a 1:1 binding model with Biacore T200 Evaluation Software.

Approximately 4 μg/ml of BA072, BA083, BA084, BA0833 and BA0834 diluted in a running buffer (10 mM HEPES, 150 mM NaCl, 3 mM EDTA, and 0.05% surfactant P20) were captured in individual flow cells of a Series S Protein A Sensor Chip (GE Healthcare Ltd, cat #29-1275-56) keeping a single flow cell as a reference. Antibodies were captured using a 15 sec injection at a flow rate of 10 μl/min to reach about 150 resonance units (RUs). Full-length isoform 2 of human CD96 with a C89S mutation (SEQ ID NO: 129) with a His tag, diluted in the running buffer at the concentration of 0.41, 1.23, 3.7, 11.1, 33.3, 100, 300 nM, was flowed over the chip surface at a flow rate of 30 μl/min with a 3-min association phase and either a 10-min or 15-min dissociation phase. The sensor chip was regenerated between cycles with a 30-sec injection of 10 mM glycine, pH 1.5. Sensorgrams were evaluated and fit to a simple Langmuir 1:1 interaction model using the global data analysis option of BIAevaluation 3.1 software. Data quality was verified by visually inspecting deviations and curve fitting, and by evaluating the parameters of $R_{max}$, Chi2, and Tc. The binding kinetics ($K_a$, $K_d$ and $K_D$) were determined from the sensorgram analyses and are shown in Table 3.

TABLE 3

Kinetic parameters of anti-CD96 antibody binding to full-length isoform 2 of human CD96 with a C89S mutation (SEQ ID NO: 129).

| Antibody | $K_a$ (1/Ms) | $K_d$ (1/s) | $K_D$ (M) |
|---|---|---|---|
| BA072 | 8.95E+04 | 3.08E−04 | 4.34E−09 |
| BA083 | 1.71E+05 | 2.98E−04 | 3.11E−09 |
| BA084 | 8.98E+04 | 4.03E−04 | 4.80E−09 |

Binding of Parental and Germlined Anti-CD96 Antibodies to His Tagged Isoform 2 of Human CD96 with a C89S Mutation The binding affinity of the parental antibody BA101, and germline variants BA102, BA103, BA104, BA105, BA106 and BA107, to full-length isoform 2 of human CD96 with a C89S mutation (SEQ ID NO: 129) with a His tag, was assessed by surface plasmon resonance.

Briefly, surface plasmon resonance experiments were performed using a Biacore T200 instrument, and the association rate (Ka), dissociation rate (Kd), and dissociation constant ($K_D$) were calculated from each experiment using a 1:1 binding model with Biacore T200 Evaluation Software.

Approximately 4 μg/ml of BA102, BA103, BA104, BA105, BA106 and BA107 diluted in a running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56) keeping a single flow cell as a reference. Antibodies were captured using a 15 sec injection at a flow rate of 10 μl/min to reach about 200 resonance units (RUs). Full-length isoform 2 of human CD96 with a C89S mutation (SEQ ID NO: 129) with a His tag, diluted in the running buffer at the concentration of 0.41, 1.23, 3.7, 11.1, 33.3, 100, 300 nM, was flowed over the chip surface at a flow rate of 30 μl/min with a 3-min association phase and either a 10-min (for g16) or a 15-min dissociation phase. The sensor chip was regenerated between cycles with a 30-sec injection of 10 mM glycine, pH 1.5. Sensorgrams were evaluated and fit to a simple Langmuir 1:1 interaction model using the global data analysis option of BIAevaluation 3.1 software. Data quality was verified by visually inspecting deviations and curve fitting, and by evaluating the parameters of $R_{max}$, Chi2, and Tc. The binding kinetics (Ka, Kd and $K_D$) were determined from the sensorgram analyses and are shown in Table 4.

TABLE 4

Kinetic parameters of anti-CD96 antibody binding to full-length isoform 2 of human CD96 with a C89S mutation (SEQ ID NO: 129)

| Antibody | $K_a$ (1/Ms) | $K_d$ (1/s) | $K_D$ (M) |
|---|---|---|---|
| BA101 | 2.77E+05 | 9.57E−04 | 4.52E−09 |
| BA102 | 3.19E+05 | 8.34E−04 | 2.61E−09 |
| BA103 | 3.53E+05 | 0.001272 | 3.61E−09 |
| BA104 | 3.36E+05 | 9.90E−04 | 2.95E−09 |
| BA105 | 3.28E+05 | 8.41E−04 | 2.56E−09 |
| BA106 | 3.08E+05 | 8.72E−04 | 2.83E−09 |
| BA107 | 1.15E+05 | 1.59E−03 | 1.38E−08 |

Binding of Affinity-Matured Anti-CD96 Antibodies to His Tagged Domain 1 of Human CD96 with a C89S Mutation or to His-Tagged Domain 1 of Cynomolgus Monkey CD96

The binding affinity of the parental antibody BA072, the germlined antibody BA083, and the affinity-matured variants BA093, BA092, BA091, BA089, BA086, BA094, BA088, BA090, BA087, and BA085 to domain 1 of human CD96 with a C89S mutation (SEQ ID NO: 131) with a His tag, or domain 1 of cynomolgus monkey CD96 (SEQ ID NO: 134) with a His tag, was assessed by surface plasmon resonance. The affinity-matured variants were selected for increased affinity to cynomolgus monkey CD96.

Briefly, surface plasmon resonance experiments were performed using a Biacore T200 instrument, and the association rate ($K_a$), dissociation rate ($K_d$), and dissociation constant ($K_D$) were calculated from each experiment using a 1:1 binding model with Biacore T200 Evaluation Software.

Specifically, antibodies diluted in a running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56) keeping a single flow cell as a reference. Antibodies were captured using a 15 sec injection at a flow rate of 10 µl/min to reach capture levels optimal for kinetic analysis (about 430 RU). The concentration of antibody to reach the optimal capture level was determined separately for each experiment (with about 8 µg/ml used for each antibody). Domain 1 of human CD96 with a C89S mutation (SEQ ID NO: 131) with a His tag, or domain 1 of cynomolgus monkey CD96 (SEQ ID NO: 134) with a His tag, diluted in running buffer at the concentration of 0.41, 1.23, 3.7, 11.1, 33.3, 100, 300 nM, were flowed over the chip surface at a flow rate of 30 µl/min with a 3-min association phase and a 15-min dissociation phase. The sensor chip was regenerated between cycles with a 30-sec injection of 10 mM glycine, pH 1.5. Sensorgrams were evaluated and fit to a simple Langmuir 1:1 interaction model using the global data analysis option of BIAevaluation 3.1 software. Data quality was verified by visually inspecting deviations and curve fitting, and by evaluating the parameters of $R_{max}$, Chi2, and Tc. The binding kinetics ($K_a$, $K_d$ and $K_D$) were determined from the sensorgram analyses and are shown in Table 5 (human) and Table 6 (cynomolgus).

TABLE 5

Kinetic parameters of anti-CD96 antibody binding to domain 1 of human CD96 with a C89S mutation (SEQ ID NO: 131).

| Antibody | $K_a$ (1/Ms) | $K_d$ (1/s) | $K_D$ (M) |
| --- | --- | --- | --- |
| BA093 | 3.33E+05 | 4.32E−04 | 1.30E−09 |
| BA092 | 9.46E+05 | 4.66E−04 | 4.93E−10 |
| BA091 | 8.13E+05 | 4.35E−04 | 5.35E−10 |
| BA089 | 1.23E+07 | 2.16E−03 | 1.76E−09 |
| BA086 | 9.80E+05 | 4.40E−04 | 4.49E−10 |
| BA083 | 1.02E+06 | 4.99E−05 | 4.88E−10 |
| BA094 | 8.23E+05 | 4.53E−04 | 5.51E−10 |
| BA088 | 7.79E+05 | 4.04E−04 | 5.18E−10 |
| BA090 | 7.75E+05 | 4.58E−04 | 9.13E−10 |
| BA087 | 6.43E+05 | 4.10E−04 | 6.39E−10 |
| BA085 | 6.43E+05 | 3.94E−04 | 6.12E−10 |
| BA072 | 6.87E+05 | 4.20E−04 | 6.11E−10 |

TABLE 6

Kinetic parameters of anti-CD96 antibody binding to domain 1 of cynomolgus monkey CD96 (SEQ ID NO: 134).

| Antibody | $K_a$ (1/Ms) | $K_d$ (1/s) | $K_D$ (M) |
| --- | --- | --- | --- |
| BA093 | 3.95E+05 | 4.10E−04 | 1.04E−09 |
| BA092 | 2.33E+05 | 5.46E−04 | 2.44E−09 |
| BA091 | 3.36E+05 | 3.70E−04 | 1.10E−09 |
| BA089 | 4.72E+05 | 4.14E−04 | 8.77E−09 |

TABLE 6-continued

Kinetic parameters of anti-CD96 antibody binding to domain 1 of cynomolgus monkey CD96 (SEQ ID NO: 134).

| Antibody | $K_a$ (1/Ms) | $K_d$ (1/s) | $K_D$ (M) |
| --- | --- | --- | --- |
| BA086 | 3.03E+05 | 7.69E−04 | 2.54E−09 |
| BA083 | 4.23E+05 | 3.39E−03 | 8.03E−09 |
| BA094 | 3.69E+05 | 5.42E−04 | 1.47E−09 |
| BA088 | 3.43E+05 | 7.73E−04 | 2.26E−09 |
| BA090 | 3.57E+05 | 1.40E−03 | 3.93E−09 |
| BA087 | 3.67E+05 | 3.94E−04 | 1.075 − 9 |
| BA085 | 3.14E+05 | 5.33E−04 | 1.70E−09 |
| BA072 | 4.33E+05 | 5.09E−03 | 1.18E−08 |

Binding of Affinity-Matured Anti-CD96 Antibodies to His Tagged Domain 1 of Human CD96 with a C89S Mutation or to His-Tagged Domain 1 of Cynomolgus Monkey CD96

The binding affinity of the parental antibody BA072, the germlined antibody BA083, and affinity-matured variants BA073, BA074, BA078, BA079, BA080, BA081, BA076, BA077, BA082, BA075 to domain 1 of human CD96 with a C89S mutation (SEQ ID NO: 131) with a His tag, or domain 1 of cynomolgus monkey CD96 (SEQ ID NO: 134) with a His tag, was assessed by surface plasmon resonance. The affinity-matured variants were selected for increased affinity to cynomolgus monkey CD96.

Briefly, surface plasmon resonance experiments were performed using a Biacore T200 instrument, and the association rate ($K_a$), dissociation rate ($K_d$), and dissociation constant ($K_D$) were calculated from each experiment using a 1:1 binding model with Biacore T200 Evaluation Software.

Specifically, antibodies diluted in a running buffer (10 mM HEPES, 150 mM NaCl, 3 mM EDTA, and 0.05% surfactant P20) were captured on individual flow cells of a Series S Protein A Sensor Chip (GE Healthcare Ltd, cat #29-1275-56) keeping a single flow cell as a reference. Antibodies were captured using a 15 sec injection at a flow rate of 10 µl/min to reach capture levels optimal for kinetic analysis (about 250 RU). The concentration of antibody to reach the optimal capture level was determined separately for each experiment (with about 4 µg/ml used for each antibody). Domain 1 of human CD96 with a C89S mutation (SEQ ID NO: 131) with a His tag, or domain 1 of cynomolgus monkey CD96 (SEQ ID NO: 134) with a His tag, diluted in running buffer at the concentration of 0.75, 1.56, 3.13, 6.25, 12.5, 25, 50, 100 nM, were flowed over the chip surface at a flow rate of 30 µl/min with a 3-min association phase and a 15-min dissociation phase. The sensor chip was regenerated between cycles with a 30-sec injection of 10 mM glycine, pH 1.5. Sensorgrams were evaluated and fit to a simple Langmuir 1:1 interaction model using the global data analysis option of BIAevaluation 3.1 software. Data quality was verified by visually inspecting deviations and curve fitting, and by evaluating the parameters of $R_{max}$, Chi2, and Tc. The binding kinetics ($K_a$, $K_d$ and $K_D$) were determined from the sensorgram analyses and are shown in Table 7 (human) and Table 8 (cynomolgus).

TABLE 7

Kinetic parameters of anti-CD96 antibody binding to domain 1 of human CD96 with a C89S mutation (SEQ ID NO: 131).

| Antibody | $K_a$ (1/Ms) | $K_d$ (1/s) | $K_D$ (M) |
|---|---|---|---|
| BA073 | 9.32E+05 | 3.25E−04 | 3.48E−10 |
| BA074 | 9.15E+05 | 4.42E−04 | 4.83E−10 |
| BA078 | 8.32E+05 | 3.57E−04 | 4.29E−10 |
| BA079 | 5.54E+05 | 3.18E−04 | 5.75E−10 |
| BA080 | 9.95E+05 | 4.41E−04 | 4.43E−10 |
| BA081 | 7.80E+05 | 4.60E−04 | 5.90E−10 |
| BA076 | 6.67E+05 | 2.77E−04 | 4.15E−10 |
| BA077 | 5.65E+05 | 3.01E−04 | 5.32E−10 |
| BA082 | 7.53E+05 | 4.39E−04 | 5.83E−10 |
| BA075 | 5.29E+05 | 3.83E−04 | 7.25E−10 |
| BA083 | 1.14E+06 | 4.91E−04 | 4.31E−10 |
| BA072 | 9.69E+05 | 5.01E−04 | 5.17E−10 |

TABLE 8

Kinetic parameters of anti-CD96 antibody binding to domain 1 of cynomolgus monkey CD96 (SEQ ID NO: 134).

| Antibody | $K_a$ (1/Ms) | $K_d$ (1/s) | $K_D$ (M) |
|---|---|---|---|
| BA073 | 5.38E+05 | 2.36E−04 | 4.38E−10 |
| BA074 | 4.59E+05 | 2.18E−04 | 4.74E−10 |
| BA078 | 5.11E+05 | 2.79E−04 | 5.46E−10 |
| BA079 | 4.46E+05 | 2.66E−04 | 5.97E−10 |
| BA080 | 5.31E+05 | 2.86E−04 | 5.40E−10 |
| BA081 | 4.05E+05 | 3.06E−04 | 7.55E−10 |
| BA076 | 3.46E+05 | 2.25E−04 | 6.50E−10 |
| BA077 | 2.90E+05 | 2.17E−04 | 7.47E−10 |
| BA082 | 4.91E+05 | 2.85E−04 | 5.81E−10 |
| BA075 | 2.81E+05 | 2.75E−04 | 9.78E−10 |
| BA083 | 4.40E+05 | 0.003536 | 8.04E−09 |
| BA072 | 5.18E+05 | 0.006013 | 1.16E−08 |

6.1.2 Anti-Human CD96 Antibodies Bind to Cells Expressing Human and Cynomolgus Monkey CD96

The capacity of the human anti-CD96 IgG1 antibodies to bind to cells expressing human CD96 or cynomolgus monkey CD96 was tested in a variety of cell types.

Binding of Anti-CD96 Antibodies to Jurkat Cells Expressing Isoform 2 of Human CD96

The ability of the parental antibodies BA072 and BA101 to bind to isoform 2 of human CD96 expressed on the surface of Jurkat cells was assessed. Briefly, Jurkat cells were transfected with a vector encoding full-length isoform 2 of human CD96 (SEQ ID NO: 128), and a clone stably expressing a high level of CD96 was selected. This stable cell line was cultured in RPMI-1640 medium supplemented with 10% heat-inactivated FBS and 1% puromycin (R10 media).

For the antibody binding assay, the cells were seeded in a 96-well U-bottom tissue culture plate at a density of 5×10⁴ cells per well and were incubated for 30 minutes at 4° C. with a series dilution of BA072, BA101, or isotype control antibody at concentrations from 10 μg/mL to 0.3 ng/mL diluted in PBS supplemented with 2% heat-inactivated FBS (FACS Buffer).

For antibody staining, the cells were washed twice with cold FACS Buffer and resuspended in FACS Buffer containing R-Phycoerythrin goat anti-human IgG (Fab'2) (Fitzgerald/43C-CJ0123) at 1:20 dilution. After a 10-minute incubation 4° C., the cells were washed twice with cold FACS Buffer, and the cells were analyzed by flow cytometry (BD LSR Fortessa Flow Cytometer). Unstained control cells were used to gate on the lymphocyte population using a plot of forward scatter-area (FSC-A) versus side scatter area (SSC-A) and another plot of FSC-A versus FSC-height (FSC-H) for selection of single cells. Samples were analyzed by sequentially gating on the following populations: FSC-A vs SSC-A, FSC-H vs FSC-A, and SSC-A vs PE. Mean fluorescence intensity (MFI) was calculated and the data were plotted by GraphPad Prism software.

As shown in FIG. 1A and FIG. 1B, BA072 (FIG. 1A) and BA101 (FIG. 1B) bound to human CD96-expressing Jurkat cells in a dose-dependent manner. The calculated area under the curve (AUC) and EC50 values for the anti-CD96 antibodies presented in FIGS. 1A and 1B are listed in Table 9 and Table 10.

TABLE 9

AUC values for anti-CD96 antibodies in FIGS. 1A and 1B.

| Antibody | Area under the curve (AUC) | Standard error |
|---|---|---|
| BA072 | 417270 | 2658 |
| BA101 | 733360 | 10440 |
| Isotype | 4763 | 359.5 |

TABLE 10

EC50 values for anti-CD96 antibodies in FIGS. 1A and 1B.*

| Antibody | $EC_{50}$ (ng/ml) | 95% CI (ng/ml) |
|---|---|---|
| BA072 | 28.23 | 23.45-33.91 |
| BA101 | 157.2 | 144-171.6 |

*Calculated from 2 experiments.

Binding of Anti-CD96 Antibodies to CHO Cells Expressing Isoform 1 of Human CD96 or Isoform 2 of Human CD96

The ability of the parental antibodies BA072 and BA101 to bind to human CD96 expressed on the surface of CHO cells was assessed. Briefly, CHO cells were transfected with a vector encoding full-length isoform 1 of human CD96 (SEQ ID NO: 127) or full-length isoform 2 of human CD96 (SEQ ID NO: 128), and clones stably expressing CD96 isoform 1 or isoform 2 were selected. These stable cell lines were cultured in Power CHO-2 medium containing 4 mM L-Glutamine, 100 U/mL Penicillin, 100 μg/mL Streptomycin, 1×HT-Supplement, and 2.5 μg/ml Puromycin.

For the antibody binding assay, a frozen aliquot of human CD96-CHO cells (isoform 1 or isoform 2) was thawed at 37° C. and then transferred to a tube containing PBS supplemented with 0.5% Bovine Serum Albumin and 0.05% Sodium Azide (FACS Buffer). Cells were centrifuged at 300 g for five minutes. The supernatant was discarded, and cells resuspended in FACS buffer were seeded in a 96-well U-bottom tissue culture plate at a density of 2×10⁵ cells per well in 50 μL. In a separate microplate, a 2× concentrated intermediate stock of each antibody (i.e., BA072, BA101 and isotype control) was prepared. Antibodies were serially diluted 1-to-3 in FACS buffer. A total of 11 working dilutions ranging from 60 μg/mL to 0.000339 μg/mL was prepared. Fifty μL of each dilution were then transferred to the microplate containing human CD96-CHO cells. The cells were then incubated for 30 minutes at 4° C. For antibody staining, the cells were washed twice with cold FACS Buffer and re-suspended in FACS Buffer containing R-Phycoerythrin (PE) AffiniPure F(ab')₂ Fragment Goat Anti-Human IgG, Fcγ fragment specific (Jackson, Cat ##109-116-098) at a 1:800 final dilution. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating the FSC-A vs. SSC-A, and SSC-H vs SSC-A. Mean fluorescence intensity (MFI) values for PE were calculated, and the data were plotted by GraphPad Prism software. The software was used to determine the concentration of antibody resulting in 50% of maximal binding (Effective Concentration 50, [EC50]) by curve fitting using a four-parameter logistic equation.

Figure 2A:
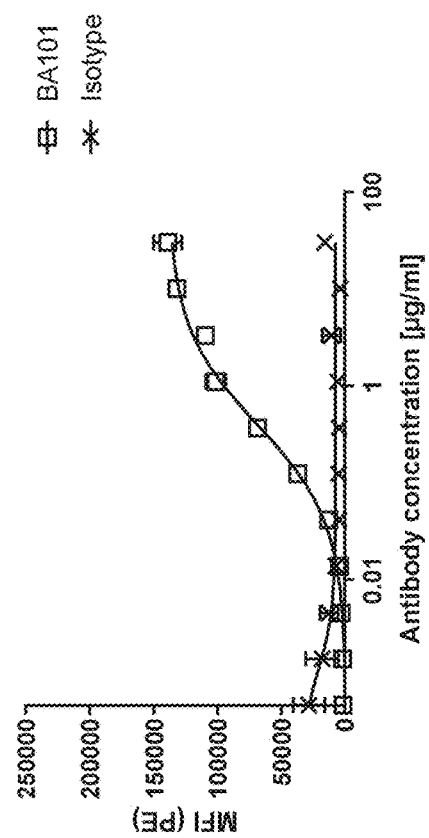
Figure 2B:
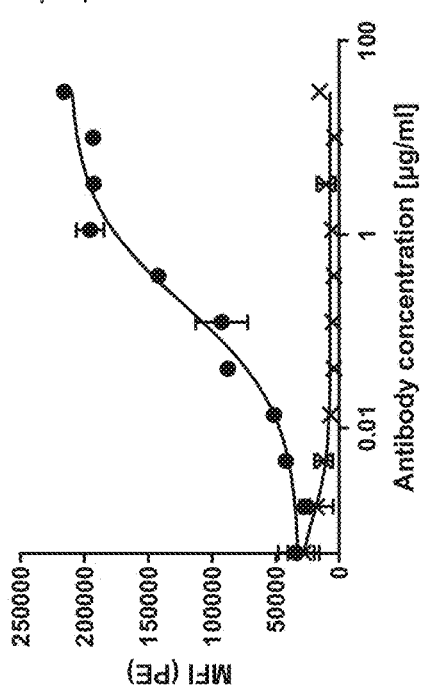

As shown in FIG. 2A and FIG. 2B, BA072 (FIG. 2A) and BA101 (FIG. 2B) bound to CHO cells expressing full-length isoform 1 of human CD96 (SEQ ID NO: 127) in a dose-dependent manner. The calculated area under the curve (AUC) and EC50 values for the anti-CD96 antibodies presented in FIGS. 2A and 2B are listed in Table 11 and Table 12.

TABLE 11

AUC values for anti-CD96 antibodies in FIGS. 2A and 2B.

| Antibody | Area under the curve (AUC) | Standard error |
|---|---|---|
| BA072 | 548231 | 12784 |
| BA101 | 257360 | 6734 |
| Isotype | 43478 | 9434 |

TABLE 12

EC50 values for anti-CD96 antibodies in FIGS. 2A and 2B.*

| Antibody | $EC_{50}$ (ng/ml) | 95% CI (ng/ml) |
|---|---|---|
| BA072 | 258 | 169-393 |
| BA101 | 393 | 185-834 |

*Calculated from 4 experiments.

As shown in FIG. 3A and FIG. 3B, BA072 (FIG. 3A) and BA101 (FIG. 3B) bound to CHO cells expressing full-length isoform 2 of human CD96 (SEQ ID NO: 128) in a dose-dependent manner. The calculated area under the curve (AUC) and EC50 values for the anti-CD96 antibodies presented in FIGS. 3A and 3B are listed in Table 13 and Table 14.

TABLE 13

AUC values for anti-CD96 antibodies in FIGS. 3A and 3B.

| Antibody | Area under the curve (AUC) | Standard error |
|---|---|---|
| BA072 | 122641 | 3382 |
| BA101 | 115846 | 2318 |
| Isotype | 5811 | 851.6 |

TABLE 14

EC50 values for anti-CD96 antibodies in FIGS. 3A and 3B.*

| Antibody | $EC_{50}$ (ng/ml) | 95% CI (ng/ml) |
|---|---|---|
| BA072 | 221 | 17-2932 |
| BA101 | 348 | 89-1352 |

*Calculated from 3 experiments.

Binding of Anti-CD96 Antibodies to CHO Cells Expressing Isoform 2 of Cynomolgus Monkey CD96

In similar experiments to those described in this section above, the capacity of parental antibodies BA072 and BA101 to bind to CHO cells engineered to express isoform 2 of cynomolgus monkey CD96 (SEQ ID NO: 133) on their cell surfaces was tested. Briefly, CHO cells were transfected with a vector encoding isoform 2 of cynomolgus monkey CD96, and a clone stably expressing CD96 was selected. This stable cell line was cultured in Power CHO-2 medium containing 4 mM L-Glutamine, 100 U/mL Penicillin, 100 μg/mL Streptomycin, 1×HT-Supplement, and 2.5 μg/ml Puromycin. The ability of antibodies BA072 and BA101 to bind to isoform 2 of cynomolgus monkey CD96-CHO was determined as described for human CD96-CHO cells above.

As shown in FIG. 4A and FIG. 4B, BA072 (FIG. 4A) and BA101 (FIG. 4B) bound to CHO cells expressing isoform 2 of cynomolgus monkey CD96 (SEQ ID NO: 133) in a dose-dependent manner. The calculated area under the curve (AUC) and EC50 values for the anti-CD96 antibodies presented in FIGS. 4A and 4B are listed in Table 15 and Table 16.

TABLE 15

AUC values for anti-CD96 antibodies in FIGS. 4A and 4B.

| Antibody | Area under the curve (AUC) | Standard error |
|---|---|---|
| BA072 | 160331 | 3674 |
| BA101 | 21400 | 689.3 |
| Isotype | 6028 | 1824 |

TABLE 16

EC50 values for anti-CD96 antibodies in FIGS. 4A and 4B.*

| Antibody | $EC_{50}$ (ng/ml) | 95% CI (ng/ml) |
|---|---|---|
| BA072 | 29 | 4-200 |
| BA101 | N/A | N/A |

*Calculated from 3 experiments.

Binding of Anti-CD96 Antibodies to Activated Primary Human Cells

In this experiment the capacity of anti-CD96 antibodies to bind to activated human T cells was tested.

For activated T cells, a frozen aliquot of human PBMC was retrieved from liquid nitrogen and immediately thawed in 37° C. water until floating ice was observed. T cells were isolated using the Pan T Cell Isolation Kit (Miltenyi Biotec/130-096-535). T cells were then transferred to 10 mL of pre-warmed R10 media. 20 μL was removed and added to 380 μL viability dye to count cells and check viability using a Muse apparatus. Samples were centrifuged at 1200 rpm for five minutes and then suspended to a final concentration of 1×10$^6$ cells/mL with R10 media.

Concanavalin A (Sigma/C-5275) was added to isolated T cells prepared as described above to a final concentration of 5 μg/ml with 50 U of IL-2 (R&D Systems/202-IL) and 100 μL of stimulated cells were pipetted into each well of a 96 well round-bottom tissue culture plate and incubated at 37° C. in 5% $CO_2$ for eight days.

A dose range of antibody was prepared in a 96-well round bottom plate. First, 600 μL of 50 μg/ml of each antibody (i.e., BA072, BA101, or an IgG1 isotype control) was prepared in buffer. Antibodies were then titrated with three-fold dilutions by pipetting 200 μL of the previous dilution into 400 µL of sample buffer. A total of 9 dilutions ranging from 10 µg/ml to 0.3 ng/mL were prepared.

After eight days, the sample plate was centrifuged for two minutes at 2000 rpm, and supernatants were discarded. Samples were stained with LIVE/DEAD® Fixable Near-IR Dead Cell Stain (Life Technologies/L10119) in PBS for 10 minutes. Sample plates were then centrifuged for two minutes at 2000 rpm, and the supernatant was discarded. The cells were then resuspended in 100 µL of BA072, BA101 or an IgG1 isotype control at the concentrations shown in FIG. 5, FIG. 6, and FIG. 7. Sample plates were incubated for 20 minutes at 4° C. Cells were washed by addition of cold sample buffer and centrifuged for two minutes at 2000 rpm, and the supernatant was discarded. This wash was repeated once.

A final cocktail of PE-labeled secondary anti-human IgG (Fab'2) antibody was prepared in 11 mL of FACs buffer. 50 µL of secondary antibody was added per well to a round-bottom 96-well plate. After a 10-minute incubation at 4° C., the cells were washed twice with cold FACS Buffer and resuspended in 1.6% paraformaldehyde in PBS.

Antibody binding was measured by flow cytometry using a BD LSR Fortessa Flow Cytometer. Unstained control cells were used to gate on the lymphocyte population using a plot of FSC-A versus side scatter area SSC-A and another plot of FSC-A versus FSC-H for selection of single cells. Tubes of cells stained with each individual antibody were used to calculate compensation of the various colors used in the experiment. 50,000 events were recorded for each sample. Samples were analyzed by sequentially gating on the following populations: FSC-A vs SSC-A, FSC-H vs FSC-A, SSC-A vs LIVE/DEAD, and SSC-A vs PE. MFI was calculated.

Figure 5A:
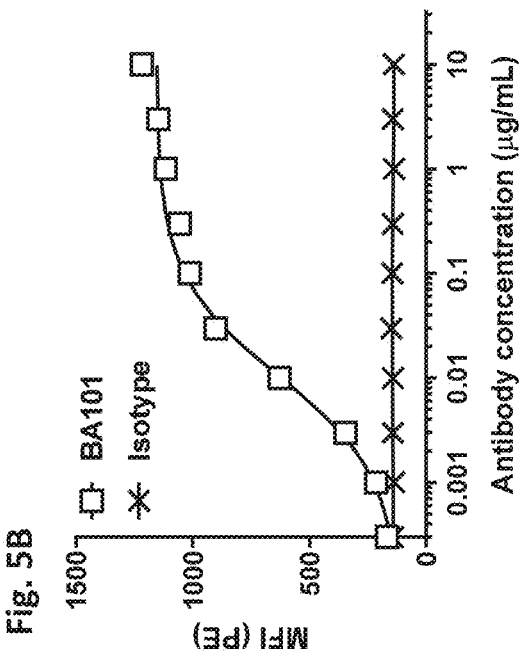
Figure 5B:
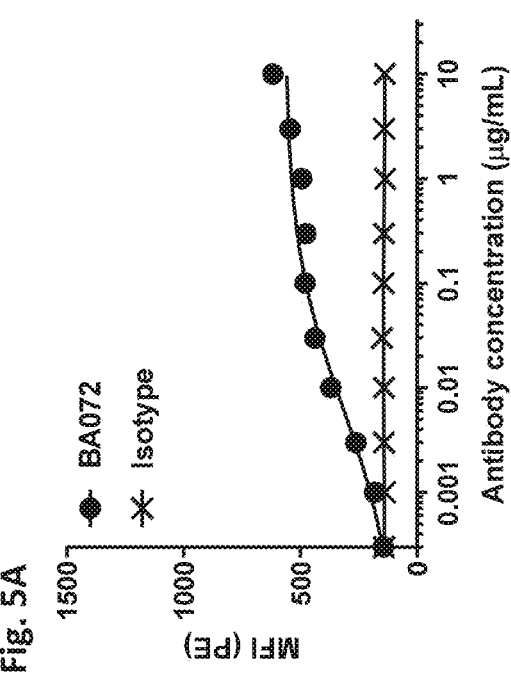

As shown in FIG. 5A and FIG. 5B, BA072 (FIG. 5A) and BA101 (FIG. 5B) bound to activated primary human T cells expressing CD96 in a dose-dependent manner. The calculated area under the curve (AUC) and EC50 values for the anti-CD96 antibodies presented in FIGS. 5A and 5B are listed in Table 17 and Table 18.

TABLE 17

AUC values for anti-CD96 antibodies in FIGS. 5A and 5B.

| Antibody | Area under the curve (AUC) | Standard error |
|---|---|---|
| BA072 | 5587 | 57.92 |
| BA101 | 11603 | 207.5 |
| Isotype | 1409 | 90.83 |

TABLE 18

EC50 values for anti-CD96 antibodies in FIGS. 5A and 5B.

| Antibody | $EC_{50}$ (ng/ml) | 95% CI (ng/ml) |
|---|---|---|
| BA072 | 6.67 | 3.61-14.74 |
| BA101 | 10.54 | 8.58-12.95 |

Figure 6A:
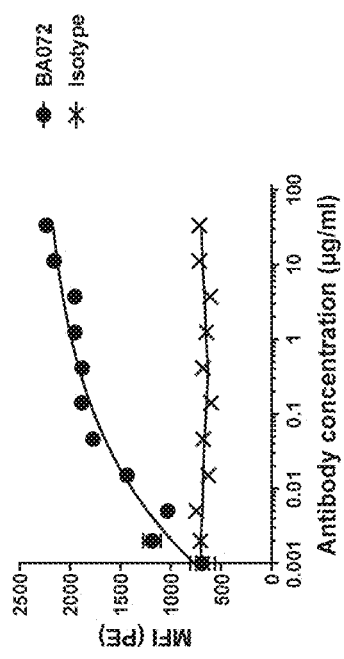
Figure 6B:
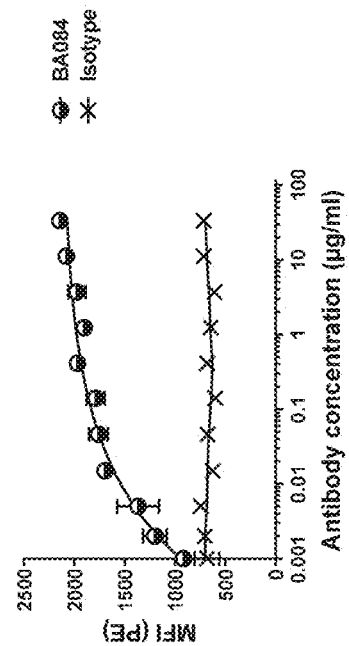
Figure 6C:
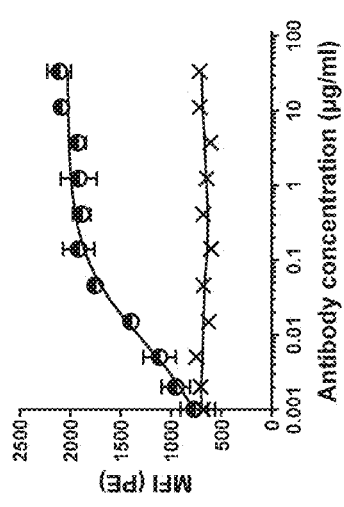
Figure 8A:
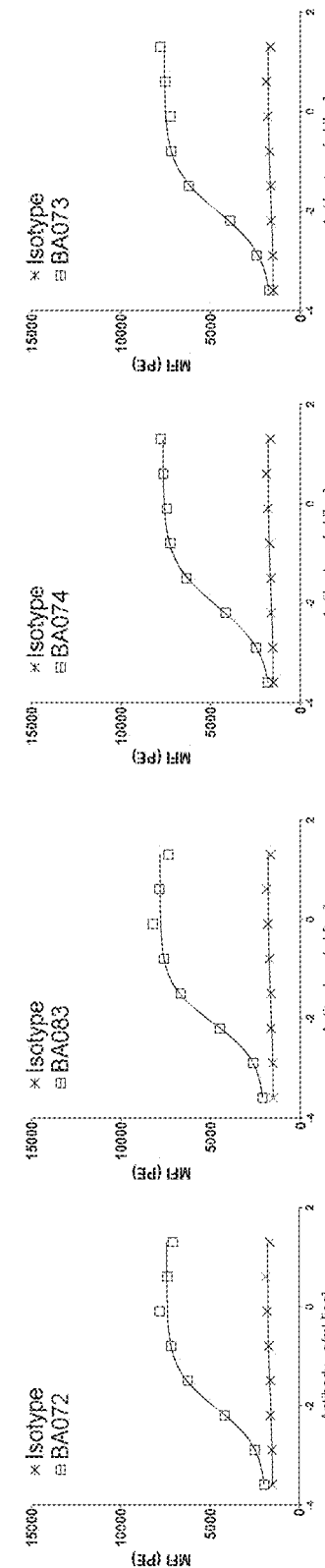
Figure 8B:
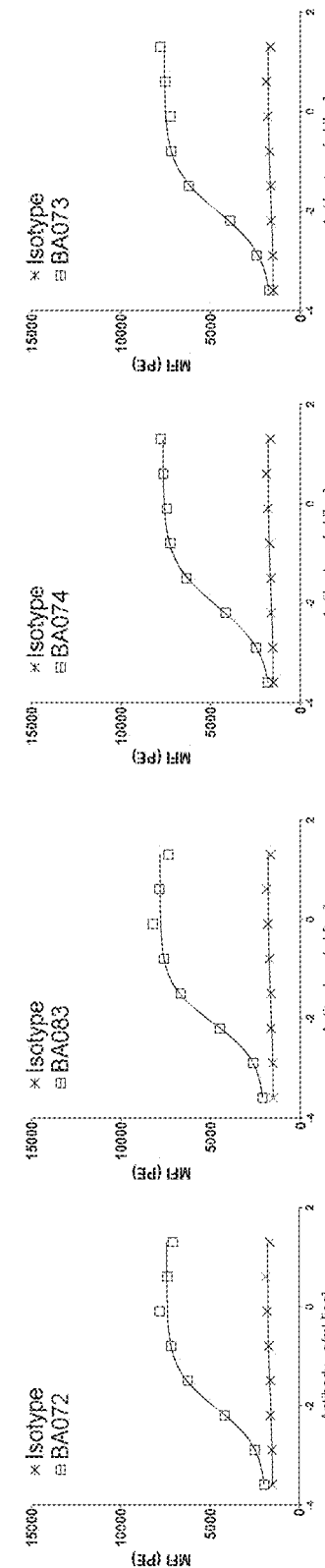
Figure 8C:
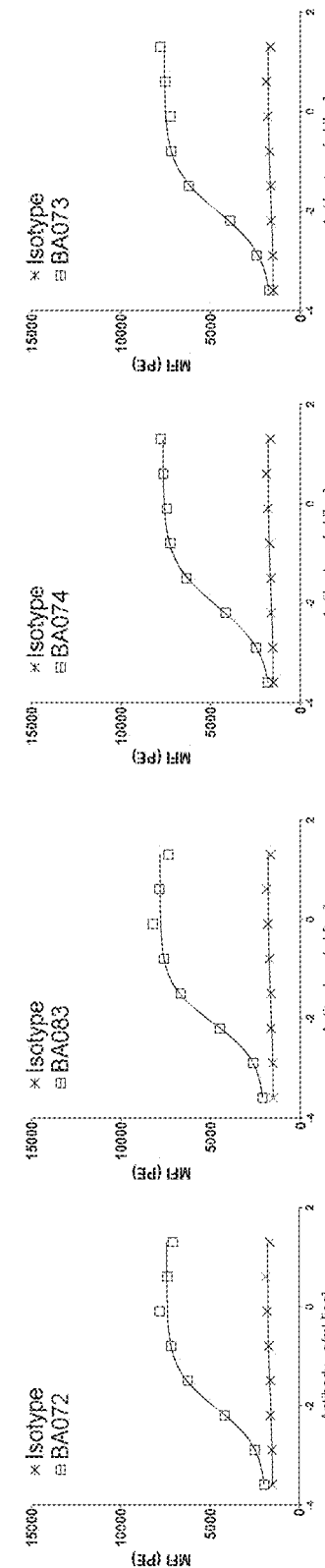
Figure 8D:
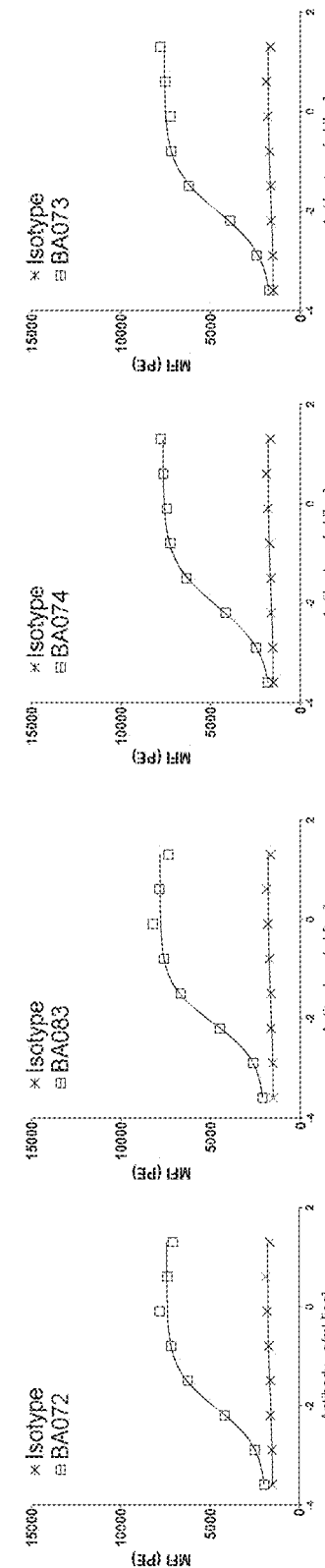
Figure 8E:
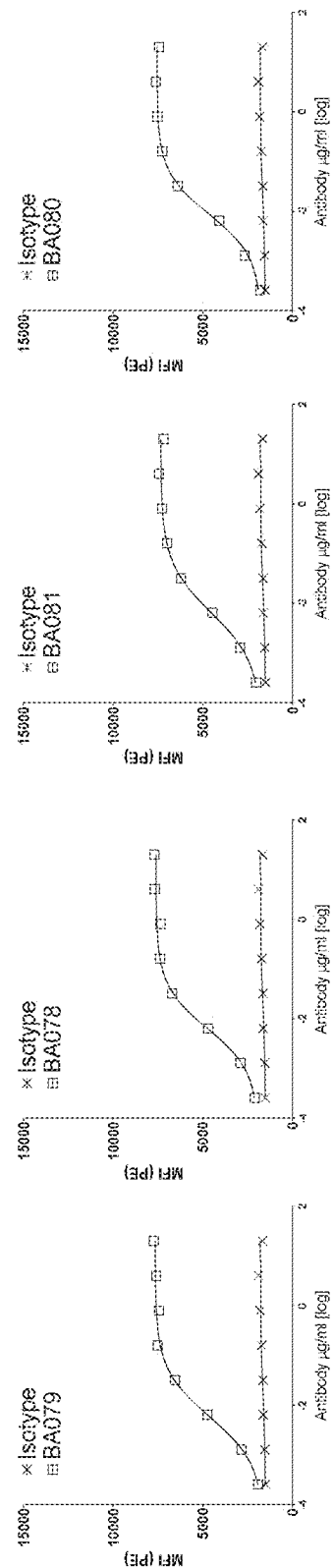
Figure 8F:
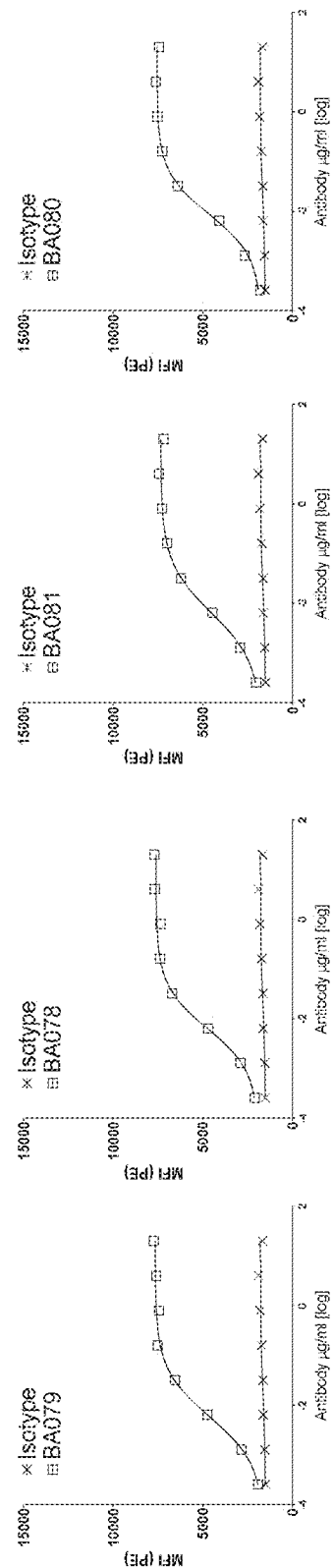
Figure 8G:
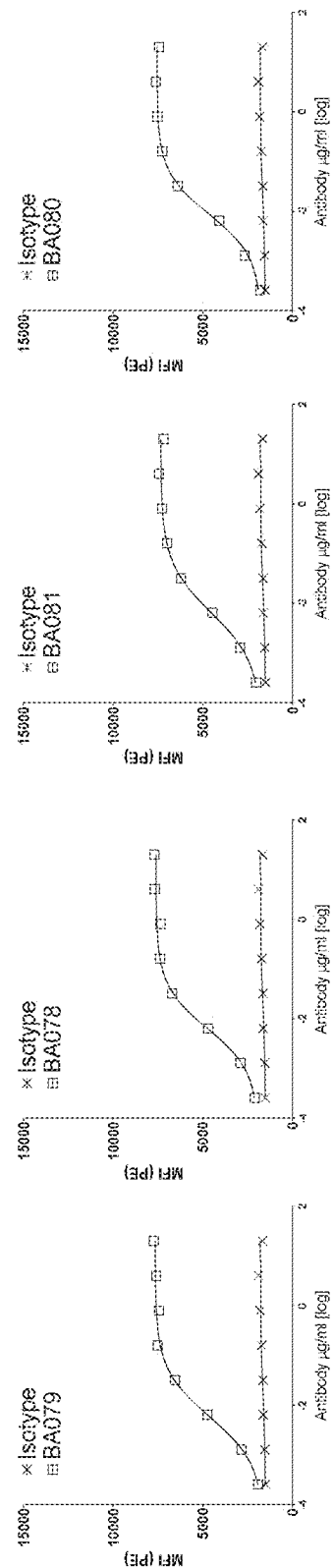
Figure 8H:
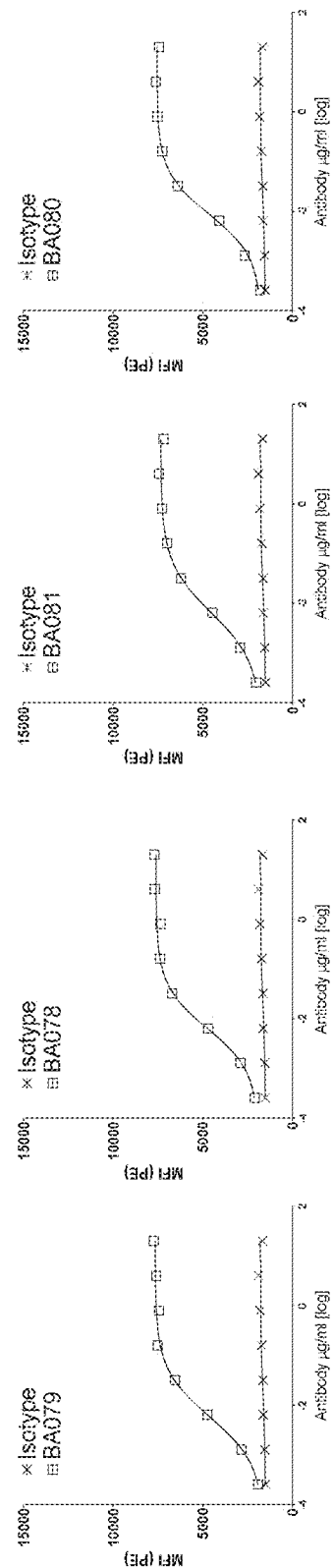

As shown in FIGS. 6A-6C, BA072 (FIG. 6A), BA083 (FIG. 6B), and BA084 (FIG. 6C) bound to activated primary human T cells in a dose-dependent manner. The calculated area under the curve (AUC) values for the anti-CD96 antibodies presented in FIGS. 6A-C are listed in Table 19.

TABLE 19

AUC values for anti-CD96 antibodies in FIGS. 6A-C.

| Antibody | Area under the curve (AUC) | Standard error |
|---|---|---|
| BA072 | 71147 | 714.2 |
| BA083 | 68546 | 2250 |
| BA084 | 69040 | 775.7 |
| Isotype | 23135 | 515.5 |

As shown in FIGS. 7A-F, BA101 (FIG. 7A), BA102 (FIG. 7B), BA103 (FIG. 7C), BA104 (FIG. 7D), BA105 (FIG. 7E), and BA106 (FIG. 7F) bound to activated primary human T cells in a dose-dependent manner. The calculated area under the curve (AUC) values for the anti-CD96 antibodies presented in FIGS. 7A-F are listed in Table 20.

TABLE 20

AUC values for anti-CD96 antibodies in FIGS. 7A-F.

| Antibody | Area under the curve (AUC) | Standard error |
|---|---|---|
| BA101 | 120826 | 1037 |
| BA102 | 124947 | 2067 |
| BA103 | 123323 | 1053 |
| BA104 | 122312 | 1367 |
| BA105 | 123476 | 1864 |
| BA106 | 125241 | 4917 |
| Isotype | 23135 | 515.5 |

Binding of Affinity-Matured Anti-CD96 Antibodies to Activated Primary Human Cells The capacity of BA072, BA083, BA073, BA074, BA078, BA079, BA080, BA081, BA076, BA077, BA075, BA082, and BA101 to bind to NY-ESO-1 transfected CD8$^+$ T cells was tested. Briefly, a frozen aliquot of NY-ESO-1 transduced T cells was retrieved from liquid nitrogen and immediately thawed in 37° C. water until floating ice was observed. Cells were then transferred to 9 mL of pre-warmed R10 NY-ESO-1 media. Samples were centrifuged at 300 g for 5 minutes and then suspended to a final concentration of 1×10$^6$ cells/mL with R10 media. T cells were added at a 1:1 dilution to tissue culture flasks that contain irradiated U251MG cell transduced with NY-ESO-1 peptide and incubated in a tissue culture incubator at 37° C. in 5% CO$_2$ until all U251MG cells were killed. The T cells were transferred to a flask with fresh irradiated U251MG NYESO cells and the incubation repeated. This cycle was repeated 3 times over 8 days.

A dose range of antibody was prepared in a 96 well round bottom plate. First, 300 µL of 40 µg/mL of each antibody was prepared in buffer. Antibodies were then serially diluted 1-to-5 by pipetting 62.5 µL of the previous dilution into 250 µL of sample buffer. A total of 8 dilutions ranging from 40 µg/mL to 0.000512 µg/mL were prepared. Activated T cells from above were stained with 2 µL LIVE/DEAD® Fixable Near-IR Dead Cell Stain (Life Technologies, Cat #L10119) in 500 µL PBS for 15 minutes at 4° C. The cells were brought up to 10 mL with PBS and then centrifuged at 300 g for 5 minutes and the supernatant was discarded. The cells were resuspended in 500 µL cold FACS buffer and incubated with Human TruStain FcX™ (Fc Receptor Blocking Solution, BioLegend, Cat #422302) diluted 1:10 for 15 minutes at 4° C. The cells were then re-suspended in 15 mL of FACS buffer and 50 incubated with Human TruStain FcX™ (Fc Receptor Blocking Solution, BioLegend, Cat #422302)

diluted 1:50 added to 50 µL of anti-CD96 antibody or a relevant isotype control at the concentrations shown in FIGS. 8A-8M. Sample plates were incubated for 60 minutes at 4° C. Cells were washed by addition of cold sample buffer and centrifuged for 5 minutes at 300 g, and the supernatant was discarded. This wash was repeated once.

Cells were then resuspended in a cocktail of fluorescently labeled antibodies. For antibody staining, the cells were washed twice with cold FACS Buffer and re-suspended in FACS A cocktail of fluorescently labeled antibodies sufficient for all samples was prepared in FACs buffer. 50 µL of buffer containing R-Phycoerythrin AffiniPure F(ab')2 Fragment Donkey Anti-Human IgG (H+L) (Jackson, Cat #09-116-149) at 1:100 dilution and CD4 BUV496 at 1:200 dilution and CD8 APC at 1:200 dilution was then added to the sample plate. The sample plate was incubated for 30 minutes on ice. Cells were washed by addition of cold sample buffer, centrifuged for 5 minutes at 300 g, and supernatants discarded. This wash was repeated once. Cells were resuspended in 1.6% PFA in FAC buffer.

Antibody binding was measured by flow cytometry using a BD LSR Fortessa Flow Cytometer. Unstained control cells were used to gate on the lymphocyte population using a plot of forward scatter-area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 20,000 events were recorded for each sample. Samples were analyzed by sequentially gating on the following populations: FSC-A vs SSC-A, FSC-H vs FSC-A, SSC-A vs LIVE/DEAD and CD4 vs CD8. Mean fluorescence intensity (MFI) of PE was calculated.

As shown in FIGS. 8A-8M, BA072 (FIG. 8A), BA083 (FIG. 8B), BA074 (FIG. 8C), BA073 (FIG. 8D), BA079 (FIG. 8E), BA078 (FIG. 8F), BA081 (FIG. 8G), BA080 (FIG. 8H), BA077 (FIG. 8I), BA076 (FIG. 8J), BA082 (FIG. 8K), BA075 (FIG. 8L), and BA101 (FIG. 8M) bound to NY-ESO-1 transfected CD8+ T cells in a dose-dependent manner. The calculated area under the curve (AUC) values for the anti-CD96 antibodies presented in FIGS. 8A-8M are listed in Table 21. The experiment was performed twice, and results presented for a single repeat are representative.

TABLE 21

AUC values for anti-CD96 antibodies in FIGS. 8A-8M.

| Antibody | Area under the curve (AUC) | Standard error |
| --- | --- | --- |
| BA072 | 146011 | 2840 |
| BA083 | 153719 | 705.1 |
| BA073 | 152117 | 1510 |
| BA074 | 153273 | 847.4 |
| BA078 | 152808 | 731.6 |
| BA079 | 152593 | 1000 |
| BA080 | 150253 | 736.6 |
| BA081 | 146170 | 1925 |
| BA076 | 168753 | 777.1 |
| BA077 | 166930 | 1468 |
| BA082 | 168052 | 853 |
| BA075 | 170820 | 1379 |
| BA101 | 248634 | 3574 |
| Isotype | 35746 | 647.6 |

Binding of Anti-CD96 Antibodies to Activated Primary Cynomolgus Monkey Cells

In this example, the capacity of BA072 and BA101 to bind to activated cynomolgus monkey cells was tested.

A frozen aliquot of cynomolgus peripheral blood mononuclear cells (PBMC) was retrieved from liquid nitrogen and immediately thawed in 37° C. water until floating ice was observed. Cells were then transferred to 9 mL of pre-warmed R10 media. 20 µL was removed and added to 380 µL viability dye to count cells and check viability using a Muse apparatus. Samples were centrifuged at 2000 rpm for two minutes and then suspended to a final concentration of $1\times10^6$ cells/mL with R10 media.

Concanavalin A (Sigma/C-5275) was added to the PBMC cells prepared as described above to a final concentration of 5 µg/ml with 50 U of IL-2 (R&D Systems/202-IL) and 100 µL of stimulated cells were pipetted to each well of a 96-well round-bottom tissue culture plate and incubated at 37° C. in 5% $CO_2$ for eight days.

A dose range of antibody was prepared in a 96 well round bottom plate. First, 600 µL of 50 µg/ml of each antibody (i.e., BA072, BA101 or an IgG1 isotype control) was prepared in buffer. Antibodies were then titrated with three-fold dilutions by pipetting 200 µL of the previous dilution into 400 µL of sample buffer. A total of 9 dilutions ranging from 10 µg/ml to 0.3 ng/mL were prepared. After eight days, the sample plate was centrifuged for two minutes at 2000 rpm, and supernatants were discarded. Samples were stained with LIVE/DEAD® Fixable Near-IR Dead Cell Stain (Life Technologies/L10119) in PBS for 10 minutes. Sample plates were then centrifuged for two minutes at 2000 rpm, and the supernatant was discarded. The cells were then resuspended in 100 µL of BA072, BA101, or an IgG1 isotype control at the concentrations shown in FIGS. 9A and 9B. Sample plates were incubated for 20 minutes at 4° C. Cells were washed by addition of cold sample buffer and centrifuged for two minutes at 2000 rpm, and the supernatant was discarded. This wash was repeated once.

A final cocktail of PE-labeled secondary anti-human IgG (Fab'2) antibody was prepared in 11 mL of FACs buffer. 50 µL of secondary antibody was added per well to a round-bottom 96-well plate. After a 10-minute incubation 4° C., the cells were washed twice with cold FACS Buffer and resuspended in 1.6% paraformaldehyde in PBS.

Antibody binding was measured by flow cytometry using a BD LSR Fortessa Flow Cytometer. Unstained control cells were used to gate on the lymphocyte population using a plot of FSC-A versus SSC-A and another plot of FSC-A versus FSC-H for selection of single cells. Tubes of cells stained with each individual antibody were used to calculate compensation of the various colors used in the experiment. 50,000 events were recorded for each sample. Samples were analyzed by sequentially gating on the following populations: FSC-A vs SSC-A, FSC-H vs FSC-A, SSC-A vs LIVE/DEAD, and SSC-A vs PE. MFI was calculated.

Figure 9A:
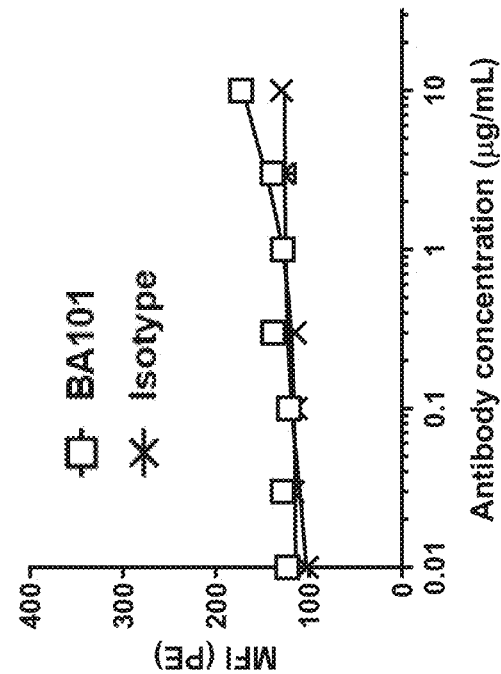
Figure 9B:
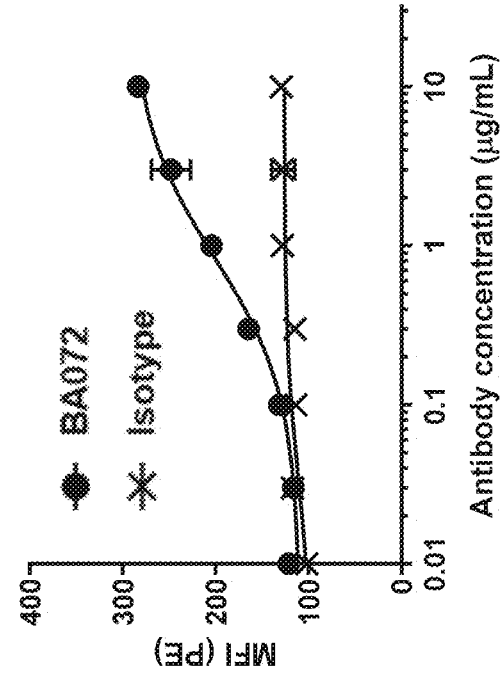

As shown in FIGS. 9A and 9B, BA072 (FIG. 9A) and BA101 (FIG. 9B) bound to activated primary cynomolgus T cells expressing CD96. The calculated area under the curve (AUC) values for the anti-CD96 antibodies presented in FIGS. 9A and 9B are listed in Table 22.

TABLE 22

AUC values for anti-CD96 antibodies in FIGS. 9A and 9B.

| Antibody | Area under the curve (AUC) | Standard error |
| --- | --- | --- |
| BA072 | 2484 | 114.7 |
| BA101 | 1494 | 57.97 |
| Isotype | 1274 | 76.96 |

6.1.3 Anti-CD96 Antibodies Block Ligand Binding to CD96

In this example, the capacity of anti-CD96 antibodies to block binding between CD96 and its ligand PVR (also referred to as CD155) was tested.

Parental Anti-CD96 Antibodies Block Binding of CD155/PVR-Fc to CHO Cells Expression Human Isoform 2 of CD96

CD96-expressing CHO cells were resuspended at $1\times10^6$ cells/mL with PBS. 100 µL of cells were aliquoted into a 96-well round bottom plate, centrifuged at 1200 rpm for five minutes, and the supernatant was discarded. Each antibody (i.e., BA07, BA101, or an IgG1 isotype control) was prepared at 30 µg/mL in FACs buffer. Antibodies were then titrated with three-fold dilutions by pipetting 112 µL of the previous dilution into 224 µL of sample buffer. A total of 7 working dilutions ranging from 30 µg/mL to 0.033 µg/mL was prepared. 50 µL of each antibody concentration was added to the cells in the 96-well plate and incubated for 1 hour at 4° C.

PVR-Fc (Sino Biological/10109-H02H-100) was conjugated with R-Phycoerythrin using the LYNX Rapid R-PE Antibody Conjugation Kit (Bio-Rad/LNK022RPE). PVR-Fc-PE was resuspended at 5 µg/mL in PBS and 50 µL of the solution was added to the cells with antibody and incubated for 1 hour at 4° C. Cells were washed by the addition of cold FACs buffer. This wash was repeated once, and cells were resuspended in 1.6% paraformaldehyde in PBS.

Antibody binding was measured by flow cytometry using a BD LSR Fortessa Flow Cytometer. Unstained control cells were used to gate on the lymphocyte population using a plot of FSC-A versus SSC-A and another plot of FSC-A versus FSC-H for selection of single cells. Tubes of cells stained with each individual antibody were used to calculate compensation of the various colors used in the experiment. 50,000 events were recorded for each sample. Samples were analyzed by sequentially gating on the following populations: FSC-A vs SSC-A, FSC-H vs FSC-A, and SSC-A vs PE. MFI was calculated. Percent binding was calculated as: (MFI (sample)−MFI (streptavidin alone$^{background}$))/(MFI (no antibody$^{full\ binding}$)))*100.

Figure 10A:
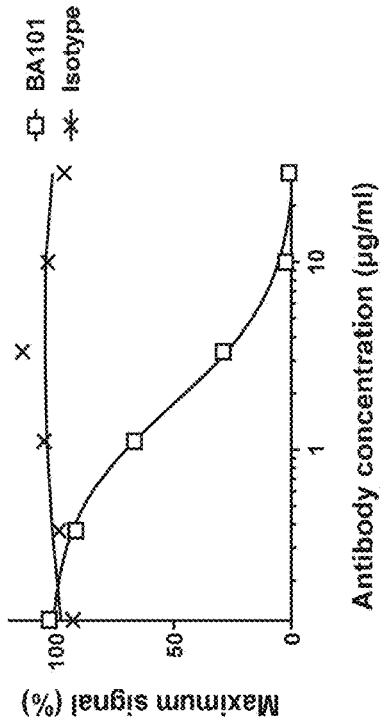
Figure 10B:
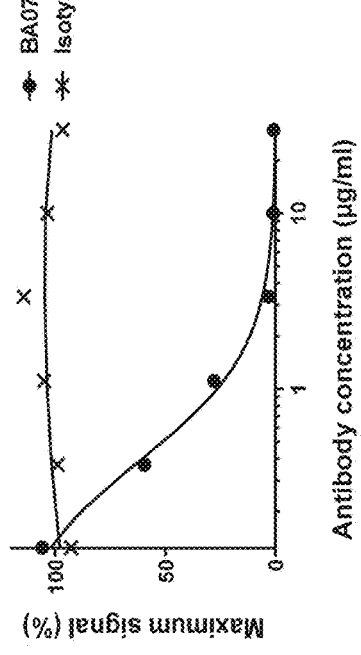

As shown in FIGS. 10A and 10B, BA072 (FIG. 10A) and BA101 (FIG. 10B) blocked binding of PVR-Fc to CD96-expressing cells.

Blocking of Human CD96-CHO Cells Binding to Soluble Human CD155/PVR by Parental Anti-CD96 Antibodies In this example, the capacity of BA072 and BA101 to block binding between human CD96 and its ligand human CD155 (also referred to as PVR) was tested. Specifically, BA072, BA101 and isotype control were tested in vitro for their ability to block binding between human isoform 2 of CD96 over-expressed on CHO cells and soluble human CD155 by flow cytometry.

Briefly, a 4× concentrated intermediate stock of each antibody (i.e., BA072, BA101 and isotype control) was prepared in a microplate. Antibodies were serially diluted 1-to-3 in FACS buffer. A total of 11 working dilutions ranging from 120 µg/mL to 0.000677 µg/mL were prepared. Twenty-five microlitres of each dilution were then transferred to a 96-well U-bottom microplate containing 25 µL of human CD96-CHO cells prepared as described in section 6.1.2. The cells were pre-incubated with the antibody dilutions for 30 minutes at 4° C. before addition of the CD96 ligand as follows. A solution containing 300 ng/mL of human CD155-His conjugated to R-Phycoerythrin (CD155-His-PE) was prepared in FACS buffer. Fifty microlitres of this working stock of human CD155-His-PE were then added to the wells of the microtitre plate containing human CD96-CHO cells and the antibodies. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs SSC-A. Mean fluorescence intensity (MFI) values for PE were calculated, and the data were plotted by GraphPad Prism software. For each antibody concentration, experimental data were normalized using MFI values obtained for human CD96-CHO cells incubated with CD155-His-PE in absence of antibody and MFI values for human CD96-CHO cell autofluorescence (background) according to equation 1.

$$\%\ \text{Maximal signal} = (\text{MFI "antibody"} - \text{MFI "background"})/(\text{MFI "total"} - \text{MFI "background"}) \quad \text{Equation 1}$$

where

"Antibody" is BA072 or BA101

"Background" is cells alone (no antibody or CD155-his-PE)

"Total" is cells incubated with CD155-His-PE in absence of antibodies

The concentration of antibody inhibiting 50% (IC50) of CD155-His-PE binding to human CD96-CHO cells was determined. IC50 values were calculated using GraphPad Prism software by curve fitting using a four-parameter logistic equation.

As shown in FIGS. 11A and 11B, BA072 (FIG. 11A) and BA101 (FIG. 11B) blocked human CD96 binding to CD155. Mean IC50 values and 95% confidence intervals were calculated for each antibody and are reported in Table 23.

TABLE 23

IC50 values for antibodies BA072 and BA101 blocking isoform 2 of human CD96 binding to human CD155.*

| Antibody Name | IC50 (Geomean), ng/ml | 95% CI, ng/ml |
|---|---|---|
| BA072 | 97 | 56-165 |
| BA101 | 317 | 364-382 |

*Calculated from 4 experiments.

Blocking of Human Isoform 2 CD96 Expressing CHO Cells Binding to Soluble Human CD155/PVR by Germlined Anti-CD96 Antibodies In this example, the capacity of BA072, BA083, and BA084 to block binding between human CD96 and its ligand human CD155 (also referred to as PVR) was tested. Specifically, these antibodies and isotype control were tested in vitro for their ability to block binding between isoform 2 of human CD96 over-expressed on CHO cells and soluble human CD155 by flow cytometry.

Briefly, a solution containing 200 ng/mL of human CD155-Fc conjugated to R-Phycoerythrin (CD155-Fc-PE) was prepared in FACS buffer. Fifty microlitres of this working stock of human CD155-Fc-PE were then added to the wells of a 96-well U-bottom microplate. A 4× concentrated intermediate stock of each antibody (i.e., BA072, BA083, BA084 and isotype control) was prepared in a separate microplate. Antibodies were serially diluted 1-to-3 in FACS buffer starting at 40 µg/ml. A total of 11 working dilutions was prepared. Twenty-five microlitres of each dilution were then transferred to the microplate containing 50 µL of CD155-Fc-PE. Lastly, 25 µL of human CD96-CHO cells (isoform 2) prepared as described in section 6.1.1. were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs SSC-A. Mean fluorescence intensity (MFI) values for PE were calculated, and the data were plotted by GraphPad Prism software and analyzed as described in section 6.1.1.

As shown in FIGS. 12A-12C, BA072 (FIG. 12A), and germlined variants BA083 (FIG. 12B) and BA084 (FIG. 12C), blocked human CD96 binding to CD155. Their respective IC50 values are reported in Table 24.

TABLE 24

IC50 values for antibodies BA072, BA083 and BA084 blocking isoform 2 of human CD96 binding to human CD155.*

| Antibody Name | IC50, ng/ml |
| --- | --- |
| BA072 | 235 |
| BA083 | 296 |
| BA084 | 271 |

*Calculated from 1 experiment.

Blocking of Human Isoform 2 CD96 Expressing CHO Cells Binding to Soluble Human CD155/PVR by Affinity-Matured Anti-CD96 Antibodies In this example, the capacity of parental antibody BA072, germlined antibody BA083, and affinity-matured variants BA085, BA086, BA087, BA089, BA090, BA088, BA091, BA092, BA093, and BA094 to block binding between human CD96 and its ligand human CD155 (also referred to as PVR) was tested. Specifically, these antibodies and isotype control were tested in vitro for their ability to block binding between isoform 2 of human CD96 over-expressed on CHO cells and soluble human CD155 by flow cytometry. The experiment was set up as described in section 6.1.3 except that the antibody titration was started at 30 µg/ml final top concentration and CD155-Fc-PE concentration was 1 µg/ml final.

As shown in FIGS. 13A-13L, anti-CD96 antibodies BA072 (FIG. 13A), BA083 (FIG. 13B), BA085 (FIG. 13C), BA086 (FIG. 13D), BA087 (FIG. 13E), BA089 (FIG. 13F), BA090 (FIG. 13G), BA088 (FIG. 13H), BA091 (FIG. 13I), BA092 (FIG. 13J), BA093 (FIG. 13K), and BA094 (FIG. 13L) blocked human CD96 binding to CD155. Their respective IC50 values are reported in Table 25.

TABLE 25

IC50 values for affinity-matured anti-CD96 antibody variants blocking isoform 2 of human CD96 binding to human CD155.*

| Antibody Name | IC50, ng/ml |
| --- | --- |
| BA072 | 1655 |
| BA083 | 1421 |
| BA085 | 321 |
| BA086 | 1185 |
| BA088 | 84 |
| BA087 | 209 |
| BA089 | 1408 |
| BA090 | 2244 |
| BA091 | 2449 |
| BA092 | 2856 |
| BA093 | 998 |
| BA094 | 559 |

*Calculated from 1 experiment.

Blocking of Isoform 1 of Human CD96 Expressing CHO Cells Binding to Soluble Human CD155/PVR by Affinity-Matured Anti-CD96 Antibodies In this example, the capacity of parental antibody BA072, germlined antibody BA083 and affinity-matured variants, BA073, BA074, BA078, BA079, BA080, BA081, BA076, BA077, BA082, and BA075 to block binding between isoform 1 of human CD96 and its ligand human CD155 (also referred to as PVR) was tested. Specifically, these antibodies and isotype control were tested in vitro for their ability to block binding between human CD96 (isoform 1) over-expressed on CHO cells and soluble human CD155 by flow cytometry. The experiment was set up as described for BA072 germlined variant antibodies (section 6.1.3) except that the antibody titration was started at 30 µg/ml final top concentration and CD155-Fc-PE concentration was 1 µg/ml final.

As shown in FIGS. 14A-14L, anti-CD96 antibodies BA073 (FIG. 14A), BA074 (FIG. 14B), BA078 (FIG. 14C), BA079 (FIG. 14D), BA080 (FIG. 14E), BA081 (FIG. 14F), BA076 (FIG. 14G), BA077 (FIG. 14H), BA082 (FIG. 14I), BA075 (FIG. 14J), BA083 (FIG. 14K), and BA072 (FIG. 14L) blocked human CD96 binding to CD155. Their respective IC50 values are reported in Table 26.

TABLE 26

IC50 values for affinity-matured anti-CD96 antibody variants blocking isoform 1 of human CD96 binding to human CD155.*

| Antibody Name | IC50 (Geomean), ng/ml |
| --- | --- |
| BA073 | 111.86 |
| BA074 | 153.17 |
| BA078 | 124.24 |
| BA079 | 135.54 |
| BA080 | 150.74 |
| BA081 | 132.33 |
| BA076 | 135.82 |
| BA077 | 127.3 |
| BA082 | 144.32 |
| BA075 | 172.05 |
| BA083 | 136.65 |
| BA072 | 141 |

*Calculated from 2 experiments.

Blocking of Human Isoform 2 CD96 Expressing CHO Cells Binding to Soluble Human CD155/PVR by Affinity-Matured Anti-CD96 Antibodies In this example, the capacity of capacity of parental antibody BA072, germlined antibody BA083 and affinity-matured variants, BA073, BA074, BA078, BA079, BA080, BA081, BA076, BA077, BA082, and BA075 to block binding between isoform 2 of human CD96 and its ligand human CD155 (also referred to as PVR) was tested. Specifically, these antibodies and isotype control were tested in vitro for their ability to block binding between human CD96 (isoform 2) over-expressed on CHO cells and soluble human CD155 by flow cytometry. The experiment was set up as described for BA072 germlined variant antibodies (section 6.1.3) except that the antibody titration was started at 30 µg/ml final top concentration and CD155-Fc-PE concentration was 1 µg/ml final.

As shown in FIGS. 15A-15L, anti-CD96 antibodies BA073 (FIG. 15A), BA074 (FIG. 15B), BA078 (FIG. 15C), BA079 (FIG. 15D), BA080 (FIG. 15E), BA081 (FIG. 15F), BA076 (FIG. 15G), BA077 (FIG. 15H), BA082 (FIG. 15I), BA075 (FIG. 15J), BA083 (FIG. 15K), BA072, and (FIG.

15L) blocked human CD96 binding to CD155. Their respective IC50 values are reported in Table 27.

TABLE 27

IC50 values for affinity-matured anti-CD96 antibody variants blocking isoform 2 of human CD96 binding to human CD155.*

| Antibody Name | IC50 (Geomean), ng/ml |
| --- | --- |
| BA073 | 155 |
| BA074 | 142 |
| BA078 | 134 |
| BA079 | 123 |
| BA080 | 195 |
| BA081 | 173 |
| BA076 | 157 |
| BA077 | 106 |
| BA082 | 193 |
| BA075 | 230 |
| BA083 | 176 |
| BA072 | 165 |

*Calculated from 2 experiments.

Blocking of Human Isoform 2 CD96 Expressing CHO Cells Binding to Soluble Human CD155/PVR by Germlined Anti-CD96 Antibodies In this example, the capacity of BA101, and germlined variants BA102, BA103, BA104, BA105 and BA106 to block binding between isoform 2 of human CD96 and its ligand human CD155 (also referred to as PVR) was tested. Specifically, these antibodies and isotype control were tested in vitro for their ability to block binding between human CD96 (isoform 2) over-expressed on CHO cells and soluble human CD155 by flow cytometry as described above for BA072 germlined variant antibodies (Section 6.1.3) except that the antibody titration was started at 30 µg/ml final top concentration.

As shown in FIGS. 16A-16F, anti-CD96 antibodies BA101 (FIG. 16A), BA102 (FIG. 16B), BA103 (FIG. 16C), BA104 (FIG. 16D), BA105 (FIG. 16E), and BA106 (FIG. 16F) blocked human CD96 binding to CD155. Their respective IC50 values are reported in Table 28.

TABLE 28

IC50 values for antibodies BA101, BA102, BA103, BA104, BA105 and BA106 blocking human CD96 binding to human CD155.*

| Antibody Name | IC50, ng/ml |
| --- | --- |
| BA101 | 1421 |
| BA102 | 1383 |
| BA103 | 1379 |
| BA104 | 1488 |
| BA105 | 1499 |
| BA106 | 1571 |

*Calculated from 1 experiment.

Blocking of Human Isoform 2 CD96 Expressing CHO Cells Binding to Soluble Human CD155/PVR by a Germlined Anti-CD96 Antibody In this example, the capacity of BA101 and variant BA107 to block binding between human CD96 and its ligand human CD155 (also referred to as PVR) was tested. Specifically, these antibodies and isotype control were tested in vitro for their ability to block binding between isoform 2 of human CD96 over-expressed on CHO cells and soluble human CD155 by flow cytometry. The experiment was set up as described for BA072 germlined variant antibodies (section 6.1.3) except that the antibody titration was started at 15 µg/ml final top concentration.

As shown in FIGS. 17A and 17B, BA101 (FIG. 17A) and BA107 (FIG. 17B) antibodies blocked human CD96 binding to CD155. Their respective IC50 values are reported in Table 29.

TABLE 29

IC50 values for antibodies BA101 and AB107 blocking human CD96 binding to human CD155.*

| Antibody Name | IC50, ng/ml |
| --- | --- |
| BA101 | 1419 |
| BA107 | 2302 |

*Calculated from 1 experiment.

Blocking of Isoform 2 of Cynomolgus Monkey CD96 Expressing CHO Cells Binding to Soluble Human CD155/PVR by Germlined Anti-CD96 Antibodies In this example, the capacity of BA072, and germlined variants BA083 and BA084 to block binding between isoform 2 of cynomolgus monkey CD96 (SEQ ID NO: 133) and human CD155 (also referred to as PVR) was tested. Specifically, these antibodies and isotype control were tested in vitro for their ability to block binding between isoform 2 of cynomolgus monkey CD96 over-expressed on CHO cells and soluble human CD155 by flow cytometry.

Briefly, a solution containing 200 ng/mL of human CD155-Fc conjugated to R-Phycoerythrin (CD155-Fc-PE) was prepared in FACS buffer. Fifty microliters of this working stock of human CD155-Fc-PE were then added to the wells of a 96-well U-bottom microplate. A 4× concentrated intermediate stock of each antibody (i.e., BA072, BA083, BA084 and isotype control) was prepared in a separate microplate. Antibodies were serially diluted 1-to-3 in FACS buffer starting at 30 µg/ml. A total of 11 working dilutions was prepared. Twenty-five microlitres of each dilution were then transferred to the microplate containing 50 µL of CD155-Fc-PE. Lastly, 25 µL of isoform 2 of cynomolgus monkey CD96 expressing CHO cells prepared as described in section 6.1.2. were added to each well. After a 30-minute incubation on ice, the cells were washed twice with cold FACS Buffer, and the cells were analyzed by flow cytometry (BD LSR Fortessa Flow Cytometer). The data were analyzed using the FlowJo software by sequentially gating on the FSC-A vs. SSC-A and SSC-H vs SSC-A. Mean fluorescence intensity (MFI) values for PE were calculated, and the data were plotted by GraphPad Prism software and analysed as described in section 6.1.2.

Figure 18A:
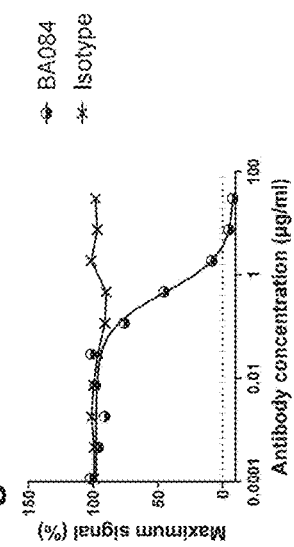
Figure 18B:
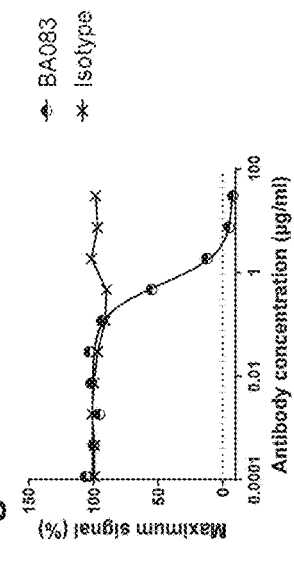
Figure 18C:
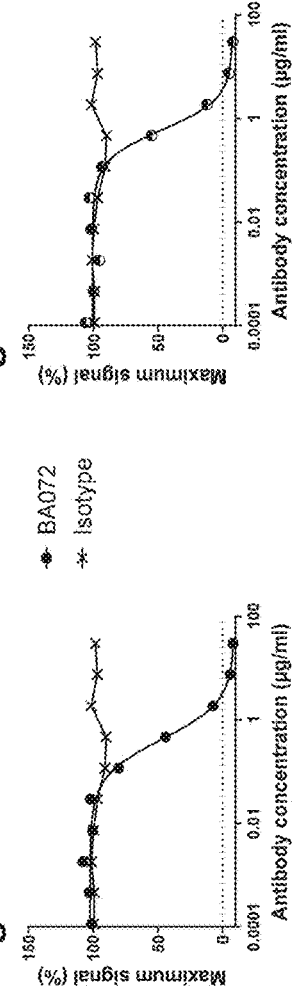

As shown in FIGS. 18A-18C, BA072 (FIG. 18A) and germlined variants BA083 (FIG. 18B) and BA084 (FIG. 18C) blocked isoform 2 of cynomolgus monkey CD96 binding to CD155. Their respective IC50 values are reported in Table 30.

TABLE 30

IC50 values for antibodies BA072, BA083 and BA084 blocking isoform 2 of cynomolgus monkey CD96 binding to human CD155.*

| Antibody Name | IC50, ng/ml |
| --- | --- |
| BA072 | 425 |
| BA083 | 611 |
| BA084 | 459 |

*Calculated from 1 experiment.

Blocking of Isoform 2 of Cynomolgus Monkey CD96 Expressing CHO Cells Binding to Soluble Human CD155/PVR by Affinity-Matured Anti-CD96 Antibodies In this example, the capacity of capacity of parental antibody BA072, germlined antibody BA083 and affinity-matured variants, BA085, BA086, BA088, BA087, BA089, BA090, BA091, BA092, BA093, and BA094 to block binding between isoform 2 of cynomolgus monkey CD96 and human CD155 (also referred to as PVR) was tested. Specifically, these antibodies and isotype control were tested in vitro for their ability to block binding between isoform 2 of cynomolgus monkey CD96 over-expressed on CHO cells and soluble human CD155 by flow cytometry. The experiment was set up as described for BA072 germlined variant antibodies (section 6.1.3) except that the antibody titration was started at 30 μg/ml final top concentration and CD155-Fc-PE concentration was 1 μg/ml final.

As shown in FIGS. 19A-19L, anti-CD96 antibodies BA072 (FIG. 19A), BA083 (FIG. 19B), BA085 (FIG. 19C), BA086 (FIG. 19D), BA088 (FIG. 19E), BA087 (FIG. 19F), BA089 (FIG. 19G), BA090 (FIG. 19H), BA091 (FIG. 19I), BA092 (FIG. 19J), BA093 (FIG. 19K), and BA094 (FIG. 19L) blocked isoform 2 of cynomolgus monkey CD96 binding to CD155. Their respective IC50 values are reported in Table 31.

TABLE 31

IC50 values for affinity-matured anti-CD96 antibody variants blocking isoform 2 of cynomolgus monkey CD96 binding to human CD155.*

| Antibody Name | IC50, ng/ml |
|---|---|
| BA072 | 645 |
| BA083 | 821 |
| BA085 | 537 |
| BA086 | 378 |
| BA088 | 390 |
| BA087 | 451 |
| BA089 | 401 |
| BA090 | 941 |
| BA091 | 886 |
| BA092 | 1725 |
| BA093 | 347 |
| BA094 | 238 |

*Calculated from 1 experiment.

Blocking of Isoform 1 of Cynomolgus Monkey CD96 CHO Cells Binding to Soluble Human CD155/PVR In this example, the capacity of parental antibody BA072, germlined antibody BA083 and affinity-matured variants, BA074, BA078, BA079, BA080, BA081, BA076, BA077, BA082, BA075, and BA072 to block binding between isoform 1 of cynomolgus monkey CD96 and human CD155 (also referred to as PVR) was tested. Specifically, these antibodies and isotype control were tested in vitro for their ability to block binding between isoform 1 of cynomolgus monkey isoform 1 of CD96 over-expressed on CHO cells and soluble human CD155 by flow cytometry. The experiment was set up as described for BA072 germlined variant antibodies (section 6.1.3) except that the antibody titration was started at 30 μg/ml final top concentration and CD155-Fc-PE concentration was 1 μg/ml final.

As shown in FIGS. 20A-20L, anti-CD96 antibodies BA073 (FIG. 20A), BA074 (FIG. 20B), BA078 (FIG. 20C), BA079 (FIG. 20D), BA080 (FIG. 20E), BA081 (FIG. 20F), BA076 (FIG. 20G), BA077 (FIG. 20H), BA082 (FIG. 20I), BA075 (FIG. 20J), BA083 (FIG. 20K), and BA072 (FIG. 20L) blocked human CD96 binding to CD155. Their respective IC50 values are reported in Table 32.

TABLE 32

IC50 values for affinity-matured anti-CD96 antibody variants blocking isoform 1 of cynomolgus CD96 binding to human CD155.*

| Antibody Name | IC50 (Geomean), ng/ml |
|---|---|
| BA073 | 74 |
| BA074 | 74 |
| BA078 | 62 |
| BA079 | 54 |
| BA080 | 96 |
| BA081 | 121 |
| BA076 | N/A |
| BA077 | N/A |
| BA082 | 99 |
| BA075 | 142 |
| BA083 | 298 |
| BA072 | 365 |

*Calculated from 2 experiments, except BA074 which was calculated from 1 experiment.

Blocking of Isoform 2 of Cynomolgus CD96-Expressing CHO Cells Binding to Soluble Human CD155/PVR In this example, the capacity of capacity of parental antibody BA072, germlined antibody BA083 and affinity-matured variants, BA073, BA074, BA078, BA079, BA080, BA081, BA076, BA077, BA082, and BA075 to block binding between isoform 2 of cynomolgus CD96 and human CD155 (also referred to as PVR) was tested. Specifically, these antibodies and isotype control were tested in vitro for their ability to block binding between isoform 2 of cynomolgus CD96 over-expressed on CHO cells and soluble human CD155 by flow cytometry. The experiment was set up as described for BA072 germlined variant antibodies (section 6.1.3) except that the antibody titration was started at 30 μg/ml final top concentration and CD155-Fc-PE concentration was 1 μg/ml final.

As shown in FIGS. 21A-21L, anti-CD96 antibodies BA073 (FIG. 21A), BA074 (FIG. 21B), BA078 (FIG. 21C), BA079 (FIG. 21D), BA080 (FIG. 21E), BA081 (FIG. 21F), BA076 (FIG. 21G), BA077 (FIG. 21H), BA082 (FIG. 21I), BA075 (FIG. 21J), BA083 (FIG. 21K), or BA072 (FIG. 21L) fully or partially blocked human CD96 binding to CD155. Their respective IC50 values are reported in Table 33.

TABLE 33

IC50 values for affinity-matured anti-CD96 antibody variants blocking isoform 2 of cynomolgus CD96 binding to human CD155.*

| Antibody Name | IC50 (Geomean), ng/ml |
|---|---|
| BA073 | 102 |
| BA074 | 93 |
| BA078 | 55 |
| BA079 | 54 |
| BA080 | 44 |
| BA081 | 26 |
| BA076 | N/A |
| BA077 | N/A |
| BA082 | 66 |
| BA075 | 135 |
| BA083 | 97 |
| BA072 | 123 |

*Calculated from 2 experiments.

Anti-CD96 Antibodies Block Binding of CD155/PVR-Expressing Cells to CD96-Expressing Cells CD96-expressing CHO cells and PVR-expressing CHO cells were washed twice with PBS and spun down at 1200 rpm for five minutes. 20 µL was removed and added to 380 µL viability dye to count cells and check viability using a Muse apparatus. Samples were centrifuged at 1200 rpm for five minutes and then suspended to a final concentration of $1\times10^7$ cells/mL with Diluent C from either the PKH26 Cell Linker Kit (Sigma/PKH26GL) or PKH67 Cell Linker Kit (Sigma/PKH67GL). 4 µL of PKH26 red dye was prepared in 1 mL of Diluent C and added to 1 mL of the resuspended PVR-expressing CHO cells, and 4 µL of PKH67 green dye was prepared in 1 mL of Diluent C and added to 1 mL of the resuspended CD96-expressing CHO cells. Cells were incubated with the dye at room temperature for five minutes.

10 mL of PowerCHO media was added to each tube of labeled cells and incubated at room temperature for 1 minute. Cells were spun down as 1200 rpm for five minutes and washed twice with 10 mL of PowerCHO media.

Labeled cells were resuspended in 1 mL of HBSS supplemented with 10% heat-inactivated FBS and 1% HEPES buffer and resuspended at $8\times10^5$ cells/mL. 25 µL of labeled CD96-expressing CHO cells were added to each well of a 96-well round bottom plate.

Each antibody (i.e., BA072, BA101, germline variants thereof, or an IgG1 isotype control) was prepared at 30 µg/mL in FACs buffer. Antibodies were then titrated with three-fold dilutions by pipetting 112 µL of the previous dilution into 224 µL of sample buffer ranging from 30 µg/mL to 0.1 µg/mL was prepared. 25 µL of each antibody concentration was added to the cells in the 96-well plate and incubated for 30 minutes at room temperature. Without washing between, 25 µL of labeled PVR-expressing CHO cells were added to each well of a 96-well plate, for a total of 75 µL per well, and incubated for 45 minutes at 37° C. and 5% $CO_2$.

Conjugation formation was measured immediately by flow cytometry using a BD LSR Fortessa Flow Cytometer. Tubes of cells stained with each dye were used to calculate compensation of the red PKH26-labeled cells (PE channel) and green PKH67-labeled cells (FITC channel). 50,000 events were recorded for each sample. Samples were analyzed by sequentially gating on the following populations: FSC-A vs SSC-A, and FITC vs PE. As shown in FIG. 22C, when blocking does not occur, conjugates appear in quadrant Q2 of the scatter plot. When the block antibody is present conjugates are not able to form and no conjugates are detected in quadrant Q2 of the scatter plot. Percent conjugation was calculated and plotted with GraphPad Prism software.

Figure 22A:
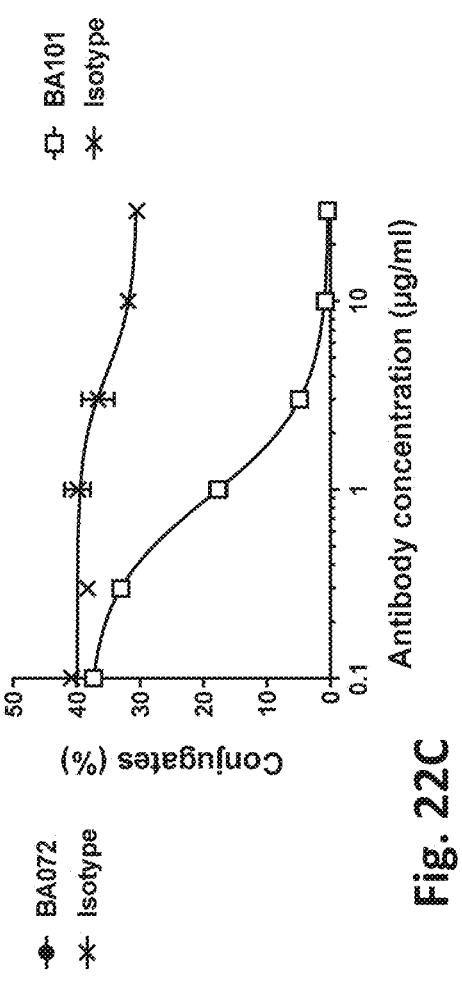
Figure 22B:
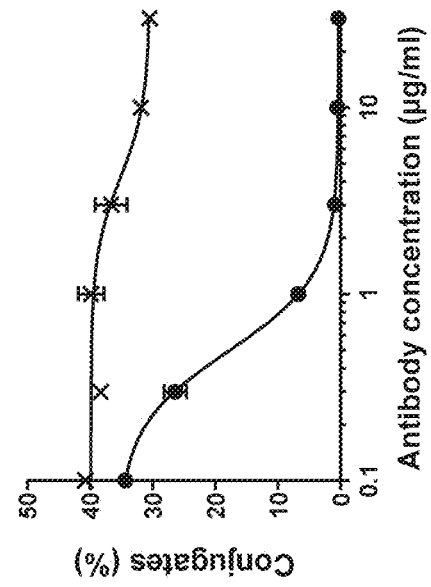
Figure 22C:
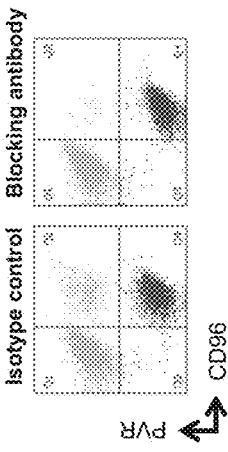
Figure 23:
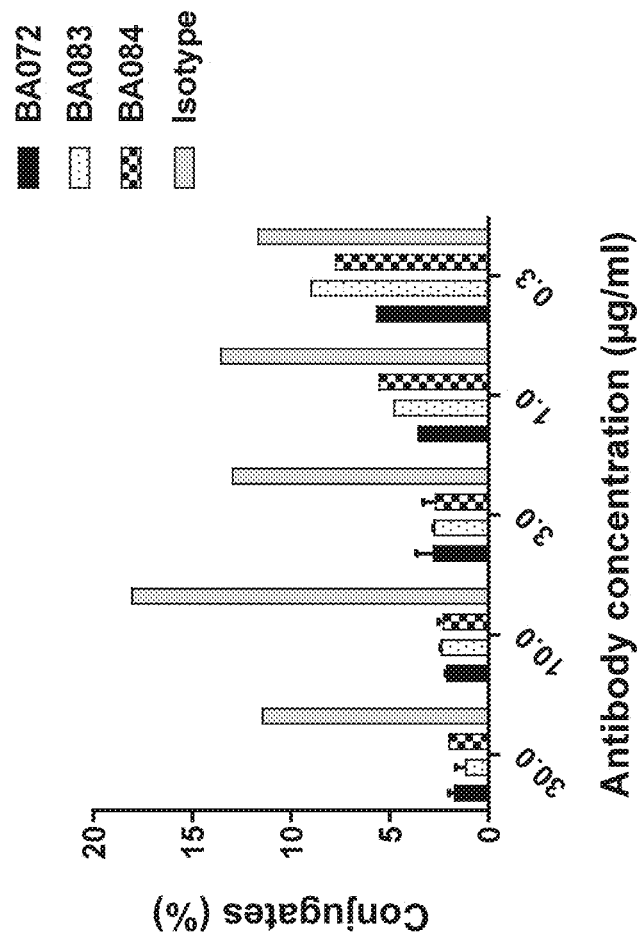
Figure 24:
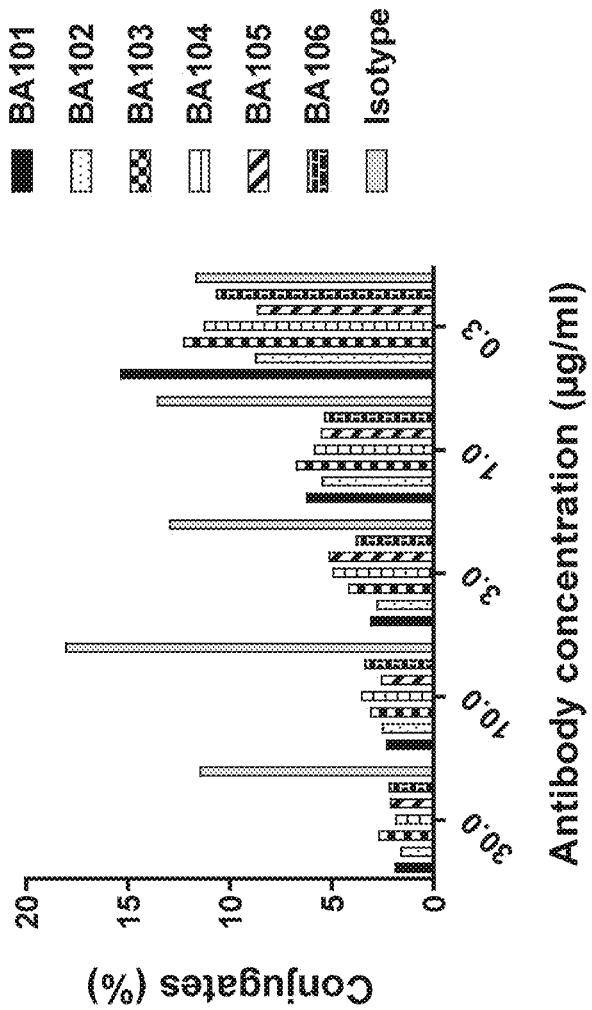
FIG. 24 is a graph showing the conjugate formation of CHO cells, engineered to express high levels of isoform 2 of human CD96 or PVR, in the presence of anti-CD96 antibodies BA101, BA102, BA103, BA104, BA105, or BA106. The percent of conjugates formed, in each case in comparison to IgG1 isotype control, are plotted against the concentrations of the respective antibody incubated with the cells.

As shown in FIGS. 22A and 22B, BA072 and BA101 blocked binding of PVR-expressing cells to CD96-expressing cells (conjugate formation) in a dose-dependent manner. As shown in FIG. 23, BA072, BA083, and BA084 blocked binding of PVR-expressing cells to CD96-expressing cells in a dose-dependent manner. As shown in FIG. 24, BA101, BA102, BA103, BA104, BA105, and BA106 blocked binding of PVR-expressing cells to CD96-expressing cells.

6.2 Example 2: Functionality of Anti-CD96 Antibodies and Combination Treatments 6.2.1 Anti-CD96 Antibodies Enhance $T_H1$ Cytokine Secretion by Primary Cells
Anti-CD96 Antibodies Enhance IL-2 Secretion by Stimulated PBMC in a Dose-Dependent Manner A dose range of the anti-CD96 (BA072 and BA101) and isotype control antibody were prepared in 1.2 ml bullet tubes at 4× concentrations. First, 600 µL of 200 µg/ml (final concentration of 50 µg/ml) of each antibody was prepared in R10 media. Antibodies were then titrated with 10-fold dilutions from a final concentration of 50 µg/ml to 0.5 ng/mL. In a 96-well round bottom plate, 25 µl of each anti-CD96 antibody or isotype control antibody were pipetted into corresponding wells.

Anti-PD-1 antibody with its respective isotype control was prepared at 4× final concentration of 20 µg/mL (final concentration of 5 µg/mL) in R10 media. 25 µl of anti-PD-1 or isotype antibody were added to the corresponding wells with the previously prepared antibodies. Frozen aliquots of human PBMC were retrieved from liquid nitrogen and immediately thawed in 37° C. water until floating ice was observed. Cells were transferred to 10 mL of pre-warmed R10 media and immediately centrifuged at 1200 rpm for five minutes. To count cells and check viability, 20 µL of sample was removed and added to 380 µL of viability dye, mixed, and read using a Muse apparatus.

Samples were centrifuged at 1200 rpm for five minutes and resuspended to a concentration of $2\times10^6$ cells/mL in R10 media. An intermediate stock concentration of SEA was made by adding 1 µL of 1000 µg/mL SEA to 99 µL R10 to make an intermediate concentration of 10 µg/mL. To stimulate the cells, 2× final concentration of 2 ng/mL (final concentration of 1 ng/mL) of SEA was added to the cells prepared above. 50 µL of cells ($0.1\times10^6$ cells/well) and SEA mixture was added into corresponding wells with the antibodies and incubated at 37° C. and 5% $CO_2$ within a humidified chamber for four days.

After four days of incubation, plates were removed from the incubator. The plates were then centrifuged for two minutes at 2000 rpm. 5 µL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 µL was added to each well and incubated in darkness at room temperature. AlphaLISA plates were briefly centrifuged at 2000 rpm. A 2.3× Streptavidin Donor Bead intermediate stock was prepared in assay buffer. 10 µL was added to each well and incubated in darkness at room temperature. AlphaLISA plates were briefly centrifuged at 2000 rpm. Relative light units (RLU) were measured using the AlphaScreen protocol on an EnVision Plate Reader. Results were plotted in GraphPad Prism and statistical analyses were performed using an unpaired t-test.

As shown in FIGS. 25A-25H, BA072 or BA101 enhanced IL-2 secretion relative to isotype control, on average, both without and with anti-PD-1. This response was generally dose dependent. FIGS. 25A-25D represent a first experiment with a first donor, and FIGS. 25E-25H represent a second experiment with a second donor.

Anti-CD96 Affinity-Matured Anti-CD96 Antibodies Enhance IL-2 Secretion by Stimulated PBMC The experiment in this example was carried out following the procedure outline in this section above, with the following changes. Antibodies (BA072, affinity-matured variants thereof, or an IgG1 isotype control antibody) were prepared in 1.2 ml bullet tubes at 4× concentration of 0.2 µg/ml (final concentration of 0.05 µg/ml) and 25 µl of each antibody was added to the corresponding wells in the 96-well plate.

As shown in FIGS. 26A-26F, BA083, BA073, BA080, and BA076, with and without anti-PD-1, resulted in an increase in IL-2 secretion in all donors, as compared to isotype control. FIGS. 26A and 26B represent one experiment without (FIG. 26A) and with (FIG. 26B) an anti-PD-1 antibody. FIGS. 26C and 26D represent a second experiment, with a different donor, without (FIG. 26C) and with (FIG. 26D) an anti-PD-1 antibody. FIGS. 26E and 26F represent a third experiment, with a different donor, without (FIG. 26E) and with (FIG. 26F) an anti-PD-1 antibody.

As shown in FIGS. 27A-27F, BA072, BA074, BA079, BA081, BA077, BA082 and BA075, enhanced IL-2 secretion relative to isotype control, on average, both without and with anti-PD-1. FIGS. 27A and 27B represent one experiment without (FIG. 27A) and with (FIG. 27B) an anti-PD-1. FIGS. 27C and 27D represent a second experiment, with a different donor, without (FIG. 27C) and with (FIG. 27D) an anti-PD-1 antibody. FIGS. 27E and 27F represent a third experiment, with a different donor, without (FIG. 27E) and with (FIG. 27F) an anti-PD-1 antibody.

6.2.2 Anti-CD96 Antibody Blocks CD96 and Increases TCR-NFAT and NFκB Signaling in a Human CD96 T Cell Reporter Assay CD96 Blockade on NFAT-Luc and NFκB-Luc Jurkat Cells Jurkat cells engineered in-house to express CD96 and either NFAT-Luciferase or NFκB-Luciferase were cultured in R10 media with 1 μg/mL of puromycin. These Jurkat reporter cells were spun down at 1200 rpm for five minutes and resuspended in R10 media at $1 \times 10^6$ cells/mL. Anti-CD28 antibody (BD Biosciences/347698) was added only to the NFκB-Luciferase reporter Jurkat cells at 4× final concentration of 2 μg/mL (final concentration of 0.5 μg/mL). 25 μL of the reporter cells were added (not together) to the corresponding wells with CHO cells and antibodies on the assay plate and incubated for 4 hours at 37° C. and 5% $CO_2$.

In this example, the capacity of soluble BA072 to block binding between CD96-expressing reporter cells and PVR-expressing cells and enhance T cell receptor (TCR) signaling through NFAT and NFκB was tested.

Sorted and clonal CHO cells engineered in-house to express high levels of PVR and anti-CD3 (clone OKT3) were resuspended in R10 media at $5 \times 10^5$ cells/mL. 50 μL of cells ($2.5 \times 10^4$ cells) were plated on a white 96-well flat bottom assay plate and incubated for 4 hours at 37° C. and 5% $CO_2$ to adhere.

BA072 and an IgG1 isotype control antibody were prepared at 4× final concentration of 40 μg/mL (final concentration of 10 μg/mL) in R10 media and titrated with three-fold dilutions by pipetting 112 μL of the previous dilution into 224 μL of sample buffer. After the 4-hour incubation, 25 μL of each antibody concentration was added to the corresponding wells with adhered CHO cells in the assay plate.

After 4 hours, plates were equilibrated to room temperature for 15 minutes and then 100 μL of Nano-Glo Luciferase Assay Reagent (Promega/N1120) was added per well. The mixtures were then incubated at room temperature for five minutes, and luminescence was measured using a plate reader (Envision). RLU was calculated: $RLU_{(induced)} - RLU_{(background)}$. The delta RLU was calculated as: RLU (BA072)–RLU (isotype) and plotted using GraphPad Prism.

As shown in FIGS. 28A and 28B, BA072 increased both TCR-NFAT (FIG. 28A) and NFκB (FIG. 28B) signaling, relative to isotype control, in human CD96-expressing Jurkat reporter cells (FIG. 28C).

In a similar experiment, the influence of CD266 expression on CD96 induced signaling was investigated. The experiment was performed as described above for FIGS. 28A-28C; however, the reporter cells used were Jurkat cells engineered in-house to express CD96 and NFAT-Luciferase (FIG. 29A) or Jurkat cells engineered in-house to express CD96 and NFAT-Luciferase with CD226 knocked out (FIG. 29B). As shown in FIGS. 29A and 29B, BA072 increased TCR-NFAT, relative to isotype control, showing that, this effect was not dependent on CD226 expression.

6.3 Example 3: Fc Variants of Anti-CD96 Antibodies

In this example, the impact of Fc region/FcγR interaction on the binding and functional activity of BA072 was analyzed. In particular, the VH region of BA072 was expressed with various Fc backbones, as summarized in Table 34.

TABLE 34

Fc variants of BA072.

| Antibody Name | Antibody Description (numbered according to the EU numbering system) | Heavy Chain SEQ ID NO: | Light Chain SEQ ID NO: |
|---|---|---|---|
| BA072 | IgG1 | 76 | 102 |
| BA108 | N297A variant of BA072 | 116 | 102 |
| BA109 | S239D/A330L/I332E variant of BA072 | 118 | 102 |
| BA110 | S267E/L328F variant of BA072 | 120 | 102 |

These Fc variants of BA072 were then tested in functional assays, as described below.

6.3.1 Fc Variants of BA072 Enhanced Killing of $CD96^+$ Jurkat Cells in Co-Culture with $CD16^+$ NK Cells Fc variants of BA072 were examined for their capacity to induce antibody-dependent cell-mediated cytotoxicity (ADCC) activity in a co-culture of CD96-expressing Jurkat cells and CD16-expressing natural killer (NK) cells. Briefly, Jurkat cells were cultured in RPMI 1640 (Corning Catalog #10-040-CM) supplemented with 10% fetal bovine serum (Benchmark Catalog #100-106, Lot A69E00F) and 1% Pen Strep Glutamine (Gibco Catalog #10378-016). NK cells were cultured in RPMI 1640 (Corning Catalog #10-040-CM) supplemented with 5% human serum (Sigma Catalog #H4522), 1% Pen Strep Glutamine (Gibco Catalog #10378-016), 100 Units/mL IL-2 (R&D Systems Catalog #202-16), and 100 Units/mL IL-15 (R&D Systems Catalog #247-ILB). Two million Jurkat cells were pelleted by centrifugation for 5 minutes at 1200 rpm. The cells were stained by resuspending the pellet in 1 mL of 0.5 μM CellTrace Far Red (Invitrogen Catalog #C34565) in PBS (Corning Catalog #21-040-CV) and incubating for 30 minutes at 37° C. and 5% $CO_2$. After incubation, 9 mL of PBS was added, and the cells were pelleted by centrifugation for 5 minutes at 300 g. The cell pellet was then resuspended in Jurkat culture media containing 1 μM CellEvent Caspase-3/7 Green Detection Reagent (Invitrogen Catalog #C10423). Antibodies were diluted in NK culture media at three times their final concentration. Stained Jurkat cells were diluted to 0.625 million cells per mL and NK cells to 0.625 million cells per mL. The assay was performed in 384-well microscopy plates (Greiner, Cat. No. 781936) by pipetting 20 μL of the antibodies, 20 μL stained Jurkat cells (12500 cells), and 20 μL NK cells (12500 cells) per well.

Live imaging was performed immediately afterwards, using an ImageXpress Micro Confocal High-Content microscope (Molecular Devices) under environmental control (37° C., 5% $CO_2$) and images were acquired every 30 minutes from the Cy5 (CellTrace Far Red) and FITC (Caspase 3/7) channels for Jurkat cells and Caspase 3/7-positive Jurkat cells, respectively, over the course of four hours. Image analysis was performed using the MetaXpress analysis software (Molecular Devices). Jurkat cells were identified from the Cy5 channel and the amount of Caspase 3/7 signal was quantified per cell from the FITC channel. Cells with Caspase 3/7 intensity above the background were designated as apoptotic. The number of apoptotic cells was normalized against the total cell count per condition to determine a percent killing measurement.

As shown in FIGS. 30A-30C, Fc enhanced BA072 (BA109) (FIG. 30B) promoted killing of CD96-expressing Jurkat cells to a greater degree than BA072 (FIG. 30A) and the "Fc-silent" N297A mutation of BA072 (BA108) (FIG. 30C), and isotype control.

6.3.2 Anti-CD96 Antibody Fc Variant Signaling Through FcγRIIIA

In another example, the capacity of BA072 Fc variants to activate reporter cells expressing FcγRIIIA$^{V158}$ was tested.

25 μL of target cells (i.e., Jurkat cells engineered in-house to express high levels of human CD96 described in Section 6.1.2) were added to the wells of an ADCC assay plate (1.5×10$^6$ cells/mL). Three-fold serial dilutions of antibody (i.e., BA072, Fc variants thereof, or corresponding isotype controls) were prepared at 3× final concentration ranging from 30 μg/mL to 0.0003 μg/mL (final concentration ranging from 10 μg/mL to 0.0001 μg/mL) in RPMI-1640 supplemented with 4% low-IgG FBS (Promega/G711A) (ADCC assay buffer). 25 μL of the 3× antibody dilutions were added to the assay plate wells containing the target cells. Effector cells (i.e., Jurkat NFAT-luciferase reporter cells overexpressing the FcγRIIIA CD16A with a high affinity 158 V/V polymorphism, less than six weeks in culture; Promega/G7102) were resuspended at 6×10$^6$ cells/mL in ADCC assay buffer and 25 μL were added to each well on the assay plate (150,000 cells/well). The assay plate was then incubated for 20 hours at 37° C. and 5% CO$_2$. Binding of antibody/antigen complex on target cell surfaces to CD16A on effector cell surfaces would result in signaling to the reporter construct and expression of luciferase.

The next day, plates were equilibrated to room temperature for 15 minutes and then 75 μL of Bio-Glo Luciferase Assay Reagent (Promega/G7940) was added per well. The mixtures were then incubated at room temperature for 5-10 minutes, and luminescence was measured using a plate reader (Envision). RLU was calculated: RLU$_{(induced)}$ −RLU$_{(background)}$.

As shown in FIGS. 31A-31C, for FcγRIIIA binding and signaling, BA072 (FIG. 31A), BA108 (FIG. 31C) and isotype controls demonstrated no signaling, whereas BA109 (FIG. 31B) exhibited signaling through FcγRIIIA.

6.3.3 T Cell Response to Anti-CD96 Antibody Fc Variants

In this example, the ability of Fc variants of BA072 to elicit T cell response in primary T cell:APC co-culture assay was tested.

A dose range of the anti-CD96 antibodies BA072 (IgG1) and BA108 (an Fc silent variant of BA072), as well as isotype control antibody were prepared in 1.2 ml bullet tubes at 2× concentrations. First, 600 μL of 100 μg/ml (final concentration of 50 μg/ml) of each antibody was prepared in R10 media. Antibodies were then titrated with 10-fold dilutions from a final concentration of 50 μg/ml to 0.05 ng/mL. In a 96-well round bottom plate, 50 μl of each anti-CD96 antibody or isotype control antibody were pipetted into corresponding wells.

Frozen aliquots of human PBMC were retrieved from liquid nitrogen and immediately thawed in 37° C. water until floating ice was observed. Cells were transferred to 10 mL of pre-warmed R10 media and immediately centrifuged at 1200 rpm for 5 minutes. 20 μL of each sample was removed and added to 380 μL of viability dye to count cells and check viability using a Muse apparatus.

Samples were centrifuged at 1200 rpm for 5 minutes and resuspended to a concentration of 2×10$^6$ cells/mL in R10 media. An intermediate stock concentration of SEA was made by adding 1 μL of 1000 μg/mL SEA to 99 μL R10 to make an intermediate concentration of 10 μg/mL. To stimulate the cells, 1 ng/mL of SEA was added to the cells prepared above. 50 μL of cells (0.1×10$^6$ cells/well) and SEA mixture was added into corresponding wells with the antibodies and incubated at 37° C. and 5% CO$_2$ within a humidified chamber for 4 days.

After four days of incubation, plates were removed from the incubator. The plates were then centrifuged for 2 minutes at 2000 rpm. 5 μL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 μL was added to each well and incubated in darkness at room temperature. AlphaLISA plates were briefly centrifuged at 2000 rpm. A 2.3× Streptavidin Donor Bead intermediate stock was prepared in assay buffer. 10 μL was added to each well and incubated in darkness at room temperature. AlphaLISA plates were briefly centrifuged at 2000 rpm. Relative light units (RLU) were measured using the AlphaScreen protocol on an EnVision Plate Reader. Results were plotted in GraphPad Prism, and statistical analyses were performed using an unpaired t-test.

As shown in FIGS. 32A and 32B, BA072 elicited enhanced IL-2 secretion relative to isotype control in the PBMC samples from both donor 1 and donor 2. This response was generally dose-dependent. IL-2 secretion elicited by BA108 was comparable to isotype control.

6.4 Example 4: CD96 Internalization 6.4.1 CD96 Internalization in CD96-Expressing Jurkat Cells Variants of BA072 were examined for their capacity to induce antibody-dependent internalization of CD96 on CD96-expressing Jurkat cells. Briefly, Jurkat cells were cultured in RPMI 1640 (Corning Catalog #10-040-CM) supplemented with 10% fetal bovine serum (Benchmark Catalog #100-106, Lot A69E00F) and 1% Pen Strep Glutamine (Gibco Catalog #10378-016). Two million Jurkat cells were pelleted by centrifugation for 5 minutes at 1200 rpm. The cells were stained by resuspending the pellet in 1 mL of 0.5 μM CellTrace Far Red (Invitrogen Catalog #C34565) and 1:500 dilution of HaloTag Ligand AF488 (Promega Catalog #G100A) in PBS (Corning Catalog #21-040-CV) and incubating for 15 minutes at 37° C. and 5% CO$_2$. After incubation, 9 mL of PBS was added, and the cells were pelleted by centrifugation for 5 minutes at 300 g. The cell pellet was then resuspended in Jurkat culture media. Antibodies were diluted in culture media at 2× their final concentration (10 μg/mL). Stained Jurkat cells were diluted to 0.4 million cells per mL. The assay was performed in 384-well microscopy plates (Greiner, Cat. No. 781936) by pipetting 30 μL of the antibodies and 30 μL stained Jurkat cells (12500 cells) per well.

Live imaging was performed immediately afterward, using an ImageXpress Micro Confocal High-Content microscope (Molecular Devices) under environmental control (37° C., 5% CO$_2$) and images were acquired every hour from the Cy5 (CellTrace Far Red) and FITC (HaloTag Ligand) channels for Jurkat cells over the course of eight hours. Image analysis was performed using the MetaXpress analysis software (Molecular Devices). Jurkat cells were identified from the Cy5 channel and the amount of HaloTag Ligand signal was quantified per cell from the FITC channel. Cells with HaloTag Ligand intensity above the background were designated as internalized. The number of internalized cells was normalized against the total cell count per condition to determine a percent internalization measurement.

As shown in FIGS. 33A-33D, BA072 (FIG. 33A), BA101 (FIG. 33B), Reference A (FIG. 33C) and PVR-Fc (FIG. 33D) promoted higher levels of internalization of CD96 on CD96-expressing Jurkat cells, relative to isotype control.

As shown in FIG. 34, BA072 (FIG. 34A), and the germlined variants BA083 (FIG. 34B) and BA084 (FIG. 34C) promoted higher levels of internalization of CD96 on CD96-expressing Jurkat cells, relative to isotype control.

6.4.2 CD96 Internalization in Primary Cells

In this example, internalization of anti-CD96 antibody, BA072, into primary activated T cells expressing CD96 was analyzed. Internalization of BA072 or an IgG1 isotype control antibody was assessed using anti-human IgG Fc antibody conjugated to pyrrolobenzodiazepine (PBD). This secondary antibody drug conjugate αHFc-PBD binds to an antibody (e.g., BA072) and results in release of the cytotoxic payload PBD into the cytoplasm of the cell upon internalization.

Briefly, pre-activated primary T cells expressing CD96 were plated in white-bottom tissue culture plates at a density of 5×10$^4$ per well. Using the secondary antibody drug conjugate αHFc-PBD, a seven-point dose titration with three-fold dilutions (3.3 μg/ml to 0.003 μg/ml) of either BA072 or IgG isotype control antibody in concert with αHFc-PBD (1:1 with the primary antibody) was added to the cells at a final volume of 100 μl/well. The cells were incubated with the primary antibodies and the secondary antibody drug conjugate at 37° C. and 5% CO$_2$ for 72 hours.

Following incubation, 90 μl of reconstituted CellTiter-Glo (Promega) was added to each well and the cells were incubated at room temperature for 5 minutes. The resulting luminescence was recorded using Envision instrument (Perkin Elmer).

As shown in FIGS. 35A and 35B, BA072 induced a greater reduction of cell survival, in two separate donors, than did the isotype control. Because cell death is a marker of internalization, this result indicates that BA072 enhances internalization of CD96, relative to isotype control.

6.5 Example 5: Epitope Binding of Anti-CD96 Antibodies 6.5.1 BA072 and BA101 Fab Binding to Fc-Tagged Full-Length Isoform 2 of Human CD96 or Fc-Tagged Domain 1 of Human CD96

The binding of BA072 Fab and BA101 Fab to full-length isoform 2 of human CD96 (SEQ ID NO: 128) with an Fc tag, or domain 1 of human CD96 (SEQ ID NO: 130) with an Fc tag, was assessed by surface plasmon resonance.

Briefly, surface plasmon resonance experiments were performed using a Biacore T200 instrument, and sensorgrams were visually inspected using Biacore T200 Evaluation Software 3.0.

Specifically, 17 μg/ml of full-length isoform 2 of human CD96 (SEQ ID NO: 128) with an Fc tag and 5 μg/ml of domain 1 of human CD96 (SEQ ID NO: 130) with an Fc tag, diluted in a running buffer (10 mM HEPES, 150 mM NaCl, 3 mM EDTA, and 0.05% surfactant P20) were captured on individual flow cells of a series S Protein A sensor chip GE Healthcare Ltd, cat #29-1275-56) using a 60 sec injection at a flow rate of 10 μl/min to reach about 900 resonance units (RUs). A single flow cell was kept as a reference. BA072 Fab, BA101 Fab or Reference A Fab at a concentration of 100 nM were flowed over each the flow cell at a rate of 30 μl/min with a 3-min association phase followed by a 20-min disassociation phase. The sensor chip was regenerated between cycles with a 40-sec injection of 10 mM glycine, pH 1.5. The sensorgrams were visually inspected using Biacore T200 Evaluation Software 3.0.

As shown in FIG. 36A, anti-human CD96 antibodies BA072 Fab, BA101 Fab and Reference A Fab bound to purified recombinant full-length isoform 2 of human CD96 (SEQ ID NO: 128). As shown in FIG. 36B, BA072 Fab bound to domain 1 of human CD96 (SEQ ID NO: 130). More limited binding was observed with BA101 Fab to domain 1 of human CD96 (SEQ ID NO: 130). No binding was observed between domain 1 of human CD96 (SEQ ID NO: 130) and Reference A Fab.

6.5.2 Epitope Binding of BA072 and BA101 Fabs

The binding of BA072 Fab and BA101 Fab to full-length isoform 2 of human CD96 (SEQ ID NO: 128) with an Fc tag, or domain 1 human CD96 (SEQ ID NO: 130) with an Fc tag, was assessed by surface plasmon resonance.

Briefly, surface plasmon resonance experiments were performed using a Biacore T200 instrument, and sensorgrams were visually inspected using Biacore T200 Evaluation Software 3.0.

Specifically, 17 μg/ml of full-length isoform 2 of human CD96 (SEQ ID NO: 128) with an Fc tag, and 5 μg/ml of domain 1 human CD96 (SEQ ID NO: 130) with an Fc tag, diluted in a running buffer (10 mM HEPES, 150 mM NaCl, 3 mM EDTA, and 0.05% surfactant P20) were captured on individual flow cells of a series S Protein A sensor chip (GE Healthcare Ltd, cat #29-1275-56) using a 60 sec injection at a flow rate of 10 μl/min to reach about 900 resonance units (RUs). A single flow cell was kept as a reference. BA072 Fab, or BA101 Fab at a concentration of 100 nM were flowed over each of the flow cells at a rate of 30 μl/min with a 3-min association phase. Using the Biacore T200's Dual injection protocol, the association phase was immediately followed by a second injection of a combination of the initial Fab plus a second Fab at equimolar concentrations (i.e., 100 nM BA072 Fab+BA101 Fab, 100 nM BA072 Fab+Reference A Fab, 100 nM BA101 Fab+BA072 Fab, or 100 nM BA101 Fab+BA072 Fab). The dual Fab injection was flowed over the flow cells at a rate of 30 μl/min with a 3-min association phase, followed by a 10-min disassociation phase. The sensor chip was regenerated between cycles with a 40-sec injection of 10 mM glycine, pH 1.5. The sensorgrams were visually inspected using Biacore T200 Evaluation Software 3.0.

As shown in FIG. 37A, Reference A Fab was able to bind to full-length isoform 2 of human CD96 after binding of BA072 Fab, suggesting that BA072 binds a different epitope on CD96 relative to Reference A. As shown in FIG. 37B, Reference A Fab was able to bind to full-length human CD96 after BA101 Fab had bound, suggesting that BA101 binds a different epitope on CD96 relative to Reference A. As shown in FIG. 37C, neither Reference A Fab nor BA101 were able to bind to domain 1 of human CD96 following binding of BA072 Fab. As shown in FIG. 37D, BA101 Fab was able to bind domain 1 of CD96. Reference A Fab was unable to bind to domain 1 of CD96 after BA101 Fab binding. BA072 Fab was able to bind domain 1 of CD96 following binding of BA101 Fab, indicating that BA072 binds to a different epitope relative to BA101.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody that specifically binds to human CD96, the antibody comprising a heavy chain variable region (VH) comprising the CDRH1, CDRH2, and CDRH3 amino acid sequences of the VH amino acid sequence of SEQ ID NO: 46, and a light chain variable region (VL) comprising the CDRL1, CDRL2, and CDRL3 amino acid sequences of the VL amino acid sequence of SEQ ID NO: 63.

2. The isolated antibody of claim 1, wherein CDRH1, CDRH2, CDRH3, CDRL1, CDRL2, and CDRL3 comprise the amino acid sequences of SEQ ID NOs: 2, 10, 18, 21, 29, and 33, respectively.

3. The isolated antibody of claim 1, wherein the VH comprises the amino acid sequence of SEQ ID NO: 46; and/or the VL comprises the amino acid sequence of SEQ ID NO: 63.

4. The isolated antibody of claim 1, wherein the antibody comprises a heavy chain constant region selected from the group consisting of human IgG$_1$, IgG$_2$, IgG$_3$, IgG$_4$, IgA$_1$, and IgA$_2$.

5. The isolated antibody of claim 4, wherein the heavy chain constant region is an IgG$_1$ heavy chain constant region.

6. The isolated antibody of claim 4, wherein the heavy chain constant region comprises an amino acid sequence selected from the group consisting of SEQ ID NOs: 121, 124-126 or 175-178.

7. The isolated antibody of claim 1, wherein the antibody comprises a human kappa light chain constant region or a human lambda light chain constant region.

8. The isolated antibody of claim 7, wherein the light chain constant region comprises the amino acid sequence of SEQ ID NO: 122 or 123.

9. The isolated antibody of claim 1, wherein the antibody comprises a heavy chain comprising the amino acid sequence of SEQ ID NO: 86 or 154, and/or a light chain comprising the amino acid sequence of SEQ ID NO: 103.

10. A composition comprising the antibody of claim 1 and a pharmaceutically acceptable excipient.

11. An isolated antibody that specifically binds to human CD96, the antibody comprising a VH comprising the amino acid sequence of SEQ ID NO: 46, and a VL comprising the amino acid sequence of SEQ ID NO: 63.

12. The isolated antibody of claim 11, wherein the antibody comprises a heavy chain constant region selected from the group consisting of human IgG$_1$, IgG$_2$, IgG$_3$, IgG$_4$, IgA$_1$, and IgA$_2$.

13. The isolated antibody of claim 12, wherein the heavy chain constant region is an IgG$_1$ heavy chain constant region.

14. The isolated antibody of claim 12, wherein the heavy chain constant region comprises an amino acid sequence selected from the group consisting of SEQ ID NOs: 121, 124-126 or 175-178.

15. The isolated antibody of claim 11, wherein the antibody comprises a human kappa light chain constant region or a human lambda light chain constant region.

16. The isolated antibody of claim 15, wherein the light chain constant region comprises the amino acid sequence of SEQ ID NO: 122 or 123.

17. The isolated antibody of claim 11, wherein the antibody comprises a heavy chain comprising the amino acid sequence of SEQ ID NO: 86 or 154, and/or a light chain comprising the amino acid sequence of SEQ ID NO: 103.

18. A composition comprising the antibody of claim 11 and a pharmaceutically acceptable excipient.

19. An isolated antibody that specifically binds to human CD96, the antibody comprising a heavy chain comprising the amino acid sequence of SEQ ID NO: 86 or 154, and a light chain comprising the amino acid sequence of SEQ ID NO: 103.

20. The isolated antibody of claim 19, wherein the heavy chain comprises the amino acid sequence of SEQ ID NO: 86, and the light chain comprises the amino acid sequence of SEQ ID NO: 103.

21. A composition comprising the antibody of claim 19 and a pharmaceutically acceptable excipient.

22. A composition comprising the antibody of claim 20 and a pharmaceutically acceptable excipient.

* * * * *

SEQUENCE LISTING

```
<160> NUMBER OF SEQ ID NOS: 180

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ala Met His
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Tyr Ala Met His
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Ser Met His
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Ala Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Trp Ile Asn Ala Gly Asn Gly Asn Thr Lys Tyr Ser Gln Lys Phe Gln
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Ile Asn Ala Val Ser Gly Asp Thr Lys Tyr Ser Gln Lys Phe Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ile Asn Ala Gly Thr Gly Asp Thr Lys Tyr Ser Gln Lys Phe Gln
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ile Asn Glu Gly Tyr Gly Asn Thr Lys Tyr Ser Gln Lys Phe Gln
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Ile Asn Ala Gly Tyr Gly Tyr Thr Lys Tyr Ser Gln Lys Phe Gln
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 10

Trp Ile Asn Ala Gly Thr Gly Asn Thr Lys Tyr Ser Gln Lys Phe Gln
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Asn Ala Gly Tyr Gly Asn Thr Lys Tyr Ser Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ile Asn Ala Trp Asn Gly Asn Thr Lys Tyr Ser Gln Lys Phe Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ile Asn Val Gly Thr Gly Thr Thr Lys Tyr Ser Gln Lys Phe Gln
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ile Asn Ala Val Asn Gly Asn Thr Lys Tyr Ser Gln Lys Phe Gln
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Trp Ile Asn Ala Gly Asn Trp Asn Thr Lys Tyr Ser Gln Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Asn Ala Trp Thr Gly Asn Thr Lys Tyr Ser Gln Lys Phe Gln
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ile Ile Pro Ile Phe Gly Thr Ala Asn Tyr Ala Gln Lys Phe Gln
1               5                   10                  15

Gly

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Trp Gly Met Ser Tyr Gly Met Asp Val
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Tyr Asp Ser Arg Pro Leu Asp Val
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Asp Ser Arg Pro Leu Asp Tyr
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Ser Ile Ser Ser Tyr Leu Asn
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Gln Ser Ile Ser Pro Tyr Leu Asn
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ala Ser Gln Ser Ile Leu Ser Tyr Leu Asn
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Ser Ile Ser Trp Tyr Leu Asn
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Ser Ile Thr Ser Tyr Leu Asn
1               5                   10

<210> SEQ ID NO 26
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 26

Gly Gly Asn Asn Ile Gly Ser Lys Ile Val His
1               5                   10

<210> SEQ ID NO 27

<400> SEQUENCE: 27

000

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Ser Ser Leu Gln Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Ser Ser Leu Gln Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Glu Ser Ser Leu Gln Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Ser Ser Leu Gln Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 32

Asp Asp Arg Asp Arg Pro Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Ser Tyr Ser Thr Pro Ala Leu Thr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Ala Tyr Ser Thr Pro Ala Leu Ser
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Val Trp Asp Ile Asn Val His His Val Ile
1               5                   10

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 36

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80
```

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser
        115

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 37

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
        115

<210> SEQ ID NO 38
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 38

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Val Ser Gly Asp Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys 85                  90                  95

Ala Arg Asn Trp Gly Met Ser Tyr Gly Met Asp Val Trp Gly Gln Gly
                100                 105                 110

Thr Met Val Thr Val Ser Ser
            115

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 39

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
                20                  25                  30

Ala Met His Trp Val Arg Gln Ala Pro Gly Gln Arg Leu Glu Trp Met
            35                  40                  45

Gly Trp Ile Asn Ala Val Ser Gly Asp Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
                100                 105                 110

Thr Thr Val Thr Val Ser Ser
            115

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 40

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Thr Gly Asp Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

```
Ala Arg Asn Trp Gly Met Ser Tyr Gly Met Asp Val Trp Gly Gln Gly
            100                 105                 110

Thr Met Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 41

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
        115

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 42

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gln Tyr
            20                  25                  30

Ala Met His Trp Val Arg Gln Ala Pro Gly Gln Arg Leu Glu Trp Met
        35                  40                  45

Gly Trp Ile Asn Glu Gly Tyr Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95
```

```
Ala Arg Asn Trp Gly Met Ser Tyr Gly Met Asp Val Trp Gly Gln Gly
            100                 105                 110

Thr Met Val Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 43

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Tyr Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 44

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Tyr Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
```

```
                100                 105                 110

Thr Thr Val Thr Val Ser Ser
        115

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 45

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gln Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser
        115

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 46

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gln Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110
```

Thr Thr Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 47

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 48

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Trp Gly Met Ser Tyr Gly Met Asp Val Trp Gly Gln Gly
            100                 105                 110

```
Thr Thr Val Thr Val Ser Ser
        115
```

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 49

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Trp Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
        115
```

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 50

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Val Gly Thr Gly Thr Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
```

```
<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 51

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
                20                  25                  30

Ala Met His Trp Val Arg Gln Ala Pro Gly Gln Arg Leu Glu Trp Met
            35                  40                  45

Gly Trp Ile Asn Ala Val Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 52

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
                20                  25                  30

Ser Met His Trp Val Arg Gln Ala Pro Gly Gln Arg Leu Glu Trp Met
            35                  40                  45

Gly Trp Ile Asn Ala Gly Asn Trp Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
        115
```

-continued

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 53

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Trp Thr Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 54

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Leu Asp Val Trp Gly Gln Gly
            100                 105                 110

Thr Met Val Thr Val Ser Ser
        115

```
<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 55

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Leu Ser Tyr Gly Met Asp Val Trp Gly Gln Gly
            100                 105                 110

Thr Met Val Thr Val Ser Ser
        115

<210> SEQ ID NO 56
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 56

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Leu Ser Tyr Gly Leu Asp Val Trp Gly Gln Gly
            100                 105                 110

Thr Met Val Thr Val Ser Ser
        115
```

```
<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 57

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Leu Asp Val Trp Gly Gln Gly
            100                 105                 110

Thr Thr Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 58

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Leu Ser Tyr Gly Met Asp Val Trp Gly Gln Gly
            100                 105                 110

Thr Thr Val Thr Val Ser Ser
        115

<210> SEQ ID NO 59
```

<211> LENGTH: 119
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Gln or pyroglutamate

<400> SEQUENCE: 59

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Leu Ser Tyr Gly Leu Asp Val Trp Gly Gln Gly
            100                 105                 110

Thr Thr Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Gln or pyroglutamate

<400> SEQUENCE: 60

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Val Trp Gly Gln Gly Thr
            100                 105                 110

Leu Val Thr Val Ser Ser
        115

<210> SEQ ID NO 61
<211> LENGTH: 118

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 61

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Tyr Trp Gly Gln Gly Thr
            100                 105                 110

Leu Val Thr Val Ser Ser
            115

<210> SEQ ID NO 62
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 63
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Glu Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ser Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 66
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 67
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Trp Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 68
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Leu Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys
            100                 105

<210> SEQ ID NO 69
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Thr Pro Ala
                85                  90                  95

Leu Ser Phe Gly Gly Gly Thr Lys Val Asp Ile Lys
            100                 105

<210> SEQ ID NO 70
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Val Ser
        35                  40                  45

Asp Asp Arg Asp Arg Pro Ser Gly Ile Pro Glu Arg Phe Ser Gly Ser
50                  55                  60

Asn Ser Gly Asn Thr Ala Thr Leu Thr Ile Asn Thr Val Glu Ala Gly

```
                65                  70                  75                  80
Asp Glu Ala Asp Tyr Tyr Cys Gln Val Trp Asp Ile Asn Val His His
                    85                  90                  95
Val Ile Phe Gly Gly Gly Thr Lys Val Thr Val Leu
                100                 105

<210> SEQ ID NO 71
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
                20                  25                  30

His Trp Tyr Gln Gln Lys Pro Gly Gln Ala Pro Val Leu Val Val Ser
                35                  40                  45

Asp Asp Arg Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu
                100                 105

<210> SEQ ID NO 72
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
                20                  25                  30

His Trp Tyr Gln Gln Lys Ser Gly Gln Ala Pro Val Leu Val Ile Tyr
                35                  40                  45

Asp Asp Arg Asp Arg Pro Ser Gly Ile Pro Glu Arg Phe Ser Gly Ser
50                  55                  60

Asn Ser Gly Asn Thr Ala Thr Leu Thr Ile Asn Thr Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu
                100                 105

<210> SEQ ID NO 73
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 73

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Pro Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Asn Thr Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu
            100                 105

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu
            100                 105

<210> SEQ ID NO 75
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

```
Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ile Asn Val His His
                 85                  90                  95

Val Ile Phe Gly Gly Gly Thr Lys Leu Thr Val Leu
            100                 105

<210> SEQ ID NO 76
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 76

Xaa Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Ala Met His Trp Val Arg Gln Ala Pro Gly Gln Arg Leu Glu Trp Met
         35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Thr Ser Thr Ala Tyr
 65                  70                  75                  80

Met Glu Leu Arg Ser Leu Arg Ser Asp Asp Thr Ala Met Tyr Tyr Cys
                 85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 77
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 77

Xaa Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Ala Met His Trp Val Arg Gln Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asn Trp Gly Met Ser Tyr Gly Met Asp Val Trp Gly Gln Gly
            100                 105                 110
Thr Thr Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 78
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 78

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
                20                  25                  30

Ala Met His Trp Val Arg Gln Ala Pro Gly Gln Arg Leu Glu Trp Met
            35                  40                  45

Gly Trp Ile Asn Ala Val Ser Gly Asp Thr Lys Tyr Ser Gln Lys Phe
```

```
            50                  55                  60
Gln Gly Arg Val Thr Ile Thr Arg Asp Thr Ser Thr Ser Thr Ala Tyr
 65                  70                  75                  80
Met Glu Leu Arg Ser Leu Arg Ser Asp Asp Thr Ala Met Tyr Tyr Cys
                 85                  90                  95
Ala Arg Asn Trp Gly Met Ser Tyr Gly Met Asp Val Trp Gly Gln Gly
                100                 105                 110
Thr Met Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Arg Val Glu Pro Lys Ser Cys Asp Lys
                210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 79
<211> LENGTH: 449
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 79

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Val Ser Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
                355                 360                 365
Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 80
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 80

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Thr Gly Asp Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 81
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 81

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 82
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 82

Xaa Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Asn Gln Tyr
                20                  25                  30

Ala Met His Trp Val Arg Gln Ala Pro Gly Gln Arg Leu Glu Trp Met
                35                  40                  45

Gly Trp Ile Asn Glu Gly Tyr Gly Asn Thr Lys Tyr Ser Gln Lys Phe
 50                  55                  60

Gln Gly Arg Val Thr Ile Thr Arg Asp Thr Ser Thr Ser Thr Ala Tyr
 65                  70                  75                  80

Met Glu Leu Arg Ser Leu Arg Ser Asp Thr Ala Met Tyr Tyr Cys
                85                  90                  95

Ala Arg Asn Trp Gly Met Ser Tyr Gly Met Asp Val Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
 145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
 210                 215                 220

Thr His Thr Cys Pro Pro Cys Pro Ala Pro Glu Leu Leu Gly Gly Pro
 225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
 305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
 385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro Gly
        435                 440                 445

Lys

<210> SEQ ID NO 83
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 83

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Tyr Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
                305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 84
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 84

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
                20                  25                  30

Ala Met His Trp Val Arg Gln Ala Pro Gly Gln Arg Leu Glu Trp Met
            35                  40                  45

Gly Trp Ile Asn Ala Gly Tyr Gly Tyr Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190
```

```
Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 85
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 85

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gln Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80
```

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 86
<211> LENGTH: 449
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<221> NAME/KEY: MOD_RES
<222> LOCATION: (1)..(1)
<223> OTHER INFORMATION: Gln or pyroglutamate

<400> SEQUENCE: 86

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gln Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 87
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 87

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                    260                 265                 270
Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 88
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 88

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 89
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 89

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ile Asn Ala Trp Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 90
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Gln or pyroglutamate

<400> SEQUENCE: 90

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Val Gly Thr Gly Thr Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

-continued

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 91
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 91
```

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Ala Met His Trp Val Arg Gln Ala Pro Gly Gln Arg Leu Glu Trp Met
        35                  40                  45

Gly Trp Ile Asn Ala Val Asn Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
```

```
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 92
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 92

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Ser Met His Trp Val Arg Gln Ala Pro Gly Gln Arg Leu Glu Trp Met
        35                  40                  45

Gly Trp Ile Asn Ala Gly Asn Trp Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Asn Trp Gly Met Ser Tyr Gly Met Asp Val Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 93
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
```

<223> OTHER INFORMATION: Gln or pyroglutamate

<400> SEQUENCE: 93

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Trp Thr Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Trp Gly Met Ser Tyr Gly Met Asp Val Trp Gly Gln Gly
        100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 94
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 94

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Leu Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

-continued

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

```
<210> SEQ ID NO 95
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 95
```

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Leu Ser Tyr Gly Met Asp Val Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 96
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 96

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45
```

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
 65              70                  75                  80

Met Glu Leu Arg Ser Leu Arg Ser Asp Asp Thr Ala Met Tyr Tyr Cys
                 85                  90                  95

Ala Arg Asn Trp Gly Leu Ser Tyr Gly Leu Asp Val Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 97

-continued

```
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 97

Xaa Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
                35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Leu Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 98
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 98

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Leu Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 99
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 99

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Leu Ser Tyr Gly Leu Asp Val Trp Gly Gln Gly
            100                 105                 110

Thr Thr Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 100
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 100
```

```
Xaa Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Val Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

-continued

```
                420                 425                 430
Leu His Asn His Tyr Thr Gln Lys Ser Leu Ser Leu Ser Pro Gly Lys
        435                 440                 445

<210> SEQ ID NO 101
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 101

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 102
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 103
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 104
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Glu Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
```

```
                    85                  90                  95
Leu Thr Phe Gly Gly Gly Thr Lys Val Asp Ile Lys Arg Thr Val Ala
                100                 105                 110

Ala Pro Ser Val Phe Ile Phe Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 105
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ser Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys Arg Thr Val Ala
                100                 105                 110

Ala Pro Ser Val Phe Ile Phe Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215
```

```
<210> SEQ ID NO 106
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 107
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Trp Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 108
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Leu Ser Tyr
            20                  25                  30

Leu Asn Trp Tyr Gln Gln Lys Pro Gly Lys Ala Pro Lys Leu Leu Ile
            35                  40                  45

Tyr Ser Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Leu Thr Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 109
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Thr Pro Ala
                85                  90                  95

Leu Ser Phe Gly Gly Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Asn Thr Val Glu Ala Gly
65                  70                  75                  80
```

Asp Glu Ala Asp Tyr Tyr Cys Gln Val Trp Asp Ile Asn Val His His
                85                  90                  95

Val Ile Phe Gly Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
    210

<210> SEQ ID NO 111
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Pro Gly Gln Ala Pro Val Leu Val Val Ser
        35                  40                  45

Asp Asp Arg Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser

<210> SEQ ID NO 112
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Ile Tyr
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Asn Thr Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 113
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Pro Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Asn Thr Val Glu Ala Gly

```
            65                  70                  75                  80
Asp Glu Ala Asp Tyr Tyr Cys Gln Val Trp Asp Ile Asn Val His His
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 114
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

```
Ala Pro Thr Glu Cys Ser
    210
```

<210> SEQ ID NO 115
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Ser Tyr Glu Leu Thr Gln Pro Leu Ser Val Ser Val Ala Leu Gly Gln
1               5                   10                  15

Thr Ala Ser Ile Thr Cys Gly Gly Asn Asn Ile Gly Ser Lys Ile Val
            20                  25                  30

His Trp Tyr Gln Gln Lys Ser Gly Gln Ala Pro Val Leu Val Val Ser
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ile Asn Val His His
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 116
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 116

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45
```

```
Gly Trp Ile Asn Ala Gly Asn Gly Asn Thr Lys Tyr Ser Gln Lys Phe
         50                  55                  60

Gln Gly Arg Val Thr Ile Thr Arg Asp Thr Ser Thr Ser Thr Ala Tyr
 65                  70                  75                  80

Met Glu Leu Arg Ser Leu Arg Ser Asp Asp Thr Ala Met Tyr Tyr Cys
                 85                  90                  95

Ala Arg Asn Trp Gly Met Ser Tyr Gly Met Asp Val Trp Gly Gln Gly
                100                 105                 110

Thr Met Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 117
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 117

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 118
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 118

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240
```

Asp Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 119
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 119

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Val Trp Gly Gln Gly Thr
            100                 105                 110

Leu Val Thr Val Ser Ser Ala Ser Thr Lys Gly Pro Ser Val Phe Pro
        115                 120                 125

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 120
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 120

Xaa Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
             20                  25                  30

Ala Met His Trp Val Arg Gln Ala Pro Gly Gln Arg Leu Glu Trp Met
         35                  40                  45

Gly Trp Ile Asn Ala Gly Asn Gly Asn Thr Lys Tyr Ser Gln Lys Phe
     50                  55                  60

Gln Gly Arg Val Thr Ile Thr Arg Asp Thr Ser Thr Ser Thr Ala Tyr
 65                  70                  75                  80

Met Glu Leu Arg Ser Leu Arg Ser Asp Asp Thr Ala Met Tyr Tyr Cys
                 85                  90                  95

Ala Arg Asn Trp Gly Met Ser Tyr Gly Met Asp Val Trp Gly Gln Gly
             100                 105                 110

Thr Met Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Arg Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Glu His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
```

Lys

<210> SEQ ID NO 121
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 123
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 124
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 125
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser

```
                    50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Asp Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Leu Pro Glu Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 126
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 127
<211> LENGTH: 498
<212> TYPE: PRT
<213> ORGANISM: Homo sapiens

<400> SEQUENCE: 127

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
                20                  25                  30

Val Gln Met Gln Trp Ser Lys Val Thr Asn Lys Ile Asp Leu Ile Ala
            35                  40                  45

Val Tyr His Pro Gln Tyr Gly Phe Tyr Cys Ala Tyr Gly Arg Pro Cys
        50                  55                  60

Glu Ser Leu Val Thr Phe Thr Glu Thr Pro Glu Asn Gly Ser Lys Trp
65                  70                  75                  80

Thr Leu His Leu Arg Asn Met Ser Cys Ser Val Ser Gly Arg Tyr Glu
                85                  90                  95

Cys Met Leu Val Leu Tyr Pro Glu Gly Ile Gln Thr Lys Ile Tyr Asn
            100                 105                 110

Leu Leu Ile Gln Thr His Val Thr Ala Asp Glu Trp Asn Ser Asn His
        115                 120                 125
```

Thr Ile Glu Ile Glu Ile Asn Gln Thr Leu Glu Ile Pro Cys Phe Gln
        130                 135                 140

Asn Ser Ser Ser Lys Ile Ser Ser Glu Phe Thr Tyr Ala Trp Ser Val
145                 150                 155                 160

Glu Asn Ser Ser Thr Asp Ser Trp Val Leu Leu Ser Lys Gly Ile Lys
                165                 170                 175

Glu Asp Asn Gly Thr Gln Glu Thr Leu Ile Ser Gln Asn His Leu Ile
            180                 185                 190

Ser Asn Ser Thr Leu Leu Lys Asp Arg Val Lys Leu Gly Thr Asp Tyr
        195                 200                 205

Arg Leu His Leu Ser Pro Val Gln Ile Phe Asp Asp Gly Arg Lys Phe
210                 215                 220

Ser Cys His Ile Arg Val Gly Pro Asn Lys Ile Leu Arg Ser Ser Thr
225                 230                 235                 240

Thr Val Lys Val Phe Ala Lys Pro Glu Ile Pro Val Ile Val Glu Asn
                245                 250                 255

Asn Ser Thr Asp Val Leu Val Glu Arg Arg Phe Thr Cys Leu Leu Lys
            260                 265                 270

Asn Val Phe Pro Lys Ala Asn Ile Thr Trp Phe Ile Asp Gly Ser Phe
        275                 280                 285

Leu His Asp Glu Lys Glu Gly Ile Tyr Ile Thr Asn Glu Glu Arg Lys
290                 295                 300

Gly Lys Asp Gly Phe Leu Glu Leu Lys Ser Val Leu Thr Arg Val His
305                 310                 315                 320

Ser Asn Lys Pro Ala Gln Ser Asp Asn Leu Thr Ile Trp Cys Met Ala
                325                 330                 335

Leu Ser Pro Val Pro Gly Asn Lys Val Trp Asn Ile Ser Ser Glu Lys
            340                 345                 350

Ile Thr Phe Leu Leu Gly Ser Glu Ile Ser Ser Thr Asp Pro Pro Leu
        355                 360                 365

Ser Val Thr Glu Ser Thr Leu Asp Thr Gln Pro Ser Pro Ala Ser Ser
370                 375                 380

Val Ser Pro Ala Arg Tyr Pro Ala Thr Ser Ser Val Thr Leu Val Asp
385                 390                 395                 400

Val Ser Ala Leu Arg Pro Asn Thr Thr Pro Gln Pro Ser Asn Ser Ser
                405                 410                 415

Met Thr Thr Arg Gly Phe Asn Tyr Pro Trp Thr Ser Ser Gly Thr Asp
            420                 425                 430

Thr Lys Lys Ser Val Ser Arg Ile Pro Ser Glu Thr Tyr Ser Ser Ser
        435                 440                 445

Pro Ser Gly Ala Gly Ser Thr Leu His Asp Asn Val Phe Thr Ser Thr
450                 455                 460

Ala Arg Ala Phe Ser Glu Val Pro Thr Thr Ala Asn Gly Ser Thr Lys
465                 470                 475                 480

Thr Asn His Val His Ile Thr Gly Ile Val Val Asn Lys Pro Lys Asp
                485                 490                 495

Gly Met

<210> SEQ ID NO 128
<211> LENGTH: 482
<212> TYPE: PRT
<213> ORGANISM: Homo sapiens

<400> SEQUENCE: 128

-continued

Val Trp Glu Lys Thr Val Asn Thr Glu Asn Val Tyr Ala Thr Leu
1               5                   10                  15

Gly Ser Asp Val Asn Leu Thr Cys Gln Thr Gln Val Gly Phe Phe
            20                  25                  30

Val Gln Met Gln Trp Ser Lys Val Thr Asn Lys Ile Asp Leu Ile Ala
        35                  40                  45

Val Tyr His Pro Gln Tyr Gly Phe Tyr Cys Ala Tyr Gly Arg Pro Cys
    50                  55                  60

Glu Ser Leu Val Thr Phe Thr Glu Thr Pro Glu Asn Gly Ser Lys Trp
65                  70                  75                  80

Thr Leu His Leu Arg Asn Met Ser Cys Ser Val Ser Gly Arg Tyr Glu
                85                  90                  95

Cys Met Leu Val Leu Tyr Pro Glu Gly Ile Gln Thr Lys Ile Tyr Asn
                100                 105                 110

Leu Leu Ile Gln Thr His Val Thr Ala Asp Glu Trp Asn Ser Asn His
        115                 120                 125

Thr Ile Glu Ile Glu Ile Asn Gln Thr Leu Glu Ile Pro Cys Phe Gln
    130                 135                 140

Asn Ser Ser Ser Lys Ile Ser Ser Glu Phe Thr Tyr Ala Trp Ser Val
145                 150                 155                 160

Glu Asp Asn Gly Thr Gln Glu Thr Leu Ile Ser Gln Asn His Leu Ile
                165                 170                 175

Ser Asn Ser Thr Leu Leu Lys Asp Arg Val Lys Leu Gly Thr Asp Tyr
            180                 185                 190

Arg Leu His Leu Ser Pro Val Gln Ile Phe Asp Asp Gly Arg Lys Phe
        195                 200                 205

Ser Cys His Ile Arg Val Gly Pro Asn Lys Ile Leu Arg Ser Ser Thr
    210                 215                 220

Thr Val Lys Val Phe Ala Lys Pro Glu Ile Pro Val Ile Val Glu Asn
225                 230                 235                 240

Asn Ser Thr Asp Val Leu Val Glu Arg Arg Phe Thr Cys Leu Leu Lys
                245                 250                 255

Asn Val Phe Pro Lys Ala Asn Ile Thr Trp Phe Ile Asp Gly Ser Phe
            260                 265                 270

Leu His Asp Glu Lys Glu Gly Ile Tyr Ile Thr Asn Glu Glu Arg Lys
        275                 280                 285

Gly Lys Asp Gly Phe Leu Glu Leu Lys Ser Val Leu Thr Arg Val His
    290                 295                 300

Ser Asn Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
                325                 330                 335

Ile Thr Phe Leu Leu Gly Ser Glu Ile Ser Ser Thr Asp Pro Pro Leu
            340                 345                 350

Ser Val Thr Glu Ser Thr Leu Asp Thr Gln Pro Ser Pro Ala Ser Ser
        355                 360                 365

Val Ser Pro Ala Arg Tyr Pro Ala Thr Ser Ser Val Thr Leu Val Asp
    370                 375                 380

Val Ser Ala Leu Arg Pro Asn Thr Thr Pro Gln Pro Ser Asn Ser Ser
385                 390                 395                 400

Met Thr Thr Arg Gly Phe Asn Tyr Pro Trp Thr Ser Ser Gly Thr Asp
                405                 410                 415

```
Thr Lys Lys Ser Val Ser Arg Ile Pro Ser Glu Thr Tyr Ser Ser
            420                 425                 430

Pro Ser Gly Ala Gly Ser Thr Leu His Asp Asn Val Phe Thr Ser Thr
        435                 440                 445

Ala Arg Ala Phe Ser Glu Val Pro Thr Thr Ala Asn Gly Ser Thr Lys
    450                 455                 460

Thr Asn His Val His Ile Thr Gly Ile Val Asn Lys Pro Lys Asp
465                 470                 475                 480

Gly Met

<210> SEQ ID NO 129
<211> LENGTH: 482
<212> TYPE: PRT
<213> ORGANISM: Homo sapiens

<400> SEQUENCE: 129

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
            20                  25                  30

Val Gln Met Gln Trp Ser Lys Val Thr Asn Lys Ile Asp Leu Ile Ala
        35                  40                  45

Val Tyr His Pro Gln Tyr Gly Phe Tyr Cys Ala Tyr Gly Arg Pro Cys
    50                  55                  60

Glu Ser Leu Val Thr Phe Thr Glu Thr Pro Glu Asn Gly Ser Lys Trp
65                  70                  75                  80

Thr Leu His Leu Arg Asn Met Ser Ser Ser Val Ser Gly Arg Tyr Glu
                85                  90                  95

Cys Met Leu Val Leu Tyr Pro Glu Gly Ile Gln Thr Lys Ile Tyr Asn
            100                 105                 110

Leu Leu Ile Gln Thr His Val Thr Ala Asp Glu Trp Asn Ser Asn His
        115                 120                 125

Thr Ile Glu Ile Glu Ile Asn Gln Thr Leu Glu Ile Pro Cys Phe Gln
130                 135                 140

Asn Ser Ser Ser Lys Ile Ser Ser Glu Phe Thr Tyr Ala Trp Ser Val
145                 150                 155                 160

Glu Asp Asn Gly Thr Gln Glu Thr Leu Ile Ser Gln Asn His Leu Ile
                165                 170                 175

Ser Asn Ser Thr Leu Leu Lys Asp Arg Val Lys Leu Gly Thr Asp Tyr
            180                 185                 190

Arg Leu His Leu Ser Pro Val Gln Ile Phe Asp Asp Gly Arg Lys Phe
        195                 200                 205

Ser Cys His Ile Arg Val Gly Pro Asn Lys Ile Leu Arg Ser Ser Thr
    210                 215                 220

Thr Val Lys Val Phe Ala Lys Pro Glu Ile Pro Val Ile Val Glu Asn
225                 230                 235                 240

Asn Ser Thr Asp Val Leu Val Glu Arg Arg Phe Thr Cys Leu Leu Lys
                245                 250                 255

Asn Val Phe Pro Lys Ala Asn Ile Thr Trp Phe Ile Asp Gly Ser Phe
            260                 265                 270

Leu His Asp Glu Lys Glu Gly Ile Tyr Ile Thr Asn Glu Glu Arg Lys
        275                 280                 285

Gly Lys Asp Gly Phe Leu Glu Leu Lys Ser Val Leu Thr Arg Val His
    290                 295                 300
```

```
Ser Asn Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
                325                 330                 335

Ile Thr Phe Leu Leu Gly Ser Glu Ile Ser Ser Thr Asp Pro Pro Leu
            340                 345                 350

Ser Val Thr Glu Ser Thr Leu Asp Thr Gln Pro Ser Pro Ala Ser Ser
        355                 360                 365

Val Ser Pro Ala Arg Tyr Pro Ala Thr Ser Ser Val Thr Leu Val Asp
    370                 375                 380

Val Ser Ala Leu Arg Pro Asn Thr Thr Pro Gln Pro Ser Asn Ser Ser
385                 390                 395                 400

Met Thr Thr Arg Gly Phe Asn Tyr Pro Trp Thr Ser Ser Gly Thr Asp
                405                 410                 415

Thr Lys Lys Ser Val Ser Arg Ile Pro Ser Glu Thr Tyr Ser Ser Ser
                420                 425                 430

Pro Ser Gly Ala Gly Ser Thr Leu His Asp Asn Val Phe Thr Ser Thr
            435                 440                 445

Ala Arg Ala Phe Ser Glu Val Pro Thr Thr Ala Asn Gly Ser Thr Lys
450                 455                 460

Thr Asn His Val His Ile Thr Gly Ile Val Asn Lys Pro Lys Asp
465                 470                 475                 480

Gly Met

<210> SEQ ID NO 130
<211> LENGTH: 119
<212> TYPE: PRT
<213> ORGANISM: Homo sapiens

<400> SEQUENCE: 130

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
                20                  25                  30

Val Gln Met Gln Trp Ser Lys Val Thr Asn Lys Ile Asp Leu Ile Ala
            35                  40                  45

Val Tyr His Pro Gln Tyr Gly Phe Tyr Cys Ala Tyr Gly Arg Pro Cys
    50                  55                  60

Glu Ser Leu Val Thr Phe Thr Glu Thr Pro Glu Asn Gly Ser Lys Trp
65                  70                  75                  80

Thr Leu His Leu Arg Asn Met Ser Cys Ser Val Ser Gly Arg Tyr Glu
                85                  90                  95

Cys Met Leu Val Leu Tyr Pro Gly Ile Gln Thr Lys Ile Tyr Asn
                100                 105                 110

Leu Leu Ile Gln Thr His Val
        115

<210> SEQ ID NO 131
<211> LENGTH: 119
<212> TYPE: PRT
<213> ORGANISM: Homo sapiens

<400> SEQUENCE: 131

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
```

```
            20                  25                  30
Val Gln Met Gln Trp Ser Lys Val Thr Asn Lys Ile Asp Leu Ile Ala
         35                  40                  45

Val Tyr His Pro Gln Tyr Gly Phe Tyr Cys Ala Tyr Gly Arg Pro Cys
     50                  55                  60

Glu Ser Leu Val Thr Phe Thr Glu Thr Pro Glu Asn Gly Ser Lys Trp
 65                  70                  75                  80

Thr Leu His Leu Arg Asn Met Ser Ser Val Ser Gly Arg Tyr Glu
                 85                  90                  95

Cys Met Leu Val Leu Tyr Pro Glu Gly Ile Gln Thr Lys Ile Tyr Asn
             100                 105                 110

Leu Leu Ile Gln Thr His Val
            115
```

<210> SEQ ID NO 132
<211> LENGTH: 499
<212> TYPE: PRT
<213> ORGANISM: Macaca fascicularis

<400> SEQUENCE: 132

```
Val Trp Gly Lys Pro Phe Asn Thr Glu Glu Asn Ile Tyr Ala Thr Leu
 1               5                  10                  15

Gly Ser Asp Val Asn Leu Thr Cys Gln Thr Gln Ala Lys Gly Phe Leu
             20                  25                  30

Val Gln Met Gln Trp Ser Lys Val Thr Asp Lys Ala Asp Leu Ile Ala
         35                  40                  45

Leu Tyr His Pro Gln Tyr Gly Phe His Cys Ala Tyr Gly Ser Pro Cys
     50                  55                  60

Glu Ser Leu Val Thr Phe Thr Gln Thr Pro Glu Asn Gly Ser Lys Trp
 65                  70                  75                  80

Thr Leu His Leu Arg Asn Met Ser Ser Val Ser Gly Arg Tyr Glu
                 85                  90                  95

Cys Met Leu Thr Leu Tyr Pro Glu Gly Met Gln Thr Lys Ile Tyr Asn
             100                 105                 110

Leu Leu Ile Gln Thr His Val Thr Pro Asp Glu Trp Lys Ser Asn His
            115                 120                 125

Thr Ile Glu Ile Glu Ile Asn Gln Thr Leu Glu Ile Pro Cys Phe Gln
130                 135                 140

Asn Ser Ser Ser Glu Ile Ser Ser Glu Phe Thr Tyr Ala Trp Leu Val
145                 150                 155                 160

Val Lys Asn Ser Ser Thr Asp Ser Trp Val Leu Leu Ser Lys Gly Lys
                165                 170                 175

Arg Tyr Asp Asn Gly Thr Gln Leu Thr Leu Ile Ser Gln Asp His Leu
            180                 185                 190

Ile Ser Ser Ser Thr Leu Leu Lys Asp Arg Val Lys Val Gly Ile Asp
        195                 200                 205

Tyr Arg Leu His Leu Ser Pro Val Gln Ile Phe Asp Asp Gly Arg Lys
    210                 215                 220

Phe Ser Cys His Ile Arg Val Gly Pro Asp Lys Ile Leu Arg Ser Ser
225                 230                 235                 240

Thr Thr Ile Lys Val Phe Ala Lys Pro Glu Ile Pro Met Ile Val Glu
                245                 250                 255

Asn Asn Ser Thr Asp Val Leu Val Glu Arg Thr Phe Thr Cys Leu Leu
            260                 265                 270
```

```
Lys Asn Val Phe Pro Lys Ala Asn Ile Ile Trp Phe Ile Asp Gly Ser
            275                 280                 285

Phe Leu His Asp Glu Lys Glu Gly Ile Tyr Ile Thr Asn Glu Arg
290                 295                 300

Lys Gly Lys Asp Gly Phe Leu Glu Leu Lys Ser Val Leu Thr Arg Val
305                 310                 315                 320

His Ser Asp Lys Pro Ala Gln Ser Asp Asn Leu Thr Ile Trp Cys Met
                325                 330                 335

Ala Leu Ser Pro Val Pro Gly Asn Lys Val Trp Asn Ile Ser Ser Glu
            340                 345                 350

Lys Ile Thr Phe Leu Leu Gly Ser Glu Met Ser Thr Thr Asp Leu Pro
            355                 360                 365

Pro Ser Val Thr Glu Ser Thr Leu Asp Thr Gln Pro Ser Pro Ala Ser
            370                 375                 380

Ser Val Ser Pro Thr Arg Tyr Pro Ala Thr Ser Ser Val Thr Leu Ala
385                 390                 395                 400

Asp Val Ser Ala Leu Arg Pro Asn Thr Thr Pro Gln Ser Ser Ser Ser
                405                 410                 415

Ser Val Thr Thr Gln Asp Phe Asn Tyr Pro Trp Thr Ser Ser Gly Thr
            420                 425                 430

Asp Ala Lys Lys Ser Phe Ser Gln Ile Pro Ser Glu Thr Tyr Ser Ser
            435                 440                 445

Ser Pro Ser Gly Ala Gly Ser Thr Leu His Asp Asn Val Phe Thr Ser
            450                 455                 460

Thr Thr Arg Ala Leu Ser Glu Val Pro Thr Thr Ala Asn Gly Ser Thr
465                 470                 475                 480

Lys Thr Asn His Val His Ile Thr Gly Ile Val Val Ser Lys Pro Lys
                485                 490                 495

Asp Gly Met

<210> SEQ ID NO 133
<211> LENGTH: 482
<212> TYPE: PRT
<213> ORGANISM: Macaca fascicularis

<400> SEQUENCE: 133

Val Trp Gly Lys Pro Phe Asn Thr Glu Glu Asn Ile Tyr Ala Thr Leu
1               5                   10                  15

Gly Ser Asp Val Asn Leu Thr Cys Gln Thr Gln Ala Lys Gly Phe Leu
                20                  25                  30

Val Gln Met Gln Trp Ser Lys Val Thr Asp Lys Ala Asp Leu Ile Ala
            35                  40                  45

Leu Tyr His Pro Gln Tyr Gly Phe His Cys Ala Tyr Gly Ser Pro Cys
50                  55                  60

Glu Ser Leu Val Thr Phe Thr Gln Thr Pro Glu Asn Gly Ser Lys Trp
65                  70                  75                  80

Thr Leu His Leu Arg Asn Met Ser Ser Ser Val Ser Gly Arg Tyr Glu
                85                  90                  95

Cys Met Leu Thr Leu Tyr Pro Glu Gly Met Gln Thr Lys Ile Tyr Asn
                100                 105                 110

Leu Leu Ile Gln Thr His Val Thr Pro Asp Glu Trp Lys Ser Asn His
            115                 120                 125

Thr Ile Glu Ile Glu Ile Asn Gln Thr Leu Glu Ile Pro Cys Phe Gln
130                 135                 140
```

Asn Ser Ser Ser Glu Ile Ser Glu Phe Thr Tyr Ala Trp Leu Val
145                 150                 155                 160

Glu Asp Asn Gly Thr Gln Gln Thr Leu Ile Ser Gln Asp His Leu Ile
                165                 170                 175

Ser Ser Ser Thr Leu Leu Lys Asp Arg Val Lys Val Gly Ile Asp Tyr
            180                 185                 190

Arg Leu His Leu Ser Pro Val Gln Ile Phe Asp Asp Gly Arg Lys Phe
        195                 200                 205

Ser Cys His Ile Arg Val Gly Pro Asp Lys Ile Leu Arg Ser Ser Thr
    210                 215                 220

Thr Ile Lys Val Phe Ala Lys Pro Glu Ile Pro Met Ile Val Glu Asn
225                 230                 235                 240

Asn Ser Thr Asp Val Leu Val Glu Arg Thr Phe Thr Cys Leu Leu Lys
                245                 250                 255

Asn Val Phe Pro Lys Ala Asn Ile Ile Trp Phe Ile Asp Gly Ser Phe
            260                 265                 270

Leu His Asp Glu Lys Glu Gly Ile Tyr Ile Thr Asn Glu Glu Arg Lys
        275                 280                 285

Gly Lys Asp Gly Phe Leu Glu Leu Lys Ser Val Leu Thr Arg Val His
    290                 295                 300

Ser Asp Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
                325                 330                 335

Ile Thr Phe Leu Leu Gly Ser Glu Met Ser Thr Thr Asp Leu Pro Pro
            340                 345                 350

Ser Val Thr Glu Ser Thr Leu Asp Thr Gln Pro Ser Pro Ala Ser Ser
        355                 360                 365

Val Ser Pro Thr Arg Tyr Pro Ala Thr Ser Ser Val Thr Leu Ala Asp
    370                 375                 380

Val Ser Ala Leu Arg Pro Asn Thr Thr Pro Gln Ser Ser Ser Ser Ser
385                 390                 395                 400

Val Thr Thr Gln Asp Phe Asn Tyr Pro Trp Thr Ser Ser Gly Thr Asp
                405                 410                 415

Ala Lys Lys Ser Phe Ser Gln Ile Pro Ser Glu Thr Tyr Ser Ser Ser
            420                 425                 430

Pro Ser Gly Ala Gly Ser Thr Leu His Asp Asn Val Phe Thr Ser Thr
        435                 440                 445

Thr Arg Ala Leu Ser Glu Val Pro Thr Thr Ala Asn Gly Ser Thr Lys
    450                 455                 460

Thr Asn His Val His Ile Thr Gly Ile Val Val Ser Lys Pro Lys Asp
465                 470                 475                 480

Gly Met

<210> SEQ ID NO 134
<211> LENGTH: 119
<212> TYPE: PRT
<213> ORGANISM: Macaca fascicularis

<400> SEQUENCE: 134

Val Trp Gly Lys Pro Phe Asn Thr Glu Glu Asn Ile Tyr Ala Thr Leu
1               5                   10                  15

Gly Ser Asp Val Asn Leu Thr Cys Gln Thr Gln Ala Lys Gly Phe Leu
            20                  25                  30

```
Val Gln Met Gln Trp Ser Lys Val Thr Asp Lys Ala Asp Leu Ile Ala
             35                  40                  45

Leu Tyr His Pro Gln Tyr Gly Phe His Cys Ala Tyr Gly Ser Pro Cys
 50                  55                  60

Glu Ser Leu Val Thr Phe Thr Gln Thr Pro Glu Asn Gly Ser Lys Trp
 65                  70                  75                  80

Thr Leu His Leu Arg Asn Met Ser Ser Val Ser Gly Arg Tyr Glu
                 85                  90                  95

Cys Met Leu Thr Leu Tyr Pro Glu Gly Met Gln Thr Lys Ile Tyr Asn
                100                 105                 110

Leu Leu Ile Gln Thr His Val
        115
```

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Ser
<220> FEATURE:
<221> NAME/KEY: MOD_RES
<222> LOCATION: (3)..(3)
<223> OTHER INFORMATION: Ala or Ser
<220> FEATURE:
<221> NAME/KEY: MOD_RES
<222> LOCATION: (4)..(4)
<223> OTHER INFORMATION: Met or Ile
<220> FEATURE:
<221> NAME/KEY: MOD_RES
<222> LOCATION: (5)..(5)
<223> OTHER INFORMATION: Ser or His

<400> SEQUENCE: 135

Xaa Tyr Xaa Xaa Xaa
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Ser
<220> FEATURE:
<221> NAME/KEY: MOD_RES
<222> LOCATION: (3)..(3)
<223> OTHER INFORMATION: Ala or Ser

<400> SEQUENCE: 136

Xaa Tyr Xaa Met His
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: Trp or Gly
<220> FEATURE:
<221> NAME/KEY: MOD_RES
<222> LOCATION: (3)..(3)
<223> OTHER INFORMATION: Asn or Ile
<220> FEATURE:
<221> NAME/KEY: MOD_RES
<222> LOCATION: (4)..(4)
<223> OTHER INFORMATION: Ala, Glu, Val, or Pro
<220> FEATURE:
<221> NAME/KEY: MOD_RES
<222> LOCATION: (5)..(5)
<223> OTHER INFORMATION: Val, Gly, Trp, or Ile
<220> FEATURE:
<221> NAME/KEY: MOD_RES
<222> LOCATION: (6)..(6)
<223> OTHER INFORMATION: Ser, Tyr, Thr, Asn, or Phe
<220> FEATURE:
<221> NAME/KEY: MOD_RES
<222> LOCATION: (7)..(7)
<223> OTHER INFORMATION: Gly or Trp
<220> FEATURE:
<221> NAME/KEY: MOD_RES
<222> LOCATION: (8)..(8)
<223> OTHER INFORMATION: Asp, Tyr, Asn, or Thr
<220> FEATURE:
<221> NAME/KEY: MOD_RES
<222> LOCATION: (9)..(9)
<223> OTHER INFORMATION: Thr or Ala
<220> FEATURE:
<221> NAME/KEY: MOD_RES
<222> LOCATION: (10)..(10)
<223> OTHER INFORMATION: Lys or Asn
<220> FEATURE:
<221> NAME/KEY: MOD_RES
<222> LOCATION: (12)..(12)
<223> OTHER INFORMATION: Ser or Ala

<400> SEQUENCE: 137

Xaa Ile Xaa Xaa Xaa Xaa Xaa Xaa Xaa Xaa Tyr Xaa Gln Lys Phe Gln
1               5                   10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Val, or Glu
<220> FEATURE:
<221> NAME/KEY: MOD_RES
<222> LOCATION: (5)..(5)
<223> OTHER INFORMATION: Val, Trp, or Gly
<220> FEATURE:
<221> NAME/KEY: MOD_RES
<222> LOCATION: (6)..(6)
<223> OTHER INFORMATION: Ser, Tyr, Thr, or Asn
<220> FEATURE:
<221> NAME/KEY: MOD_RES
<222> LOCATION: (7)..(7)
<223> OTHER INFORMATION: Gly or Trp
<220> FEATURE:
<221> NAME/KEY: MOD_RES
<222> LOCATION: (8)..(8)
<223> OTHER INFORMATION: Asp, Asn, Tyr, or Thr

<400> SEQUENCE: 138

Trp Ile Asn Xaa Xaa Xaa Xaa Xaa Thr Lys Tyr Ser Gln Lys Phe Gln
```

```
1               5                   10                  15

Gly

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser, Thr, or Leu
<220> FEATURE:
<221> NAME/KEY: MOD_RES
<222> LOCATION: (8)..(8)
<223> OTHER INFORMATION: Ser, Pro, or Trp

<400> SEQUENCE: 139

Arg Ala Ser Gln Ser Ile Xaa Xaa Tyr Leu Asn
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Trp Gly Met Ser Tyr Gly Leu Asp Val
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Ala
<220> FEATURE:
<221> NAME/KEY: MOD_RES
<222> LOCATION: (2)..(2)
<223> OTHER INFORMATION: Ala, Ser, or Glu

<400> SEQUENCE: 141

Xaa Xaa Ser Ser Leu Gln Ser
1               5

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Trp Gly Leu Ser Tyr Gly Met Asp Val
1               5                   10

<210> SEQ ID NO 143
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (10)..(10)
<223> OTHER INFORMATION: Thr or Ser

<400> SEQUENCE: 143

Gln Gln Xaa Tyr Ser Thr Pro Ala Leu Xaa
1               5                   10

<210> SEQ ID NO 144
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 144

Xaa Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 145
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 145

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 146
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 146

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30
```

-continued

```
Ala Met His Trp Val Arg Gln Ala Pro Gly Gln Arg Leu Glu Trp Met
            35                  40                  45
Gly Trp Ile Asn Ala Val Ser Gly Asp Thr Lys Tyr Ser Gln Lys Phe
 50                  55                  60
Gln Gly Arg Val Thr Ile Thr Arg Asp Thr Ser Thr Ser Thr Ala Tyr
 65                  70                  75                  80
Met Glu Leu Arg Ser Leu Arg Ser Asp Asp Thr Ala Met Tyr Tyr Cys
                 85                  90                  95
Ala Arg Asn Trp Gly Met Ser Tyr Gly Met Asp Val Trp Gly Gln Gly
                100                 105                 110
Thr Met Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
<210> SEQ ID NO 147
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 147

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Val Ser Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
                340                 345                 350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 148
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 148

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asp Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 149
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 149

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Thr Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 150
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 150

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gln Tyr
```

```
                   20                  25                  30
Ala Met His Trp Val Arg Gln Ala Pro Gly Gln Arg Leu Glu Trp Met
            35                  40                  45
Gly Trp Ile Asn Glu Gly Tyr Gly Asn Thr Lys Tyr Ser Gln Lys Phe
        50                  55                  60
Gln Gly Arg Val Thr Ile Thr Arg Asp Thr Ser Thr Ser Thr Ala Tyr
65                  70                  75                  80
Met Glu Leu Arg Ser Leu Arg Ser Asp Asp Thr Ala Met Tyr Tyr Cys
                85                  90                  95
Ala Arg Asn Trp Gly Met Ser Tyr Gly Met Asp Val Trp Gly Gln Gly
            100                 105                 110
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
<210> SEQ ID NO 151
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 151

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Tyr Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 152
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 152

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Ala Met His Trp Val Arg Gln Ala Pro Gly Gln Arg Leu Glu Trp Met
        35                  40                  45

Gly Trp Ile Asn Ala Gly Tyr Gly Tyr Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
```

-continued

```
            225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 153
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 153

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gln Tyr
                20                  25                  30

Ala Met His Trp Val Arg Gln Ala Pro Gly Gln Arg Leu Glu Trp Met
            35                  40                  45

Gly Trp Ile Asn Ala Gly Thr Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 154
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 154

Xaa Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Ser Gln Tyr
             20                  25                  30

Ala Met His Trp Val Arg Gln Ala Pro Gly Gln Arg Leu Glu Trp Met
             35                  40                  45

Gly Trp Ile Asn Ala Gly Thr Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Asn Trp Gly Met Ser Tyr Gly Met Asp Val Trp Gly Gln Gly
             100                 105                 110

Thr Thr Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
 145                 150                 155                 160

Asn Ser Gly Ala Leu Thr Ser Gly Val His Thr Phe Pro Ala Val Leu
             165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
             195                 200                 205

Ser Asn Thr Lys Val Asp Lys Arg Val Glu Pro Lys Ser Cys Asp Lys
 210                 215                 220

Thr His Thr Cys Pro Pro Cys Pro Ala Pro Glu Leu Leu Gly Gly Pro
 225                 230                 235                 240

Ser Val Phe Leu Phe Pro Pro Lys Pro Lys Asp Thr Leu Met Ile Ser
             245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
             275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
 305                 310                 315                 320

Tyr Lys Cys Lys Val Ser Asn Lys Ala Leu Pro Ala Pro Ile Glu Lys
             325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
             355                 360                 365

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
 385                 390                 395                 400

Asp Ser Asp Gly Ser Phe Phe Leu Tyr Ser Lys Leu Thr Val Asp Lys
             405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
```

435 440 445

<210> SEQ ID NO 155
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Gln or pyroglutamate

<400> SEQUENCE: 155

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Gln Tyr
                20                  25                  30

Ala Met His Trp Val Arg Gln Ala Pro Gly Gln Arg Leu Glu Trp Met
            35                  40                  45

Gly Trp Ile Asn Ala Gly Tyr Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

-continued

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 156
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 156

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 157
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 157

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Trp Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Trp Gly Met Ser Tyr Gly Met Asp Val Trp Gly Gln Gly
        100                 105                 110

Thr Thr Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 158
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 158

Xaa Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30
Ala Met His Trp Val Arg Gln Ala Pro Gly Gln Arg Leu Glu Trp Met
        35                  40                  45
Gly Trp Ile Asn Val Gly Thr Gly Thr Thr Lys Tyr Ser Gln Lys Phe
 50                  55                  60
Gln Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Asn Trp Gly Met Ser Tyr Gly Met Asp Val Trp Gly Gln Gly
            100                 105                 110
Thr Thr Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
            435                 440                 445
```

<210> SEQ ID NO 159
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 159

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Ala Met His Trp Val Arg Gln Ala Pro Gly Gln Arg Leu Glu Trp Met
        35                  40                  45

Gly Trp Ile Asn Ala Val Asn Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                        325                 330                 335
Thr Ile Ser Lys Ala Lys Gly Gln Pro Arg Glu Pro Gln Val Tyr Thr
                    340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 160
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 160

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Ser Met His Trp Val Arg Gln Ala Pro Gly Gln Arg Leu Glu Trp Met
        35                  40                  45

Gly Trp Ile Asn Ala Gly Asn Trp Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 161
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 161

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Trp Thr Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Met Asp Val Trp Gly Gln Gly
            100                 105                 110
```

```
Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 162
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 162

Xaa Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Thr Phe Thr Ser Tyr
                20                  25                  30
Ala Met His Trp Val Arg Gln Ala Pro Gly Gln Arg Leu Glu Trp Met
                35                  40                  45
Gly Trp Ile Asn Ala Gly Asn Gly Asn Thr Lys Tyr Ser Gln Lys Phe
            50                  55                  60
Gln Gly Arg Val Thr Ile Thr Arg Asp Thr Ser Thr Ser Thr Ala Tyr
65                  70                  75                  80
Met Glu Leu Arg Ser Leu Arg Ser Asp Thr Ala Met Tyr Tyr Cys
                85                  90                  95
Ala Arg Asn Trp Gly Met Ser Tyr Gly Leu Asp Val Trp Gly Gln Gly
                100                 105                 110
Thr Met Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Arg Val Glu Pro Lys Ser Cys Asp Lys
                210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
```

-continued

Ala Leu His Asn His Tyr Thr Gln Lys Ser Leu Ser Leu Ser Pro Gly
             435                 440                 445

<210> SEQ ID NO 163
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 163

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Leu Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

-continued

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 164
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 164

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Leu Ser Tyr Gly Leu Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys

```
                210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 165
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 165

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Met Ser Tyr Gly Leu Asp Val Trp Gly Gln Gly
                100                 105                 110
```

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 166
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 166

-continued

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Leu Ser Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                     420                 425                 430
Ala Leu His Asn His Tyr Thr Gln Lys Ser Leu Ser Leu Ser Pro Gly
            435                 440                 445

<210> SEQ ID NO 167
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 167

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Gly Leu Ser Tyr Gly Leu Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 168
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 168

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 169
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 169

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Tyr Trp Gly Gln Gly Thr
```

```
                    100                 105                 110
Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 170
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 170
```

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 171
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 171

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Arg Pro Leu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr

```
                305                 310                 315                 320
Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                    420                 425                 430

Leu His Asn His Tyr Thr Gln Lys Ser Leu Ser Leu Ser Pro Gly
                435                 440                 445

<210> SEQ ID NO 172
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 172

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 173
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 173

Xaa Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Tyr Asp Ser Arg Pro Leu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 174
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyroglutamate

<400> SEQUENCE: 174

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asn Trp Gly Met Ser Tyr Gly Met Asp Val Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 175
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
```

<210> SEQ ID NO 176
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 177
<211> LENGTH: 329

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 178
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 178

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asn Trp Gly Leu Ser Tyr Gly Leu Asp Val
1               5                   10

```
<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Met or Leu
<220> FEATURE:
<221> NAME/KEY: MOD_RES
<222> LOCATION: (8)..(8)
<223> OTHER INFORMATION: Met or Leu

<400> SEQUENCE: 180

Asn Trp Gly Xaa Ser Tyr Gly Xaa Asp Val
1               5                   10
```